US011939392B2

(12) United States Patent
Hernandez-Hoyos et al.

(10) Patent No.: US 11,939,392 B2
(45) **Date of Patent: *Mar. 26, 2024**

(54) CD123 BINDING PROTEINS AND RELATED COMPOSITIONS AND METHODS

(71) Applicant: APTEVO RESEARCH AND DEVELOPMENT LLC, Seattle, WA (US)

(72) Inventors: Gabriela Hernandez-Hoyos, Seattle, WA (US); Elaine T. Sewell, Seattle, WA (US); Catherine J. McMahan, Seattle, WA (US); David Bienvenue, Seattle, WA (US); John W. Blankenship, Seattle, WA (US); Danielle Mitchell, Seattle, WA (US); Peter Pavlik, Seattle, WA (US)

(73) Assignee: Aptevo Research and Development LLC, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/557,440

(22) Filed: Dec. 21, 2021

(65) Prior Publication Data

US 2022/0363773 A1 Nov. 17, 2022

Related U.S. Application Data

(63) Continuation of application No. 16/335,561, filed as application No. PCT/US2017/052808 on Sep. 21, 2017, now Pat. No. 11,242,400.

(60) Provisional application No. 62/466,192, filed on Mar. 2, 2017, provisional application No. 62/397,736, filed on Sep. 21, 2016.

(51) Int. Cl.

| | |
|---|---|
| ***C07K 16/28*** | (2006.01) |
| ***A61K 47/68*** | (2017.01) |
| ***A61P 35/00*** | (2006.01) |
| ***A61P 35/02*** | (2006.01) |
| ***C07K 16/30*** | (2006.01) |
| ***C12N 15/62*** | (2006.01) |
| *A61K 39/00* | (2006.01) |
| *C07K 16/00* | (2006.01) |

(52) U.S. Cl.

CPC ...... *C07K 16/2896* (2013.01); *A61K 47/6803* (2017.08); *A61P 35/00* (2018.01); *A61P 35/02* (2018.01); *C07K 16/2809* (2013.01); *C07K 16/2866* (2013.01); *C07K 16/3061* (2013.01); *C12N 15/62* (2013.01); *A61K 2039/505* (2013.01); *A61K 2039/545* (2013.01); *C07K 16/005* (2013.01); *C07K 2317/24* (2013.01); *C07K 2317/31* (2013.01); *C07K 2317/33* (2013.01); *C07K 2317/524* (2013.01); *C07K 2317/526* (2013.01); *C07K 2317/53* (2013.01); *C07K 2317/565* (2013.01); *C07K 2317/622* (2013.01); *C07K 2317/73* (2013.01); *C07K 2317/732* (2013.01); *C07K 2317/734* (2013.01); *C07K 2317/75* (2013.01); *C07K 2317/90* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | | |
|---|---|---|---|---|
| 5,731,168 | A | 3/1998 | Carter et al. | |
| 5,821,337 | A | 10/1998 | Carter et al. | |
| 5,834,597 | A * | 11/1998 | Tso | C07K 16/2809 530/387.3 |
| 6,180,370 | B1 * | 1/2001 | Queen | C07K 16/087 435/69.6 |
| 6,551,592 | B2 | 4/2003 | Lindhofer et al. | |
| 7,612,181 | B2 | 11/2009 | Wu et al. | |
| 9,745,381 | B2 | 8/2017 | Liu et al. | |
| 9,856,327 | B2 * | 1/2018 | Bernett | C07K 16/2866 |
| 10,676,533 | B2 | 6/2020 | Hernandez-Hoyos et al. | |
| 11,242,400 | B2 | 2/2022 | Hernandez-Hoyos et al. | |
| 2005/0009743 | A1 | 1/2005 | Sundquist et al. | |
| 2005/0163782 | A1 | 7/2005 | Glaser et al. | |
| 2005/0208048 | A1 | 9/2005 | McMahan et al. | |
| 2006/0035320 | A1 | 2/2006 | Tissot et al. | |
| 2006/0234302 | A1 | 10/2006 | Hoet et al. | |
| 2007/0077246 | A1 | 4/2007 | Koenig et al. | |
| 2011/0293619 | A1 * | 12/2011 | Kufer | A61P 35/00 435/69.6 |

(Continued)

FOREIGN PATENT DOCUMENTS

| | | | | |
|---|---|---|---|---|
| WO | WO-2006124784 A2 * | 11/2006 | | C12N 15/1034 |
| WO | WO-2007146948 A2 | 12/2007 | | |

(Continued)

OTHER PUBLICATIONS

Hezareh, M et al. Journal of virology vol. 75,24 (2001): 12161-8 (Year: 2001).*

(Continued)

*Primary Examiner* — Michael Szperka
*Assistant Examiner* — Lia E Taylor
(74) *Attorney, Agent, or Firm* — COOLEY LLP

(57) ABSTRACT

The present disclosure relates to protein molecules that specifically bind to CD123, which may have at least one humanized or human CD123-binding domain. Such molecules are useful for the treatment of cancer. The protein molecule binding to CD123 may have a second binding domain that binds to another target. In one embodiment, multi-specific polypeptide molecules bind both CD123-expressing cells and the T-cell receptor complex on T-cells to induce target-dependent T-cell cytotoxicity, activation, and proliferation. The disclosure also provides pharmaceutical compositions comprising the CD123-binding polypeptide molecules, nucleic acid molecules encoding these polypeptides and methods of making these molecules.

15 Claims, 23 Drawing Sheets

Specification includes a Sequence Listing.

(56) References Cited

U.S. PATENT DOCUMENTS

2012/0082670 A1 4/2012 Konopitzky et al.
2013/0266569 A1 10/2013 Gurney et al.
2015/0110789 A1 4/2015 Liu et al.
2015/0232557 A1* 8/2015 Tan ........................ A61P 35/00 435/254.11
2016/0068605 A1 3/2016 Nemeth et al.
2016/0176953 A1 6/2016 Purcell Ngambo et al.
2017/0349660 A1 12/2017 Saville et al.
2018/0273622 A1 9/2018 Tan et al.
2019/0071513 A1 3/2019 Hernandez-Hoyos et al.
2020/0165346 A1 5/2020 Hernandez-Hoyos et al.

FOREIGN PATENT DOCUMENTS

WO WO-2009017823 A2 2/2009
WO WO-2011034969 A1 3/2011
WO WO-2011090761 A1 7/2011
WO WO-2012021934 A1 2/2012
WO WO-2012065161 A2 5/2012
WO WO-2013173820 A2 11/2013
WO WO-2014143807 A2 9/2014
WO WO-2016116626 A1 7/2016
WO WO-2016130819 A2 8/2016
WO WO-2017053469 A2 3/2017
WO WO-2018057802 A1 3/2018

OTHER PUBLICATIONS

Buss, Nicholas APS, et al. Current opinion in pharmacology 12.5 (2012): 615-622 (Year: 2012).*
Dechant, Michael, et al. Blood, The Journal of the American Society of Hematology 100.13 (2002): 4574-4580 (Year: 2002).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Baeuerle, Patrick A., and Carsten Reinhardt. Cancer research 69.12 (2009): 4941-4944 (Year: 2009).
Bargou et al., "Tumor Regression in Cancer Patients by Very Low Doses of a T Cell-Engaging Antibody," Science, 2008, 321:974-977.
Bortoletto et al., "Optimizing anti-CD3 affinity for effective T cell targeting against tumor cells," Eur. J. Immunol. 32(11):3102-3107 (2002).
Chichili et al., "ACD3xCD123 bispecific DART for redirecting host Tcells to my elogenous leukemia: Preclinical activity and safety in non human primates",Science Translational Medicine, 7 (289): 289ra82-289ra82, 2015.
Chu et al., "Immunotherapy with Long Lived Anti CD123x Anti CD3 Bispecific Antibodies Stimulates Potent T Cell Mediated Killing of Human AML Cell Lines and of CD123+ Cells in Monkeys: A Potential Therapy for Acute Myeloqenous Leukemia," Blood, 124 (21): 2316, 2014.
Clinical Trials.gov, History of Changes for Study: NCT00635596: Phase I Study MT110101 in CDC; Gland Lung Cancer, first published Mar. 7, 2008, 7 pages, retrieved from https:clinicaltrials.govct2historyNCT00635596?A=1&B=1&C=merged#StudyPageTop.
Co-pending U.S. Appl. No. 17/238,522, inventors Hernandez-Hoyos; Gabriela et al., filed Apr. 23, 2021.
Croasdale et al., "Development of Tetravalent IgG1 Dual Targeting IGF1 REGFR Antibodies with Potent Tumor Inhibition," Archives of Biochemistry and Biophysics, 526: 206-218, 2012.
Dechant M., et al., "Chimeric IgA Antibodies Against HLA Class II Effectively Trigger Lymphoma Cell Killing," Blood, Dec. 15, 2002, vol. 100, No. 13, pp. 4574-4580.
Dong et al., "A Stable IgG Like Bispecific Antibody Targeting the Epidermal Growth Factor Receptor and the Type I Insulin like Growth Factor Receptor Demonstrates Superior Anti Tumor Activity," mAbs, 3(3): 373288, 2011.
Dreier et al., "Extremely Potent, Rapid, and Costimulation Independent Cytotoxic T Cell Response Against Lymphoma Cells Catalyzed by a Single Chain Bispecific Antibody," International Journal of Cancer, 100(6): 690-692, 2002.
Enver et al., "Next generation immunotherapeutics honing the magic bullet," Current Opinion in Biotechnology, 20: 405-411 (2009), published on Aug. 24, 2009.
Extended European Search Report for European Application No. 13790217.7, dated Mar. 21, 2016, 12 pages.
Extended European Search Report for European Application No. 17853936.7 dated Aug. 19, 2020, 14 pages.
Fiedler et al., "A Phase I Study of EpCAMCD3 Bispecific Antibody (MT110) in Patients with Advanced Solid Tumors," Abstract, Journal of Clinical Oncology, 30(15) Suppl. 2504, 2012.
Genbank AEV 43323.1 , "FelgG1 Heavy Chain Constant Region, Partial [*Homo sapiens*]", published Jul. 6, 2011, 1 page.
Henn et al., "Pre clinical characterization of MT114, a novel CD33CD 3 bispecific BiTE antibody for the treatment of acutemyeloid leukemia(AML)", Cancer Research, Apr. 15, 2012, XP055251939, Retrieved from the internet: URL: http//cancerres.aacrjournals.orgcontenV728_SupplemenV3523 [retrieved on Feb. 22, 2016] 2 pages, abstract only.
Hezareh, M. et al., "Effector Function Activities of a Panel of Mutants of a Broadly Neutralizing Antibody against Human Immunodeficiency Virus Type 1", Journal of Virology 75.24 (2001): 12161-12168.
International Search Report and Written Opinion for International Application No. PCT/US2017/052808, dated Jan. 23, 2018, 14 pages.
Janeway, A. C., et al., "The interaction of the antibody molecule with specific antigen," immunobiology: The Immune System in Health and Disease, 5th Edition, Garland Science, 2001, 5 pages.
Janeway C.A., et al., "Immunobiology: the Immune System in Health and Disease", Current Biology, 1997, 14 pages.
Kiewe et al., "Phase I trial of the trifunctional anti HER2x anti CD3 antibody ertumaxomab in metastatic breast cancer," Clinical Cancer Research, 2006, vol. 12, No. 10, pp. 3085-3091.
Kipriyanov S.M., et al., "Generation and Production of Engineered Antibodies," Molecular Biotechnology (2004); 26(1): 39-60.
Konterman, R.E. (Mar./Apr. 2012) "Dual targeting strategies with bispecific antibodies" MAbs, 4(2):182-197.
Kugleretal., "Are combinant trispecific single chain Fv derivative directed against CD123 and CD33 mediates effective elimination of acutemyeloid leukaemia cells by dual targeting," British Journal of Haematology 150; 574-586 (2010), published on Jul. 16, 2010.
Kuo et al., "Antibody Internalization After Cell Surface Antigen Binding is Critical for Immunotoxin Development," Bioconjugate Chemistry, 20(10): 1975-1982, 2009.
Kuo, et al., "Engineering a CD123xCD3 bispecific scFv immunofusion for the treatment of leukemia and elimination of leukemia stem cells." Protein Engineering, Design and Selection (2012); 25 (10): 561-570.
Liu et al., "CD123 and its potential clinical application in leukemias," Life Sciences (2015) 122: 59-64.
Müller et al., "Bispecific antibodies for cancer immunotherapy: Current perspectives," BioDrugs 24(2):89-98 (2010).
Moore G.L., et al., "A Novel Bispecific Antibody Format Enables Simultaneous Bivalent and Monovalent Co-Engagement of Distinct Target Antigens," MAbs, Nov.-Dec. 2011, vol. 3, No. 6, pp. 546-557, DOI: 10.4161/mabs.3.6.18123.
Naujokat, "Targeting Human Cancer Stem Cells with Monoclonal Antibodies," Journal of Clinical & Cellular Immunology, 85: 007, 2012, 15 pages.
Niranjana et al. "AEV43323.1. Fe IgG1 Heavy Chain Constant Region, partial [*Homo sapiens*]", Genbank, Jul. 6, 2011, 1 page.
Non-Final Office Action dated Jul. 16, 2021 for U.S. Appl. No. 16/335,561, filed Mar. 21, 2019, 25 pages.
Pohl et al., "A Cassette Vector System for the Rapid Cloning and Production of Bispecific Tetravalent Antibodies," Antibodies, 1: 19-38, 2012.
Radcliff et al., "Mobilization of dendritic cells in cancer patients treated with granulocy tecolony stimulating factor and chemotherapy," British Journal of Haematology 119; 20411 (2002).

(56) References Cited

OTHER PUBLICATIONS

Ramos, et al., "Current Approaches in the Treatment of Relapsed and Refractory Acute Myeloid Leukemia." J. Clin. Med. (2015); 4 (4): 665-695.
Request for Ex Parte Reexamination filed Jul. 13, 2018 in U.S. Pat. No. 9,745,381 (57 pages).
Request for Ex Parte Reexamination filed May 3, 2019 in U.S. Pat. No. 9,745,381 (67 pages).
Robinson, W.H., "Sequencing the functional antibody repertoire-diagnostic and therapeutic discovery," Nature Reviews Rheumatology (2015) 11: 171-182.
Roopenian and Akilesh, "FcRn: the neonatal Fc receptor comes of age," Nature Reviews Immunology, 2007, vol. 7, pp. 715-725.
Rudikoff, S. et al., "Single amino acid substitution altering antigen-binding specificity," Proc. Natl. Acad. Sci. USA, 79:1979-1983 (Mar. 1, 1982).
Schlereth et al., "Eradication of Tumors from a Human Colon Cancer Cell Line and from Ovarian Cancer Metastases in Immunodeficient Mice by a Single-Chain-Ep-CAM-/CD3-Bispecific Antibody Construct," Cancer Research, 65(7): 2882-2889, 2005.
Sievers and Senter, "Antibody-Drug Conjugates in Cancer Therapy," Annual Review of Medicine (2013) 64: 15-29.
Stamova et al., "Simultaneous engagement of the activatory receptors NKG2D and CD3 for retargeting of effector cells to CD33-positive malignant cells," Leukemia 25; 1053-1056 (2011), published on Mar. 18, 2011.
Stein et al., "Novel conjugates of single-chain Fv antibody fragments specific for stem cell antigen CD123 mediate potent death of acute myeloid leukaemia cells," British Journal of Haematology (2010) 148, 879-889.
Testa, et al., "CD 123 is a membrane biomarker and a therapeutic target in hematologic malignancies." Biomarker Research (2014); 2: 4, 11 pages.
Third Party Observations Issued in Corresponding European Application No. 13790217.7, dated Apr. 11, 2019 (12 pages).
Third Party Observations Issued in Corresponding European Application No. 13790217.7, dated Apr. 25, 2019 (31 pages).
Wang et al., "Monoclonal antibodies with identical Fe sequences can bind to FcRn differentially with pharmacokinetic consequences," Drug Metabolism and Disposition, 2011, vol. 39, No. 9, pp. 1469-1477.
Wolf et al., "BiTEs: bispecific antibody constructs with unique anti-tumor activity," Drug Discov. Today 10(18):1237-1244 (2005).
Yalcintepe et al., "Expression of interleukin-3 receptor subunits on defined subpopulations of acute myeloid leukemia blasts predicts the cytotoxicity of diphtheria toxin interleukin-3 fusion protein against malignant progenitors that engraft in immunodeficient mice," Blood, 2006, vol. 108, pp. 3530-3537.

* cited by examiner

| | TRI125 |
|---|---|
| EC50 (nM) | 3.14 |

| | TRI129 | TRI130 |
|---|---|---|
| EC50 (nM) | 5.33 | 4.31 |

| | TRI139 |
|---|---|
| EC50 (nM) | 2.33 |

| | TRI129 | TRI130 | TRI139 |
|---|---|---|---|
| EC50 (nM) | 9.69 | 4.65 | 2.81 |

| | TRI123 | TRI126 |
|---|---|---|
| EC50 (nM) | 7.38 | 37.18 |

| | TRI129 | TRI130 | TRI132 |
|---|---|---|---|
| EC50 (nM) | 8.77 | 12.12 | 4.23 |

| | TRI137 | TRI139 |
|---|---|---|
| EC50 (nM) | 4.79 | 3.64 |

| | TRI123 | TRI125 | TRI126 | TRI127 | TRI128 | TRI129 | TRI130 | TRI131 | TRI132 | TRI134 |
|---|---|---|---|---|---|---|---|---|---|---|
| EC50 (pM) | 19.70 | 4.99 | 7.96 | 10.94 | 3.54 | 10.4 | 3.66 | 22.80 | 6.74 | 22.69 |

| | TRI137 | TRI138 | TRI139 |
|---|---|---|---|
| EC50 (pM) | 36.39 | 15.17 | 7.96 |

Proliferation of CD4+ T cells in the Presence of Bispecific anti-CD123 x anti-CD3ε Molecules and Molm-13 Target Cells

| CD4 | TRI129 | TRI130 | TRI139 |
|---|---|---|---|
| EC50 (pM) | 1.65 | 1.53 | 1.54 |

Proliferation of CD8+ T cells in the Presence of Bispecific anti-CD123 x anti-CD3ε Molecules and Molm-13 Target Cells

| CD8 | TRI129 | TRI130 | TRI139 |
|---|---|---|---|
| EC50 (pM) | 2.29 | 1.46 | 2.06 |

| CD4 | TRI129 | TRI130 | TRI139 |
|---|---|---|---|
| EC50 (pM) | 2.63 | 3.40 | 2.71 |

| CD8 | TRI129 | TRI130 | TRI139 |
|---|---|---|---|
| EC50 (pM) | 5.79 | 6.50 | 6.36 |

*Tumor volumes are plotted as the mean + SEM of tumor volume measurement
*Last recorded volume carried forward after endpoint reached
*Groups plotted until all mice in group reached endpoint, or until study terminiated FIG. 13 WinNonlin NCA Estimates and Fit of Half-life for Treatment Groups FIG. 14 Change in Lymphocyte Population Over Time in Cynomolgus Monkeys
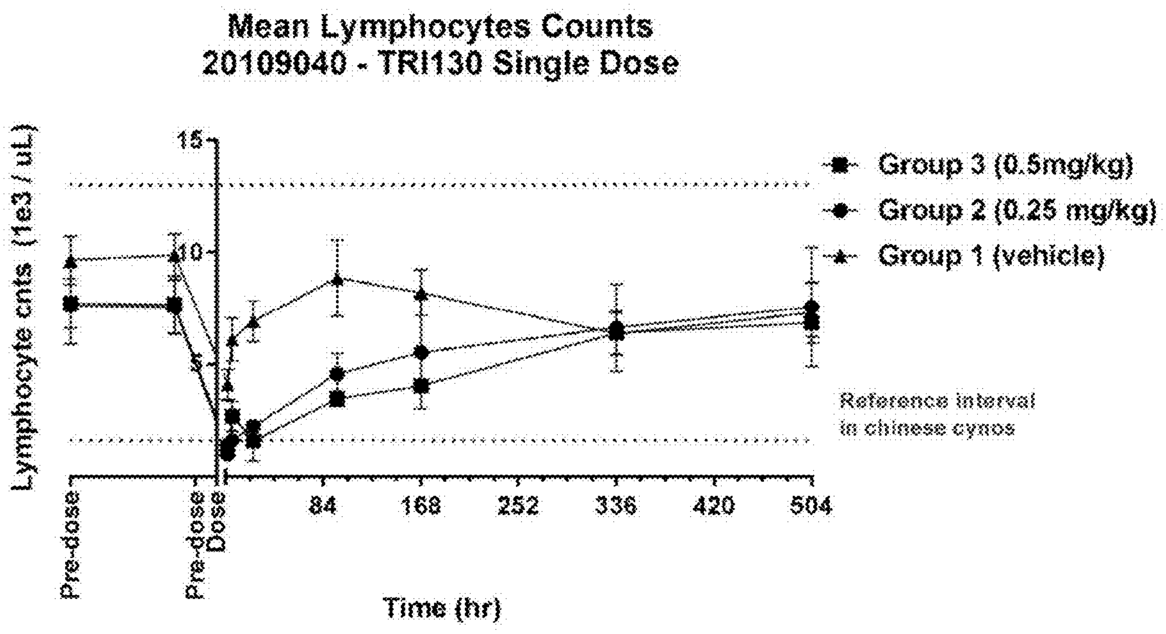
FIG. 15 Change in Basophil Population Over Time in Cynomolgus Monkeys
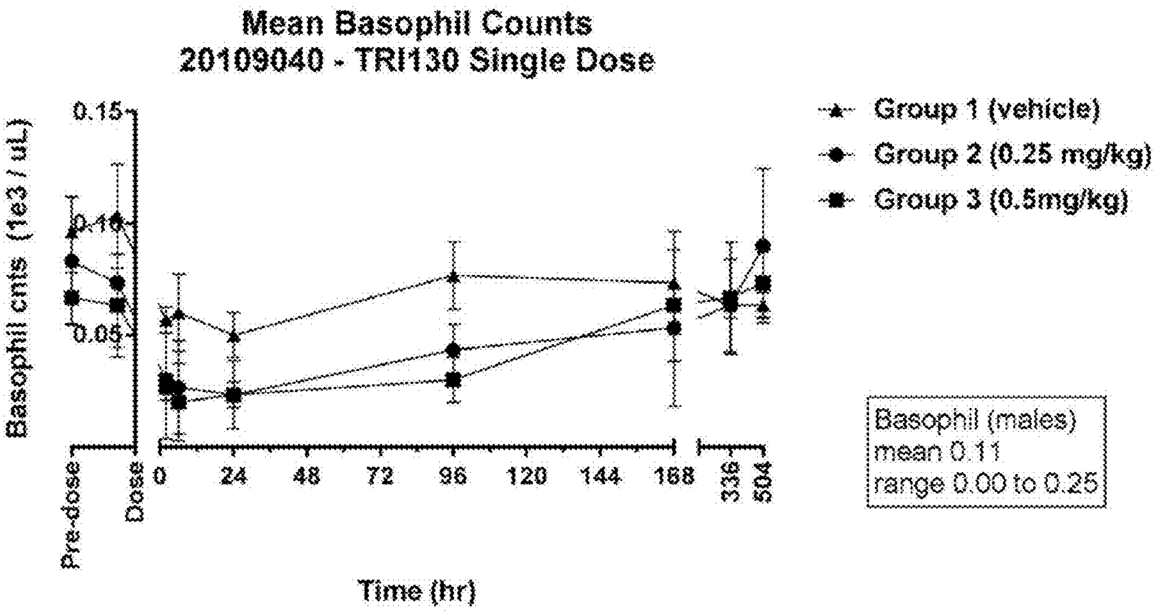

FIG. 16 Bioluminescent Tumor Burden of MOLM-13 Disseminated Xenograft Study
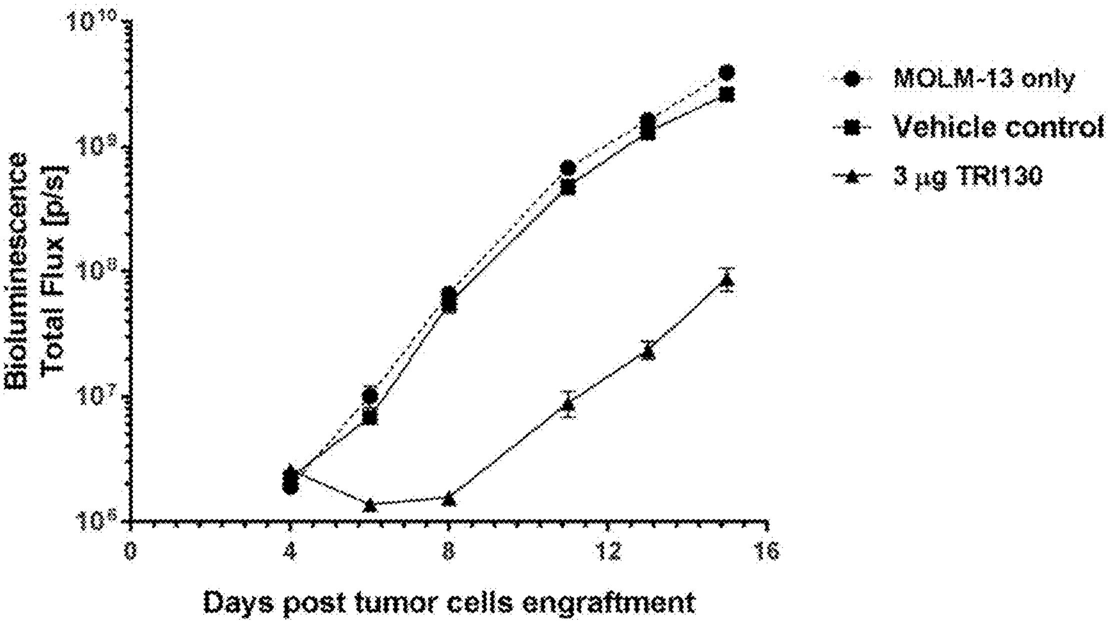
FIG. 17 Bioluminescent Images of Day 14 Tumor Burden
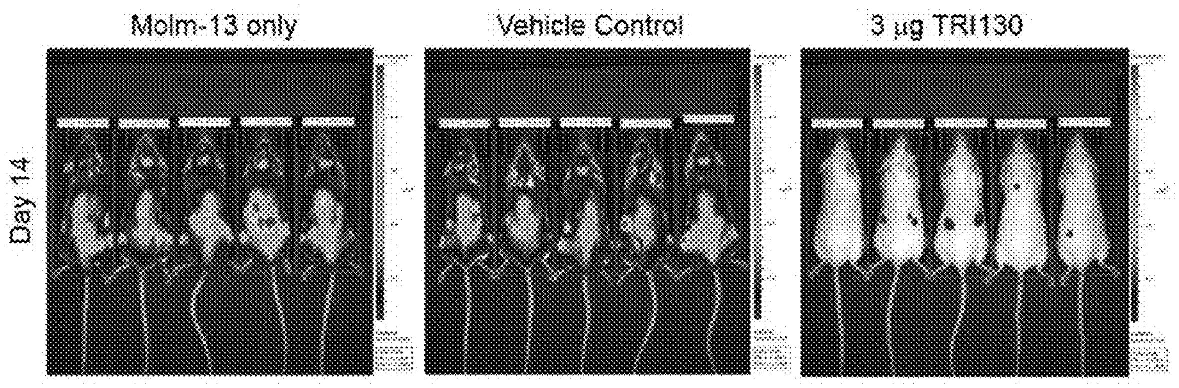

FIG. 18 TRI130 and TRI168 Induced T-cell Activation with Molm-13 Target Cells
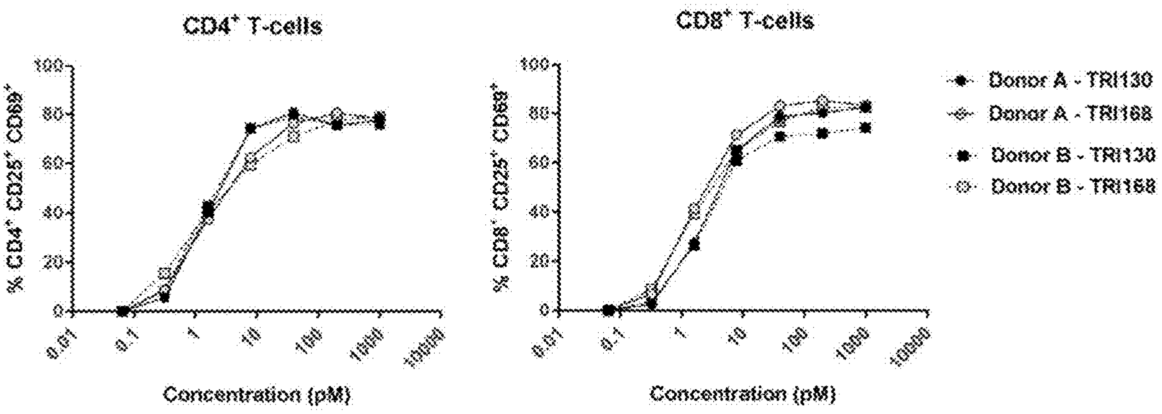
| EC50 (pM) | TRI130 | TRI168 |
|---|---|---|
| Donor A | 1.5 | 1.7 |
| Donor B | 1.4 | 1.0 |
| EC50 (pM) | TRI130 | TRI168 |
|---|---|---|
| Donor A | 2.6 | 1.6 |
| Donor B | 2.4 | 1.7 |
FIG. 19 TRI130 and TRI168 Induced T-cell Cytotoxicity of CD123+ Molm-13 Target Cells
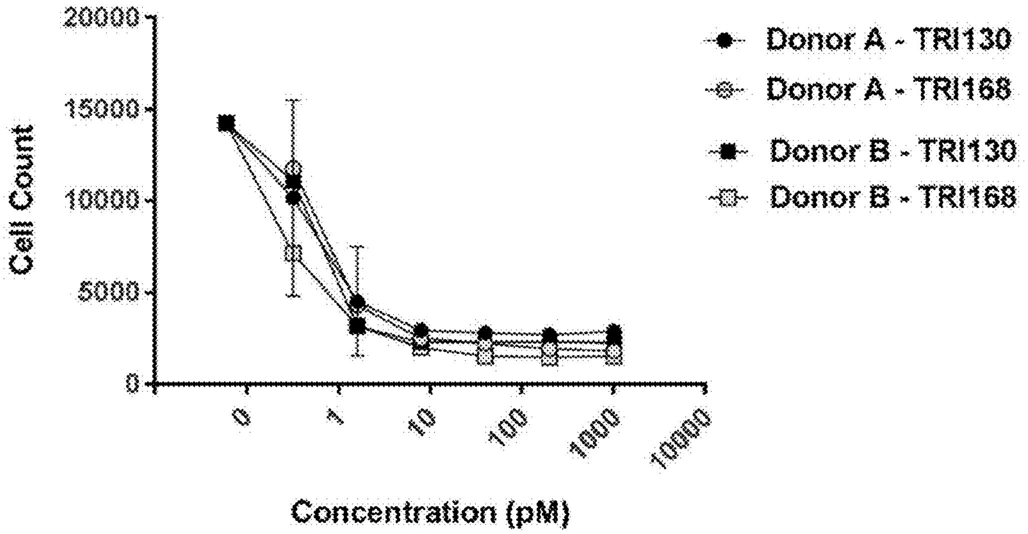

FIG. 20 TRI130 and TRI168 Induced T-cell Cytokine Release with Molm-13 Target Cells
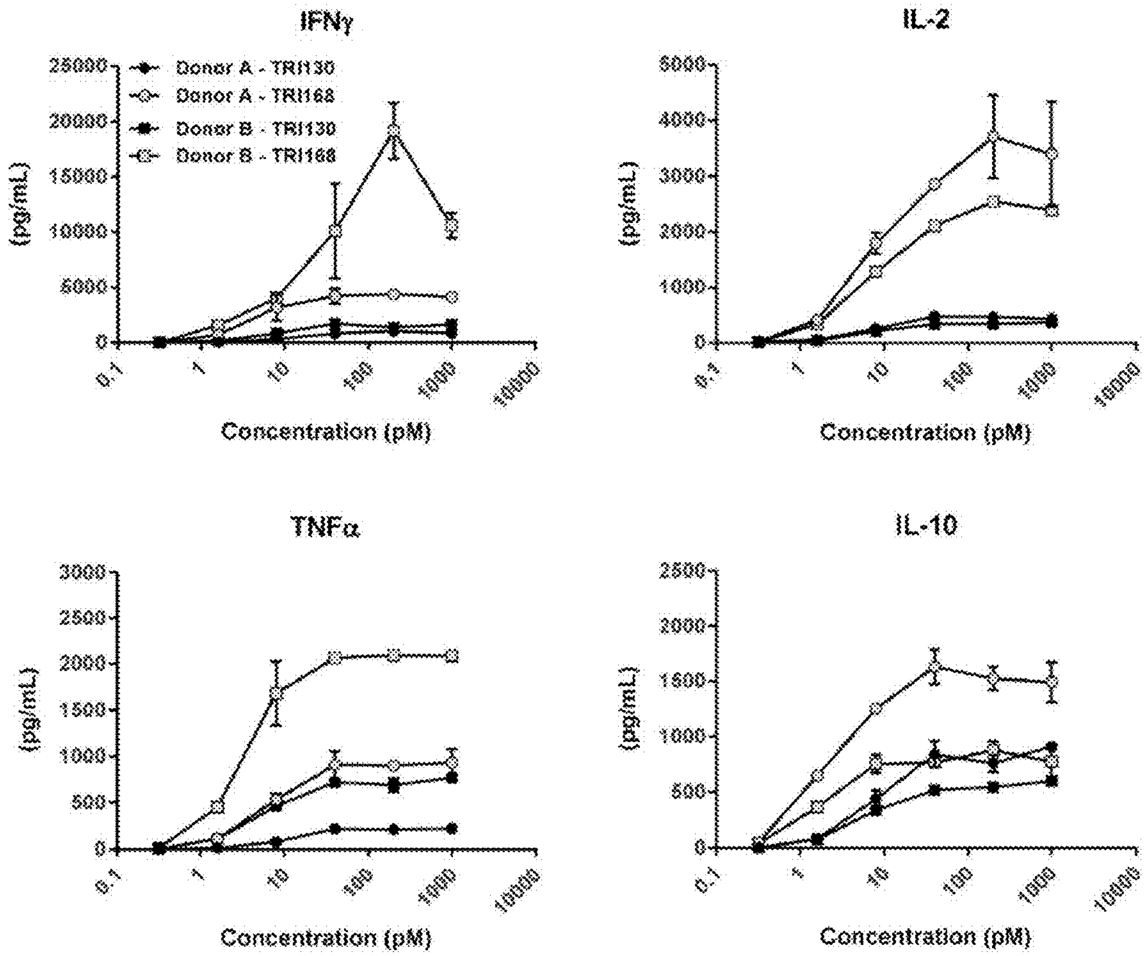

FIG. 21 TRI130 and TRI168 Induced Cytokine Release in PBMC Cultures
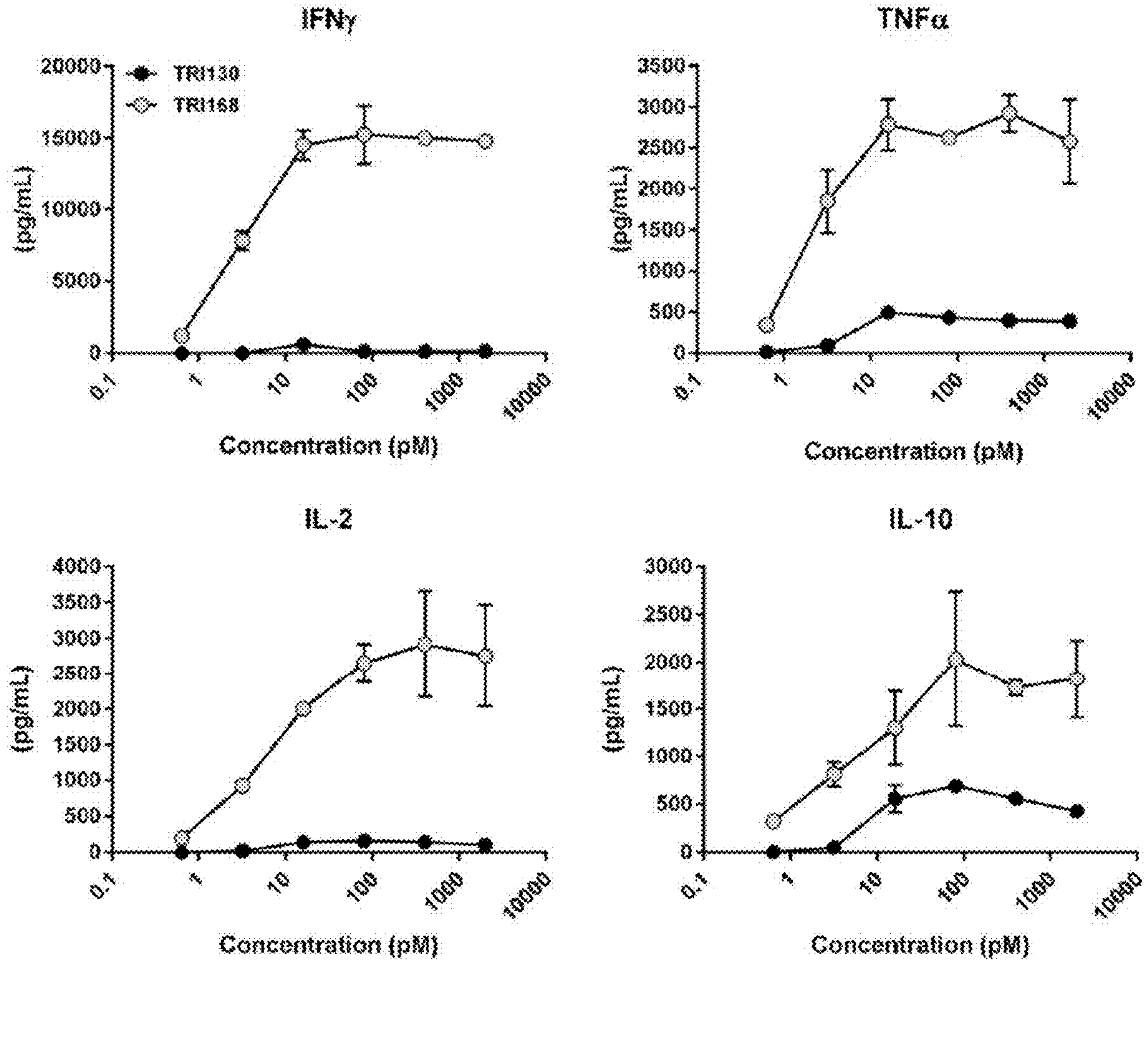

FIG. 22 Cytotoxicity of TRI130 Incubated with AML Cell Samples
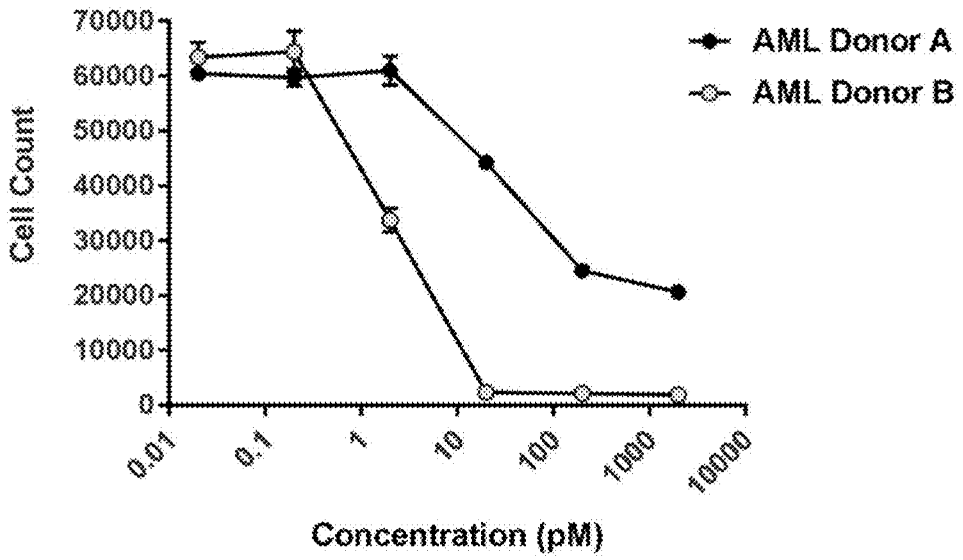

SEQUENCE LISTING

```
<160> NUMBER OF SEQ ID NOS: 316

<210> SEQ ID NO 1
<211> LENGTH: 342
<212> TYPE: DNA
<213> ORGANISM: Artificial Sequence
<220> FEATURE:
<223> OTHER INFORMATION: OMT1 variable light chain domain

<400> SEQUENCE: 1

gacatcgtga tgacccagtc tccagactcc ctggctgtgt ctctgggcga gagggccacc     60

atcaactgca agtccagcca cagtgtttta tacagctcca acaataagaa ctacttagct    120

tggtaccagc agaaaccagg acagcctcct aagctgctca tttactgggc atctacccgg    180

gaatccgggg tccctgaccg attcagtggc agcgggtctg ggacagattt cactctcacc    240

atcagcagcc tgcaggctga agatgtggca gtttattact gtcagcaata ttatagtact    300

cctccgacca ctttcggcgg agggaccaag gtggagatca aa                       342


<210> SEQ ID NO 2
<211> LENGTH: 114
<212> TYPE: PRT
<213> ORGANISM: Artificial Sequence
<220> FEATURE:
<223> OTHER INFORMATION: OMT1 variable light chain domain

<400> SEQUENCE: 2

Asp Ile Val Met Thr Gln Ser Pro Asp Ser Leu Ala Val Ser Leu Gly
1               5                   10                  15
```

```
Glu Arg Ala Thr Ile Asn Cys Lys Ser Ser His Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Thr Phe Gly Gly Gly Thr Lys Val Glu
            100                 105                 110

Ile Lys


<210> SEQ ID NO 3
<211> LENGTH: 372
<212> TYPE: DNA
<213> ORGANISM: Artificial Sequence
<220> FEATURE:
<223> OTHER INFORMATION: OMT1 variable heavy chain domain

<400> SEQUENCE: 3

gaggtgcagc tgttggagtc tgggggaggc ttggtacagc ctggggggtc cctgagactc      60

tcctgtgcag cctctggatt cacctttagc agctatggca tgagctgggt ccgccaggct     120

ccagggaagg ggctggaggg ggtctcagct attagtggta gtggtggtag cacatactac     180

gcagactccg tgaagggccg gttcaccatc tccagagaca attccaagaa cacgctgtat     240

ctgcaaatga acagcctgag agccgaggac acggccgtat attactgtgc gaaagaaaag     300

ttacgatatt ttgactggtt atccgatgct tttgatatct ggggccaagg gacaatggtc     360

accgtctctt ca                                                         372


<210> SEQ ID NO 4
<211> LENGTH: 124
<212> TYPE: PRT
<213> ORGANISM: Artificial Sequence
<220> FEATURE:
<223> OTHER INFORMATION: OMT1 variable heavy chain domain

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Gly Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Lys Leu Arg Tyr Phe Asp Trp Leu Ser Asp Ala Phe Asp
            100                 105                 110

Ile Trp Gly Gln Gly Thr Met Val Thr Val Ser Ser
        115                 120
```

<210> SEQ ID NO 5
<211> LENGTH: 36
<212> TYPE: DNA
<213> ORGANISM: Artificial Sequence
<220> FEATURE:
<223> OTHER INFORMATION: OMT1 CDR L1

<400> SEQUENCE: 5
cacagtgttt tatacagctc caacaataag aactac 36

<210> SEQ ID NO 6
<211> LENGTH: 12
<212> TYPE: PRT
<213> ORGANISM: Artificial Sequence
<220> FEATURE:
<223> OTHER INFORMATION: OMT1 CDR L1

<400> SEQUENCE: 6

His Ser Val Leu Tyr Ser Ser Asn Asn Lys Asn Tyr
1 5 10

<210> SEQ ID NO 7
<211> LENGTH: 9
<212> TYPE: DNA
<213> ORGANISM: Artificial Sequence
<220> FEATURE:
<223> OTHER INFORMATION: OMT1 CDR L2

<400> SEQUENCE: 7 tgggcatct 9

<210> SEQ ID NO 8
<211> LENGTH: 3
<212> TYPE: PRT
<213> ORGANISM: Artificial Sequence
<220> FEATURE:
<223> OTHER INFORMATION: OMT1 CDR L2

<400> SEQUENCE: 8

Trp Ala Ser
1

<210> SEQ ID NO 9
<211> LENGTH: 30
<212> TYPE: DNA
<213> ORGANISM: Artificial Sequence
<220> FEATURE:
<223> OTHER INFORMATION: OMT1 CDR L3

<400> SEQUENCE: 9
cagcaatatt atagtactcc tccgaccact 30

<210> SEQ ID NO 10
<211> LENGTH: 10
<212> TYPE: PRT
<213> ORGANISM: Artificial Sequence
<220> FEATURE:
<223> OTHER INFORMATION: OMT1 CDR L3

<400> SEQUENCE: 10

Gln Gln Tyr Tyr Ser Thr Pro Pro Thr Thr
1 5 10

<210> SEQ ID NO 11
<211> LENGTH: 24
<212> TYPE: DNA
<213> ORGANISM: Artificial Sequence -continued

<220> FEATURE:
<223> OTHER INFORMATION: OMT1 CDR H1

<400> SEQUENCE: 11
ggattcacct ttagcagcta tggc 24

<210> SEQ ID NO 12
<211> LENGTH: 8
<212> TYPE: PRT
<213> ORGANISM: Artificial Sequence
<220> FEATURE:
<223> OTHER INFORMATION: OMT1 CDR H1

<400> SEQUENCE: 12

Gly Phe Thr Phe Ser Ser Tyr Gly
1 5

<210> SEQ ID NO 13
<211> LENGTH: 24
<212> TYPE: DNA
<213> ORGANISM: Artificial Sequence
<220> FEATURE:
<223> OTHER INFORMATION: OMT1 CDR H2

<400> SEQUENCE: 13
attagtggta gtggtggtag caca 24

<210> SEQ ID NO 14
<211> LENGTH: 8
<212> TYPE: PRT
<213> ORGANISM: Artificial Sequence
<220> FEATURE:
<223> OTHER INFORMATION: OMT1 CDR H2

<400> SEQUENCE: 14

Ile Ser Gly Ser Gly Gly Ser Thr
1 5

<210> SEQ ID NO 15
<211> LENGTH: 51
<212> TYPE: DNA
<213> ORGANISM: Artificial Sequence
<220> FEATURE:
<223> OTHER INFORMATION: OMT1 CDR H3

<400> SEQUENCE: 15
gcgaaagaaa agttacgata ttttgactgg ttatccgatg cttttgatat c 51

<210> SEQ ID NO 16
<211> LENGTH: 17
<212> TYPE: PRT
<213> ORGANISM: Artificial Sequence
<220> FEATURE:
<223> OTHER INFORMATION: OMT1 CDR H3

<400> SEQUENCE: 16

Ala Lys Glu Lys Leu Arg Tyr Phe Asp Trp Leu Ser Asp Ala Phe Asp
1 5 10 15

Ile

<210> SEQ ID NO 17
<211> LENGTH: 321
<212> TYPE: DNA
<213> ORGANISM: Artificial Sequence
<220> FEATURE:
<223> OTHER INFORMATION: DB8, DB60, DB65, DB280, DB331, DB415, DB435
variable light chain domain

<400> SEQUENCE: 17

```
gacatccaga tgacccagtc tccatcctcc ctgtctgcat ctgtaggaga cagagtcacc      60

atcacttgcc gggcaagtca gagcattagc agctatctga attggtatca gcagaaacca     120

gggaaagccc ctaagctcct gatctatgct gcatccagtt tgcaaagtgg ggtcccatca     180

aggttcagtg gcagtggatc tgggacagat ttcactctca ccatcagcag tctgcaacct     240

gaagattttg caacttacta ctgtcaacag agttacagta cccctctcac tttcggcgga     300

ggtaccaagg tggagatcaa a                                               321
```

<210> SEQ ID NO 18
<211> LENGTH: 107
<212> TYPE: PRT
<213> ORGANISM: Artificial Sequence
<220> FEATURE:
<223> OTHER INFORMATION: DB8, DB60, DB65, DB280, DB331, DB415, DB435
variable light chain domain

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 19
<211> LENGTH: 366
<212> TYPE: DNA
<213> ORGANISM: Artificial Sequence
<220> FEATURE:
<223> OTHER INFORMATION: DB8 variable heavy chain domain

<400> SEQUENCE: 19

```
caggtgcagc tggtgcagtc tggggctgag gtgaagaagc ctggggcctc agtgaaggtt      60

tcctgcaagg catctggata catcttcacc gactactata tgcactgggt gcgtcaggcc     120

cctggacaag ggcttgagtg gatgggatgg atgagcccta acagtggtaa cacaggctat     180

gcacagaagt tccagggccg tgtcaccatg acccgcgaca cgtccacgag cacagtctac     240

atggagctga gcagcctgcg ttctgaggac acggccgtgt attactgtgc gagagatgcg     300

gcggattacg gtgactacgt tgcttttgat atctggggcc aagggacaat ggtcaccgtc     360

tcttca                                                                366
```

<210> SEQ ID NO 20
<211> LENGTH: 122
<212> TYPE: PRT
<213> ORGANISM: Artificial Sequence
<220> FEATURE:
<223> OTHER INFORMATION: DB8 variable heavy chain domain

<400> SEQUENCE: 20

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Asp Tyr
20 25 30

Tyr Met His Trp Val Arg Gln Ala Pro Gly Gln Gly Leu Glu Trp Met
35 40 45

Gly Trp Met Ser Pro Asn Ser Gly Asn Thr Gly Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Asp Ala Ala Asp Tyr Gly Asp Tyr Val Ala Phe Asp Ile Trp
100 105 110

Gly Gln Gly Thr Met Val Thr Val Ser Ser
115 120

<210> SEQ ID NO 21
<211> LENGTH: 18
<212> TYPE: DNA
<213> ORGANISM: Artificial Sequence
<220> FEATURE:
<223> OTHER INFORMATION: DB8, DB60, DB65, DB280, DB331, DB415, DB435 CDR L1

<400> SEQUENCE: 21
cagagcatta gcagctat 18

<210> SEQ ID NO 22
<211> LENGTH: 6
<212> TYPE: PRT
<213> ORGANISM: Artificial Sequence
<220> FEATURE:
<223> OTHER INFORMATION: DB8, DB60, DB65, DB280, DB331, DB415, DB435 CDR L1

<400> SEQUENCE: 22

Gln Ser Ile Ser Ser Tyr
1 5

<210> SEQ ID NO 23
<211> LENGTH: 9
<212> TYPE: DNA
<213> ORGANISM: Artificial Sequence
<220> FEATURE:
<223> OTHER INFORMATION: DB8, DB60, DB65, DB280, DB331, DB415, DB435 CDR L2

<400> SEQUENCE: 23 gctgcatcc 9

<210> SEQ ID NO 24
<211> LENGTH: 3
<212> TYPE: PRT
<213> ORGANISM: Artificial Sequence
<220> FEATURE:
<223> OTHER INFORMATION: DB8, DB60, DB65, DB280, DB331, DB415, DB435 CDR L2

<400> SEQUENCE: 24

Ala Ala Ser
1

<210> SEQ ID NO 25
<211> LENGTH: 27
<212> TYPE: DNA
<213> ORGANISM: Artificial Sequence
<220> FEATURE:
<223> OTHER INFORMATION: DB8, DB60, DB65, DB280, DB331, DB415, DB435 CDR L3

<400> SEQUENCE: 25
caacagagtt acagtacccc tctcact 27

<210> SEQ ID NO 26
<211> LENGTH: 9
<212> TYPE: PRT
<213> ORGANISM: Artificial Sequence
<220> FEATURE:
<223> OTHER INFORMATION: DB8, DB60, DB65, DB280, DB331, DB415, DB435 CDR L3

<400> SEQUENCE: 26

Gln Gln Ser Tyr Ser Thr Pro Leu Thr
1 5

<210> SEQ ID NO 27
<211> LENGTH: 24
<212> TYPE: DNA
<213> ORGANISM: Artificial Sequence
<220> FEATURE:
<223> OTHER INFORMATION: DB8 and DB60 CDR H1

<400> SEQUENCE: 27
ggatacatct tcaccgacta ctat 24

<210> SEQ ID NO 28
<211> LENGTH: 8
<212> TYPE: PRT
<213> ORGANISM: Artificial Sequence
<220> FEATURE:
<223> OTHER INFORMATION: DB8 CDR H1

<400> SEQUENCE: 28

Gly Tyr Ile Phe Thr Asp Tyr Tyr
1 5

<210> SEQ ID NO 29
<211> LENGTH: 24
<212> TYPE: DNA
<213> ORGANISM: Artificial Sequence
<220> FEATURE:
<223> OTHER INFORMATION: DB8 CDR H2

<400> SEQUENCE: 29
atgagcccta acagtggtaa caca 24

<210> SEQ ID NO 30
<211> LENGTH: 8
<212> TYPE: PRT
<213> ORGANISM: Artificial Sequence
<220> FEATURE:
<223> OTHER INFORMATION: DB8 CDR H2

<400> SEQUENCE: 30

Met Ser Pro Asn Ser Gly Asn Thr
1 5

<210> SEQ ID NO 31
<211> LENGTH: 45
<212> TYPE: DNA
<213> ORGANISM: Artificial Sequence
<220> FEATURE:
<223> OTHER INFORMATION: DB8 CDR H3

<400> SEQUENCE: 31
gcgagagatg cggcggatta cggtgactac gttgcttttg atatc 45

<210> SEQ ID NO 32
<211> LENGTH: 15
<212> TYPE: PRT
<213> ORGANISM: Artificial Sequence
<220> FEATURE:
<223> OTHER INFORMATION: DB8 CDR H3

<400> SEQUENCE: 32

Ala Arg Asp Ala Ala Asp Tyr Gly Asp Tyr Val Ala Phe Asp Ile
1 5 10 15

<210> SEQ ID NO 33
<211> LENGTH: 357
<212> TYPE: DNA
<213> ORGANISM: Artificial Sequence
<220> FEATURE:
<223> OTHER INFORMATION: DB60 variable heavy chain domain

<400> SEQUENCE: 33
caggtgcagc tggtgcagtc tggggctgag gtgaagaagc ctggggcctc agtgaaggtt 60
tcctgcaagg catctggata caccttcacc agctactata tgcactgggt gcgtcaggcc 120
cctggacaag ggcttgagtg gatggggtgg atcaacccta acagtggtga cacaagctat 180
gcacagaagt tccagggccg tgtcaccatg acccgcgaca cgtccacgag cacagtctac 240
atggagctga gcagcctgcg ttctgaggac acggccgtgt attactgtgc gcaggatagt 300
agtggttccg ggcttttga tatctggggc caagggacaa tggtcaccgt ctcttca 357

<210> SEQ ID NO 34
<211> LENGTH: 119
<212> TYPE: PRT
<213> ORGANISM: Artificial Sequence
<220> FEATURE:
<223> OTHER INFORMATION: DB60 variable heavy chain domain

<400> SEQUENCE: 34

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Trp Ile Asn Pro Asn Ser Gly Asp Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

-continued

Ala Gln Asp Ser Ser Gly Ser Gly Ala Phe Asp Ile Trp Gly Gln Gly
100 105 110

Thr Met Val Thr Val Ser Ser
115

<210> SEQ ID NO 35
<211> LENGTH: 24
<212> TYPE: DNA
<213> ORGANISM: Artificial Sequence
<220> FEATURE:
<223> OTHER INFORMATION: DB60 CDR H1

<400> SEQUENCE: 35
ggatacacct tcaccagcta ctat 24

<210> SEQ ID NO 36
<211> LENGTH: 8
<212> TYPE: PRT
<213> ORGANISM: Artificial Sequence
<220> FEATURE:
<223> OTHER INFORMATION: DB60 CDR H1

<400> SEQUENCE: 36

Gly Tyr Thr Phe Thr Ser Tyr Tyr
1 5

<210> SEQ ID NO 37
<211> LENGTH: 24
<212> TYPE: DNA
<213> ORGANISM: Artificial Sequence
<220> FEATURE:
<223> OTHER INFORMATION: DB60 CDR H2

<400> SEQUENCE: 37
atcaacccta acagtggtga caca 24

<210> SEQ ID NO 38
<211> LENGTH: 8
<212> TYPE: PRT
<213> ORGANISM: Artificial Sequence
<220> FEATURE:
<223> OTHER INFORMATION: DB60 CDR H2

<400> SEQUENCE: 38

Ile Asn Pro Asn Ser Gly Asp Thr
1 5

<210> SEQ ID NO 39
<211> LENGTH: 36
<212> TYPE: DNA
<213> ORGANISM: Artificial Sequence
<220> FEATURE:
<223> OTHER INFORMATION: DB60 CDR H3

<400> SEQUENCE: 39
gcgcaggata gtagtggttc cggggctttt gatatc 36

<210> SEQ ID NO 40
<211> LENGTH: 12
<212> TYPE: PRT
<213> ORGANISM: Artificial Sequence
<220> FEATURE:
<223> OTHER INFORMATION: DB60 CDR H3

<400> SEQUENCE: 40

Ala Gln Asp Ser Ser Gly Ser Gly Ala Phe Asp Ile
1 5 10

<210> SEQ ID NO 41
<211> LENGTH: 369
<212> TYPE: DNA
<213> ORGANISM: Artificial Sequence
<220> FEATURE:
<223> OTHER INFORMATION: DB65 variable heavy chain domain

<400> SEQUENCE: 41
caggtgcagc tggtgcagtc tggggctgag gtgaagaagc ctggggcctc agtgaaggtt 60
tcctgcaagg catctggata caccttcacc ggctactata tgcactgggt gcgtcaggcc 120
cctggacaag ggcttgagtg gatgggatgg atgaacccta acagtggtaa cacaggctat 180
gcacagaagt tccagggccg tgtcaccatg acccgcgaca cgtccacgag cacagtctac 240
atggagctga gcagcctgcg ttctgaggac acggccgtgt attactgtgc gaaagaggaa 300
ccgatttttg gagtggttat ggatgctttt gatatctggg gccaagggac aatggtcacc 360
gtctcctca 369

<210> SEQ ID NO 42
<211> LENGTH: 123
<212> TYPE: PRT
<213> ORGANISM: Artificial Sequence
<220> FEATURE:
<223> OTHER INFORMATION: DB65 variable heavy chain domain

<400> SEQUENCE: 42

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Met Asn Pro Asn Ser Gly Asn Thr Gly Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Lys Glu Glu Pro Ile Phe Gly Val Val Met Asp Ala Phe Asp Ile
100 105 110

Trp Gly Gln Gly Thr Met Val Thr Val Ser Ser
115 120

<210> SEQ ID NO 43
<211> LENGTH: 24
<212> TYPE: DNA
<213> ORGANISM: Artificial Sequence
<220> FEATURE:
<223> OTHER INFORMATION: DB65 CDR H1

<400> SEQUENCE: 43
ggatacacct tcaccggcta ctat 24

<210> SEQ ID NO 44
<211> LENGTH: 8
<212> TYPE: PRT

<213> ORGANISM: Artificial Sequence
<220> FEATURE:
<223> OTHER INFORMATION: DB65 CDR H1

<400> SEQUENCE: 44

Gly Tyr Thr Phe Thr Gly Tyr Tyr
1 5

<210> SEQ ID NO 45
<211> LENGTH: 24
<212> TYPE: DNA
<213> ORGANISM: Artificial Sequence
<220> FEATURE:
<223> OTHER INFORMATION: DB65 CDR H2

<400> SEQUENCE: 45
atgaacccta acagtggtaa caca 24

<210> SEQ ID NO 46
<211> LENGTH: 8
<212> TYPE: PRT
<213> ORGANISM: Artificial Sequence
<220> FEATURE:
<223> OTHER INFORMATION: DB65 CDR H2

<400> SEQUENCE: 46

Met Asn Pro Asn Ser Gly Asn Thr
1 5

<210> SEQ ID NO 47
<211> LENGTH: 48
<212> TYPE: DNA
<213> ORGANISM: Artificial Sequence
<220> FEATURE:
<223> OTHER INFORMATION: DB65 CDR H3

<400> SEQUENCE: 47
gcgaaagagg aaccgatttt tggagtggtt atggatgctt ttgatatc 48

<210> SEQ ID NO 48
<211> LENGTH: 16
<212> TYPE: PRT
<213> ORGANISM: Artificial Sequence
<220> FEATURE:
<223> OTHER INFORMATION: DB65 CDR H3

<400> SEQUENCE: 48

Ala Lys Glu Glu Pro Ile Phe Gly Val Val Met Asp Ala Phe Asp Ile
1 5 10 15

<210> SEQ ID NO 49
<211> LENGTH: 321
<212> TYPE: DNA
<213> ORGANISM: Artificial Sequence
<220> FEATURE:
<223> OTHER INFORMATION: DB82 variable light chain domain

<400> SEQUENCE: 49
gacatccaga tgacccagtc tccatcctcc ctgtctgcat ctgtaggaga ccgcgtcacc 60
atcacttgcc gggcaagtca gaccataaac aactatttga actggtatca gcagaaacca 120
gggaaagccc ctaagctcct gatctattct gcatctactt tgcaaagtgg ggtcccatca 180
cgtttcagtg gcagtggatc tgggacagat ttcactctca ccatcagcag tctgcaacct 240

```
gaagattttg caacttacta ctgtcaccag agttacactt cacctctcac tttcggcgga    300

ggtaccaagg tggagatcaa a                                              321
```

<210> SEQ ID NO 50
<211> LENGTH: 107
<212> TYPE: PRT
<213> ORGANISM: Artificial Sequence
<220> FEATURE:
<223> OTHER INFORMATION: DB82 variable light chain domain

<400> SEQUENCE: 50

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Thr Ile Asn Asn Tyr
            20                  25                  30

Leu Asn Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Ser Tyr Thr Ser Pro Leu
                85                  90                  95

Thr Phe Gly Gly Gly Thr Lys Val Glu Ile Lys
            100                 105
```

<210> SEQ ID NO 51
<211> LENGTH: 363
<212> TYPE: DNA
<213> ORGANISM: Artificial Sequence
<220> FEATURE:
<223> OTHER INFORMATION: DB82 variable heavy chain domain

<400> SEQUENCE: 51

```
gaggtgcagc tggtggagtc tgggggaggc ttggtacagc ctggggggtc cctgcgcctc     60

tcctgtgcag cctctggatt cacctttagc agctatgcca tgagctgggt ccgccaggct    120

ccagggaagg ggctggagtg ggtctcagtt attagtgcca atagtgctgg tctaggccat    180

gcggactctg tgaagggccg gttcaccatc tcccgcgaca attccaagaa cacgctgtat    240

ctgcaaatga acagcctgcg cgccgaggac acggccgtat attactgtgc gagagtgggc    300

tatagcagct cggctgatgc ttttgatatc tggggccaag ggacaatggt caccgtctcc    360

tcg                                                                  363
```

<210> SEQ ID NO 52
<211> LENGTH: 121
<212> TYPE: PRT
<213> ORGANISM: Artificial Sequence
<220> FEATURE:
<223> OTHER INFORMATION: DB82 variable heavy chain domain

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

-continued

```
Ser Val Ile Ser Ala Asn Ser Ala Gly Leu Gly His Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly Tyr Ser Ser Ser Ala Asp Ala Phe Asp Ile Trp Gly
            100                 105                 110

Gln Gly Thr Met Val Thr Val Ser Ser
        115                 120
```

<210> SEQ ID NO 53
<211> LENGTH: 18
<212> TYPE: DNA
<213> ORGANISM: Artificial Sequence
<220> FEATURE:
<223> OTHER INFORMATION: DB82 CDR L1

<400> SEQUENCE: 53
cagaccataa acaactat 18

<210> SEQ ID NO 54
<211> LENGTH: 6
<212> TYPE: PRT
<213> ORGANISM: Artificial Sequence
<220> FEATURE:
<223> OTHER INFORMATION: DB82 CDR L1

<400> SEQUENCE: 54

```
Gln Thr Ile Asn Asn Tyr
1               5
```

<210> SEQ ID NO 55
<211> LENGTH: 9
<212> TYPE: DNA
<213> ORGANISM: Artificial Sequence
<220> FEATURE:
<223> OTHER INFORMATION: DB82 CDR L2

<400> SEQUENCE: 55 tctgcatct 9

<210> SEQ ID NO 56
<211> LENGTH: 3
<212> TYPE: PRT
<213> ORGANISM: Artificial Sequence
<220> FEATURE:
<223> OTHER INFORMATION: DB82 CDR L2

<400> SEQUENCE: 56

```
Ser Ala Ser
1
```

<210> SEQ ID NO 57
<211> LENGTH: 27
<212> TYPE: DNA
<213> ORGANISM: Artificial Sequence
<220> FEATURE:
<223> OTHER INFORMATION: DB82 CDR L3

<400> SEQUENCE: 57
caccagagtt acacttcacc tctcact 27

<210> SEQ ID NO 58
<211> LENGTH: 9
<212> TYPE: PRT
<213> ORGANISM: Artificial Sequence
<220> FEATURE:
<223> OTHER INFORMATION: DB82 CDR L3

<400> SEQUENCE: 58

His Gln Ser Tyr Thr Ser Pro Leu Thr
1               5

<210> SEQ ID NO 59
<211> LENGTH: 24
<212> TYPE: DNA
<213> ORGANISM: Artificial Sequence
<220> FEATURE:
<223> OTHER INFORMATION: DB82 CDR H1

<400> SEQUENCE: 59
ggattcacct ttagcagcta tgcc 24

<210> SEQ ID NO 60
<211> LENGTH: 8
<212> TYPE: PRT
<213> ORGANISM: Artificial Sequence
<220> FEATURE:
<223> OTHER INFORMATION: DB82 CDR H1

<400> SEQUENCE: 60

Gly Phe Thr Phe Ser Ser Tyr Ala
1               5

<210> SEQ ID NO 61
<211> LENGTH: 24
<212> TYPE: DNA
<213> ORGANISM: Artificial Sequence
<220> FEATURE:
<223> OTHER INFORMATION: DB82 CDR H2

<400> SEQUENCE: 61
attagtgcca atagtgctgg tcta 24

<210> SEQ ID NO 62
<211> LENGTH: 8
<212> TYPE: PRT
<213> ORGANISM: Artificial Sequence
<220> FEATURE:
<223> OTHER INFORMATION: DB82 CDR H2

<400> SEQUENCE: 62

Ile Ser Ala Asn Ser Ala Gly Leu
1               5

<210> SEQ ID NO 63
<211> LENGTH: 42
<212> TYPE: DNA
<213> ORGANISM: Artificial Sequence
<220> FEATURE:
<223> OTHER INFORMATION: DB82 CDR H3

<400> SEQUENCE: 63
gcgagagtgg gctatagcag ctcggctgat gcttttgata tc 42

<210> SEQ ID NO 64
<211> LENGTH: 14
<212> TYPE: PRT
<213> ORGANISM: Artificial Sequence

<220> FEATURE:
<223> OTHER INFORMATION: DB82 CDR H3

<400> SEQUENCE: 64

Ala Arg Val Gly Tyr Ser Ser Ser Ala Asp Ala Phe Asp Ile
1               5                   10

<210> SEQ ID NO 65
<211> LENGTH: 336
<212> TYPE: DNA
<213> ORGANISM: Artificial Sequence
<220> FEATURE:
<223> OTHER INFORMATION: DB83 variable light chain domain

<400> SEQUENCE: 65
gatgttgtga tgactcagtc tccactctcc ctgcccgtca cccctggaga gccggcctcc 60
atctcctgca ggtctagtca gagcctcctg catagtaatg gagacaacta tttggattgg 120
tacctgcaga agccagggca gtctccacag ctcctgatct atttgggttc taatcgggcc 180
tccggggtcc ctgaccgttt cagtggcagt ggatcaggca cagattttac actgaaaatc 240
agccgtgtgg aggctgagga tgttggggtt tattactgca tgcaagctac acactggcca 300
ctcactttcg gccctggtac caaagtggat atcaaa 336

<210> SEQ ID NO 66
<211> LENGTH: 112
<212> TYPE: PRT
<213> ORGANISM: Artificial Sequence
<220> FEATURE:
<223> OTHER INFORMATION: DB83 variable light chain domain

<400> SEQUENCE: 66

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asp Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr His Trp Pro Leu Thr Phe Gly Pro Gly Thr Lys Val Asp Ile Lys
            100                 105                 110

<210> SEQ ID NO 67
<211> LENGTH: 375
<212> TYPE: DNA
<213> ORGANISM: Artificial Sequence
<220> FEATURE:
<223> OTHER INFORMATION: DB83 variable heavy chain domain

<400> SEQUENCE: 67
caggtgcagc tggtgcagtc tggggctgag gtgaagaagc ctggggcctc agtgaaggtt 60
tcctgcaagg catctggata caccttcact agctatgcta tgcattgggt gcgtcaggcc 120
cctggacaag ggcttgagtg gatgggactt gttgatcctg aagatggtga aacaatatat 180
gcagagaagt tccagggccg tgtcaccatg acccgcgaca cgtccacgag cacagtctac 240

```
atggagctga gcagcctgcg ttctgaggac acggccgtgt attactgtgc gagacgaacg    300

tattactatg atagtagtgg ttcccgttat gcttttgata tctggggcca agggaccacg    360

gtcaccgtct cttca                                                     375


<210> SEQ ID NO 68
<211> LENGTH: 125
<212> TYPE: PRT
<213> ORGANISM: Artificial Sequence
<220> FEATURE:
<223> OTHER INFORMATION: DB83 variable heavy chain domain

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Thr Tyr Tyr Tyr Asp Ser Ser Gly Ser Arg Tyr Ala Phe
            100                 105                 110

Asp Ile Trp Gly Gln Gly Thr Thr Val Thr Val Ser Ser
        115                 120                 125


<210> SEQ ID NO 69
<211> LENGTH: 33
<212> TYPE: DNA
<213> ORGANISM: Artificial Sequence
<220> FEATURE:
<223> OTHER INFORMATION: DB83 CDR L1

<400> SEQUENCE: 69

cagagcctcc tgcatagtaa tggagacaac tat                                  33


<210> SEQ ID NO 70
<211> LENGTH: 11
<212> TYPE: PRT
<213> ORGANISM: Artificial Sequence
<220> FEATURE:
<223> OTHER INFORMATION: DB83 CDR L1

<400> SEQUENCE: 70

Gln Ser Leu Leu His Ser Asn Gly Asp Asn Tyr
1               5                   10


<210> SEQ ID NO 71
<211> LENGTH: 9
<212> TYPE: DNA
<213> ORGANISM: Artificial Sequence
<220> FEATURE:
<223> OTHER INFORMATION: DB83 CDR L2

<400> SEQUENCE: 71

ttgggttct                                                              9
```

<210> SEQ ID NO 72
<211> LENGTH: 3
<212> TYPE: PRT
<213> ORGANISM: Artificial Sequence
<220> FEATURE:
<223> OTHER INFORMATION: DB83 CDR L2

<400> SEQUENCE: 72

Leu Gly Ser
1

<210> SEQ ID NO 73
<211> LENGTH: 27
<212> TYPE: DNA
<213> ORGANISM: Artificial Sequence
<220> FEATURE:
<223> OTHER INFORMATION: DB83 CDR L3

<400> SEQUENCE: 73
atgcaagcta cacactggcc actcact 27

<210> SEQ ID NO 74
<211> LENGTH: 9
<212> TYPE: PRT
<213> ORGANISM: Artificial Sequence
<220> FEATURE:
<223> OTHER INFORMATION: DB83 CDR L3

<400> SEQUENCE: 74

Met Gln Ala Thr His Trp Pro Leu Thr
1 5

<210> SEQ ID NO 75
<211> LENGTH: 24
<212> TYPE: DNA
<213> ORGANISM: Artificial Sequence
<220> FEATURE:
<223> OTHER INFORMATION: DB83 CDR H1

<400> SEQUENCE: 75
ggatacacct tcactagcta tgct 24

<210> SEQ ID NO 76
<211> LENGTH: 8
<212> TYPE: PRT
<213> ORGANISM: Artificial Sequence
<220> FEATURE:
<223> OTHER INFORMATION: DB83 CDR H1

<400> SEQUENCE: 76

Gly Tyr Thr Phe Thr Ser Tyr Ala
1 5

<210> SEQ ID NO 77
<211> LENGTH: 24
<212> TYPE: DNA
<213> ORGANISM: Artificial Sequence
<220> FEATURE:
<223> OTHER INFORMATION: DB83 CDR H2

<400> SEQUENCE: 77
gttgatcctg aagatggtga aaca 24

<210> SEQ ID NO 78
<211> LENGTH: 8
<212> TYPE: PRT
<213> ORGANISM: Artificial Sequence

<220> FEATURE:
<223> OTHER INFORMATION: DB83 CDR H2

<400> SEQUENCE: 78

Val Asp Pro Glu Asp Gly Glu Thr
1               5

<210> SEQ ID NO 79
<211> LENGTH: 54
<212> TYPE: DNA
<213> ORGANISM: Artificial Sequence
<220> FEATURE:
<223> OTHER INFORMATION: DB83 CDR H3

<400> SEQUENCE: 79
gcgagacgaa cgtattacta tgatagtagt ggttcccgtt atgcttttga tatc 54

<210> SEQ ID NO 80
<211> LENGTH: 18
<212> TYPE: PRT
<213> ORGANISM: Artificial Sequence
<220> FEATURE:
<223> OTHER INFORMATION: DB83 CDR H3

<400> SEQUENCE: 80

Ala Arg Arg Thr Tyr Tyr Tyr Asp Ser Ser Gly Ser Arg Tyr Ala Phe
1               5                   10                  15

Asp Ile

<210> SEQ ID NO 81
<211> LENGTH: 321
<212> TYPE: DNA
<213> ORGANISM: Artificial Sequence
<220> FEATURE:
<223> OTHER INFORMATION: DB86 variable light chain domain

<400> SEQUENCE: 81
gacatccaga tgacccagtc tccatcctcc ctgtctgcat ctgtaggaga ccgcgtcacc 60
atcacttgcc gggcaagtca gggcatcaga aatgatttag gttggtatca gcagaaacca 120
gggaaagccc ctaagctcct gatctatgct gcatccactt tgcaatcagg ggtcccatca 180
cgtttcagtg gcagtggatc tgggacagat ttcactctca ccatcagcag tctgcaacct 240
gaagattttg caacttacta ctgtcaacag agttacggtg cccccctcac tttcggcgga 300
ggtaccaagg tggagatcaa a 321

<210> SEQ ID NO 82
<211> LENGTH: 107
<212> TYPE: PRT
<213> ORGANISM: Artificial Sequence
<220> FEATURE:
<223> OTHER INFORMATION: DB86 variable light chain domain

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Gly Ala Pro Leu
                85                  90                  95

Thr Phe Gly Gly Gly Thr Lys Val Glu Ile Lys
            100                 105


<210> SEQ ID NO 83
<211> LENGTH: 360
<212> TYPE: DNA
<213> ORGANISM: Artificial Sequence
<220> FEATURE:
<223> OTHER INFORMATION: DB86 variable heavy chain domain

<400> SEQUENCE: 83

caggtgcagc tggtgcagtc tggggctgag gtgaagaagc ctggggcctc agtgaaggtt      60

tcctgcaagg catctggata tatgttcagt ggccattctg cacactgggt gcgtcaggcc     120

cctggacaag ggcttgagtg gatgggatgg atgaacccta acagtggtaa cacaggctat     180

gcacagaagt tccagggccg tgtcaccatg acccgcgaca cgtccacgag cacagtctac     240

atggagctga gcagcctgcg ttctgaggac acggccgtgt attactgtgc gagagatagc     300

agtggctggt acgatgtctt tgactactgg ggccagggga ccctggtcac cgtctcctca     360


<210> SEQ ID NO 84
<211> LENGTH: 120
<212> TYPE: PRT
<213> ORGANISM: Artificial Sequence
<220> FEATURE:
<223> OTHER INFORMATION: DB86 variable heavy chain domain

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Ser Gly His
            20                  25                  30

Ser Ala His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Tyr Asp Val Phe Asp Tyr Trp Gly Gln
            100                 105                 110

Gly Thr Leu Val Thr Val Ser Ser
        115                 120


<210> SEQ ID NO 85
<211> LENGTH: 18
<212> TYPE: DNA
<213> ORGANISM: Artificial Sequence
<220> FEATURE:
<223> OTHER INFORMATION: DB86 CDR L1

<400> SEQUENCE: 85

cagggcatca gaaatgat                                                    18
```

<210> SEQ ID NO 86
<211> LENGTH: 6
<212> TYPE: PRT
<213> ORGANISM: Artificial Sequence
<220> FEATURE:
<223> OTHER INFORMATION: DB86 CDR L1

<400> SEQUENCE: 86

Gln Gly Ile Arg Asn Asp
1 5

<210> SEQ ID NO 87
<211> LENGTH: 9
<212> TYPE: DNA
<213> ORGANISM: Artificial Sequence
<220> FEATURE:
<223> OTHER INFORMATION: DB86 CDR L2

<400> SEQUENCE: 87 gctgcatcc 9

<210> SEQ ID NO 88
<211> LENGTH: 3
<212> TYPE: PRT
<213> ORGANISM: Artificial Sequence
<220> FEATURE:
<223> OTHER INFORMATION: DB86 CDR L2

<400> SEQUENCE: 88

Ala Ala Ser
1

<210> SEQ ID NO 89
<211> LENGTH: 24
<212> TYPE: DNA
<213> ORGANISM: Artificial Sequence
<220> FEATURE:
<223> OTHER INFORMATION: DB86 CDR L3

<400> SEQUENCE: 89
caacagagtt acggtgcccc cctc 24

<210> SEQ ID NO 90
<211> LENGTH: 9
<212> TYPE: PRT
<213> ORGANISM: Artificial Sequence
<220> FEATURE:
<223> OTHER INFORMATION: DB86 CDR L3

<400> SEQUENCE: 90

Gln Gln Ser Tyr Gly Ala Pro Leu Thr
1 5

<210> SEQ ID NO 91
<211> LENGTH: 24
<212> TYPE: DNA
<213> ORGANISM: Artificial Sequence
<220> FEATURE:
<223> OTHER INFORMATION: DB86 CDR H1

<400> SEQUENCE: 91
ggatatatgt tcagtggcca ttct 24

<210> SEQ ID NO 92
<211> LENGTH: 8
<212> TYPE: PRT
<213> ORGANISM: Artificial Sequence

<220> FEATURE:
<223> OTHER INFORMATION: DB86 CDR H1

<400> SEQUENCE: 92

Gly Tyr Met Phe Ser Gly His Ser
1               5

<210> SEQ ID NO 93
<211> LENGTH: 24
<212> TYPE: DNA
<213> ORGANISM: Artificial Sequence
<220> FEATURE:
<223> OTHER INFORMATION: DB86 CDR H2

<400> SEQUENCE: 93
atgaacccta acagtggtaa caca 24

<210> SEQ ID NO 94
<211> LENGTH: 8
<212> TYPE: PRT
<213> ORGANISM: Artificial Sequence
<220> FEATURE:
<223> OTHER INFORMATION: DB86 CDR H2

<400> SEQUENCE: 94

Met Asn Pro Asn Ser Gly Asn Thr
1               5

<210> SEQ ID NO 95
<211> LENGTH: 39
<212> TYPE: DNA
<213> ORGANISM: Artificial Sequence
<220> FEATURE:
<223> OTHER INFORMATION: DB86 CDR H3

<400> SEQUENCE: 95
gcgagagata gcagtggctg gtacgatgtc tttgactac 39

<210> SEQ ID NO 96
<211> LENGTH: 13
<212> TYPE: PRT
<213> ORGANISM: Artificial Sequence
<220> FEATURE:
<223> OTHER INFORMATION: DB86 CDR H3

<400> SEQUENCE: 96

Ala Arg Asp Ser Ser Gly Trp Tyr Asp Val Phe Asp Tyr
1               5                   10

<210> SEQ ID NO 97
<211> LENGTH: 378
<212> TYPE: DNA
<213> ORGANISM: Artificial Sequence
<220> FEATURE:
<223> OTHER INFORMATION: DB280 variable heavy chain domain

<400> SEQUENCE: 97
caggtgcagc tggtgcagtc tggggctgag gtgaagaagc ctggggcctc agtgaaggtt 60
tcctgcaagg catctggata cagcctcaac ttatactata tgcactgggt gcgtcaggcc 120
cctggacaag ggcttgagtg gatgggatgg atgaacccta acagtggtaa cacaggctat 180
gcacagaagt tccagggccg tgtcaccatg acccgcgaca cgtccacgag cacagtctac 240
atggagctga gcagcctgcg ttctgaggac acggccgtgt attactgtgc gagcctcgat 300

-continued tgtagtggtg gtagctgcta ctccgaatat gatgcttttg atatctgggg ccaagggacc 360
acggtcaccg tctcctca 378

<210> SEQ ID NO 98
<211> LENGTH: 126
<212> TYPE: PRT
<213> ORGANISM: Artificial Sequence
<220> FEATURE:
<223> OTHER INFORMATION: DB280 variable heavy chain domain

<400> SEQUENCE: 98

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Asn Leu Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Leu Asp Cys Ser Gly Gly Ser Cys Tyr Ser Glu Tyr Asp Ala
            100                 105                 110

Phe Asp Ile Trp Gly Gln Gly Thr Thr Val Thr Val Ser Ser
        115                 120                 125

<210> SEQ ID NO 99
<211> LENGTH: 24
<212> TYPE: DNA
<213> ORGANISM: Artificial Sequence
<220> FEATURE:
<223> OTHER INFORMATION: DB280 CDR H1

<400> SEQUENCE: 99
ggatacagcc tcaacttata ctat 24

<210> SEQ ID NO 100
<211> LENGTH: 8
<212> TYPE: PRT
<213> ORGANISM: Artificial Sequence
<220> FEATURE:
<223> OTHER INFORMATION: DB280 CDR H1

<400> SEQUENCE: 100

Gly Tyr Ser Leu Asn Leu Tyr Tyr
1               5

<210> SEQ ID NO 101
<211> LENGTH: 24
<212> TYPE: DNA
<213> ORGANISM: Artificial Sequence
<220> FEATURE:
<223> OTHER INFORMATION: DB280 CDR H2

<400> SEQUENCE: 101
atgaacccta acagtggtaa caca 24

<210> SEQ ID NO 102
<211> LENGTH: 8
<212> TYPE: PRT

<213> ORGANISM: Artificial Sequence
<220> FEATURE:
<223> OTHER INFORMATION: DB280 CDR H2

<400> SEQUENCE: 102

Met Asn Pro Asn Ser Gly Asn Thr
1               5

<210> SEQ ID NO 103
<211> LENGTH: 57
<212> TYPE: DNA
<213> ORGANISM: Artificial Sequence
<220> FEATURE:
<223> OTHER INFORMATION: DB280 CDR H3

<400> SEQUENCE: 103
gcgagcctcg attgtagtgg tggtagctgc tactccgaat atgatgcttt tgatatc        57

<210> SEQ ID NO 104
<211> LENGTH: 19
<212> TYPE: PRT
<213> ORGANISM: Artificial Sequence
<220> FEATURE:
<223> OTHER INFORMATION: DB280 CDR H3

<400> SEQUENCE: 104

Ala Ser Leu Asp Cys Ser Gly Gly Ser Cys Tyr Ser Glu Tyr Asp Ala
1               5                   10                  15

Phe Asp Ile

<210> SEQ ID NO 105
<211> LENGTH: 357
<212> TYPE: DNA
<213> ORGANISM: Artificial Sequence
<220> FEATURE:
<223> OTHER INFORMATION: DB331 variable heavy chain domain

<400> SEQUENCE: 105
caggtgcagc tggtgcagtc tggggctgag gtgaagaagc ctggggcctc agtgaaggtt      60
tcctgcaagg catctggata caccttcacc agctactata tgcactgggt gcgtcaggcc     120
cctggacaag ggcttgagtg gatgggatgg atgaacccta acagtggtaa cacaggctat     180
gcacagaagt tccagggccg tgtcaccatg acccgcgaca cgtccacgag cacagtctac     240
atggagctga gcagcctgcg ttctgaggac acggccgtgt attactgtgc aacagatctc     300
gcgggggaag ccttgttcga cccctggggc cagggcaccc tggtcaccgt ctcctca        357

<210> SEQ ID NO 106
<211> LENGTH: 119
<212> TYPE: PRT
<213> ORGANISM: Artificial Sequence
<220> FEATURE:
<223> OTHER INFORMATION: DB331 variable heavy chain domain

<400> SEQUENCE: 106

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Thr Asp Leu Ala Gly Glu Ala Leu Phe Asp Pro Trp Gly Gln Gly
100 105 110

Thr Leu Val Thr Val Ser Ser
115

<210> SEQ ID NO 107
<211> LENGTH: 24
<212> TYPE: DNA
<213> ORGANISM: Artificial Sequence
<220> FEATURE:
<223> OTHER INFORMATION: DB331 CDR H1

<400> SEQUENCE: 107
ggatacacct tcaccagcta ctat 24

<210> SEQ ID NO 108
<211> LENGTH: 8
<212> TYPE: PRT
<213> ORGANISM: Artificial Sequence
<220> FEATURE:
<223> OTHER INFORMATION: DB331 CDR H1

<400> SEQUENCE: 108

Gly Tyr Thr Phe Thr Ser Tyr Tyr
1 5

<210> SEQ ID NO 109
<211> LENGTH: 24
<212> TYPE: DNA
<213> ORGANISM: Artificial Sequence
<220> FEATURE:
<223> OTHER INFORMATION: DB331 CDR H2

<400> SEQUENCE: 109
atgaacccta acagtggtaa caca 24

<210> SEQ ID NO 110
<211> LENGTH: 8
<212> TYPE: PRT
<213> ORGANISM: Artificial Sequence
<220> FEATURE:
<223> OTHER INFORMATION: DB331 CDR H2

<400> SEQUENCE: 110

Met Asn Pro Asn Ser Gly Asn Thr
1 5

<210> SEQ ID NO 111
<211> LENGTH: 36
<212> TYPE: DNA
<213> ORGANISM: Artificial Sequence
<220> FEATURE:
<223> OTHER INFORMATION: DB331 CDR H3

<400> SEQUENCE: 111
gcaacagatc tcgcggggga agccttgttc gacccc 36

<210> SEQ ID NO 112
<211> LENGTH: 12
<212> TYPE: PRT
<213> ORGANISM: Artificial Sequence

<220> FEATURE:
<223> OTHER INFORMATION: DB331 CDR H3

<400> SEQUENCE: 112

Ala Thr Asp Leu Ala Gly Glu Ala Leu Phe Asp Pro
1               5                   10

<210> SEQ ID NO 113
<211> LENGTH: 351
<212> TYPE: DNA
<213> ORGANISM: Artificial Sequence
<220> FEATURE:
<223> OTHER INFORMATION: DB415 variable heavy chain domain

<400> SEQUENCE: 113
gaggtgcagc tggtggagtc tgggggaggc ttggtacagc ctggggggtc cctgcgcctc     60
tcctgtgcag cctctggaat caccttcagt agttatggca tgcattgggt ccgccaggct    120
ccagggaagg ggctggagtg ggtctcaggt attagttgga atagtggtaa cagagtctat    180
gtggactctg tgaagggccg gttcaccatc tcccgcgaca attccaagaa cacgctgtat    240
ctgcaaatga acagcctgcg cgccgaggac acggccgtat attactgtgc gagagatact    300
aatgatgctt ttgatatctg gggccaaggg accacggtca ccgtctcctc a             351

<210> SEQ ID NO 114
<211> LENGTH: 117
<212> TYPE: PRT
<213> ORGANISM: Artificial Sequence
<220> FEATURE:
<223> OTHER INFORMATION: DB415 variable heavy chain domain

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Gly Met His Trp Val Arg Gln Ala Pro Gly Lys Gly Leu Glu Trp Val
        35                  40                  45

Ser Gly Ile Ser Trp Asn Ser Gly Asn Arg Val Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asn Asp Ala Phe Asp Ile Trp Gly Gln Gly Thr Thr
            100                 105                 110

Val Thr Val Ser Ser
        115

<210> SEQ ID NO 115
<211> LENGTH: 24
<212> TYPE: DNA
<213> ORGANISM: Artificial Sequence
<220> FEATURE:
<223> OTHER INFORMATION: DB415 CDR H1

<400> SEQUENCE: 115
ggaatcacct tcagtagtta tggc                                            24

<210> SEQ ID NO 116
<211> LENGTH: 8
<212> TYPE: PRT
<213> ORGANISM: Artificial Sequence
<220> FEATURE:
<223> OTHER INFORMATION: DB415 CDR H1

<400> SEQUENCE: 116

Gly Ile Thr Phe Ser Ser Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: DB415 CDR H2

<400> SEQUENCE: 117
attagttgga atagtggtaa caga 24

<210> SEQ ID NO 118
<211> LENGTH: 8
<212> TYPE: PRT
<213> ORGANISM: Artificial Sequence
<220> FEATURE:
<223> OTHER INFORMATION: DB415 CDR H2

<400> SEQUENCE: 118

Ile Ser Trp Asn Ser Gly Asn Arg
1               5

<210> SEQ ID NO 119
<211> LENGTH: 30
<212> TYPE: DNA
<213> ORGANISM: Artificial Sequence
<220> FEATURE:
<223> OTHER INFORMATION: DB415 CDR H3

<400> SEQUENCE: 119
gcgagagata ctaatgatgc ttttgatatc 30

<210> SEQ ID NO 120
<211> LENGTH: 10
<212> TYPE: PRT
<213> ORGANISM: Artificial Sequence
<220> FEATURE:
<223> OTHER INFORMATION: DB415 CDR H3

<400> SEQUENCE: 120

Ala Arg Asp Thr Asn Asp Ala Phe Asp Ile
1               5                   10

<210> SEQ ID NO 121
<211> LENGTH: 357
<212> TYPE: DNA
<213> ORGANISM: Artificial Sequence
<220> FEATURE:
<223> OTHER INFORMATION: DB435 variable heavy chain domain

<400> SEQUENCE: 121
caggtgcagc tggtgcagtc tggggctgag gtgaagaagc ctggggcctc agtgaaggtt 60
tcctgcaagg catctggagg caccttcagc agctatgcta tcagctgggt gcgtcaggcc 120
cctggacaag ggcttgagtg gatgggctgg atcacccctc acaatggtaa cataaagtat 180
gcacgggagt tccagggccg tgtcaccatg acccgcgaca cgtccacgag cacagtctac 240

-continued

```
atggagctga gcagcctgcg ttctgaggac acggccgtgt attactgtgc gaaagatctg    300

aactggaacg cagcctttga ctactggggc caggggaccc tggtcaccgt ctcctca       357


<210> SEQ ID NO 122
<211> LENGTH: 119
<212> TYPE: PRT
<213> ORGANISM: Artificial Sequence
<220> FEATURE:
<223> OTHER INFORMATION: DB435 variable heavy chain domain

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Trp Ile Thr Pro His Asn Gly Asn Ile Lys Tyr Ala Arg Glu Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Asp Leu Asn Trp Asn Ala Ala Phe Asp Tyr Trp Gly Gln Gly
            100                 105                 110

Thr Leu Val Thr Val Ser Ser
        115


<210> SEQ ID NO 123
<211> LENGTH: 24
<212> TYPE: DNA
<213> ORGANISM: Artificial Sequence
<220> FEATURE:
<223> OTHER INFORMATION: DB435 CDR H1

<400> SEQUENCE: 123

ggaggcacct tcagcagcta tgct                                            24


<210> SEQ ID NO 124
<211> LENGTH: 8
<212> TYPE: PRT
<213> ORGANISM: Artificial Sequence
<220> FEATURE:
<223> OTHER INFORMATION: DB435 CDR H1

<400> SEQUENCE: 124

Gly Gly Thr Phe Ser Ser Tyr Ala
1               5


<210> SEQ ID NO 125
<211> LENGTH: 24
<212> TYPE: DNA
<213> ORGANISM: Artificial Sequence
<220> FEATURE:
<223> OTHER INFORMATION: DB435 CDR H2

<400> SEQUENCE: 125

atcacccctc acaatggtaa cata                                            24


<210> SEQ ID NO 126
<211> LENGTH: 8
<212> TYPE: PRT
```

<213> ORGANISM: Artificial Sequence
<220> FEATURE:
<223> OTHER INFORMATION: DB435 CDR H2

<400> SEQUENCE: 126

Ile Thr Pro His Asn Gly Asn Ile
1               5

<210> SEQ ID NO 127
<211> LENGTH: 36
<212> TYPE: DNA
<213> ORGANISM: Artificial Sequence
<220> FEATURE:
<223> OTHER INFORMATION: DB435 CDR H3

<400> SEQUENCE: 127
gcgaaagatc tgaactggaa cgcagccttt gactac 36

<210> SEQ ID NO 128
<211> LENGTH: 12
<212> TYPE: PRT
<213> ORGANISM: Artificial Sequence
<220> FEATURE:
<223> OTHER INFORMATION: DB435 CDR H3

<400> SEQUENCE: 128

Ala Lys Asp Leu Asn Trp Asn Ala Ala Phe Asp Tyr
1               5                   10

<210> SEQ ID NO 129
<211> LENGTH: 2340
<212> TYPE: DNA
<213> ORGANISM: Artificial Sequence
<220> FEATURE:
<223> OTHER INFORMATION: OMT1 VHVL x TSC456 scFv-Fc-scFv
      TRI129

<400> SEQUENCE: 129
atggaagcac cagcgcagct tctcttcctc ctgctactct ggctcccaga taccaccggt 60
gaggtgcagc tgttggagtc tgggggaggc ttggtacagc ctggggggtc cctgagactc 120
tcctgtgcag cctctggatt cacctttagc agctatggca tgagctgggt ccgccaggct 180
ccagggaagg ggctggaggg ggtctcagct attagtggta gtggtggtag cacatactac 240
gcagactccg tgaagggccg gttcaccatc tccagagaca attccaagaa cacgctgtat 300
ctgcaaatga acagcctgag agccgaggac acggccgtat attactgtgc gaaagaaaag 360
ttacgatatt ttgactggtt atccgatgct tttgatatct ggggccaagg gacaatggtc 420
accgtctctt caggtggagg cggttcaggc ggaggtggat ccggcggtgg cggctccggt 480
ggcggcggat ctgacatcgt gatgacccag tctccagact ccctggctgt gtctctgggc 540
gagagggcca ccatcaactg caagtccagc cacagtgttt tatacagctc caacaataag 600
aactacttag cttggtacca gcagaaacca ggacagcctc ctaagctgct catttactgg 660
gcatctaccc gggaatccgg ggtccctgac cgattcagtg gcagcgggtc tgggacagat 720
ttcactctca ccatcagcag cctgcaggct gaagatgtgg cagtttatta ctgtcagcaa 780
tattatagta ctcctccgac cactttcggc ggagggacca aggtggagat caaatcctcg 840
agtgagccca aatcttctga caaaactcac acatgcccac cgtgcccagc acctgaagcc 900
gcgggtgcac cgtcagtctt cctcttcccc ccaaaaccca aggacaccct catgatctcc 960
cggacccctg aggtcacatg cgtggtggtg gacgtgagcc acgaagaccc tgaggtcaag 1020

-continued

```
ttcaactggt acgtggacgg cgtggaggtg cataatgcca agacaaagcc gcgggaggag   1080

cagtacaaca gcacgtaccg tgtggtcagc gtcctcaccg tcctgcacca ggactggctg   1140

aatggcaagg aatacaagtg cgcggtctcc aacaaagccc tcccagcccc catcgagaaa   1200

accatctcca aagccaaagg gcagccccga gaaccacagg tgtacaccct gcccccatcc   1260

cgggatgagc tgaccaagaa ccaggtcagc ctgacctgcc tggtcaaagg cttctatcca   1320

agcgacatcg ccgtggagtg ggagagcaat gggcagccgg agaacaacta caagaccacg   1380

cctcccgtgc tggactccga cggctccttc ttcctctaca gcaagctcac cgtggacaag   1440

agcaggtggc agcaggggaa cgtcttctca tgctccgtga tgcatgaggc tctgcacaac   1500

cactacacgc agaagagcct ctccctgtct ccgggttccg gaggaggggg ttcaggtggg   1560

ggaggttctg gcggcggggg aagcccttca caggtgcaac tggtgcagag tggacccgag   1620

gttaaaaaac cagggtcctc cgttaaggtt agctgcaaag cctctggcta cacattttcc   1680

aggagtacaa tgcactgggt gaggcaggct cctggacagg gactcgagtg gatcgggtat   1740

atcaacccat ctagcgccta taccaattac aaccaaaagt ttaaggaccg agttaccatt   1800

accgctgaca aatccaccag tacagcttat atggagctgt catctcttag gtccgaggac   1860

actgctgttt attactgcgc tcgtcctcag gttcactatg actataatgg ttttccctac   1920

tggggtcagg gaaccctggt gactgtctct tctggcggtg gaggcagcgg tgggggtggg   1980

tctggaggcg gtggcagtgg cggcggaggc tctgatattc agatgactca gtctcctagc   2040

actctcagcg ccagcgtggg ggatcgtgtg acaatgactt gctccgctag cagtagtgtg   2100

tcttacatga attggtatca gcagaagccc gggaaagcac ctaagcgctg gatctatgac   2160

tcttccaagc tggcaagtgg tgtcccctca cggttctctg gctcaggttc tggtactgac   2220

tatactttga ctatctcctc cctccagccc gatgatttcg ctacctatta ttgtcagcag   2280

tggagccgta acccacccac tttcggaggc ggtaccaaag tggagatcaa gaggtcataa   2340
```

<210> SEQ ID NO 130
<211> LENGTH: 759
<212> TYPE: PRT
<213> ORGANISM: Artificial Sequence
<220> FEATURE:
<223> OTHER INFORMATION: OMT1 VHVL x TSC456 scFv-Fc-scFv
      TRI129

<400> SEQUENCE: 130

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Gly Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Lys Leu Arg Tyr Phe Asp Trp Leu Ser Asp Ala Phe Asp
            100                 105                 110

Ile Trp Gly Gln Gly Thr Met Val Thr Val Ser Ser Gly Gly Gly Gly
        115                 120                 125
```

-continued

```
Ser Gly Gly Gly Gly Ser Gly Gly Gly Gly Ser Gly Gly Gly Gly Ser
    130                 135                 140

Asp Ile Val Met Thr Gln Ser Pro Asp Ser Leu Ala Val Ser Leu Gly
145                 150                 155                 160

Glu Arg Ala Thr Ile Asn Cys Lys Ser Ser His Ser Val Leu Tyr Ser
                165                 170                 175

Ser Asn Asn Lys Asn Tyr Leu Ala Trp Tyr Gln Gln Lys Pro Gly Gln
            180                 185                 190

Pro Pro Lys Leu Leu Ile Tyr Trp Ala Ser Thr Arg Glu Ser Gly Val
        195                 200                 205

Pro Asp Arg Phe Ser Gly Ser Gly Ser Gly Thr Asp Phe Thr Leu Thr
    210                 215                 220

Ile Ser Ser Leu Gln Ala Glu Asp Val Ala Val Tyr Tyr Cys Gln Gln
225                 230                 235                 240

Tyr Tyr Ser Thr Pro Pro Thr Thr Phe Gly Gly Gly Thr Lys Val Glu
                245                 250                 255

Ile Lys Ser Ser Ser Glu Pro Lys Ser Ser Asp Lys Thr His Thr Cys
            260                 265                 270

Pro Pro Cys Pro Ala Pro Glu Ala Ala Gly Ala Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Ala
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Ser Gly Gly Gly
                485                 490                 495

Gly Ser Gly Gly Gly Gly Ser Gly Gly Gly Gly Ser Pro Ser Gln Val
            500                 505                 510

Gln Leu Val Gln Ser Gly Pro Glu Val Lys Lys Pro Gly Ser Ser Val
        515                 520                 525

Lys Val Ser Cys Lys Ala Ser Gly Tyr Thr Phe Ser Arg Ser Thr Met
    530                 535                 540
```

-continued

His Trp Val Arg Gln Ala Pro Gly Gln Gly Leu Glu Trp Ile Gly Tyr
545 550 555 560

Ile Asn Pro Ser Ser Ala Tyr Thr Asn Tyr Asn Gln Lys Phe Lys Asp
565 570 575

Arg Val Thr Ile Thr Ala Asp Lys Ser Thr Ser Thr Ala Tyr Met Glu
580 585 590

Leu Ser Ser Leu Arg Ser Glu Asp Thr Ala Val Tyr Tyr Cys Ala Arg
595 600 605

Pro Gln Val His Tyr Asp Tyr Asn Gly Phe Pro Tyr Trp Gly Gln Gly
610 615 620

Thr Leu Val Thr Val Ser Ser Gly Gly Gly Gly Ser Gly Gly Gly Gly
625 630 635 640

Ser Gly Gly Gly Gly Ser Gly Gly Gly Gly Ser Asp Ile Gln Met Thr
645 650 655

Gln Ser Pro Ser Thr Leu Ser Ala Ser Val Gly Asp Arg Val Thr Met
660 665 670

Thr Cys Ser Ala Ser Ser Ser Val Ser Tyr Met Asn Trp Tyr Gln Gln
675 680 685

Lys Pro Gly Lys Ala Pro Lys Arg Trp Ile Tyr Asp Ser Ser Lys Leu
690 695 700

Ala Ser Gly Val Pro Ser Arg Phe Ser Gly Ser Gly Ser Gly Thr Asp
705 710 715 720

Tyr Thr Leu Thr Ile Ser Ser Leu Gln Pro Asp Asp Phe Ala Thr Tyr
725 730 735

Tyr Cys Gln Gln Trp Ser Arg Asn Pro Pro Thr Phe Gly Gly Gly Thr
740 745 750

Lys Val Glu Ile Lys Arg Ser
755

<210> SEQ ID NO 131
<211> LENGTH: 2334
<212> TYPE: DNA
<213> ORGANISM: Artificial Sequence
<220> FEATURE:
<223> OTHER INFORMATION: OMT1 VLVH x TSC456 scFv-Fc-scFv TRI130

<400> SEQUENCE: 131
atggaagcac cagcgcagct tctcttcctc ctgctactct ggctcccaga taccaccggt 60
gacatcgtga tgacccagtc tccagactcc ctggctgtgt ctctgggcga gagggccacc 120
atcaactgca agtccagcca cagtgtttta tacagctcca acaataagaa ctacttagct 180
tggtaccagc agaaaccagg acagcctcct aagctgctca tttactgggc atctacccgg 240
gaatccgggg tccctgaccg attcagtggc agcgggtctg ggacagattt cactctcacc 300
atcagcagcc tgcaggctga agatgtggca gtttattact gtcagcaata ttatagtact 360
cctccgacca ctttcggcgg agggaccaag gtggagatca aaggtggagg cggttcaggc 420
ggaggtggat ccggcggtgg cggctccggt ggcggcggat ctgaggtgca gctgttggag 480
tctgggggag gcttggtaca gcctgggggg tccctgagac tctcctgtgc agcctctgga 540
ttcaccttta gcagctatgg catgagctgg gtccgccagg ctccagggaa ggggctggag 600
ggggtctcag ctattagtgg tagtggtggt agcacatact acgcagactc cgtgaagggc 660
cggttcacca tctccagaga caattccaag aacacgctgt atctgcaaat gaacagcctg 720
agagccgagg acacggccgt atattactgt gcgaaagaaa agttacgata ttttgactgg 780
ttatccgatg cttttgatat ctggggccaa gggacaatgg tcaccgtctc ctcgagtgag 840

```
cccaaatctt ctgacaaaac tcacacatgc ccaccgtgcc cagcacctga agccgcgggt    900
gcaccgtcag tcttcctctt ccccccaaaa cccaaggaca ccctcatgat ctcccggacc    960
cctgaggtca catgcgtggt ggtggacgtg agccacgaag accctgaggt caagttcaac   1020
tggtacgtgg acggcgtgga ggtgcataat gccaagacaa agccgcggga ggagcagtac   1080
aacagcacgt accgtgtggt cagcgtcctc accgtcctgc accaggactg gctgaatggc   1140
aaggaataca agtgcgcggt ctccaacaaa gccctcccag cccccatcga gaaaaccatc   1200
tccaaagcca aagggcagcc ccgagaacca caggtgtaca ccctgccccc atcccgggat   1260
gagctgacca agaaccaggt cagcctgacc tgcctggtca aaggcttcta tccaagcgac   1320
atcgccgtgg agtgggagag caatgggcag ccggagaaca actacaagac cacgcctccc   1380
gtgctggact ccgacggctc cttcttcctc tacagcaagc tcaccgtgga caagagcagg   1440
tggcagcagg ggaacgtctt ctcatgctcc gtgatgcatg aggctctgca caaccactac   1500
acgcagaaga gcctctccct gtctccgggt tccggaggag gggggttcagg tgggggaggt   1560
tctggcggcg gggaagccc ttcacaggtg caactggtgc agagtggacc cgaggttaaa   1620
aaaccagggt cctccgttaa ggttagctgc aaagcctctg gctacacatt ttccaggagt   1680
acaatgcact gggtgaggca ggctcctgga cagggactcg agtggatcgg gtatatcaac   1740
ccatctagcg cctataccaa ttacaaccaa aagtttaagg accgagttac cattaccgct   1800
gacaaatcca ccagtacagc ttatatggag ctgtcatctc ttaggtccga ggacactgct   1860
gtttattact gcgctcgtcc tcaggttcac tatgactata atggttttcc ctactggggt   1920
cagggaaccc tggtgactgt ctcttctggc ggtggaggca gcggtggggg tgggtctgga   1980
ggcggtggca gtggcggcgg aggctctgat attcagatga ctcagtctcc tagcactctc   2040
agcgccagcg tgggggatcg tgtgacaatg acttgctccg ctagcagtag tgtgtcttac   2100
atgaattggt atcagcagaa gcccgggaaa gcacctaagc gctggatcta tgactcttcc   2160
aagctggcaa gtggtgtccc ctcacggttc tctggctcag gttctggtac tgactatact   2220
ttgactatct cctccctcca gcccgatgat ttcgctacct attattgtca gcagtggagc   2280
cgtaacccac ccactttcgg aggcggtacc aaagtggaga tcaagaggtc ataa         2334
```

```
<210> SEQ ID NO 132
<211> LENGTH: 757
<212> TYPE: PRT
<213> ORGANISM: Artificial Sequence
<220> FEATURE:
<223> OTHER INFORMATION: OMT1 VLVH x TSC456 scFv-Fc-scFv TRI130

<400> SEQUENCE: 132

Asp Ile Val Met Thr Gln Ser Pro Asp Ser Leu Ala Val Ser Leu Gly
1               5                   10                  15

Glu Arg Ala Thr Ile Asn Cys Lys Ser Ser His Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

-continued

```
Tyr Tyr Ser Thr Pro Pro Thr Thr Phe Gly Gly Gly Thr Lys Val Glu
            100                 105                 110

Ile Lys Gly Gly Gly Gly Ser Gly Gly Gly Gly Ser Gly Gly Gly Gly
        115                 120                 125

Ser Gly Gly Gly Gly Ser Glu Val Gln Leu Leu Glu Ser Gly Gly Gly
    130                 135                 140

Leu Val Gln Pro Gly Gly Ser Leu Arg Leu Ser Cys Ala Ala Ser Gly
145                 150                 155                 160

Phe Thr Phe Ser Ser Tyr Gly Met Ser Trp Val Arg Gln Ala Pro Gly
                165                 170                 175

Lys Gly Leu Glu Gly Val Ser Ala Ile Ser Gly Ser Gly Gly Ser Thr
            180                 185                 190

Tyr Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Ala Glu Asp
    210                 215                 220

Thr Ala Val Tyr Tyr Cys Ala Lys Glu Lys Leu Arg Tyr Phe Asp Trp
225                 230                 235                 240

Leu Ser Asp Ala Phe Asp Ile Trp Gly Gln Gly Thr Met Val Thr Val
                245                 250                 255

Ser Ser Ser Glu Pro Lys Ser Ser Asp Lys Thr His Thr Cys Pro Pro
            260                 265                 270

Cys Pro Ala Pro Glu Ala Ala Gly Ala Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Asn Ser Thr Tyr Arg Val Val Ser Val Leu Thr Val
            340                 345                 350

Leu His Gln Asp Trp Leu Asn Gly Lys Glu Tyr Lys Cys Ala Val Ser
        355                 360                 365

Asn Lys Ala Leu Pro Ala Pro Ile Glu Lys Thr Ile Ser Lys Ala Lys
    370                 375                 380

Gly Gln Pro Arg Glu Pro Gln Val Tyr Thr Leu Pro Pro Ser Arg Asp
385                 390                 395                 400

Glu Leu Thr Lys Asn Gln Val Ser Leu Thr Cys Leu Val Lys Gly Phe
                405                 410                 415

Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
        435                 440                 445

Phe Leu Tyr Ser Lys Leu Thr Val Asp Lys Ser Arg Trp Gln Gln Gly
    450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly Ser Gly Gly Gly Gly Ser
                485                 490                 495

Gly Gly Gly Gly Ser Gly Gly Gly Gly Ser Pro Ser Gln Val Gln Leu
            500                 505                 510
```

-continued

```
Val Gln Ser Gly Pro Glu Val Lys Lys Pro Gly Ser Ser Val Lys Val
        515                 520                 525

Ser Cys Lys Ala Ser Gly Tyr Thr Phe Ser Arg Ser Thr Met His Trp
    530                 535                 540

Val Arg Gln Ala Pro Gly Gln Gly Leu Glu Trp Ile Gly Tyr Ile Asn
545                 550                 555                 560

Pro Ser Ser Ala Tyr Thr Asn Tyr Asn Gln Lys Phe Lys Asp Arg Val
                565                 570                 575

Thr Ile Thr Ala Asp Lys Ser Thr Ser Thr Ala Tyr Met Glu Leu Ser
            580                 585                 590

Ser Leu Arg Ser Glu Asp Thr Ala Val Tyr Tyr Cys Ala Arg Pro Gln
        595                 600                 605

Val His Tyr Asp Tyr Asn Gly Phe Pro Tyr Trp Gly Gln Gly Thr Leu
    610                 615                 620

Val Thr Val Ser Ser Gly Gly Gly Gly Ser Gly Gly Gly Gly Ser Gly
625                 630                 635                 640

Gly Gly Gly Ser Gly Gly Gly Gly Ser Asp Ile Gln Met Thr Gln Ser
                645                 650                 655

Pro Ser Thr Leu Ser Ala Ser Val Gly Asp Arg Val Thr Met Thr Cys
            660                 665                 670

Ser Ala Ser Ser Ser Val Ser Tyr Met Asn Trp Tyr Gln Gln Lys Pro
        675                 680                 685

Gly Lys Ala Pro Lys Arg Trp Ile Tyr Asp Ser Ser Lys Leu Ala Ser
    690                 695                 700

Gly Val Pro Ser Arg Phe Ser Gly Ser Gly Ser Gly Thr Asp Tyr Thr
705                 710                 715                 720

Leu Thr Ile Ser Ser Leu Gln Pro Asp Asp Phe Ala Thr Tyr Tyr Cys
                725                 730                 735

Gln Gln Trp Ser Arg Asn Pro Pro Thr Phe Gly Gly Gly Thr Lys Val
            740                 745                 750

Glu Ile Lys Arg Ser
        755
```

<210> SEQ ID NO 133
<211> LENGTH: 2313
<212> TYPE: DNA
<213> ORGANISM: Artificial Sequence
<220> FEATURE:
<223> OTHER INFORMATION: DB8 VHVL x TSC456 scFv-Fc-scFv TRI123

<400> SEQUENCE: 133

```
atggaagcac cagcgcagct tctcttcctc ctgctactct ggctcccaga taccaccggt     60

caggtgcagc tggtgcagtc tggggctgag gtgaagaagc ctggggcctc agtgaaggtt    120

tcctgcaagg catctggata catcttcacc gactactata tgcactgggt gcgtcaggcc    180

cctggacaag ggcttgagtg gatgggatgg atgagcccta acagtggtaa cacaggctat    240

gcacagaagt tccagggccg tgtcaccatg acccgcgaca cgtccacgag cacagtctac    300

atggagctga gcagcctgcg ttctgaggac acggccgtgt attactgtgc gagagatgcg    360

gcggattacg gtgactacgt tgcttttgat atctggggcc aagggacaat ggtcaccgtc    420

tcttcaggcg gcggcggcag cggcggcggc ggcagcggcg gcggaggctc cggcggcggc    480

ggcagcgaca tccagatgac ccagtctcca tcctccctgt ctgcatctgt aggagacaga    540

gtcaccatca cttgccgggc aagtcagagc attagcagct atctgaattg gtatcagcag    600

aaaccaggga aagcccctaa gctcctgatc tatgctgcat ccagtttgca aagtggggtc    660
```

-continued

```
ccatcaaggt tcagtggcag tggatctggg acagatttca ctctcaccat cagcagtctg    720
caacctgaag attttgcaac ttactactgt caacagagtt acagtacccc tctcactttc    780
ggcggaggta ccaaggtgga gatcaaatcc tcgagtgagc ccaaatcttc tgacaaaact    840
cacacatgcc caccgtgccc agcacctgaa gccgcgggtg caccgtcagt cttcctcttc    900
cccccaaaac ccaaggacac cctcatgatc tcccggaccc ctgaggtcac atgcgtggtg    960
gtggacgtga gccacgaaga ccctgaggtc aagttcaact ggtacgtgga cggcgtggag   1020
gtgcataatg ccaagacaaa gccgcgggag gagcagtaca acagcacgta ccgtgtggtc   1080
agcgtcctca ccgtcctgca ccaggactgg ctgaatggca aggaatacaa gtgcgcggtc   1140
tccaacaaag ccctcccagc ccccatcgag aaaaccatct ccaaagccaa agggcagccc   1200
cgagaaccac aggtgtacac cctgccccca tcccgggatg agctgaccaa gaaccaggtc   1260
agcctgacct gcctggtcaa aggcttctat ccaagcgaca tcgccgtgga gtgggagagc   1320
aatgggcagc cggagaacaa ctacaagacc acgcctcccg tgctggactc cgacggctcc   1380
ttcttcctct acagcaagct caccgtggac aagagcaggt ggcagcaggg gaacgtcttc   1440
tcatgctccg tgatgcatga ggctctgcac aaccactaca cgcagaagag cctctccctg   1500
tctccgggtt ccggaggagg gggttcaggt gggggaggtt ctggcggcgg gggaagccct   1560
tcacaggtgc aactggtgca gagtggaccc gaggttaaaa aaccagggtc ctccgttaag   1620
gttagctgca aagcctctgg ctacacattt tccaggagta caatgcactg ggtgaggcag   1680
gctcctggac agggactcga gtggatcggg tatatcaacc catctagcgc ctataccaat   1740
tacaaccaaa agtttaagga ccgagttacc attaccgctg acaaatccac cagtacagct   1800
tatatggagc tgtcatctct taggtccgag gacactgctg tttattactg cgctcgtcct   1860
caggttcact atgactataa tggttttccc tactggggtc agggaaccct ggtgactgtc   1920
tcttctggcg gtggaggcag cggtgggggt gggtctggag gcggtggcag tggcggcgga   1980
ggctctgata ttcagatgac tcagtctcct agcactctca gcgccagcgt gggggatcgt   2040
gtgacaatga cttgctccgc tagcagtagt gtgtcttaca tgaattggta tcagcagaag   2100
cccgggaaag cacctaagcg ctggatctat gactcttcca agctggcaag tggtgtcccc   2160
tcacggttct ctggctcagg ttctggtact gactatactt tgactatctc ctccctccag   2220
cccgatgatt tcgctaccta ttattgtcag cagtggagcc gtaacccacc cactttcgga   2280
ggcggtacca aagtggagat caagaggtca taa                                2313
```

<210> SEQ ID NO 134
<211> LENGTH: 750
<212> TYPE: PRT
<213> ORGANISM: Artificial Sequence
<220> FEATURE:
<223> OTHER INFORMATION: DB8 VHVL x TSC456 scFv-Fc-scFv TRI123

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Tyr Met His Trp Val Arg Gln Ala Pro Gly Gln Gly Leu Glu Trp Met
        35                  40                  45

Gly Trp Met Ser Pro Asn Ser Gly Asn Thr Gly Tyr Ala Gln Lys Phe
    50                  55                  60
```

-continued

```
Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Asp Tyr Gly Asp Tyr Val Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Thr Pro Leu Thr Phe
225                 230                 235                 240

Gly Gly Gly Thr Lys Val Glu Ile Lys Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445

Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480
```

```
Ser Pro Gly Ser Gly Gly Gly Gly Ser Gly Gly Gly Gly Ser Gly Gly
                485                 490                 495

Gly Gly Ser Pro Ser Gln Val Gln Leu Val Gln Ser Gly Pro Glu Val
            500                 505                 510

Lys Lys Pro Gly Ser Ser Val Lys Val Ser Cys Lys Ala Ser Gly Tyr
        515                 520                 525

Thr Phe Ser Arg Ser Thr Met His Trp Val Arg Gln Ala Pro Gly Gln
    530                 535                 540

Gly Leu Glu Trp Ile Gly Tyr Ile Asn Pro Ser Ser Ala Tyr Thr Asn
545                 550                 555                 560

Tyr Asn Gln Lys Phe Lys Asp Arg Val Thr Ile Thr Ala Asp Lys Ser
                565                 570                 575

Thr Ser Thr Ala Tyr Met Glu Leu Ser Ser Leu Arg Ser Glu Asp Thr
            580                 585                 590

Ala Val Tyr Tyr Cys Ala Arg Pro Gln Val His Tyr Asp Tyr Asn Gly
        595                 600                 605

Phe Pro Tyr Trp Gly Gln Gly Thr Leu Val Thr Val Ser Ser Gly Gly
    610                 615                 620

Gly Gly Ser Gly Gly Gly Gly Ser Gly Gly Gly Gly Ser Gly Gly Gly
625                 630                 635                 640

Gly Ser Asp Ile Gln Met Thr Gln Ser Pro Ser Thr Leu Ser Ala Ser
                645                 650                 655

Val Gly Asp Arg Val Thr Met Thr Cys Ser Ala Ser Ser Ser Val Ser
            660                 665                 670

Tyr Met Asn Trp Tyr Gln Gln Lys Pro Gly Lys Ala Pro Lys Arg Trp
        675                 680                 685

Ile Tyr Asp Ser Ser Lys Leu Ala Ser Gly Val Pro Ser Arg Phe Ser
    690                 695                 700

Gly Ser Gly Ser Gly Thr Asp Tyr Thr Leu Thr Ile Ser Ser Leu Gln
705                 710                 715                 720

Pro Asp Asp Phe Ala Thr Tyr Tyr Cys Gln Gln Trp Ser Arg Asn Pro
                725                 730                 735

Pro Thr Phe Gly Gly Gly Thr Lys Val Glu Ile Lys Arg Ser
            740                 745                 750
```

<210> SEQ ID NO 135
<211> LENGTH: 2307
<212> TYPE: DNA
<213> ORGANISM: Artificial Sequence
<220> FEATURE:
<223> OTHER INFORMATION: DB8 VLVH x TSC456 scFv-Fc-scFv TRI124

<400> SEQUENCE: 135

```
atggaagcac cagcgcagct tctcttcctc ctgctactct ggctcccaga taccaccggt     60

gacatccaga tgacccagtc tccatcctcc ctgtctgcat ctgtaggaga cagagtcacc    120

atcacttgcc gggcaagtca gagcattagc agctatctga attggtatca gcagaaacca    180

gggaaagccc ctaagctcct gatctatgct gcatccagtt tgcaaagtgg ggtcccatca    240

aggttcagtg gcagtggatc tgggacagat ttcactctca ccatcagcag tctgcaacct    300

gaagattttg caacttacta ctgtcaacag agttacagta cccctctcac tttcggcgga    360

ggtaccaagg tggagatcaa aggcggcggc ggcagcggcg gcggcggcag cggcggcgga    420

ggctccggcg gcggcggcag ccaggtgcag ctggtgcagt ctggggctga ggtgaagaag    480

cctggggcct cagtgaaggt ttcctgcaag gcatctggat acatcttcac cgactactat    540
```

-continued

```
atgcactggg tgcgtcaggc ccctggacaa gggcttgagt ggatgggatg gatgagccct    600
aacagtggta acacaggcta tgcacagaag ttccagggcc gtgtcaccat gacccgcgac    660
acgtccacga gcacagtcta catggagctg agcagcctgc gttctgagga cacggccgtg    720
tattactgtg cgagagatgc ggcggattac ggtgactacg ttgcttttga tatctggggc    780
caagggacaa tggtcaccgt ctcctcgagt gagcccaaat cttctgacaa aactcacaca    840
tgcccaccgt gcccagcacc tgaagccgcg ggtgcaccgt cagtcttcct cttcccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggaat acaagtgcgc ggtctccaac   1140
aaagccctcc cagcccccat cgagaaaacc atctccaaag ccaaagggca gccccgagaa   1200
ccacaggtgt acaccctgcc cccatcccgg gatgagctga ccaagaacca ggtcagcctg   1260
acctgcctgg tcaaaggctt ctatccaagc gacatcgccg tggagtggga gagcaatggg   1320
cagccggaga acaactacaa gaccacgcct cccgtgctgg actccgacgg ctccttcttc   1380
ctctacagca agctcaccgt ggacaagagc aggtggcagc aggggaacgt cttctcatgc   1440
tccgtgatgc atgaggctct gcacaaccac tacacgcaga agagcctctc cctgtctccg   1500
ggttccggag gagggggttc aggtggggga ggttctggcg gcgggggaag cccttcacag   1560
gtgcaactgg tgcagagtgg acccgaggtt aaaaaaccag ggtcctccgt taaggttagc   1620
tgcaaagcct ctggctacac attttccagg agtacaatgc actgggtgag gcaggctcct   1680
ggacagggac tcgagtggat cggggtatatc aacccatcta gcgcctatac caattacaac   1740
caaaagttta aggaccgagt taccattacc gctgacaaat ccaccagtac agcttatatg   1800
gagctgtcat ctcttaggtc cgaggacact gctgtttatt actgcgctcg tcctcaggtt   1860
cactatgact ataatggttt tccctactgg ggtcagggaa ccctggtgac tgtctcttct   1920
ggcggtggag gcagcggtgg gggtgggtct ggaggcggtg gcagtggcgg cggaggctct   1980
gatattcaga tgactcagtc tcctagcact ctcagcgcca gcgtggggga tcgtgtgaca   2040
atgacttgct ccgctagcag tagtgtgtct tacatgaatt ggtatcagca gaagcccggg   2100
aaagcaccta agcgctggat ctatgactct tccaagctgg caagtggtgt cccctcacgg   2160
ttctctggct caggttctgg tactgactat actttgacta tctcctccct ccagcccgat   2220
gatttcgcta cctattattg tcagcagtgg agccgtaacc cacccacttt cggaggcggt   2280
accaaagtgg agatcaagag gtcataa                                      2307
```

```
<210> SEQ ID NO 136
<211> LENGTH: 748
<212> TYPE: PRT
<213> ORGANISM: Artificial Sequence
<220> FEATURE:
<223> OTHER INFORMATION: DB8 VLVH x TSC456 scFv-Fc-scFv TRI124

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

-continued

```
Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Ile Phe Thr Asp Tyr Tyr
145                 150                 155                 160

Met His Trp Val Arg Gln Ala Pro Gly Gln Gly Leu Glu Trp Met Gly
                165                 170                 175

Trp Met Ser Pro Asn Ser Gly Asn Thr Gly Tyr Ala Gln Lys Phe Gln
            180                 185                 190

Gly Arg Val Thr Met Thr Arg Asp Thr Ser Thr Ser Thr Val Tyr Met
        195                 200                 205

Glu Leu Ser Ser Leu Arg Ser Glu Asp Thr Ala Val Tyr Tyr Cys Ala
    210                 215                 220

Arg Asp Ala Ala Asp Tyr Gly Asp Tyr Val Ala Phe Asp Ile Trp Gly
225                 230                 235                 240

Gln Gly Thr Met Val Thr Val Ser Ser Ser Glu Pro Lys Ser Ser Asp
                245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460
```

Glu Ala Leu His Asn His Tyr Thr Gln Lys Ser Leu Ser Leu Ser Pro
465 470 475 480

Gly Ser Gly Gly Gly Gly Ser Gly Gly Gly Gly Ser Gly Gly Gly Gly
485 490 495

Ser Pro Ser Gln Val Gln Leu Val Gln Ser Gly Pro Glu Val Lys Lys
500 505 510

Pro Gly Ser Ser Val Lys Val Ser Cys Lys Ala Ser Gly Tyr Thr Phe
515 520 525

Ser Arg Ser Thr Met His Trp Val Arg Gln Ala Pro Gly Gln Gly Leu
530 535 540

Glu Trp Ile Gly Tyr Ile Asn Pro Ser Ser Ala Tyr Thr Asn Tyr Asn
545 550 555 560

Gln Lys Phe Lys Asp Arg Val Thr Ile Thr Ala Asp Lys Ser Thr Ser
565 570 575

Thr Ala Tyr Met Glu Leu Ser Ser Leu Arg Ser Glu Asp Thr Ala Val
580 585 590

Tyr Tyr Cys Ala Arg Pro Gln Val His Tyr Asp Tyr Asn Gly Phe Pro
595 600 605

Tyr Trp Gly Gln Gly Thr Leu Val Thr Val Ser Ser Gly Gly Gly Gly
610 615 620

Ser Gly Gly Gly Gly Ser Gly Gly Gly Gly Ser Gly Gly Gly Gly Ser
625 630 635 640

Asp Ile Gln Met Thr Gln Ser Pro Ser Thr Leu Ser Ala Ser Val Gly
645 650 655

Asp Arg Val Thr Met Thr Cys Ser Ala Ser Ser Ser Val Ser Tyr Met
660 665 670

Asn Trp Tyr Gln Gln Lys Pro Gly Lys Ala Pro Lys Arg Trp Ile Tyr
675 680 685

Asp Ser Ser Lys Leu Ala Ser Gly Val Pro Ser Arg Phe Ser Gly Ser
690 695 700

Gly Ser Gly Thr Asp Tyr Thr Leu Thr Ile Ser Ser Leu Gln Pro Asp
705 710 715 720

Asp Phe Ala Thr Tyr Tyr Cys Gln Gln Trp Ser Arg Asn Pro Pro Thr
725 730 735

Phe Gly Gly Gly Thr Lys Val Glu Ile Lys Arg Ser
740 745

<210> SEQ ID NO 137
<211> LENGTH: 2313
<212> TYPE: DNA
<213> ORGANISM: Artificial Sequence
<220> FEATURE:
<223> OTHER INFORMATION: DB8 VHVL x TSC456 scFv-Fc-scFv TRI137

<400> SEQUENCE: 137
atggaagcac cagcgcagct tctcttcctc ctgctactct ggctcccaga taccaccggt 60
caggtgcagc tggtgcagtc tggggctgag gtgaagaagc ctggggcctc agtgaaggtt 120
tcctgcaagg catctggata catcttcacc gactactata tgcactgggt gcgtcaggcc 180
cctggacaag ggcttgagtg gatgggatgg atgagcccta acagtggtaa cacaggctat 240
gcacagaagt tccagggccg tgtcaccatg acccgcgaca cgtccacgag cacagtctac 300
atggagctga gcagcctgcg ttctgaggac acggccgtgt attactgtgc gagagatgcg 360
gcggattacg gtgactacgt tgcttttgat atctggggcc aagggacaat ggtcaccgtc 420
tcttcaggtg gaggcggttc aggcggaggt ggatccggcg gtggcggctc cggtggcggc 480
ggatctgaca tccagatgac ccagtctcca tcctccctgt ctgcatctgt aggagacaga 540
gtcaccatca cttgccgggc aagtcagagc attagcagct atctgaattg gtatcagcag 600
aaaccaggga aagcccctaa gctcctgatc tatgctgcat ccagtttgca aagtggggtc 660
ccatcaaggt tcagtggcag tggatctggg acagatttca ctctcaccat cagcagtctg 720
caacctgaag attttgcaac ttactactgt caacagagtt acagtacccc tctcactttc 780
ggcggaggta ccaaggtgga gatcaaatcc tcgagtgagc ccaaatcttc tgacaaaact 840
cacacatgcc caccgtgccc agcacctgaa gccgcgggtg caccgtcagt cttcctcttc 900
cccccaaaac ccaaggacac cctcatgatc tcccggaccc ctgaggtcac atgcgtggtg 960
gtggacgtga gccacgaaga ccctgaggtc aagttcaact ggtacgtgga cggcgtggag 1020
gtgcataatg ccaagacaaa gccgcgggag gagcagtaca acagcacgta ccgtgtggtc 1080
agcgtcctca ccgtcctgca ccaggactgg ctgaatggca aggaatacaa gtgcgcggtc 1140
tccaacaaag ccctcccagc ccccatcgag aaaaccatct ccaaagccaa agggcagccc 1200
cgagaaccac aggtgtacac cctgccccca tcccgggatg agctgaccaa gaaccaggtc 1260
agcctgacct gcctggtcaa aggcttctat ccaagcgaca tcgccgtgga gtgggagagc 1320
aatgggcagc cggagaacaa ctacaagacc acgcctcccg tgctggactc cgacggctcc 1380
ttcttcctct acagcaagct caccgtggac aagagcaggt ggcagcaggg gaacgtcttc 1440
tcatgctccg tgatgcatga ggctctgcac aaccactaca cgcagaagag cctctccctg 1500
tctccgggtt ccggaggagg gggttcaggt gggggaggtt ctggcggcgg gggaagccct 1560
tcacaggtgc aactggtgca gagtggaccc gaggttaaaa aaccagggtc ctccgttaag 1620
gttagctgca aagcctctgg ctacacattt tccaggagta caatgcactg ggtgaggcag 1680
gctcctggac agggactcga gtggatcggg tatatcaacc catctagcgc ctataccaat 1740
tacaaccaaa agtttaagga ccgagttacc attaccgctg acaaatccac cagtacagct 1800
tatatggagc tgtcatctct taggtccgag gacactgctg tttattactg cgctcgtcct 1860
caggttcact atgactataa tggttttccc tactggggtc agggaaccct ggtgactgtc 1920
tcttctggcg gtggaggcag cggtgggggt gggtctggag gcggtggcag tggcggcgga 1980
ggctctgata ttcagatgac tcagtctcct agcactctca gcgccagcgt gggggatcgt 2040
gtgacaatga cttgctccgc tagcagtagt gtgtcttaca tgaattggta tcagcagaag 2100
cccgggaaag cacctaagcg ctggatctat gactcttcca agctggcaag tggtgtcccc 2160
tcacggttct ctggctcagg ttctggtact gactatactt tgactatctc ctccctccag 2220
cccgatgatt tcgctaccta ttattgtcag cagtggagcc gtaacccacc cactttcgga 2280
ggcggtacca aagtggagat caagaggtca tga 2313

<210> SEQ ID NO 138
<211> LENGTH: 750
<212> TYPE: PRT
<213> ORGANISM: Artificial Sequence
<220> FEATURE:
<223> OTHER INFORMATION: DB8 VHVL x TSC456 scFv-Fc-scFv TRI137

<400> SEQUENCE: 138

Gln Val Gln Leu Val Gln Ser Gly Ala Glu Val Lys Lys Pro Gly Ala
1 5 10 15

Ser Val Lys Val Ser Cys Lys Ala Ser Gly Tyr Ile Phe Thr Asp Tyr
20 25 30

```
Tyr Met His Trp Val Arg Gln Ala Pro Gly Gln Gly Leu Glu Trp Met
        35                  40                  45

Gly Trp Met Ser Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Ala Asp Tyr Gly Asp Tyr Val Ala Phe Asp Ile Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Gly Gly Gly Gly Ser Asp Ile
    130                 135                 140

Gln Met Thr Gln Ser Pro Ser Ser Leu Ser Ala Ser Val Gly Asp Arg
145                 150                 155                 160

Val Thr Ile Thr Cys Arg Ala Ser Gln Ser Ile Ser Ser Tyr Leu Asn
                165                 170                 175

Trp Tyr Gln Gln Lys Pro Gly Lys Ala Pro Lys Leu Leu Ile Tyr Ala
            180                 185                 190

Ala Ser Ser Leu Gln Ser Gly Val Pro Ser Arg Phe Ser Gly Ser Gly
        195                 200                 205

Ser Gly Thr Asp Phe Thr Leu Thr Ile Ser Ser Leu Gln Pro Glu Asp
    210                 215                 220

Phe Ala Thr Tyr Tyr Cys Gln Gln Ser Tyr Ser Thr Pro Leu Thr Phe
225                 230                 235                 240

Gly Gly Gly Thr Lys Val Glu Ile Lys Ser Ser Ser Glu Pro Lys Ser
                245                 250                 255

Ser Asp Lys Thr His Thr Cys Pro Pro Cys Pro Ala Pro Glu Ala Ala
            260                 265                 270

Gly Ala Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Ala Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Lys Leu Thr
        435                 440                 445
```

-continued

```
Val Asp Lys Ser Arg Trp Gln Gln Gly Asn Val Phe Ser Cys Ser Val
    450                 455                 460

Met His Glu Ala Leu His Asn His Tyr Thr Gln Lys Ser Leu Ser Leu
465                 470                 475                 480

Ser Pro Gly Ser Gly Gly Gly Gly Ser Gly Gly Gly Gly Ser Gly Gly
                485                 490                 495

Gly Gly Ser Pro Ser Gln Val Gln Leu Val Gln Ser Gly Pro Glu Val
            500                 505                 510

Lys Lys Pro Gly Ser Ser Val Lys Val Ser Cys Lys Ala Ser Gly Tyr
        515                 520                 525

Thr Phe Ser Arg Ser Thr Met His Trp Val Arg Gln Ala Pro Gly Gln
    530                 535                 540

Gly Leu Glu Trp Ile Gly Tyr Ile Asn Pro Ser Ser Ala Tyr Thr Asn
545                 550                 555                 560

Tyr Asn Gln Lys Phe Lys Asp Arg Val Thr Ile Thr Ala Asp Lys Ser
                565                 570                 575

Thr Ser Thr Ala Tyr Met Glu Leu Ser Ser Leu Arg Ser Glu Asp Thr
            580                 585                 590

Ala Val Tyr Tyr Cys Ala Arg Pro Gln Val His Tyr Asp Tyr Asn Gly
        595                 600                 605

Phe Pro Tyr Trp Gly Gln Gly Thr Leu Val Thr Val Ser Ser Gly Gly
    610                 615                 620

Gly Gly Ser Gly Gly Gly Gly Ser Gly Gly Gly Gly Ser Gly Gly Gly
625                 630                 635                 640

Gly Ser Asp Ile Gln Met Thr Gln Ser Pro Ser Thr Leu Ser Ala Ser
                645                 650                 655

Val Gly Asp Arg Val Thr Met Thr Cys Ser Ala Ser Ser Ser Val Ser
            660                 665                 670

Tyr Met Asn Trp Tyr Gln Gln Lys Pro Gly Lys Ala Pro Lys Arg Trp
        675                 680                 685

Ile Tyr Asp Ser Ser Lys Leu Ala Ser Gly Val Pro Ser Arg Phe Ser
    690                 695                 700

Gly Ser Gly Ser Gly Thr Asp Tyr Thr Leu Thr Ile Ser Ser Leu Gln
705                 710                 715                 720

Pro Asp Asp Phe Ala Thr Tyr Tyr Cys Gln Gln Trp Ser Arg Asn Pro
                725                 730                 735

Pro Thr Phe Gly Gly Gly Thr Lys Val Glu Ile Lys Arg Ser
            740                 745                 750
```

<210> SEQ ID NO 139
<211> LENGTH: 2304
<212> TYPE: DNA
<213> ORGANISM: Artificial Sequence
<220> FEATURE:
<223> OTHER INFORMATION: DB60 VHVL x TSC456 scFv-Fc-scFv TRI125

<400> SEQUENCE: 139

```
atggaagcac cagcgcagct tctcttcctc ctgctactct ggctcccaga taccaccggt     60

caggtgcagc tggtgcagtc tggggctgag gtgaagaagc ctggggcctc agtgaaggtt    120

tcctgcaagg catctggata caccttcacc agctactata tgcactgggt gcgtcaggcc    180

cctggacaag ggcttgagtg gatggggtgg atcaacccta acagtggtga cacaagctat    240

gcacagaagt tccagggccg tgtcaccatg acccgcgaca cgtccacgag cacagtctac    300

atggagctga gcagcctgcg ttctgaggac acggccgtgt attactgtgc gcaggatagt    360
```

```
agtggttccg gggcttttga tatctggggc caagggacaa tggtcaccgt ctcttcaggc    420

ggcggcggca gcggcggcgg cggcagcggc ggcggaggct ccggcggcgg cggcagcgac    480

atccagatga cccagtctcc atcctccctg tctgcatctg taggagacag agtcaccatc    540

acttgccggg caagtcagag cattagcagc tatctgaatt ggtatcagca gaaaccaggg    600

aaagccccta agctcctgat ctatgctgca tccagtttgc aaagtggggt cccatcaagg    660

ttcagtggca gtggatctgg gacagatttc actctcacca tcagcagtct gcaacctgaa    720

gattttgcaa cttactactg tcaacagagt tacagtaccc ctctcacttt cggcggaggt    780

accaaggtgg agatcaaatc ctcgagtgag cccaaatctt ctgacaaaac tcacacatgc    840

ccaccgtgcc cagcacctga agccgcgggt gcaccgtcag tcttcctctt ccccccaaaa    900

cccaaggaca ccctcatgat ctcccggacc cctgaggtca catgcgtggt ggtggacgtg    960

agccacgaag accctgaggt caagttcaac tggtacgtgg acggcgtgga ggtgcataat   1020

gccaagacaa agccgcggga ggagcagtac aacagcacgt accgtgtggt cagcgtcctc   1080

accgtcctgc accaggactg gctgaatggc aaggaataca agtgcgcggt ctccaacaaa   1140

gccctcccag cccccatcga gaaaaccatc tccaaagcca aagggcagcc ccgagaacca   1200

caggtgtaca ccctgccccc atcccgggat gagctgacca agaaccaggt cagcctgacc   1260

tgcctggtca aaggcttcta tccaagcgac atcgccgtgg agtgggagag caatgggcag   1320

ccggagaaca actacaagac cacgcctccc gtgctggact ccgacggctc cttcttcctc   1380

tacagcaagc tcaccgtgga caagagcagg tggcagcagg ggaacgtctt ctcatgctcc   1440

gtgatgcatg aggctctgca caaccactac acgcagaaga gcctctccct gtctccgggt   1500

tccggaggag gggttcagg tgggggaggt tctggcggcg gggaagccc ttcacaggtg   1560

caactggtgc agagtggacc cgaggttaaa aaaccagggt cctccgttaa ggttagctgc   1620

aaagcctctg gctacacatt ttccaggagt acaatgcact gggtgaggca ggctcctgga   1680

cagggactcg agtggatcgg gtatatcaac ccatctagcg cctataccaa ttacaaccaa   1740

aagtttaagg accgagttac cattaccgct gacaaatcca ccagtacagc ttatatggag   1800

ctgtcatctc ttaggtccga ggacactgct gtttattact gcgctcgtcc tcaggttcac   1860

tatgactata atggttttcc ctactggggt cagggaaccc tggtgactgt ctcttctggc   1920

ggtggaggca gcggtggggg tgggtctgga ggcggtggca gtggcggcgg aggctctgat   1980

attcagatga ctcagtctcc tagcactctc agcgccagcg tgggggatcg tgtgacaatg   2040

acttgctccg ctagcagtag tgtgtcttac atgaattggt atcagcagaa gcccgggaaa   2100

gcacctaagc gctggatcta tgactcttcc aagctggcaa gtggtgtccc ctcacggttc   2160

tctggctcag gttctggtac tgactatact ttgactatct cctccctcca gcccgatgat   2220

ttcgctacct attattgtca gcagtggagc cgtaacccac ccactttcgg aggcggtacc   2280

aaagtggaga tcaagaggtc ataa                                          2304
```

<210> SEQ ID NO 140
<211> LENGTH: 747
<212> TYPE: PRT
<213> ORGANISM: Artificial Sequence
<220> FEATURE:
<223> OTHER INFORMATION: DB60 VHVL x TSC456 scFv-Fc-scFv TRI125

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Asp Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Gln Asp Ser Ser Gly Ser Gly Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Ser Ser Tyr Leu Asn Trp Tyr Gln
                165                 170                 175

Gln Lys Pro Gly Lys Ala Pro Lys Leu Leu Ile Tyr Ala Ala Ser Ser
            180                 185                 190

Leu Gln Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Ser Tyr Ser Thr Pro Leu Thr Phe Gly Gly Gly
225                 230                 235                 240

Thr Lys Val Glu Ile Lys Ser Ser Ser Glu Pro Lys Ser Ser Asp Lys
                245                 250                 255

Thr His Thr Cys Pro Pro Cys Pro Ala Pro Glu Ala Ala Gly Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Ala Val Ser Asn Lys Ala Leu Pro Ala Pro Ile Glu Lys
        355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
420 425 430

Asp Ser Asp Gly Ser Phe Phe Leu Tyr Ser Lys Leu Thr Val Asp Lys
435 440 445

Ser Arg Trp Gln Gln Gly Asn Val Phe Ser Cys Ser Val Met His Glu
450 455 460

Ala Leu His Asn His Tyr Thr Gln Lys Ser Leu Ser Leu Ser Pro Gly
465 470 475 480

Ser Gly Gly Gly Gly Ser Gly Gly Gly Gly Ser Gly Gly Gly Gly Ser
485 490 495

Pro Ser Gln Val Gln Leu Val Gln Ser Gly Pro Glu Val Lys Lys Pro
500 505 510

Gly Ser Ser Val Lys Val Ser Cys Lys Ala Ser Gly Tyr Thr Phe Ser
515 520 525

Arg Ser Thr Met His Trp Val Arg Gln Ala Pro Gly Gln Gly Leu Glu
530 535 540

Trp Ile Gly Tyr Ile Asn Pro Ser Ser Ala Tyr Thr Asn Tyr Asn Gln
545 550 555 560

Lys Phe Lys Asp Arg Val Thr Ile Thr Ala Asp Lys Ser Thr Ser Thr
565 570 575

Ala Tyr Met Glu Leu Ser Ser Leu Arg Ser Glu Asp Thr Ala Val Tyr
580 585 590

Tyr Cys Ala Arg Pro Gln Val His Tyr Asp Tyr Asn Gly Phe Pro Tyr
595 600 605

Trp Gly Gln Gly Thr Leu Val Thr Val Ser Ser Gly Gly Gly Gly Ser
610 615 620

Gly Gly Gly Gly Ser Gly Gly Gly Gly Ser Gly Gly Gly Gly Ser Asp
625 630 635 640

Ile Gln Met Thr Gln Ser Pro Ser Thr Leu Ser Ala Ser Val Gly Asp
645 650 655

Arg Val Thr Met Thr Cys Ser Ala Ser Ser Ser Val Ser Tyr Met Asn
660 665 670

Trp Tyr Gln Gln Lys Pro Gly Lys Ala Pro Lys Arg Trp Ile Tyr Asp
675 680 685

Ser Ser Lys Leu Ala Ser Gly Val Pro Ser Arg Phe Ser Gly Ser Gly
690 695 700

Ser Gly Thr Asp Tyr Thr Leu Thr Ile Ser Ser Leu Gln Pro Asp Asp
705 710 715 720

Phe Ala Thr Tyr Tyr Cys Gln Gln Trp Ser Arg Asn Pro Pro Thr Phe
725 730 735

Gly Gly Gly Thr Lys Val Glu Ile Lys Arg Ser
740 745

<210> SEQ ID NO 141
<211> LENGTH: 2316
<212> TYPE: DNA
<213> ORGANISM: Artificial Sequence
<220> FEATURE:
<223> OTHER INFORMATION: DB65 VHVL x TSC456 scFv-Fc-scFv TRI126

<400> SEQUENCE: 141
atggaagcac cagcgcagct tctcttcctc ctgctactct ggctcccaga taccaccggt 60
caggtgcagc tggtgcagtc tggggctgag gtgaagaagc ctggggcctc agtgaaggtt 120
tcctgcaagg catctggata caccttcacc ggctactata tgcactgggt gcgtcaggcc 180

-continued

```
cctggacaag ggcttgagtg gatgggatgg atgaacccta acagtggtaa cacaggctat    240

gcacagaagt tccagggccg tgtcaccatg acccgcgaca cgtccacgag cacagtctac    300

atggagctga gcagcctgcg ttctgaggac acggccgtgt attactgtgc gaaagaggaa    360

ccgatttttg gagtggttat ggatgctttt gatatctggg gccaagggac aatggtcacc    420

gtctcctcag gcggcggcgg cagcggcggc ggcggcagcg gcggcggagg ctccggcggc    480

ggcggcagcg acatccagat gacccagtct ccatcctccc tgtctgcatc tgtaggagac    540

agagtcacca tcacttgccg ggcaagtcag agcattagca gctatctgaa ttggtatcag    600

cagaaaccag ggaaagcccc taagctcctg atctatgctg catccagttt gcaaagtggg    660

gtcccatcaa ggttcagtgg cagtggatct gggacagatt tcactctcac catcagcagt    720

ctgcaacctg aagattttgc aacttactac tgtcaacaga gttacagtac ccctctcact    780

ttcggcggag gtaccaaggt ggagatcaaa tcctcgagtg agcccaaatc ttctgacaaa    840

actcacacat gcccaccgtg cccagcacct gaagccgcgg gtgcaccgtc agtcttcctc    900

ttccccccaa aacccaagga caccctcatg atctcccgga cccctgaggt cacatgcgtg    960

gtggtggacg tgagccacga agaccctgag gtcaagttca actggtacgt ggacggcgtg   1020

gaggtgcata atgccaagac aaagccgcgg gaggagcagt acaacagcac gtaccgtgtg   1080

gtcagcgtcc tcaccgtcct gcaccaggac tggctgaatg gcaaggaata caagtgcgcg   1140

gtctccaaca aagccctccc agcccccatc gagaaaacca tctccaaagc caaagggcag   1200

ccccgagaac cacaggtgta caccctgccc ccatcccggg atgagctgac caagaaccag   1260

gtcagcctga cctgcctggt caaaggcttc tatccaagcg acatcgccgt ggagtgggag   1320

agcaatgggc agccggagaa caactacaag accacgcctc ccgtgctgga ctccgacggc   1380

tccttcttcc tctacagcaa gctcaccgtg gacaagagca ggtggcagca ggggaacgtc   1440

ttctcatgct ccgtgatgca tgaggctctg cacaaccact acacgcagaa gagcctctcc   1500

ctgtctccgg gttccggagg agggggttca ggtgggggag gttctggcgg cgggggaagc   1560

ccttcacagg tgcaactggt gcagagtgga cccgaggtta aaaaaccagg gtcctccgtt   1620

aaggttagct gcaaagcctc tggctacaca ttttccagga gtacaatgca ctgggtgagg   1680

caggctcctg gacagggact cgagtggatc gggtatatca acccatctag cgcctatacc   1740

aattacaacc aaaagtttaa ggaccgagtt accattaccg ctgacaaatc caccagtaca   1800

gcttatatgg agctgtcatc tcttaggtcc gaggacactg ctgtttatta ctgcgctcgt   1860

cctcaggttc actatgacta taatggtttt ccctactggg gtcagggaac cctggtgact   1920

gtctcttctg gcggtggagg cagcggtggg ggtgggtctg gaggcggtgg cagtggcggc   1980

ggaggctctg atattcagat gactcagtct cctagcactc tcagcgccag cgtgggggat   2040

cgtgtgacaa tgacttgctc cgctagcagt agtgtgtctt acatgaattg gtatcagcag   2100

aagcccggga aagcacctaa gcgctggatc tatgactctt ccaagctggc aagtggtgtc   2160

ccctcacggt tctctggctc aggttctggt actgactata ctttgactat ctcctccctc   2220

cagcccgatg atttcgctac ctattattgt cagcagtgga gccgtaaccc acccactttc   2280

ggaggcggta ccaaagtgga gatcaagagg tcataa                              2316
```

<210> SEQ ID NO 142
<211> LENGTH: 751
<212> TYPE: PRT
<213> ORGANISM: Artificial Sequence
<220> FEATURE:
<223> OTHER INFORMATION: DB65 VHVL x TSC456 scFv-Fc-scFv TRI126

<400> SEQUENCE: 142

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Lys Glu Glu Pro Ile Phe Gly Val Val Met Asp Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Gly Gly Gly Gly Ser Asp
    130                 135                 140

Ile Gln Met Thr Gln Ser Pro Ser Ser Leu Ser Ala Ser Val Gly Asp
145                 150                 155                 160

Arg Val Thr Ile Thr Cys Arg Ala Ser Gln Ser Ile Ser Ser Tyr Leu
                165                 170                 175

Asn Trp Tyr Gln Gln Lys Pro Gly Lys Ala Pro Lys Leu Leu Ile Tyr
            180                 185                 190

Ala Ala Ser Ser Leu Gln Ser Gly Val Pro Ser Arg Phe Ser Gly Ser
        195                 200                 205

Gly Ser Gly Thr Asp Phe Thr Leu Thr Ile Ser Ser Leu Gln Pro Glu
    210                 215                 220

Asp Phe Ala Thr Tyr Tyr Cys Gln Gln Ser Tyr Ser Thr Pro Leu Thr
225                 230                 235                 240

Phe Gly Gly Gly Thr Lys Val Glu Ile Lys Ser Ser Ser Glu Pro Lys
                245                 250                 255

Ser Ser Asp Lys Thr His Thr Cys Pro Pro Cys Pro Ala Pro Glu Ala
            260                 265                 270

Ala Gly Ala Pro Ser Val Phe Leu Phe Pro Pro Lys Pro Lys Asp Thr
        275                 280                 285

Leu Met Ile Ser Arg Thr Pro Glu Val Thr Cys Val Val Val Asp Val
    290                 295                 300

Ser His Glu Asp Pro Glu Val Lys Phe Asn Trp Tyr Val Asp Gly Val
305                 310                 315                 320

Glu Val His Asn Ala Lys Thr Lys Pro Arg Glu Glu Gln Tyr Asn Ser
                325                 330                 335

Thr Tyr Arg Val Val Ser Val Leu Thr Val Leu His Gln Asp Trp Leu
            340                 345                 350

Asn Gly Lys Glu Tyr Lys Cys Ala Val Ser Asn Lys Ala Leu Pro Ala
        355                 360                 365

Pro Ile Glu Lys Thr Ile Ser Lys Ala Lys Gly Gln Pro Arg Glu Pro
    370                 375                 380

Gln Val Tyr Thr Leu Pro Pro Ser Arg Asp Glu Leu Thr Lys Asn Gln
385                 390                 395                 400

Val Ser Leu Thr Cys Leu Val Lys Gly Phe Tyr Pro Ser Asp Ile Ala
                405                 410                 415
```

-continued

```
Val Glu Trp Glu Ser Asn Gly Gln Pro Glu Asn Asn Tyr Lys Thr Thr
            420                 425                 430

Pro Pro Val Leu Asp Ser Asp Gly Ser Phe Phe Leu Tyr Ser Lys Leu
        435                 440                 445

Thr Val Asp Lys Ser Arg Trp Gln Gln Gly Asn Val Phe Ser Cys Ser
    450                 455                 460

Val Met His Glu Ala Leu His Asn His Tyr Thr Gln Lys Ser Leu Ser
465                 470                 475                 480

Leu Ser Pro Gly Ser Gly Gly Gly Gly Ser Gly Gly Gly Gly Ser Gly
                485                 490                 495

Gly Gly Gly Ser Pro Ser Gln Val Gln Leu Val Gln Ser Gly Pro Glu
            500                 505                 510

Val Lys Lys Pro Gly Ser Ser Val Lys Val Ser Cys Lys Ala Ser Gly
        515                 520                 525

Tyr Thr Phe Ser Arg Ser Thr Met His Trp Val Arg Gln Ala Pro Gly
    530                 535                 540

Gln Gly Leu Glu Trp Ile Gly Tyr Ile Asn Pro Ser Ser Ala Tyr Thr
545                 550                 555                 560

Asn Tyr Asn Gln Lys Phe Lys Asp Arg Val Thr Ile Thr Ala Asp Lys
                565                 570                 575

Ser Thr Ser Thr Ala Tyr Met Glu Leu Ser Ser Leu Arg Ser Glu Asp
            580                 585                 590

Thr Ala Val Tyr Tyr Cys Ala Arg Pro Gln Val His Tyr Asp Tyr Asn
        595                 600                 605

Gly Phe Pro Tyr Trp Gly Gln Gly Thr Leu Val Thr Val Ser Ser Gly
    610                 615                 620

Gly Gly Gly Ser Gly Gly Gly Gly Ser Gly Gly Gly Gly Ser Gly Gly
625                 630                 635                 640

Gly Gly Ser Asp Ile Gln Met Thr Gln Ser Pro Ser Thr Leu Ser Ala
                645                 650                 655

Ser Val Gly Asp Arg Val Thr Met Thr Cys Ser Ala Ser Ser Ser Val
            660                 665                 670

Ser Tyr Met Asn Trp Tyr Gln Gln Lys Pro Gly Lys Ala Pro Lys Arg
        675                 680                 685

Trp Ile Tyr Asp Ser Ser Lys Leu Ala Ser Gly Val Pro Ser Arg Phe
    690                 695                 700

Ser Gly Ser Gly Ser Gly Thr Asp Tyr Thr Leu Thr Ile Ser Ser Leu
705                 710                 715                 720

Gln Pro Asp Asp Phe Ala Thr Tyr Tyr Cys Gln Gln Trp Ser Arg Asn
                725                 730                 735

Pro Pro Thr Phe Gly Gly Gly Thr Lys Val Glu Ile Lys Arg Ser
            740                 745                 750
```

<210> SEQ ID NO 143
<211> LENGTH: 2304
<212> TYPE: DNA
<213> ORGANISM: Artificial Sequence
<220> FEATURE:
<223> OTHER INFORMATION: DB82 VLVH x TSC456 scFv-Fc-scFv TRI127

<400> SEQUENCE: 143

```
atggaagcac cagcgcagct tctcttcctc ctgctactct ggctcccaga taccaccggt      60

gacatccaga tgacccagtc tccatcctcc ctgtctgcat ctgtaggaga ccgcgtcacc     120

atcacttgcc gggcaagtca gaccataaac aactatttga actggtatca gcagaaacca     180
```

```
gggaaagccc ctaagctcct gatctattct gcatctactt tgcaaagtgg ggtcccatca    240
cgtttcagtg gcagtggatc tgggacagat ttcactctca ccatcagcag tctgcaacct    300
gaagattttg caacttacta ctgtcaccag agttacactt cacctctcac tttcggcgga    360
ggtaccaagg tggagatcaa aggcggcggc ggcagcggcg gcggcggcag cggcggcgga    420
ggctccggcg gcggcggcag cgaggtgcag ctggtggagt ctgggggagg cttggtacag    480
cctggggggt ccctgcgcct ctcctgtgca gcctctggat tcacctttag cagctatgcc    540
atgagctggg tccgccaggc tccagggaag gggctggagt gggtctcagt tattagtgcc    600
aatagtgctg gtctaggcca tgcggactct gtgaagggcc ggttcaccat ctcccgcgac    660
aattccaaga acacgctgta tctgcaaatg aacagcctgc gcgccgagga cacggccgta    720
tattactgtg cgagagtggg ctatagcagc tcggctgatg cttttgatat ctggggccaa    780
gggacaatgg tcaccgtctc ctcgagtgag cccaaatctt ctgacaaaac tcacacatgc    840
ccaccgtgcc cagcacctga agccgcgggt gcaccgtcag tcttcctctt ccccccaaaa    900
cccaaggaca ccctcatgat ctcccggacc cctgaggtca catgcgtggt ggtggacgtg    960
agccacgaag accctgaggt caagttcaac tggtacgtgg acggcgtgga ggtgcataat   1020
gccaagacaa agccgcggga ggagcagtac aacagcacgt accgtgtggt cagcgtcctc   1080
accgtcctgc accaggactg gctgaatggc aaggaataca agtgcgcggt ctccaacaaa   1140
gccctcccag cccccatcga gaaaaccatc tccaaagcca aagggcagcc ccgagaacca   1200
caggtgtaca ccctgccccc atcccgggat gagctgacca agaaccaggt cagcctgacc   1260
tgcctggtca aaggcttcta tccaagcgac atcgccgtgg agtgggagag caatgggcag   1320
ccggagaaca actacaagac cacgcctccc gtgctggact ccgacggctc cttcttcctc   1380
tacagcaagc tcaccgtgga caagagcagg tggcagcagg ggaacgtctt ctcatgctcc   1440
gtgatgcatg aggctctgca caaccactac acgcagaaga gcctctccct gtctccgggt   1500
tccggaggag ggggttcagg tgggggaggt tctggcggcg gggaagccc ttcacaggtg    1560
caactggtgc agagtggacc cgaggttaaa aaaccagggt cctccgttaa ggttagctgc   1620
aaagcctctg gctacacatt ttccaggagt acaatgcact gggtgaggca ggctcctgga   1680
cagggactcg agtggatcgg gtatatcaac ccatctagcg cctataccaa ttacaaccaa   1740
aagtttaagg accgagttac cattaccgct gacaaatcca ccagtacagc ttatatggag   1800
ctgtcatctc ttaggtccga ggacactgct gtttattact gcgctcgtcc tcaggttcac   1860
tatgactata atggttttcc ctactggggt cagggaaccc tggtgactgt ctcttctggc   1920
ggtggaggca gcggtggggg tgggtctgga ggcggtggca gtggcggcgg aggctctgat   1980
attcagatga ctcagtctcc tagcactctc agcgccagcg tgggggatcg tgtgacaatg   2040
acttgctccg ctagcagtag tgtgtcttac atgaattggt atcagcagaa gcccgggaaa   2100
gcacctaagc gctggatcta tgactcttcc aagctggcaa gtggtgtccc ctcacggttc   2160
tctggctcag gttctggtac tgactatact ttgactatct cctccctcca gcccgatgat   2220
ttcgctacct attattgtca gcagtggagc cgtaacccac ccactttcgg aggcggtacc   2280
aaagtggaga tcaagaggtc ataa                                          2304
```

<210> SEQ ID NO 144
<211> LENGTH: 747
<212> TYPE: PRT
<213> ORGANISM: Artificial Sequence
<220> FEATURE:
<223> OTHER INFORMATION: DB82 VLVH x TSC456 scFv-Fc-scFv TRI127

<400> SEQUENCE: 144

Asp Ile Gln Met Thr Gln Ser Pro Ser Ser Leu Ser Ala Ser Val Gly
1 5 10 15

Asp Arg Val Thr Ile Thr Cys Arg Ala Ser Gln Thr Ile Asn Asn Tyr
20 25 30

Leu Asn Trp Tyr Gln Gln Lys Pro Gly Lys Ala Pro Lys Leu Leu Ile
35 40 45

Tyr Ser Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys His Gln Ser Tyr Thr Ser Pro Leu
85 90 95

Thr Phe Gly Gly Gly Thr Lys Val Glu Ile Lys Gly Gly Gly Gly Ser
100 105 110

Gly Gly Gly Gly Ser Gly Gly Gly Gly Ser Gly Gly Gly Gly Ser Glu
115 120 125

Val Gln Leu Val Glu Ser Gly Gly Gly Leu Val Gln Pro Gly Gly Ser
130 135 140

Leu Arg Leu Ser Cys Ala Ala Ser Gly Phe Thr Phe Ser Ser Tyr Ala
145 150 155 160

Met Ser Trp Val Arg Gln Ala Pro Gly Lys Gly Leu Glu Trp Val Ser
165 170 175

Val Ile Ser Ala Asn Ser Ala Gly Leu Gly His Ala Asp Ser Val Lys
180 185 190

Gly Arg Phe Thr Ile Ser Arg Asp Asn Ser Lys Asn Thr Leu Tyr Leu
195 200 205

Gln Met Asn Ser Leu Arg Ala Glu Asp Thr Ala Val Tyr Tyr Cys Ala
210 215 220

Arg Val Gly Tyr Ser Ser Ser Ala Asp Ala Phe Asp Ile Trp Gly Gln
225 230 235 240

Gly Thr Met Val Thr Val Ser Ser Ser Glu Pro Lys Ser Ser Asp Lys
245 250 255

Thr His Thr Cys Pro Pro Cys Pro Ala Pro Glu Ala Ala Gly Ala Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Ala Val Ser Asn Lys Ala Leu Pro Ala Pro Ile Glu Lys
355 360 365

Thr Ile Ser Lys Ala Lys Gly Gln Pro Arg Glu Pro Gln Val Tyr Thr
370 375 380

Leu Pro Pro Ser Arg Asp Glu Leu Thr Lys Asn Gln Val Ser Leu Thr
385 390 395 400

Cys Leu Val Lys Gly Phe Tyr Pro Ser Asp Ile Ala Val Glu Trp Glu
405 410 415

-continued

```
Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Ser Gly Gly Gly Gly Ser Gly Gly Gly Gly Ser Gly Gly Gly Gly Ser
                485                 490                 495

Pro Ser Gln Val Gln Leu Val Gln Ser Gly Pro Glu Val Lys Lys Pro
            500                 505                 510

Gly Ser Ser Val Lys Val Ser Cys Lys Ala Ser Gly Tyr Thr Phe Ser
        515                 520                 525

Arg Ser Thr Met His Trp Val Arg Gln Ala Pro Gly Gln Gly Leu Glu
    530                 535                 540

Trp Ile Gly Tyr Ile Asn Pro Ser Ser Ala Tyr Thr Asn Tyr Asn Gln
545                 550                 555                 560

Lys Phe Lys Asp Arg Val Thr Ile Thr Ala Asp Lys Ser Thr Ser Thr
                565                 570                 575

Ala Tyr Met Glu Leu Ser Ser Leu Arg Ser Glu Asp Thr Ala Val Tyr
            580                 585                 590

Tyr Cys Ala Arg Pro Gln Val His Tyr Asp Tyr Asn Gly Phe Pro Tyr
        595                 600                 605

Trp Gly Gln Gly Thr Leu Val Thr Val Ser Ser Gly Gly Gly Gly Ser
    610                 615                 620

Gly Gly Gly Gly Ser Gly Gly Gly Gly Ser Gly Gly Gly Gly Ser Asp
625                 630                 635                 640

Ile Gln Met Thr Gln Ser Pro Ser Thr Leu Ser Ala Ser Val Gly Asp
                645                 650                 655

Arg Val Thr Met Thr Cys Ser Ala Ser Ser Ser Val Ser Tyr Met Asn
            660                 665                 670

Trp Tyr Gln Gln Lys Pro Gly Lys Ala Pro Lys Arg Trp Ile Tyr Asp
        675                 680                 685

Ser Ser Lys Leu Ala Ser Gly Val Pro Ser Arg Phe Ser Gly Ser Gly
    690                 695                 700

Ser Gly Thr Asp Tyr Thr Leu Thr Ile Ser Ser Leu Gln Pro Asp Asp
705                 710                 715                 720

Phe Ala Thr Tyr Tyr Cys Gln Gln Trp Ser Arg Asn Pro Pro Thr Phe
                725                 730                 735

Gly Gly Gly Thr Lys Val Glu Ile Lys Arg Ser
            740                 745
```

<210> SEQ ID NO 145
<211> LENGTH: 2337
<212> TYPE: DNA
<213> ORGANISM: Artificial Sequence
<220> FEATURE:
<223> OTHER INFORMATION: DB83 VHVL x TSC456 scFv-Fc-scFv TRI134

<400> SEQUENCE: 145

```
atggaagcac cagcgcagct tctcttcctc ctgctactct ggctcccaga taccaccggt      60

caggtgcagc tggtgcagtc tggggctgag gtgaagaagc ctggggcctc agtgaaggtt     120

tcctgcaagg catctggata caccttcact agctatgcta tgcattgggt gcgtcaggcc     180
```

```
cctggacaag ggcttgagtg gatgggactt gttgatcctg aagatggtga aacaatatat    240
gcagagaagt tccagggccg tgtcaccatg acccgcgaca cgtccacgag cacagtctac    300
atggagctga gcagcctgcg ttctgaggac acggccgtgt attactgtgc gagacgaacg    360
tattactatg atagtagtgg ttcccgttat gcttttgata tctggggcca agggaccacg    420
gtcaccgtct cttcaggcgg cggcggcagc ggcggcggcg gcagcggcgg cggaggctcc    480
ggcggcggcg gcagcgatgt tgtgatgact cagtctccac tctccctgcc cgtcacccct    540
ggagagccgg cctccatctc ctgcaggtct agtcagagcc tcctgcatag taatggagac    600
aactatttgg attggtacct gcagaagcca gggcagtctc cacagctcct gatctatttg    660
ggttctaatc gggcctccgg ggtccctgac cgtttcagtg gcagtggatc aggcacagat    720
tttacactga aaatcagccg tgtggaggct gaggatgttg ggtttatta ctgcatgcaa     780
gctacacact ggccactcac tttcggccct ggtaccaaag tggatatcaa atcctcgagt    840
gagcccaaat cttctgacaa aactcacaca tgcccaccgt gcccagcacc tgaagccgcg    900
ggtgcaccgt cagtcttcct cttcccccca aaacccaagg acaccctcat gatctcccgg    960
acccctgagg tcacatgcgt ggtggtggac gtgagccacg aagaccctga ggtcaagttc   1020
aactggtacg tggacggcgt ggaggtgcat aatgccaaga caaagccgcg ggaggagcag   1080
tacaacagca cgtaccgtgt ggtcagcgtc ctcaccgtcc tgcaccagga ctggctgaat   1140
ggcaaggaat acaagtgcgc ggtctccaac aaagccctcc cagcccccat cgagaaaacc   1200
atctccaaag ccaaagggca gccccgagaa ccacaggtgt acaccctgcc cccatcccgg   1260
gatgagctga ccaagaacca ggtcagcctg acctgcctgg tcaaaggctt ctatccaagc   1320
gacatcgccg tggagtggga gagcaatggg cagccggaga acaactacaa gaccacgcct   1380
cccgtgctgg actccgacgg ctccttcttc ctctacagca agctcaccgt ggacaagagc   1440
aggtggcagc aggggaacgt cttctcatgc tccgtgatgc atgaggctct gcacaaccac   1500
tacacgcaga agagcctctc cctgtctccg ggttccggag gagggggttc aggtggggga   1560
ggttctggcg gcgggggaag cccttcacag gtgcaactgg tgcagagtgg acccgaggtt   1620
aaaaaaccag ggtcctccgt taaggttagc tgcaaagcct ctggctacac attttccagg   1680
agtacaatgc actgggtgag gcaggctcct ggacagggac tcgagtggat cgggtatatc   1740
aacccatcta gcgcctatac caattacaac caaaagttta aggaccgagt taccattacc   1800
gctgacaaat ccaccagtac agcttatatg gagctgtcat ctcttaggtc cgaggacact   1860
gctgtttatt actgcgctcg tcctcaggtt cactatgact ataatggttt tccctactgg   1920
ggtcagggaa ccctggtgac tgtctcttct ggcggtggag gcagcggtgg gggtgggtct   1980
ggaggcggtg gcagtggcgg cggaggctct gatattcaga tgactcagtc tcctagcact   2040
ctcagcgcca gcgtggggga tcgtgtgaca atgacttgct ccgctagcag tagtgtgtct   2100
tacatgaatt ggtatcagca gaagcccggg aaagcaccta agcgctggat ctatgactct   2160
tccaagctgg caagtggtgt cccctcacgg ttctctggct caggttctgg tactgactat   2220
actttgacta tctcctccct ccagcccgat gatttcgcta cctattattg tcagcagtgg   2280
agccgtaacc cacccacttt cggaggcggt accaaagtgg agatcaagag gtcataa      2337
```

<210> SEQ ID NO 146
<211> LENGTH: 758
<212> TYPE: PRT
<213> ORGANISM: Artificial Sequence
<220> FEATURE:
<223> OTHER INFORMATION: DB83 VHVL x TSC456 scFv-Fc-scFv TRI134

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Thr Tyr Tyr Tyr Asp Ser Ser Gly Ser Arg Tyr Ala Phe
            100                 105                 110

Asp Ile Trp Gly Gln Gly Thr Thr Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Asp Val Val Met Thr Gln Ser Pro Leu Ser Leu Pro Val Thr Pro
145                 150                 155                 160

Gly Glu Pro Ala Ser Ile Ser Cys Arg Ser Ser Gln Ser Leu Leu His
                165                 170                 175

Ser Asn Gly Asp Asn Tyr Leu Asp Trp Tyr Leu Gln Lys Pro Gly Gln
            180                 185                 190

Ser Pro Gln Leu Leu Ile Tyr Leu Gly Ser Asn Arg Ala Ser Gly Val
        195                 200                 205

Pro Asp Arg Phe Ser Gly Ser Gly Ser Gly Thr Asp Phe Thr Leu Lys
    210                 215                 220

Ile Ser Arg Val Glu Ala Glu Asp Val Gly Val Tyr Tyr Cys Met Gln
225                 230                 235                 240

Ala Thr His Trp Pro Leu Thr Phe Gly Pro Gly Thr Lys Val Asp Ile
                245                 250                 255

Lys Ser Ser Ser Glu Pro Lys Ser Ser Asp Lys Thr His Thr Cys Pro
            260                 265                 270

Pro Cys Pro Ala Pro Glu Ala Ala Gly Ala Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Ala Val
        355                 360                 365

Ser Asn Lys Ala Leu Pro Ala Pro Ile Glu Lys Thr Ile Ser Lys Ala
    370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

```
Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
        435                 440                 445

Phe Phe Leu Tyr Ser Lys Leu Thr Val Asp Lys Ser Arg Trp Gln Gln
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Ser Gly Gly Gly Gly
                485                 490                 495

Ser Gly Gly Gly Gly Ser Gly Gly Gly Gly Ser Pro Ser Gln Val Gln
            500                 505                 510

Leu Val Gln Ser Gly Pro Glu Val Lys Lys Pro Gly Ser Ser Val Lys
        515                 520                 525

Val Ser Cys Lys Ala Ser Gly Tyr Thr Phe Ser Arg Ser Thr Met His
    530                 535                 540

Trp Val Arg Gln Ala Pro Gly Gln Gly Leu Glu Trp Ile Gly Tyr Ile
545                 550                 555                 560

Asn Pro Ser Ser Ala Tyr Thr Asn Tyr Asn Gln Lys Phe Lys Asp Arg
                565                 570                 575

Val Thr Ile Thr Ala Asp Lys Ser Thr Ser Thr Ala Tyr Met Glu Leu
            580                 585                 590

Ser Ser Leu Arg Ser Glu Asp Thr Ala Val Tyr Tyr Cys Ala Arg Pro
        595                 600                 605

Gln Val His Tyr Asp Tyr Asn Gly Phe Pro Tyr Trp Gly Gln Gly Thr
    610                 615                 620

Leu Val Thr Val Ser Ser Gly Gly Gly Gly Ser Gly Gly Gly Gly Ser
625                 630                 635                 640

Gly Gly Gly Gly Ser Gly Gly Gly Gly Ser Asp Ile Gln Met Thr Gln
                645                 650                 655

Ser Pro Ser Thr Leu Ser Ala Ser Val Gly Asp Arg Val Thr Met Thr
            660                 665                 670

Cys Ser Ala Ser Ser Ser Val Ser Tyr Met Asn Trp Tyr Gln Gln Lys
        675                 680                 685

Pro Gly Lys Ala Pro Lys Arg Trp Ile Tyr Asp Ser Ser Lys Leu Ala
    690                 695                 700

Ser Gly Val Pro Ser Arg Phe Ser Gly Ser Gly Ser Gly Thr Asp Tyr
705                 710                 715                 720

Thr Leu Thr Ile Ser Ser Leu Gln Pro Asp Asp Phe Ala Thr Tyr Tyr
                725                 730                 735

Cys Gln Gln Trp Ser Arg Asn Pro Pro Thr Phe Gly Gly Gly Thr Lys
            740                 745                 750

Val Glu Ile Lys Arg Ser
        755
```

<210> SEQ ID NO 147
<211> LENGTH: 2307
<212> TYPE: DNA
<213> ORGANISM: Artificial Sequence
<220> FEATURE:
<223> OTHER INFORMATION: DB86 VHVL x TSC456 scFv-Fc-scFv TRI128

<400> SEQUENCE: 147

```
atggaagcac cagcgcagct tctcttcctc ctgctactct ggctcccaga taccaccggt      60

caggtgcagc tggtgcagtc tggggctgag gtgaagaagc ctggggcctc agtgaaggtt     120
```

-continued

```
tcctgcaagg catctggata tatgttcagt ggccattctg cacactgggt gcgtcaggcc    180
cctggacaag ggcttgagtg gatgggatgg atgaacccta acagtggtaa cacaggctat    240
gcacagaagt tccagggccg tgtcaccatg acccgcgaca cgtccacgag cacagtctac    300
atggagctga gcagcctgcg ttctgaggac acggccgtgt attactgtgc gagagatagc    360
agtggctggt acgatgtctt tgactactgg ggccagggga ccctggtcac cgtctcctca    420
ggtggaggcg gttcaggcgg aggtggatcc ggcggtggcg gctccggtgg cggcggatct    480
gacatccaga tgacccagtc tccatcctcc ctgtctgcat ctgtaggaga ccgcgtcacc    540
atcacttgcc gggcaagtca gggcatcaga aatgatttag gttggtatca gcagaaacca    600
gggaaagccc ctaagctcct gatctatgct gcatccactt tgcaatcagg ggtcccatca    660
cgtttcagtg gcagtggatc tgggacagat ttcactctca ccatcagcag tctgcaacct    720
gaagattttg caacttacta ctgtcaacag agttacggtg ccccccctcac tttcggcgga    780
ggtaccaagg tggagatcaa atcctcgagt gagcccaaat cttctgacaa aactcacaca    840
tgcccaccgt gcccagcacc tgaagccgcg ggtgcaccgt cagtcttcct cttcccccca    900
aaacccaagg acaccctcat gatctcccgg acccctgagg tcacatgcgt ggtggtggac    960
gtgagccacg aagaccctga ggtcaagttc aactggtacg tggacggcgt ggaggtgcat   1020
aatgccaaga caaagccgcg ggaggagcag tacaacagca cgtaccgtgt ggtcagcgtc   1080
ctcaccgtcc tgcaccagga ctggctgaat ggcaaggaat acaagtgcgc ggtctccaac   1140
aaagccctcc cagcccccat cgagaaaacc atctccaaag ccaaagggca gccccgagaa   1200
ccacaggtgt acaccctgcc cccatcccgg gatgagctga ccaagaacca ggtcagcctg   1260
acctgcctgg tcaaaggctt ctatccaagc gacatcgccg tggagtggga gagcaatggg   1320
cagccggaga acaactacaa gaccacgcct cccgtgctgg actccgacgg ctccttcttc   1380
ctctacagca agctcaccgt ggacaagagc aggtggcagc aggggaacgt cttctcatgc   1440
tccgtgatgc atgaggctct gcacaaccac tacacgcaga agagcctctc cctgtctccg   1500
ggttccggag gagggggttc aggtggggga ggttctggcg gcgggggaag cccttcacag   1560
gtgcaactgg tgcagagtgg acccgaggtt aaaaaaccag ggtcctccgt taaggttagc   1620
tgcaaagcct ctggctacac attttccagg agtacaatgc actgggtgag gcaggctcct   1680
ggacagggac tcgagtggat cgggtatatc aacccatcta gcgcctatac caattacaac   1740
caaaagttta aggaccgagt taccattacc gctgacaaat ccaccagtac agcttatatg   1800
gagctgtcat ctcttaggtc cgaggacact gctgtttatt actgcgctcg tcctcaggtt   1860
cactatgact ataatggttt tccctactgg ggtcagggaa ccctggtgac tgtctcttct   1920
ggcggtggag gcagcggtgg gggtgggtct ggaggcggtg gcagtggcgg cggaggctct   1980
gatattcaga tgactcagtc tcctagcact ctcagcgcca gcgtgggggga tcgtgtgaca   2040
atgacttgct ccgctagcag tagtgtgtct tacatgaatt ggtatcagca gaagcccggg   2100
aaagcaccta agcgctggat ctatgactct tccaagctgg caagtggtgt cccctcacgg   2160
ttctctggct caggttctgg tactgactat actttgacta tctcctccct ccagcccgat   2220
gatttcgcta cctattattg tcagcagtgg agccgtaacc cacccacttt cggaggcggt   2280
accaaagtgg agatcaagag gtcataa                                       2307
```

<210> SEQ ID NO 148
<211> LENGTH: 748
<212> TYPE: PRT
<213> ORGANISM: Artificial Sequence

```
<220> FEATURE:
<223> OTHER INFORMATION: DB86 VHVL x TSC456 scFv-Fc-scFv TRI128

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Met Phe Ser Gly His
            20                  25                  30

Ser Ala His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ser Ser Gly Trp Tyr Asp Val Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Asp Ile Gln Met
    130                 135                 140

Thr Gln Ser Pro Ser Ser Leu Ser Ala Ser Val Gly Asp Arg Val Thr
145                 150                 155                 160

Ile Thr Cys Arg Ala Ser Gln Gly Ile Arg Asn Asp Leu Gly Trp Tyr
                165                 170                 175

Gln Gln Lys Pro Gly Lys Ala Pro Lys Leu Leu Ile Tyr Ala Ala Ser
            180                 185                 190

Thr Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ser Tyr Gly Ala Pro Leu Thr Phe Gly Gly
225                 230                 235                 240

Gly Thr Lys Val Glu Ile Lys Ser Ser Ser Glu Pro Lys Ser Ser Asp
                245                 250                 255

Lys Thr His Thr Cys Pro Pro Cys Pro Ala Pro Glu Ala Ala Gly Ala
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Ala Val Ser Asn Lys Ala Leu Pro Ala Pro Ile Glu
        355                 360                 365

Lys Thr Ile Ser Lys Ala Lys Gly Gln Pro Arg Glu Pro Gln Val Tyr
    370                 375                 380

Thr Leu Pro Pro Ser Arg Asp Glu Leu Thr Lys Asn Gln Val Ser Leu
385                 390                 395                 400
```

-continued

```
Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
            420                 425                 430

Leu Asp Ser Asp Gly Ser Phe Phe Leu Tyr Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Ser Gly Gly Gly Gly Ser Gly Gly Gly Gly Ser Gly Gly Gly Gly
                485                 490                 495

Ser Pro Ser Gln Val Gln Leu Val Gln Ser Gly Pro Glu Val Lys Lys
            500                 505                 510

Pro Gly Ser Ser Val Lys Val Ser Cys Lys Ala Ser Gly Tyr Thr Phe
        515                 520                 525

Ser Arg Ser Thr Met His Trp Val Arg Gln Ala Pro Gly Gln Gly Leu
    530                 535                 540

Glu Trp Ile Gly Tyr Ile Asn Pro Ser Ser Ala Tyr Thr Asn Tyr Asn
545                 550                 555                 560

Gln Lys Phe Lys Asp Arg Val Thr Ile Thr Ala Asp Lys Ser Thr Ser
                565                 570                 575

Thr Ala Tyr Met Glu Leu Ser Ser Leu Arg Ser Glu Asp Thr Ala Val
            580                 585                 590

Tyr Tyr Cys Ala Arg Pro Gln Val His Tyr Asp Tyr Asn Gly Phe Pro
        595                 600                 605

Tyr Trp Gly Gln Gly Thr Leu Val Thr Val Ser Ser Gly Gly Gly Gly
    610                 615                 620

Ser Gly Gly Gly Gly Ser Gly Gly Gly Gly Ser Gly Gly Gly Gly Ser
625                 630                 635                 640

Asp Ile Gln Met Thr Gln Ser Pro Ser Thr Leu Ser Ala Ser Val Gly
                645                 650                 655

Asp Arg Val Thr Met Thr Cys Ser Ala Ser Ser Ser Val Ser Tyr Met
            660                 665                 670

Asn Trp Tyr Gln Gln Lys Pro Gly Lys Ala Pro Lys Arg Trp Ile Tyr
        675                 680                 685

Asp Ser Ser Lys Leu Ala Ser Gly Val Pro Ser Arg Phe Ser Gly Ser
    690                 695                 700

Gly Ser Gly Thr Asp Tyr Thr Leu Thr Ile Ser Ser Leu Gln Pro Asp
705                 710                 715                 720

Asp Phe Ala Thr Tyr Tyr Cys Gln Gln Trp Ser Arg Asn Pro Pro Thr
                725                 730                 735

Phe Gly Gly Gly Thr Lys Val Glu Ile Lys Arg Ser
            740                 745
```

<210> SEQ ID NO 149
<211> LENGTH: 2325
<212> TYPE: DNA
<213> ORGANISM: Artificial Sequence
<220> FEATURE:
<223> OTHER INFORMATION: DB280 VHVL x TSC456 scFv-Fc-scFv TRI131

<400> SEQUENCE: 149

```
atggaagcac cagcgcagct tctcttcctc ctgctactct ggctcccaga taccaccggt      60

caggtgcagc tggtgcagtc tggggctgag gtgaagaagc ctggggcctc agtgaaggtt     120
```

tcctgcaagg catctggata cagcctcaac ttatactata tgcactgggt gcgtcaggcc 180
cctggacaag ggcttgagtg gatgggatgg atgaacccta acagtggtaa cacaggctat 240
gcacagaagt tccagggccg tgtcaccatg acccgcgaca cgtccacgag cacagtctac 300
atggagctga gcagcctgcg ttctgaggac acggccgtgt attactgtgc gagcctcgat 360
tgtagtggtg gtagctgcta ctccgaatat gatgcttttg atatctgggg ccaagggacc 420
acggtcaccg tctcctcagg cggcggcggc agcggcggcg gcggcagcgg cggcggaggc 480
tccggcggcg gcggcagcga catccagatg acccagtctc catcctccct gtctgcatct 540
gtaggagaca gagtcaccat cacttgccgg gcaagtcaga gcattagcag ctatctgaat 600
tggtatcagc agaaaccagg gaaagcccct aagctcctga tctatgctgc atccagtttg 660
caaagtgggg tcccatcaag gttcagtggc agtggatctg ggacagattt cactctcacc 720
atcagcagtc tgcaacctga agattttgca acttactact gtcaacagag ttacagtacc 780
cctctcactt tcggcggagg taccaaggtg gagatcaaat cctcgagtga gcccaaatct 840
tctgacaaaa ctcacacatg cccaccgtgc ccagcacctg aagccgcggg tgcaccgtca 900
gtcttcctct tcccccaaa acccaaggac accctcatga tctcccggac ccctgaggtc 960
acatgcgtgg tggtggacgt gagccacgaa gaccctgagg tcaagttcaa ctggtacgtg 1020
gacggcgtgg aggtgcataa tgccaagaca aagccgcggg aggagcagta caacagcacg 1080
taccgtgtgg tcagcgtcct caccgtcctg caccaggact ggctgaatgg caaggaatac 1140
aagtgcgcgg tctccaacaa agccctccca gcccccatcg agaaaaccat ctccaaagcc 1200
aaagggcagc cccgagaacc acaggtgtac accctgcccc catcccggga tgagctgacc 1260
aagaaccagg tcagcctgac ctgcctggtc aaaggcttct atccaagcga catcgccgtg 1320
gagtgggaga gcaatgggca gccggagaac aactacaaga ccacgcctcc cgtgctggac 1380
tccgacggct ccttcttcct ctacagcaag ctcaccgtgg acaagagcag gtggcagcag 1440
gggaacgtct tctcatgctc cgtgatgcat gaggctctgc acaaccacta cacgcagaag 1500
agcctctccc tgtctccggg ttccggagga gggggttcag gtgggggagg ttctggcggc 1560
gggggaagcc cttcacaggt gcaactggtg cagagtggac ccgaggttaa aaaaccaggg 1620
tcctccgtta aggttagctg caaagcctct ggctacacat tttccaggag tacaatgcac 1680
tgggtgaggc aggctcctgg acagggactc gagtggatcg ggtatatcaa cccatctagc 1740
gcctatacca attacaacca aaagtttaag gaccgagtta ccattaccgc tgacaaatcc 1800
accagtacag cttatatgga gctgtcatct cttaggtccg aggacactgc tgtttattac 1860
tgcgctcgtc ctcaggttca ctatgactat aatggttttc cctactgggg tcagggaacc 1920
ctggtgactg tctcttctgg cggtggaggc agcggtgggg gtgggtctgg aggcggtggc 1980
agtggcggcg gaggctctga tattcagatg actcagtctc ctagcactct cagcgccagc 2040
gtgggggatc gtgtgacaat gacttgctcc gctagcagta gtgtgtctta catgaattgg 2100
tatcagcaga agcccgggaa agcacctaag cgctggatct atgactcttc caagctggca 2160
agtggtgtcc cctcacggtt ctctggctca ggttctggta ctgactatac tttgactatc 2220
tcctccctcc agcccgatga tttcgctacc tattattgtc agcagtggag ccgtaaccca 2280
cccactttcg gaggcggtac caaagtggag atcaagaggt cataa 2325

<210> SEQ ID NO 150
<211> LENGTH: 754
<212> TYPE: PRT
<213> ORGANISM: Artificial Sequence
<220> FEATURE:
<223> OTHER INFORMATION: DB280 VHVL x TSC456 scFv-Fc-scFv TRI131

<400> SEQUENCE: 150

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Leu Asn Leu Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ser Leu Asp Cys Ser Gly Gly Ser Cys Tyr Ser Glu Tyr Asp Ala
            100                 105                 110

Phe Asp Ile Trp Gly Gln Gly Thr Thr Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Asp Ile Gln Met Thr Gln Ser Pro Ser Ser Leu Ser Ala Ser
145                 150                 155                 160

Val Gly Asp Arg Val Thr Ile Thr Cys Arg Ala Ser Gln Ser Ile Ser
                165                 170                 175

Ser Tyr Leu Asn Trp Tyr Gln Gln Lys Pro Gly Lys Ala Pro Lys Leu
            180                 185                 190

Leu Ile Tyr Ala Ala Ser Ser Leu Gln Ser Gly Val Pro Ser Arg Phe
        195                 200                 205

Ser Gly Ser Gly Ser Gly Thr Asp Phe Thr Leu Thr Ile Ser Ser Leu
    210                 215                 220

Gln Pro Glu Asp Phe Ala Thr Tyr Tyr Cys Gln Gln Ser Tyr Ser Thr
225                 230                 235                 240

Pro Leu Thr Phe Gly Gly Gly Thr Lys Val Glu Ile Lys Ser Ser Ser
                245                 250                 255

Glu Pro Lys Ser Ser Asp Lys Thr His Thr Cys Pro Pro Cys Pro Ala
            260                 265                 270

Pro Glu Ala Ala Gly Ala Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Ala Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

```
Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Ser Gly Gly Gly Gly Ser Gly Gly Gly
                485                 490                 495

Gly Ser Gly Gly Gly Gly Ser Pro Ser Gln Val Gln Leu Val Gln Ser
            500                 505                 510

Gly Pro Glu Val Lys Lys Pro Gly Ser Ser Val Lys Val Ser Cys Lys
        515                 520                 525

Ala Ser Gly Tyr Thr Phe Ser Arg Ser Thr Met His Trp Val Arg Gln
    530                 535                 540

Ala Pro Gly Gln Gly Leu Glu Trp Ile Gly Tyr Ile Asn Pro Ser Ser
545                 550                 555                 560

Ala Tyr Thr Asn Tyr Asn Gln Lys Phe Lys Asp Arg Val Thr Ile Thr
                565                 570                 575

Ala Asp Lys Ser Thr Ser Thr Ala Tyr Met Glu Leu Ser Ser Leu Arg
            580                 585                 590

Ser Glu Asp Thr Ala Val Tyr Tyr Cys Ala Arg Pro Gln Val His Tyr
        595                 600                 605

Asp Tyr Asn Gly Phe Pro Tyr Trp Gly Gln Gly Thr Leu Val Thr Val
    610                 615                 620

Ser Ser Gly Gly Gly Gly Ser Gly Gly Gly Gly Ser Gly Gly Gly Gly
625                 630                 635                 640

Ser Gly Gly Gly Gly Ser Asp Ile Gln Met Thr Gln Ser Pro Ser Thr
                645                 650                 655

Leu Ser Ala Ser Val Gly Asp Arg Val Thr Met Thr Cys Ser Ala Ser
            660                 665                 670

Ser Ser Val Ser Tyr Met Asn Trp Tyr Gln Gln Lys Pro Gly Lys Ala
        675                 680                 685

Pro Lys Arg Trp Ile Tyr Asp Ser Ser Lys Leu Ala Ser Gly Val Pro
    690                 695                 700

Ser Arg Phe Ser Gly Ser Gly Ser Gly Thr Asp Tyr Thr Leu Thr Ile
705                 710                 715                 720

Ser Ser Leu Gln Pro Asp Asp Phe Ala Thr Tyr Tyr Cys Gln Gln Trp
                725                 730                 735

Ser Arg Asn Pro Pro Thr Phe Gly Gly Gly Thr Lys Val Glu Ile Lys
            740                 745                 750

Arg Ser
```

<210> SEQ ID NO 151
<211> LENGTH: 2304
<212> TYPE: DNA
<213> ORGANISM: Artificial Sequence
<220> FEATURE:
<223> OTHER INFORMATION: DB331 VHVL x TSC456 scFv-Fc-scFv TRI132

<400> SEQUENCE: 151
atggaagcac cagcgcagct tctcttcctc ctgctactct ggctcccaga taccaccggt 60
caggtgcagc tggtgcagtc tggggctgag gtgaagaagc ctggggcctc agtgaaggtt 120
tcctgcaagg catctggata caccttcacc agctactata tgcactgggt gcgtcaggcc 180
cctggacaag ggcttgagtg gatgggatgg atgaacccta acagtggtaa cacaggctat 240
gcacagaagt tccagggccg tgtcaccatg acccgcgaca cgtccacgag cacagtctac 300
atggagctga gcagcctgcg ttctgaggac acggccgtgt attactgtgc aacagatctc 360
gcgggggaag ccttgttcga cccctggggc cagggcaccc tggtcaccgt ctcctcaggc 420
ggcggcggca gcggcggcgg cggcagcggc ggcggaggct ccggcggcgg cggcagcgac 480
atccagatga cccagtctcc atcctccctg tctgcatctg taggagacag agtcaccatc 540
acttgccggg caagtcagag cattagcagc tatctgaatt ggtatcagca gaaaccaggg 600
aaagccccta agctcctgat ctatgctgca tccagtttgc aaagtggggt cccatcaagg 660
ttcagtggca gtggatctgg gacagatttc actctcacca tcagcagtct gcaacctgaa 720
gattttgcaa cttactactg tcaacagagt tacagtaccc ctctcacttt cggcggaggt 780
accaaggtgg agatcaaatc ctcgagtgag cccaaatctt ctgacaaaac tcacacatgc 840
ccaccgtgcc cagcacctga agccgcgggt gcaccgtcag tcttcctctt ccccccaaaa 900
cccaaggaca ccctcatgat ctcccggacc cctgaggtca catgcgtggt ggtggacgtg 960
agccacgaag accctgaggt caagttcaac tggtacgtgg acggcgtgga ggtgcataat 1020
gccaagacaa agccgcggga ggagcagtac aacagcacgt accgtgtggt cagcgtcctc 1080
accgtcctgc accaggactg gctgaatggc aaggaataca agtgcgcggt ctccaacaaa 1140
gccctcccag cccccatcga gaaaaccatc tccaaagcca aagggcagcc ccgagaacca 1200
caggtgtaca ccctgccccc atcccgggat gagctgacca agaaccaggt cagcctgacc 1260
tgcctggtca aaggcttcta tccaagcgac atcgccgtgg agtgggagag caatgggcag 1320
ccggagaaca actacaagac cacgcctccc gtgctggact ccgacggctc cttcttcctc 1380
tacagcaagc tcaccgtgga caagagcagg tggcagcagg ggaacgtctt ctcatgctcc 1440
gtgatgcatg aggctctgca caaccactac acgcagaaga gcctctccct gtctccgggt 1500
tccggaggag gggggttcagg tgggggaggt tctggcggcg gggggaagccc ttcacaggtg 1560
caactggtgc agagtggacc cgaggttaaa aaaccagggt cctccgttaa ggttagctgc 1620
aaagcctctg gctacacatt ttccaggagt acaatgcact gggtgaggca ggctcctgga 1680
cagggactcg agtggatcgg gtatatcaac ccatctagcg cctataccaa ttacaaccaa 1740
aagtttaagg accgagttac cattaccgct gacaaatcca ccagtacagc ttatatggag 1800
ctgtcatctc ttaggtccga ggacactgct gtttattact gcgctcgtcc tcaggttcac 1860
tatgactata atggttttcc ctactggggt cagggaaccc tggtgactgt ctcttctggc 1920
ggtggaggca gcggtggggg tgggtctgga ggcggtggca gtggcggcgg aggctctgat 1980
attcagatga ctcagtctcc tagcactctc agcgccagcg tgggggatcg tgtgacaatg 2040
acttgctccg ctagcagtag tgtgtcttac atgaattggt atcagcagaa gcccgggaaa 2100
gcacctaagc gctggatcta tgactcttcc aagctggcaa gtggtgtccc ctcacggttc 2160
tctggctcag gttctggtac tgactatact ttgactatct cctccctcca gcccgatgat 2220
ttcgctacct attattgtca gcagtggagc cgtaacccac ccactttcgg aggcggtacc 2280
aaagtggaga tcaagaggtc ataa 2304

<210> SEQ ID NO 152
<211> LENGTH: 747
<212> TYPE: PRT
<213> ORGANISM: Artificial Sequence
<220> FEATURE:
<223> OTHER INFORMATION: DB331 VHVL x TSC456 scFv-Fc-scFv TRI132

<400> SEQUENCE: 152

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Leu Ala Gly Glu Ala Leu Phe Asp Pro Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Gly Gly Gly Gly Ser Asp Ile Gln Met Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Ser Ser Tyr Leu Asn Trp Tyr Gln
                165                 170                 175

Gln Lys Pro Gly Lys Ala Pro Lys Leu Leu Ile Tyr Ala Ala Ser Ser
            180                 185                 190

Leu Gln Ser Gly Val Pro Ser Arg Phe Ser Gly Ser Gly Ser Gly Thr
        195                 200                 205

Asp Phe Thr Leu Thr Ile Ser Ser Leu Gln Pro Glu Asp Phe Ala Thr
    210                 215                 220

Tyr Tyr Cys Gln Gln Ser Tyr Ser Thr Pro Leu Thr Phe Gly Gly Gly
225                 230                 235                 240

Thr Lys Val Glu Ile Lys Ser Ser Ser Glu Pro Lys Ser Ser Asp Lys
                245                 250                 255

Thr His Thr Cys Pro Pro Cys Pro Ala Pro Glu Ala Ala Gly Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Ala Val Ser Asn Lys Ala Leu Pro Ala Pro Ile Glu Lys
        355                 360                 365
```

```
Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Ser Gly Gly Gly Gly Ser Gly Gly Gly Gly Ser Gly Gly Gly Gly Ser
                485                 490                 495

Pro Ser Gln Val Gln Leu Val Gln Ser Gly Pro Glu Val Lys Lys Pro
            500                 505                 510

Gly Ser Ser Val Lys Val Ser Cys Lys Ala Ser Gly Tyr Thr Phe Ser
        515                 520                 525

Arg Ser Thr Met His Trp Val Arg Gln Ala Pro Gly Gln Gly Leu Glu
    530                 535                 540

Trp Ile Gly Tyr Ile Asn Pro Ser Ser Ala Tyr Thr Asn Tyr Asn Gln
545                 550                 555                 560

Lys Phe Lys Asp Arg Val Thr Ile Thr Ala Asp Lys Ser Thr Ser Thr
                565                 570                 575

Ala Tyr Met Glu Leu Ser Ser Leu Arg Ser Glu Asp Thr Ala Val Tyr
            580                 585                 590

Tyr Cys Ala Arg Pro Gln Val His Tyr Asp Tyr Asn Gly Phe Pro Tyr
        595                 600                 605

Trp Gly Gln Gly Thr Leu Val Thr Val Ser Ser Gly Gly Gly Gly Ser
    610                 615                 620

Gly Gly Gly Gly Ser Gly Gly Gly Gly Ser Gly Gly Gly Gly Ser Asp
625                 630                 635                 640

Ile Gln Met Thr Gln Ser Pro Ser Thr Leu Ser Ala Ser Val Gly Asp
                645                 650                 655

Arg Val Thr Met Thr Cys Ser Ala Ser Ser Ser Val Ser Tyr Met Asn
            660                 665                 670

Trp Tyr Gln Gln Lys Pro Gly Lys Ala Pro Lys Arg Trp Ile Tyr Asp
        675                 680                 685

Ser Ser Lys Leu Ala Ser Gly Val Pro Ser Arg Phe Ser Gly Ser Gly
    690                 695                 700

Ser Gly Thr Asp Tyr Thr Leu Thr Ile Ser Ser Leu Gln Pro Asp Asp
705                 710                 715                 720

Phe Ala Thr Tyr Tyr Cys Gln Gln Trp Ser Arg Asn Pro Pro Thr Phe
                725                 730                 735

Gly Gly Gly Thr Lys Val Glu Ile Lys Arg Ser
            740                 745
```

<210> SEQ ID NO 153
<211> LENGTH: 2298
<212> TYPE: DNA
<213> ORGANISM: Artificial Sequence
<220> FEATURE:
<223> OTHER INFORMATION: DB415 VHVL x TSC456 scFv-Fc-scFv TRI138

<400> SEQUENCE: 153

```
atggaagcac cagcgcagct tctcttcctc ctgctactct ggctcccaga taccaccggt     60
gaggtgcagc tggtggagtc tgggggaggc ttggtacagc ctggggggtc cctgcgcctc    120
tcctgtgcag cctctggaat caccttcagt agttatggca tgcattgggt ccgccaggct    180
ccagggaagg ggctggagtg ggtctcaggt attagttgga atagtggtaa cagagtctat    240
gtggactctg tgaagggccg gttcaccatc tcccgcgaca attccaagaa cacgctgtat    300
ctgcaaatga acagcctgcg cgccgaggac acggccgtat attactgtgc gagagatact    360
aatgatgctt ttgatatctg gggccaaggg accacggtca ccgtctcctc aggtggaggc    420
ggttcaggcg gaggtggatc cggcggtggc ggctccggtg gcggcggatc tgacatccag    480
atgacccagt ctccatcctc cctgtctgca tctgtaggag acagagtcac catcacttgc    540
cgggcaagtc agagcattag cagctatctg aattggtatc agcagaaacc agggaaagcc    600
cctaagctcc tgatctatgc tgcatccagt ttgcaaagtg gggtcccatc aaggttcagt    660
ggcagtggat ctgggacaga tttcactctc accatcagca gtctgcaacc tgaagatttt    720
gcaacttact actgtcaaca gagttacagt acccctctca ctttcggcgg aggtaccaag    780
gtggagatca aatcctcgag tgagcccaaa tcttctgaca aaactcacac atgcccaccg    840
tgcccagcac ctgaagccgc gggtgcaccg tcagtcttcc tcttcccccc aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag   1020
acaaagccgc gggaggagca gtacaacagc acgtaccgtg tggtcagcgt cctcaccgtc   1080
ctgcaccagg actggctgaa tggcaaggaa tacaagtgcg cggtctccaa caaagccctc   1140
ccagccccca tcgagaaaac catctccaaa gccaaagggc agccccgaga accacaggtg   1200
tacaccctgc ccccatcccg ggatgagctg accaagaacc aggtcagcct gacctgcctg   1260
gtcaaaggct tctatccaag cgacatcgcc gtggagtggg agagcaatgg gcagccggag   1320
aacaactaca agaccacgcc tcccgtgctg gactccgacg gctccttctt cctctacagc   1380
aagctcaccg tggacaagag caggtggcag caggggaacg tcttctcatg ctccgtgatg   1440
catgaggctc tgcacaacca ctacacgcag aagagcctct ccctgtctcc gggttccgga   1500
ggagggggtt caggtggggg aggttctggc ggcgggggaa gcccttcaca ggtgcaactg   1560
gtgcagagtg gacccgaggt taaaaaacca gggtcctccg ttaaggttag ctgcaaagcc   1620
tctggctaca cattttccag gagtacaatg cactgggtga ggcaggctcc tggacaggga   1680
ctggagtgga tcgggtatat caacccatct agcgcctata ccaattacaa ccaaaagttt   1740
aaggaccgag ttaccattac cgctgacaaa tccaccagta cagcttatat ggagctgtca   1800
tctcttaggt ccgaggacac tgctgtttat tactgcgctc gtcctcaggt tcactatgac   1860
tataatggtt ttccctactg ggggtcaggga accctggtga ctgtctcttc tggcggtgga   1920
ggcagcggtg ggggtgggtc tggaggcggt ggcagtggcg gcggaggctc tgatattcag   1980
atgactcagt ctcctagcac tctcagcgcc agcgtggggg atcgtgtgac aatgacttgc   2040
tccgctagca gtagtgtgtc ttacatgaat tggtatcagc agaagcccgg gaaagcacct   2100
aagcgctgga tctatgactc ttccaagctg gcaagtggtg tcccctcacg gttctctggc   2160
tcaggttctg gtactgacta tactttgact atctcctccc tccagcccga tgatttcgct   2220
acctattatt gtcagcagtg gagccgtaac ccacccactt tcggaggcgg taccaaagtg   2280
gagatcaaga ggtcatga                                                 2298
```

```
<210> SEQ ID NO 154
<211> LENGTH: 745
<212> TYPE: PRT
<213> ORGANISM: Artificial Sequence
<220> FEATURE:
<223> OTHER INFORMATION: DB415 VHVL x TSC456 scFv-Fc-scFv TRI138

<400> SEQUENCE: 154

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Thr Phe Ser Ser Tyr
            20                  25                  30

Gly Met His Trp Val Arg Gln Ala Pro Gly Lys Gly Leu Glu Trp Val
        35                  40                  45

Ser Gly Ile Ser Trp Asn Ser Gly Asn Arg Val Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Asn Asp Ala Phe Asp Ile Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Asp Ile Gln Met Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Ser Ile Ser Ser Tyr Leu Asn Trp Tyr Gln Gln Lys
                165                 170                 175

Pro Gly Lys Ala Pro Lys Leu Leu Ile Tyr Ala Ala Ser Ser Leu Gln
            180                 185                 190

Ser Gly Val Pro Ser Arg Phe Ser Gly Ser Gly Ser Gly Thr Asp Phe
        195                 200                 205

Thr Leu Thr Ile Ser Ser Leu Gln Pro Glu Asp Phe Ala Thr Tyr Tyr
    210                 215                 220

Cys Gln Gln Ser Tyr Ser Thr Pro Leu Thr Phe Gly Gly Gly Thr Lys
225                 230                 235                 240

Val Glu Ile Lys Ser Ser Ser Glu Pro Lys Ser Ser Asp Lys Thr His
                245                 250                 255

Thr Cys Pro Pro Cys Pro Ala Pro Glu Ala Ala Gly Ala Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Ala Val Ser Asn Lys Ala Leu Pro Ala Pro Ile Glu Lys Thr Ile
        355                 360                 365
```

```
Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Ser Gly
465                 470                 475                 480

Gly Gly Gly Ser Gly Gly Gly Gly Ser Gly Gly Gly Gly Ser Pro Ser
                485                 490                 495

Gln Val Gln Leu Val Gln Ser Gly Pro Glu Val Lys Lys Pro Gly Ser
            500                 505                 510

Ser Val Lys Val Ser Cys Lys Ala Ser Gly Tyr Thr Phe Ser Arg Ser
        515                 520                 525

Thr Met His Trp Val Arg Gln Ala Pro Gly Gln Gly Leu Glu Trp Ile
    530                 535                 540

Gly Tyr Ile Asn Pro Ser Ser Ala Tyr Thr Asn Tyr Asn Gln Lys Phe
545                 550                 555                 560

Lys Asp Arg Val Thr Ile Thr Ala Asp Lys Ser Thr Ser Thr Ala Tyr
                565                 570                 575

Met Glu Leu Ser Ser Leu Arg Ser Glu Asp Thr Ala Val Tyr Tyr Cys
            580                 585                 590

Ala Arg Pro Gln Val His Tyr Asp Tyr Asn Gly Phe Pro Tyr Trp Gly
        595                 600                 605

Gln Gly Thr Leu Val Thr Val Ser Ser Gly Gly Gly Gly Ser Gly Gly
    610                 615                 620

Gly Gly Ser Gly Gly Gly Gly Ser Gly Gly Gly Gly Ser Asp Ile Gln
625                 630                 635                 640

Met Thr Gln Ser Pro Ser Thr Leu Ser Ala Ser Val Gly Asp Arg Val
                645                 650                 655

Thr Met Thr Cys Ser Ala Ser Ser Ser Val Ser Tyr Met Asn Trp Tyr
            660                 665                 670

Gln Gln Lys Pro Gly Lys Ala Pro Lys Arg Trp Ile Tyr Asp Ser Ser
        675                 680                 685

Lys Leu Ala Ser Gly Val Pro Ser Arg Phe Ser Gly Ser Gly Ser Gly
    690                 695                 700

Thr Asp Tyr Thr Leu Thr Ile Ser Ser Leu Gln Pro Asp Asp Phe Ala
705                 710                 715                 720

Thr Tyr Tyr Cys Gln Gln Trp Ser Arg Asn Pro Pro Thr Phe Gly Gly
                725                 730                 735

Gly Thr Lys Val Glu Ile Lys Arg Ser
            740                 745
```

<210> SEQ ID NO 155
<211> LENGTH: 2304
<212> TYPE: DNA
<213> ORGANISM: Artificial Sequence
<220> FEATURE:
<223> OTHER INFORMATION: DB435 VHVL x TSC456 scFv-Fc-scFv TRI139

<400> SEQUENCE: 155

```
atggaagcac cagcgcagct tctcttcctc ctgctactct ggctcccaga taccaccggt     60
caggtgcagc tggtgcagtc tggggctgag gtgaagaagc ctggggcctc agtgaaggtt    120
tcctgcaagg catctggagg caccttcagc agctatgcta tcagctgggt gcgtcaggcc    180
cctggacaag ggcttgagtg gatgggctgg atcacccctc acaatggtaa cataaagtat    240
gcacgggagt tccagggccg tgtcaccatg acccgcgaca cgtccacgag cacagtctac    300
atggagctga gcagcctgcg ttctgaggac acggccgtgt attactgtgc gaaagatctg    360
aactggaacg cagcctttga ctactggggc caggggaccc tggtcaccgt ctcctcaggt    420
ggaggcggtt caggcggagg tggatccggc ggtggcggct ccggtggcgg cggatctgac    480
atccagatga cccagtctcc atcctccctg tctgcatctg taggagacag agtcaccatc    540
acttgccggg caagtcagag cattagcagc tatctgaatt ggtatcagca gaaaccaggg    600
aaagccccta agctcctgat ctatgctgca tccagtttgc aaagtggggt cccatcaagg    660
ttcagtggca gtggatctgg gacagatttc actctcacca tcagcagtct gcaacctgaa    720
gattttgcaa cttactactg tcaacagagt tacagtaccc ctctcacttt cggcggaggt    780
accaaggtgg agatcaaatc ctcgagtgag cccaaatctt ctgacaaaac tcacacatgc    840
ccaccgtgcc cagcacctga agccgcgggt gcaccgtcag tcttcctctt ccccccaaaa    900
cccaaggaca ccctcatgat ctcccggacc cctgaggtca catgcgtggt ggtggacgtg    960
agccacgaag accctgaggt caagttcaac tggtacgtgg acggcgtgga ggtgcataat   1020
gccaagacaa agccgcggga ggagcagtac aacagcacgt accgtgtggt cagcgtcctc   1080
accgtcctgc accaggactg gctgaatggc aaggaataca agtgcgcggt ctccaacaaa   1140
gccctcccag cccccatcga gaaaaccatc tccaaagcca aagggcagcc ccgagaacca   1200
caggtgtaca ccctgccccc atcccgggat gagctgacca agaaccaggt cagcctgacc   1260
tgcctggtca aaggcttcta tccaagcgac atcgccgtgg agtgggagag caatgggcag   1320
ccggagaaca actacaagac cacgcctccc gtgctggact ccgacggctc cttcttcctc   1380
tacagcaagc tcaccgtgga caagagcagg tggcagcagg ggaacgtctt ctcatgctcc   1440
gtgatgcatg aggctctgca caaccactac acgcagaaga gcctctccct gtctccgggt   1500
tccggaggag gggggttcagg tgggggaggt tctggcggcg gggaagccc ttcacaggtg   1560
caactggtgc agagtggacc cgaggttaaa aaaccagggt cctccgttaa ggttagctgc   1620
aaagcctctg gctacacatt ttccaggagt acaatgcact gggtgaggca ggctcctgga   1680
cagggactgg agtggatcgg gtatatcaac ccatctagcg cctataccaa ttacaaccaa   1740
aagtttaagg accgagttac cattaccgct gacaaatcca ccagtacagc ttatatggag   1800
ctgtcatctc ttaggtccga ggacactgct gtttattact gcgctcgtcc tcaggttcac   1860
tatgactata atggttttcc ctactggggt cagggaaccc tggtgactgt ctcttctggc   1920
ggtggaggca gcggtggggg tgggtctgga ggcggtggca gtggcggcgg aggctctgat   1980
attcagatga ctcagtctcc tagcactctc agcgccagcg tgggggatcg tgtgacaatg   2040
acttgctccg ctagcagtag tgtgtcttac atgaattggt atcagcagaa gcccgggaaa   2100
gcacctaagc gctggatcta tgactcttcc aagctggcaa gtggtgtccc ctcacggttc   2160
tctggctcag gttctggtac tgactatact ttgactatct cctccctcca gcccgatgat   2220
ttcgctacct attattgtca gcagtggagc cgtaacccac ccactttcgg aggcggtacc   2280
aaagtggaga tcaagaggtc atga                                          2304
```

<210> SEQ ID NO 156
<211> LENGTH: 747
<212> TYPE: PRT
<213> ORGANISM: Artificial Sequence
<220> FEATURE:
<223> OTHER INFORMATION: DB435 VHVL x TSC456 scFv-Fc-scFv TRI139

<400> SEQUENCE: 156

Gln Val Gln Leu Val Gln Ser Gly Ala Glu Val Lys Lys Pro Gly Ala
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Trp Ile Thr Pro His Asn Gly Asn Ile Lys Tyr Ala Arg Glu Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Lys Asp Leu Asn Trp Asn Ala Ala Phe Asp Tyr Trp Gly Gln Gly
100 105 110

Thr Leu Val Thr Val Ser Ser Gly Gly Gly Gly Ser Gly Gly Gly Gly
115 120 125

Ser Gly Gly Gly Gly Ser Gly Gly Gly Gly Ser Asp Ile Gln Met Thr
130 135 140

Gln Ser Pro Ser Ser Leu Ser Ala Ser Val Gly Asp Arg Val Thr Ile
145 150 155 160

Thr Cys Arg Ala Ser Gln Ser Ile Ser Ser Tyr Leu Asn Trp Tyr Gln
165 170 175

Gln Lys Pro Gly Lys Ala Pro Lys Leu Leu Ile Tyr Ala Ala Ser Ser
180 185 190

Leu Gln Ser Gly Val Pro Ser Arg Phe Ser Gly Ser Gly Ser Gly Thr
195 200 205

Asp Phe Thr Leu Thr Ile Ser Ser Leu Gln Pro Glu Asp Phe Ala Thr
210 215 220

Tyr Tyr Cys Gln Gln Ser Tyr Ser Thr Pro Leu Thr Phe Gly Gly Gly
225 230 235 240

Thr Lys Val Glu Ile Lys Ser Ser Ser Glu Pro Lys Ser Ser Asp Lys
245 250 255

Thr His Thr Cys Pro Pro Cys Pro Ala Pro Glu Ala Ala Gly Ala Pro
260 265 270

Ser Val Phe Leu Phe Pro Pro Lys Pro Lys Asp Thr Leu Met Ile Ser
275 280 285

Arg Thr Pro Glu Val Thr Cys Val Val Val Asp Val Ser His Glu Asp
290 295 300

Pro Glu Val Lys Phe Asn Trp Tyr Val Asp Gly Val Glu Val His Asn
305 310 315 320

Ala Lys Thr Lys Pro Arg Glu Glu Gln Tyr Asn Ser Thr Tyr Arg Val
325 330 335

Val Ser Val Leu Thr Val Leu His Gln Asp Trp Leu Asn Gly Lys Glu
340 345 350

Tyr Lys Cys Ala Val Ser Asn Lys Ala Leu Pro Ala Pro Ile Glu Lys
355 360 365

```
Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Ser Gly Gly Gly Gly Ser Gly Gly Gly Gly Ser Gly Gly Gly Gly Ser
                485                 490                 495

Pro Ser Gln Val Gln Leu Val Gln Ser Gly Pro Glu Val Lys Lys Pro
            500                 505                 510

Gly Ser Ser Val Lys Val Ser Cys Lys Ala Ser Gly Tyr Thr Phe Ser
        515                 520                 525

Arg Ser Thr Met His Trp Val Arg Gln Ala Pro Gly Gln Gly Leu Glu
    530                 535                 540

Trp Ile Gly Tyr Ile Asn Pro Ser Ser Ala Tyr Thr Asn Tyr Asn Gln
545                 550                 555                 560

Lys Phe Lys Asp Arg Val Thr Ile Thr Ala Asp Lys Ser Thr Ser Thr
                565                 570                 575

Ala Tyr Met Glu Leu Ser Ser Leu Arg Ser Glu Asp Thr Ala Val Tyr
            580                 585                 590

Tyr Cys Ala Arg Pro Gln Val His Tyr Asp Tyr Asn Gly Phe Pro Tyr
        595                 600                 605

Trp Gly Gln Gly Thr Leu Val Thr Val Ser Ser Gly Gly Gly Gly Ser
    610                 615                 620

Gly Gly Gly Gly Ser Gly Gly Gly Gly Ser Gly Gly Gly Gly Ser Asp
625                 630                 635                 640

Ile Gln Met Thr Gln Ser Pro Ser Thr Leu Ser Ala Ser Val Gly Asp
                645                 650                 655

Arg Val Thr Met Thr Cys Ser Ala Ser Ser Ser Val Ser Tyr Met Asn
            660                 665                 670

Trp Tyr Gln Gln Lys Pro Gly Lys Ala Pro Lys Arg Trp Ile Tyr Asp
        675                 680                 685

Ser Ser Lys Leu Ala Ser Gly Val Pro Ser Arg Phe Ser Gly Ser Gly
    690                 695                 700

Ser Gly Thr Asp Tyr Thr Leu Thr Ile Ser Ser Leu Gln Pro Asp Asp
705                 710                 715                 720

Phe Ala Thr Tyr Tyr Cys Gln Gln Trp Ser Arg Asn Pro Pro Thr Phe
                725                 730                 735

Gly Gly Gly Thr Lys Val Glu Ile Lys Arg Ser
                740                 745
```

<210> SEQ ID NO 157
<211> LENGTH: 108
<212> TYPE: PRT
<213> ORGANISM: Artificial Sequence
<220> FEATURE:
<223> OTHER INFORMATION: TSC455 variable light domain

<400> SEQUENCE: 157

Asp Ile Gln Met Thr Gln Ser Pro Ser Thr Leu Ser Ala Ser Val Gly
1 5 10 15

Asp Arg Val Thr Met Thr Cys Ser Ala Ser Ser Ser Val Ser Tyr Met
20 25 30

Asn Trp Tyr Gln Gln Lys Pro Gly Lys Ala Pro Lys Arg Trp Ile Tyr
35 40 45

Asp Ser Ser Lys Leu Ala Ser Gly Val Pro Ser Arg Phe Ser Gly Ser
50 55 60

Gly Ser Gly Thr Glu Tyr Thr Leu Thr Ile Ser Ser Leu Gln Pro Asp
65 70 75 80

Asp Phe Ala Thr Tyr Tyr Cys Gln Gln Trp Ser Arg Asn Pro Pro Thr
85 90 95

Phe Gly Gly Gly Thr Lys Val Glu Ile Lys Arg Ser
100 105

<210> SEQ ID NO 158
<211> LENGTH: 108
<212> TYPE: PRT
<213> ORGANISM: Artificial Sequence
<220> FEATURE:
<223> OTHER INFORMATION: TSC456 variable light domain

<400> SEQUENCE: 158

Asp Ile Gln Met Thr Gln Ser Pro Ser Thr Leu Ser Ala Ser Val Gly
1 5 10 15

Asp Arg Val Thr Met Thr Cys Ser Ala Ser Ser Ser Val Ser Tyr Met
20 25 30

Asn Trp Tyr Gln Gln Lys Pro Gly Lys Ala Pro Lys Arg Trp Ile Tyr
35 40 45

Asp Ser Ser Lys Leu Ala Ser Gly Val Pro Ser Arg Phe Ser Gly Ser
50 55 60

Gly Ser Gly Thr Asp Tyr Thr Leu Thr Ile Ser Ser Leu Gln Pro Asp
65 70 75 80

Asp Phe Ala Thr Tyr Tyr Cys Gln Gln Trp Ser Arg Asn Pro Pro Thr
85 90 95

Phe Gly Gly Gly Thr Lys Val Glu Ile Lys Arg Ser
100 105

<210> SEQ ID NO 159
<211> LENGTH: 121
<212> TYPE: PRT
<213> ORGANISM: Artificial Sequence
<220> FEATURE:
<223> OTHER INFORMATION: TSC455 and TSC456 variable heavy domain

<400> SEQUENCE: 159

Gln Val Gln Leu Val Gln Ser Gly Pro Glu Val Lys Lys Pro Gly Ser
1 5 10 15

Ser Val Lys Val Ser Cys Lys Ala Ser Gly Tyr Thr Phe Ser Arg Ser
20 25 30

Thr Met His Trp Val Arg Gln Ala Pro Gly Gln Gly Leu Glu Trp Ile
35 40 45

Gly Tyr Ile Asn Pro Ser Ser Ala Tyr Thr Asn Tyr Asn Gln Lys Phe
50 55 60

Lys Asp Arg Val Thr Ile Thr Ala Asp Lys Ser Thr Ser Thr Ala Tyr
65 70 75 80

```
Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser
        115                 120
```

<210> SEQ ID NO 160
<211> LENGTH: 107
<212> TYPE: PRT
<213> ORGANISM: Artificial Sequence
<220> FEATURE:
<223> OTHER INFORMATION: DRA222 variable light domain

<400> SEQUENCE: 160

```
Asp Ile Gln Met Thr Gln Ser Pro Ser Ser Leu Ser Ala Ser Val Gly
1               5                   10                  15

Asp Arg Val Thr Met Thr Cys Ser Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Ser Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Arg Asn Pro Pro Thr
                85                  90                  95

Phe Gly Gly Gly Thr Lys Leu Gln Ile Thr Ser
            100                 105
```

<210> SEQ ID NO 161
<211> LENGTH: 121
<212> TYPE: PRT
<213> ORGANISM: Artificial Sequence
<220> FEATURE:
<223> OTHER INFORMATION: DRA222 variable heavy domain

<400> SEQUENCE: 161

```
Gln Val Gln Leu Val Glu Ser Gly Gly Gly Val Val Gln Pro Gly Arg
1               5                   10                  15

Ser Leu Arg Leu Ser Cys Lys Ala Ser Gly Tyr Thr Phe Thr Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Phe Thr Ile Ser Ala Asp Lys Ser Lys Ser Thr Ala Phe
65                  70                  75                  80

Leu Gln Met Asp Ser Leu Arg Pro Glu Asp Thr Gly Val Tyr Phe Cys
                85                  90                  95

Ala Arg Pro Gln Val His Tyr Asp Tyr Asn Gly Phe Pro Tyr Trp Gly
            100                 105                 110

Gln Gly Thr Pro Val Thr Val Ser Ser
        115                 120
```

<210> SEQ ID NO 162
<211> LENGTH: 10
<212> TYPE: PRT
<213> ORGANISM: Artificial Sequence
<220> FEATURE:
<223> OTHER INFORMATION: Cris7 and DRA222 VL CDR1 (Kabat)

<400> SEQUENCE: 162

Ser Ala Ser Ser Ser Val Ser Tyr Met Asn
1 5 10

<210> SEQ ID NO 163
<211> LENGTH: 7
<212> TYPE: PRT
<213> ORGANISM: Artificial Sequence
<220> FEATURE:
<223> OTHER INFORMATION: Cris7 and DRA222 VL CDR2 (Kabat)

<400> SEQUENCE: 163

Asp Ser Ser Lys Leu Ala Ser
1 5

<210> SEQ ID NO 164
<211> LENGTH: 9
<212> TYPE: PRT
<213> ORGANISM: Artificial Sequence
<220> FEATURE:
<223> OTHER INFORMATION: Cris7 and DRA222 VL CDR3 (Kabat)

<400> SEQUENCE: 164

Gln Gln Trp Ser Arg Asn Pro Pro Thr
1 5

<210> SEQ ID NO 165
<211> LENGTH: 5
<212> TYPE: PRT
<213> ORGANISM: Artificial Sequence
<220> FEATURE:
<223> OTHER INFORMATION: Cris7 and DRA222 VH CDR1 (Kabat)

<400> SEQUENCE: 165

Arg Ser Thr Met His
1 5

<210> SEQ ID NO 166
<211> LENGTH: 16
<212> TYPE: PRT
<213> ORGANISM: Artificial Sequence
<220> FEATURE:
<223> OTHER INFORMATION: Cris7 and DRA222 VH CDR2 (Kabat)

<400> SEQUENCE: 166

Tyr Ile Asn Pro Ser Ser Ala Tyr Thr Asn Tyr Asn Gln Lys Phe Lys
1 5 10 15

<210> SEQ ID NO 167
<211> LENGTH: 11
<212> TYPE: PRT
<213> ORGANISM: Artificial Sequence
<220> FEATURE:
<223> OTHER INFORMATION: Cris7 and DRA222 VH CDR3 (Kabat)

<400> SEQUENCE: 167

Gln Val His Tyr Asp Tyr Asn Gly Phe Pro Tyr
1 5 10

<210> SEQ ID NO 168
<211> LENGTH: 7
<212> TYPE: PRT
<213> ORGANISM: Artificial Sequence
<220> FEATURE:
<223> OTHER INFORMATION: Cris7 and DRA222 VL CDR1 (IMGT)

<400> SEQUENCE: 168

Ala Ser Ser Ser Val Ser Tyr
1 5

<210> SEQ ID NO 169
<211> LENGTH: 3
<212> TYPE: PRT
<213> ORGANISM: Artificial Sequence
<220> FEATURE:
<223> OTHER INFORMATION: Cris7 and DRA222 VL CDR2 (IMGT)

<400> SEQUENCE: 169

Asp Ser Ser
1

<210> SEQ ID NO 170
<211> LENGTH: 9
<212> TYPE: PRT
<213> ORGANISM: Artificial Sequence
<220> FEATURE:
<223> OTHER INFORMATION: Cris7 and DRA222 VL CDR3 (IMGT)

<400> SEQUENCE: 170

Gln Gln Trp Ser Arg Asn Pro Pro Thr
1 5

<210> SEQ ID NO 171
<211> LENGTH: 8
<212> TYPE: PRT
<213> ORGANISM: Artificial Sequence
<220> FEATURE:
<223> OTHER INFORMATION: Cris7 and DRA222 VH CDR1 (IMGT)

<400> SEQUENCE: 171

Gly Tyr Thr Phe Thr Arg Ser Thr
1 5

<210> SEQ ID NO 172
<211> LENGTH: 8
<212> TYPE: PRT
<213> ORGANISM: Artificial Sequence
<220> FEATURE:
<223> OTHER INFORMATION: Cris7 and DRA222 VH CDR2 (IMGT)

<400> SEQUENCE: 172

Ile Asn Pro Ser Ser Ala Tyr Thr
1 5

<210> SEQ ID NO 173
<211> LENGTH: 9
<212> TYPE: PRT
<213> ORGANISM: Artificial Sequence
<220> FEATURE:
<223> OTHER INFORMATION: Cris7 and DRA222 VH CDR3 (IMGT)

<400> SEQUENCE: 173

Gln Gln Trp Ser Arg Asn Pro Pro Thr
1 5

<210> SEQ ID NO 174
<211> LENGTH: 5
<212> TYPE: PRT
<213> ORGANISM: Artificial Sequence
<220> FEATURE:
<223> OTHER INFORMATION: I2C VH CDR1 (Kabat)

<400> SEQUENCE: 174

Lys Tyr Ala Met Asn
1 5

<210> SEQ ID NO 175
<211> LENGTH: 19
<212> TYPE: PRT
<213> ORGANISM: Artificial Sequence
<220> FEATURE:
<223> OTHER INFORMATION: I2C VH CDR2 (Kabat)

<400> SEQUENCE: 175

Arg Ile Arg Ser Lys Tyr Asn Asn Tyr Ala Thr Tyr Tyr Ala Asp Ser
1 5 10 15

Val Lys Asp

<210> SEQ ID NO 176
<211> LENGTH: 14
<212> TYPE: PRT
<213> ORGANISM: Artificial Sequence
<220> FEATURE:
<223> OTHER INFORMATION: I2C VH CDR3 (Kabat)

<400> SEQUENCE: 176

His Gly Asn Phe Gly Asn Ser Tyr Ile Ser Tyr Trp Ala Tyr
1 5 10

<210> SEQ ID NO 177
<211> LENGTH: 3
<212> TYPE: PRT
<213> ORGANISM: Artificial Sequence
<220> FEATURE:
<223> OTHER INFORMATION: I2C VL CDR2 (IMGT)

<400> SEQUENCE: 177

Gly Thr Lys
1

<210> SEQ ID NO 178
<211> LENGTH: 9
<212> TYPE: PRT
<213> ORGANISM: Artificial Sequence
<220> FEATURE:
<223> OTHER INFORMATION: I2C VL CDR3 (IMGT)

<400> SEQUENCE: 178

Val Leu Trp Tyr Ser Asn Arg Trp Val
1 5

<210> SEQ ID NO 179
<211> LENGTH: 8
<212> TYPE: PRT
<213> ORGANISM: Artificial Sequence
<220> FEATURE:
<223> OTHER INFORMATION: I2C VH CDR1 (IMGT)

<400> SEQUENCE: 179

Gly Phe Thr Phe Asn Lys Tyr Ala
1 5

<210> SEQ ID NO 180
<211> LENGTH: 10
<212> TYPE: PRT

<213> ORGANISM: Artificial Sequence
<220> FEATURE:
<223> OTHER INFORMATION: I2C VH CDR2 (IMGT)

<400> SEQUENCE: 180

Ile Arg Ser Lys Tyr Asn Asn Tyr Ala Thr
1               5                   10

<210> SEQ ID NO 181
<211> LENGTH: 16
<212> TYPE: PRT
<213> ORGANISM: Artificial Sequence
<220> FEATURE:
<223> OTHER INFORMATION: I2C VH CDR3 (IMGT)

<400> SEQUENCE: 181

Val Arg His Gly Asn Phe Gly Asn Ser Tyr Ile Ser Tyr Trp Ala Tyr
1               5                   10                  15

<210> SEQ ID NO 182
<211> LENGTH: 10
<212> TYPE: PRT
<213> ORGANISM: Artificial Sequence
<220> FEATURE:
<223> OTHER INFORMATION: HuM291 VL CDR1 (Kabat)

<400> SEQUENCE: 182

Ser Ala Ser Ser Ser Val Ser Tyr Met Asn
1               5                   10

<210> SEQ ID NO 183
<211> LENGTH: 7
<212> TYPE: PRT
<213> ORGANISM: Artificial Sequence
<220> FEATURE:
<223> OTHER INFORMATION: HuM291 VL CDR2 (Kabat)

<400> SEQUENCE: 183

Asp Thr Ser Lys Leu Ala Ser
1               5

<210> SEQ ID NO 184
<211> LENGTH: 9
<212> TYPE: PRT
<213> ORGANISM: Artificial Sequence
<220> FEATURE:
<223> OTHER INFORMATION: HuM291 VL CDR3 (Kabat)

<400> SEQUENCE: 184

Gln Gln Trp Ser Ser Asn Pro Pro Thr
1               5

<210> SEQ ID NO 185
<211> LENGTH: 5
<212> TYPE: PRT
<213> ORGANISM: Artificial Sequence
<220> FEATURE:
<223> OTHER INFORMATION: HuM291 VH CDR1 (Kabat)

<400> SEQUENCE: 185

Ser Tyr Thr Met His
1               5

<210> SEQ ID NO 186
<211> LENGTH: 17
<212> TYPE: PRT
<213> ORGANISM: Artificial Sequence
<220> FEATURE:
<223> OTHER INFORMATION: HuM291 VH CDR2 (Kabat)

<400> SEQUENCE: 186

Tyr Ile Asn Pro Arg Ser Gly Tyr Thr His Tyr Asn Gln Lys Leu Lys
1               5                   10                  15

Asp

<210> SEQ ID NO 187
<211> LENGTH: 11
<212> TYPE: PRT
<213> ORGANISM: Artificial Sequence
<220> FEATURE:
<223> OTHER INFORMATION: HuM291 VH CDR3 (Kabat)

<400> SEQUENCE: 187

Ser Ala Tyr Tyr Asp Tyr Asp Gly Phe Ala Tyr
1               5                   10

<210> SEQ ID NO 188
<211> LENGTH: 7
<212> TYPE: PRT
<213> ORGANISM: Artificial Sequence
<220> FEATURE:
<223> OTHER INFORMATION: HuM291 VL CDR1 (IMGT)

<400> SEQUENCE: 188

Ala Ser Ser Ser Val Ser Tyr
1               5

<210> SEQ ID NO 189
<211> LENGTH: 3
<212> TYPE: PRT
<213> ORGANISM: Artificial Sequence
<220> FEATURE:
<223> OTHER INFORMATION: HuM291 VL CDR2 (IMGT)

<400> SEQUENCE: 189

Asp Thr Ser
1

<210> SEQ ID NO 190
<211> LENGTH: 9
<212> TYPE: PRT
<213> ORGANISM: Artificial Sequence
<220> FEATURE:
<223> OTHER INFORMATION: HuM291 VL CDR3 (IMGT)

<400> SEQUENCE: 190

Gln Gln Trp Ser Ser Asn Pro Pro Thr
1               5

<210> SEQ ID NO 191
<211> LENGTH: 8
<212> TYPE: PRT
<213> ORGANISM: Artificial Sequence
<220> FEATURE:
<223> OTHER INFORMATION: HuM291 VH CDR1 (IMGT)

<400> SEQUENCE: 191

Gly Tyr Thr Phe Ile Ser Tyr Thr
1               5

<210> SEQ ID NO 192
<211> LENGTH: 8
<212> TYPE: PRT

<213> ORGANISM: Artificial Sequence
<220> FEATURE:
<223> OTHER INFORMATION: HuM291 VH CDR2 (IMGT)

<400> SEQUENCE: 192

Ile Asn Pro Arg Ser Gly Tyr Thr
1               5

<210> SEQ ID NO 193
<211> LENGTH: 13
<212> TYPE: PRT
<213> ORGANISM: Artificial Sequence
<220> FEATURE:
<223> OTHER INFORMATION: HuM291 VH CDR3 (IMGT)

<400> SEQUENCE: 193

Ala Arg Ser Ala Tyr Tyr Asp Tyr Asp Gly Phe Ala Tyr
1               5                   10

<210> SEQ ID NO 194
<211> LENGTH: 339
<212> TYPE: DNA
<213> ORGANISM: Mus sp.

<400> SEQUENCE: 194
gacatcatga tgtcccagtc cccctcctcc ctggccgtgt ccgtgggcga gaagttcacc 60
atgacctgca agtcctccca gtccctgttc ttcggctcca cccagaagaa ctacctggcc 120
tggtaccagc agaagcccgg ccagtccccc aagctgctga tctactgggc ctccacccgg 180
gagtccggcg tgcccgaccg gttcaccggc tccggctccg gcaccgactt caccctggcc 240
atctcctccg tgatgcccga ggacctggcc gtgtactact gccagcagta ctacaactac 300
ccctggacct tcggcggcgg caccaagctg gagatcaag 339

<210> SEQ ID NO 195
<211> LENGTH: 113
<212> TYPE: PRT
<213> ORGANISM: Mus sp.

<400> SEQUENCE: 195

Asp Ile Met Met Ser Gln Ser Pro Ser Ser Leu Ala Val Ser Val Gly
1               5                   10                  15

Glu Lys Phe Thr Met Thr Cys Lys Ser Ser Gln Ser Leu Phe Phe Gly
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Ala
65                  70                  75                  80

Ile Ser Ser Val Met Pro Glu Asp Leu Ala Val Tyr Tyr Cys Gln Gln
                85                  90                  95

Tyr Tyr Asn Tyr Pro Trp Thr Phe Gly Gly Gly Thr Lys Leu Glu Ile
            100                 105                 110

Lys

<210> SEQ ID NO 196
<211> LENGTH: 345
<212> TYPE: DNA
<213> ORGANISM: Mus sp.

<400> SEQUENCE: 196
cagctgcagg agtccggccc cggcctggtg aagccctccc agtccctgtc cctgacctgc 60
tccgtgaccg actactccat cacctccggc tactactgga actggattcg gcagttcccc 120
ggcaacaagc tggagtggat gggctacatc tcctacgacg gctccaacaa ctacaacccc 180
tccctgaaga accggatctc catcacccgg gacacctcca agaaccagtt cttcctgaag 240
ctgtcctccg tgaccaccga ggacaccgcc acctactact gctcccgggg cgagggcttc 300
tacttcgact cctggggcca gggcaccacc ctgaccgtgt cctcg 345

<210> SEQ ID NO 197
<211> LENGTH: 116
<212> TYPE: PRT
<213> ORGANISM: Mus sp.

<400> SEQUENCE: 197

Val Gln Leu Gln Glu Ser Gly Pro Gly Leu Val Lys Pro Ser Gln Ser
1 5 10 15

Leu Ser Leu Thr Cys Ser Val Thr Asp Tyr Ser Ile Thr Ser Gly Tyr
20 25 30

Tyr Trp Asn Trp Ile Arg Gln Phe Pro Gly Asn Lys Leu Glu Trp Met
35 40 45

Gly Tyr Ile Ser Tyr Asp Gly Ser Asn Asn Tyr Asn Pro Ser Leu Lys
50 55 60

Asn Arg Ile Ser Ile Thr Arg Asp Thr Ser Lys Asn Gln Phe Phe Leu
65 70 75 80

Lys Leu Ser Ser Val Thr Thr Glu Asp Thr Ala Thr Tyr Tyr Cys Ser
85 90 95

Arg Gly Glu Gly Phe Tyr Phe Asp Ser Trp Gly Gln Gly Thr Thr Leu
100 105 110

Thr Val Ser Ser
115

<210> SEQ ID NO 198
<211> LENGTH: 20
<212> TYPE: PRT
<213> ORGANISM: Artificial Sequence
<220> FEATURE:
<223> OTHER INFORMATION: secretory signal sequence

<400> SEQUENCE: 198

Met Glu Ala Pro Ala Gln Leu Leu Phe Leu Leu Leu Leu Trp Leu Pro
1 5 10 15

Asp Thr Thr Gly
20

<210> SEQ ID NO 199
<211> LENGTH: 1074
<212> TYPE: DNA
<213> ORGANISM: Artificial Sequence
<220> FEATURE:
<223> OTHER INFORMATION: human CD123 ectodomain, with Avi-3xFLAG-His affinity tag TRI032

<400> SEQUENCE: 199
atggaagcac cagcgcagct tctcttcctc ctgctactct ggctcccaga taccaccggt 60
aaggaggacc ccaacccccc catcaccaac ctgaggatga aggccaaggc ccagcagctg 120
acctgggacc tgaacaggaa cgtgacagac atcgaatgcg tgaaggatgc cgactacagc 180
atgcccgccg tgaacaactc ctactgccag ttcggcgcca tcagcctgtg cgaggtgaca 240

```
aactacaccg tgagagtggc caacccccc ttcagcacct ggatcctgtt tcccgagaac    300
agcggcaaac cctgggctgg cgctgagaac ctgacctgct ggatccacga cgtggacttt    360
ctgtcctgca gctgggctgt gggacccgga gctcctgccg atgtgcagta cgacctgtac    420
ctgaatgtgg ccaacagaag acagcagtac gagtgcctgc attacaagac cgacgcccag    480
ggaaccagga tcggctgcag gtttgatgac atcagcaggc tgtcctccgg cagccagtcc    540
agccacatcc tggtgagagg cagatccgcc gccttcggca ttccctgcac agacaagttc    600
gtcgtcttca gccagatcga gattctgacc ccccccaaca tgaccgccaa gtgtaacaag    660
acccacagct tcatgcactg gaagatgagg agccacttca acaggaagtt caggtacgag    720
ctccagatcc agaagaggat gcagcccgtg atcaccgagc aggtgaggga caggacatcc    780
ttccagctgc tgaatcccgg cacatacacc gtgcagatca gggccaggga aagggtgtac    840
gagttcctgt ccgcctggag cacccccccag aggttcgagt gtgaccagga ggagggagcc    900
aataccaggg cctggagatc ctcgagtctc aacgatattt ttgaagccca aaaaattgag    960
tggcatgaag attacaagga cgatgacgac aaagactata aggacgacga cgataaggat   1020
tacaaggatg acgatgataa gcaccatcat catcaccatc accaccacca ctga         1074
```

```
<210> SEQ ID NO 200
<211> LENGTH: 337
<212> TYPE: PRT
<213> ORGANISM: Artificial Sequence
<220> FEATURE:
<223> OTHER INFORMATION: human CD123 ectodomain, with Avi-3xFLAG-His
      affinity tag TRI032

<400> SEQUENCE: 200

Lys Glu Asp Pro Asn Pro Pro Ile Thr Asn Leu Arg Met Lys Ala Lys
1               5                   10                  15

Ala Gln Gln Leu Thr Trp Asp Leu Asn Arg Asn Val Thr Asp Ile Glu
            20                  25                  30

Cys Val Lys Asp Ala Asp Tyr Ser Met Pro Ala Val Asn Asn Ser Tyr
        35                  40                  45

Cys Gln Phe Gly Ala Ile Ser Leu Cys Glu Val Thr Asn Tyr Thr Val
    50                  55                  60

Arg Val Ala Asn Pro Pro Phe Ser Thr Trp Ile Leu Phe Pro Glu Asn
65                  70                  75                  80

Ser Gly Lys Pro Trp Ala Gly Ala Glu Asn Leu Thr Cys Trp Ile His
                85                  90                  95

Asp Val Asp Phe Leu Ser Cys Ser Trp Ala Val Gly Pro Gly Ala Pro
            100                 105                 110

Ala Asp Val Gln Tyr Asp Leu Tyr Leu Asn Val Ala Asn Arg Arg Gln
        115                 120                 125

Gln Tyr Glu Cys Leu His Tyr Lys Thr Asp Ala Gln Gly Thr Arg Ile
    130                 135                 140

Gly Cys Arg Phe Asp Asp Ile Ser Arg Leu Ser Ser Gly Ser Gln Ser
145                 150                 155                 160

Ser His Ile Leu Val Arg Gly Arg Ser Ala Ala Phe Gly Ile Pro Cys
                165                 170                 175

Thr Asp Lys Phe Val Val Phe Ser Gln Ile Glu Ile Leu Thr Pro Pro
            180                 185                 190

Asn Met Thr Ala Lys Cys Asn Lys Thr His Ser Phe Met His Trp Lys
        195                 200                 205
```

-continued

```
Met Arg Ser His Phe Asn Arg Lys Phe Arg Tyr Glu Leu Gln Ile Gln
    210                 215                 220

Lys Arg Met Gln Pro Val Ile Thr Glu Gln Val Arg Asp Arg Thr Ser
225                 230                 235                 240

Phe Gln Leu Leu Asn Pro Gly Thr Tyr Thr Val Gln Ile Arg Ala Arg
                245                 250                 255

Glu Arg Val Tyr Glu Phe Leu Ser Ala Trp Ser Thr Pro Gln Arg Phe
            260                 265                 270

Glu Cys Asp Gln Glu Glu Gly Ala Asn Thr Arg Ala Trp Arg Ser Ser
        275                 280                 285

Ser Leu Asn Asp Ile Phe Glu Ala Gln Lys Ile Glu Trp His Glu Asp
    290                 295                 300

Tyr Lys Asp Asp Asp Asp Lys Asp Tyr Lys Asp Asp Asp Asp Lys Asp
305                 310                 315                 320

Tyr Lys Asp Asp Asp Asp Lys His His His His His His His His His
                325                 330                 335

His
```

<210> SEQ ID NO 201
<211> LENGTH: 996
<212> TYPE: DNA
<213> ORGANISM: Homo sapiens

<400> SEQUENCE: 201

```
atggtcctcc tttggctcac gctgctcctg atcgccctgc cctgtctcct gcaaacgaag     60

gaaggtggga agccttgggc aggtgcggag aatctgacct gctggattca tgacgtggat    120

ttcttgagct gcagctgggc ggtaggcccg ggggccccg cggacgtcca gtacgacctg    180

tacttgaacg ttgccaacag gcgtcaacag tacgagtgtc ttcactacaa aacggatgct    240

cagggaacac gtatcgggtg tcgtttcgat gacatctctc gactctccag cggttctcaa    300

agttcccaca tcctggtgcg gggcaggagc gcagccttcg gtatcccctg cacagataag    360

tttgtcgtct tttcacagat tgagatatta actccaccca acatgactgc aaagtgtaat    420

aagacacatt cctttatgca ctggaaaatg agaagtcatt tcaatcgcaa atttcgctat    480

gagcttcaga tacaaaagag aatgcagcct gtaatcacag aacaggtcag agacagaacc    540

tccttccagc tactcaatcc tggaacgtac acagtacaaa taagagcccg ggaaagagtg    600

tatgaattct tgagcgcctg gagcaccccc cagcgcttcg agtgcgacca ggaggagggc    660

gcaaacacac gtgcctggcg gacgtcgctg ctgatcgcgc tggggacgct gctggccctg    720

gtctgtgtct tcgtgatctg cagaaggtat ctggtgatgc agagactctt tccccgcatc    780

cctcacatga aagaccccat cggtgacagc ttccaaaacg acaagctggt ggtctgggag    840

gcgggcaaag ccggcctgga ggagtgtctg gtgactgaag tacaggtcgt gcagaaaact    900

acgcgtacgc ggccgctcga gcagaaactc atctcagaag aggatctggc agcaaatgat    960

atcctggatt acaaggatga cgacgataag gtttaa                             996
```

<210> SEQ ID NO 202
<211> LENGTH: 310
<212> TYPE: PRT
<213> ORGANISM: Homo sapiens

<400> SEQUENCE: 202

```
Gly Gly Lys Pro Trp Ala Gly Ala Glu Asn Leu Thr Cys Trp Ile His
1               5                   10                  15
```

```
Asp Val Asp Phe Leu Ser Cys Ser Trp Ala Val Gly Pro Gly Ala Pro
            20                  25                  30

Ala Asp Val Gln Tyr Asp Leu Tyr Leu Asn Val Ala Asn Arg Arg Gln
        35                  40                  45

Gln Tyr Glu Cys Leu His Tyr Lys Thr Asp Ala Gln Gly Thr Arg Ile
    50                  55                  60

Gly Cys Arg Phe Asp Asp Ile Ser Arg Leu Ser Ser Gly Ser Gln Ser
65                  70                  75                  80

Ser His Ile Leu Val Arg Gly Arg Ser Ala Ala Phe Gly Ile Pro Cys
                85                  90                  95

Thr Asp Lys Phe Val Val Phe Ser Gln Ile Glu Ile Leu Thr Pro Pro
            100                 105                 110

Asn Met Thr Ala Lys Cys Asn Lys Thr His Ser Phe Met His Trp Lys
        115                 120                 125

Met Arg Ser His Phe Asn Arg Lys Phe Arg Tyr Glu Leu Gln Ile Gln
    130                 135                 140

Lys Arg Met Gln Pro Val Ile Thr Glu Gln Val Arg Asp Arg Thr Ser
145                 150                 155                 160

Phe Gln Leu Leu Asn Pro Gly Thr Tyr Thr Val Gln Ile Arg Ala Arg
                165                 170                 175

Glu Arg Val Tyr Glu Phe Leu Ser Ala Trp Ser Thr Pro Gln Arg Phe
            180                 185                 190

Glu Cys Asp Gln Glu Glu Gly Ala Asn Thr Arg Ala Trp Arg Thr Ser
        195                 200                 205

Leu Leu Ile Ala Leu Gly Thr Leu Leu Ala Leu Val Cys Val Phe Val
    210                 215                 220

Ile Cys Arg Arg Tyr Leu Val Met Gln Arg Leu Phe Pro Arg Ile Pro
225                 230                 235                 240

His Met Lys Asp Pro Ile Gly Asp Ser Phe Gln Asn Asp Lys Leu Val
                245                 250                 255

Val Trp Glu Ala Gly Lys Ala Gly Leu Glu Glu Cys Leu Val Thr Glu
            260                 265                 270

Val Gln Val Val Gln Lys Thr Thr Arg Thr Arg Pro Leu Glu Gln Lys
        275                 280                 285

Leu Ile Ser Glu Glu Asp Leu Ala Ala Asn Asp Ile Leu Asp Tyr Lys
    290                 295                 300

Asp Asp Asp Asp Lys Val
305                 310
```

<210> SEQ ID NO 203
<211> LENGTH: 1140
<212> TYPE: DNA
<213> ORGANISM: Homo sapiens

<400> SEQUENCE: 203

```
atggaagccc ccgcccagct gctcttcctg ctgctcctgt ggctgcctga caccaccggc      60

aaggaagacc ccaatgcccc catcaggaac ctgagaatga aggagaaggc ccagcagctc     120

atgtgggatc tgaacaggaa cgtgaccgac gtggagtgta tcaagggcac cgactactcc     180

atgcccgcca tgaataacag ctattgccag ttcggcgcca tcagcctgtg cgaggtcacc     240

aactacaccg tgagagtggc cagccccccc ttctccacct ggattctgtt ccctgagaac     300

agcggcaccc ctagggctgg cgctgagaat ctgacatgct gggtccatga cgtggacttc     360

ctgagctgca gctgggtggt gggacctgct gctcccgctg acgtgcagta cgatctgtat     420
```

-continued ctgaacaacc ccaactccca cgagcagtac aggtgcctgc actacaagac agacgctaga 480
ggcacccaga tcggctgcag gttcgatgat atcgcccctc tgagcagggg atcccagagc 540
tcccatatcc tggtgagggg caggtccgcc gctgtgagca ttccttgcac cgacaagttc 600
gtcttcttca gccagatcga gaggctgacc ccccctaaca tgacaggcga gtgcaacgag 660
acccacagct tcatgcactg gaagatgaag agccatttca acaggaaatt caggtacgaa 720
ctgaggattc agaagagaat gcagcccgtg aggacagagc aggtgaggga tacaaccagc 780
ttccagctgc ccaatcctgg cacctatacc gtgcagatca gggctagaga gaccgtgtac 840
gagtttctgt ccgcctggag caccccccag aggtttgaat gtgaccagga ggagggagcc 900
tccagcaggg cttggagaac cagcctcctc atcgccctgg gcacactgct ggctctgctg 960
tgtgtgttcc tgatctgcag aaggtacctg gtgatgcaga ggctcttccc taggattccc 1020
cacatgaagg accccatcgg cgacaccttc cagcaggaca aactggtggt gtgggaagcc 1080
ggaaaggccg gcctggagga atgcctcgtg tccgaggtgc aggtggtgga gaagacctaa 1140

<210> SEQ ID NO 204
<211> LENGTH: 359
<212> TYPE: PRT
<213> ORGANISM: Homo sapiens

<400> SEQUENCE: 204

Lys Glu Asp Pro Asn Ala Pro Ile Arg Asn Leu Arg Met Lys Glu Lys
1 5 10 15

Ala Gln Gln Leu Met Trp Asp Leu Asn Arg Asn Val Thr Asp Val Glu
20 25 30

Cys Ile Lys Gly Thr Asp Tyr Ser Met Pro Ala Met Asn Asn Ser Tyr
35 40 45

Cys Gln Phe Gly Ala Ile Ser Leu Cys Glu Val Thr Asn Tyr Thr Val
50 55 60

Arg Val Ala Ser Pro Pro Phe Ser Thr Trp Ile Leu Phe Pro Glu Asn
65 70 75 80

Ser Gly Thr Pro Arg Ala Gly Ala Glu Asn Leu Thr Cys Trp Val His
85 90 95

Asp Val Asp Phe Leu Ser Cys Ser Trp Val Val Gly Pro Ala Ala Pro
100 105 110

Ala Asp Val Gln Tyr Asp Leu Tyr Leu Asn Asn Pro Asn Ser His Glu
115 120 125

Gln Tyr Arg Cys Leu His Tyr Lys Thr Asp Ala Arg Gly Thr Gln Ile
130 135 140

Gly Cys Arg Phe Asp Asp Ile Ala Pro Leu Ser Arg Gly Ser Gln Ser
145 150 155 160

Ser His Ile Leu Val Arg Gly Arg Ser Ala Ala Val Ser Ile Pro Cys
165 170 175

Thr Asp Lys Phe Val Phe Phe Ser Gln Ile Glu Arg Leu Thr Pro Pro
180 185 190

Asn Met Thr Gly Glu Cys Asn Glu Thr His Ser Phe Met His Trp Lys
195 200 205

Met Lys Ser His Phe Asn Arg Lys Phe Arg Tyr Glu Leu Arg Ile Gln
210 215 220

Lys Arg Met Gln Pro Val Arg Thr Glu Gln Val Arg Asp Thr Thr Ser
225 230 235 240

Phe Gln Leu Pro Asn Pro Gly Thr Tyr Thr Val Gln Ile Arg Ala Arg
245 250 255

```
Glu Thr Val Tyr Glu Phe Leu Ser Ala Trp Ser Thr Pro Gln Arg Phe
            260                 265                 270

Glu Cys Asp Gln Glu Glu Gly Ala Ser Ser Arg Ala Trp Arg Thr Ser
        275                 280                 285

Leu Leu Ile Ala Leu Gly Thr Leu Leu Ala Leu Leu Cys Val Phe Leu
    290                 295                 300

Ile Cys Arg Arg Tyr Leu Val Met Gln Arg Leu Phe Pro Arg Ile Pro
305                 310                 315                 320

His Met Lys Asp Pro Ile Gly Asp Thr Phe Gln Gln Asp Lys Leu Val
                325                 330                 335

Val Trp Glu Ala Gly Lys Ala Gly Leu Glu Glu Cys Leu Val Ser Glu
            340                 345                 350

Val Gln Val Val Glu Lys Thr
        355


<210> SEQ ID NO 205
<211> LENGTH: 1713
<212> TYPE: DNA
<213> ORGANISM: Homo sapiens

<400> SEQUENCE: 205

gtcaggttca tggttacgaa gctgctgacc ccaggatccc agcccgtggg agagaagggg     60

gtctctgaca gcccccaccc ctccccactg ccagatcctt attgggtctg agtttcaggg    120

gtggggcccc agctggaggt tataaaacag ctcaatcggg gagtacaacc ttcggtttct    180

cttcggggaa agctgctttc agcgcacacg ggaagatatc agaaacatcc taggatcagg    240

acaccccaga tcttctcaac tggaaccacg aaggctgttt cttccacaca gtactttgat    300

ctccatttaa gcaggcacct ctgtcctgcg ttccggagct gcgttcccga tggtcctcct    360

ttggctcacg ctgctcctga tcgccctgcc ctgtctcctg caaacgaagg aagatccaaa    420

cccaccaatc acgaacctaa ggatgaaagc aaaggctcag cagttgacct gggaccttaa    480

cagaaatgtg accgatatcg agtgtgttaa agacgccgac tattctatgc cggcagtgaa    540

caatagctat tgccagtttg gagcaatttc cttatgtgaa gtgaccaact acaccgtccg    600

agtggccaac ccaccattct ccacgtggat cctcttccct gagaacagtg ggaagccttg    660

ggcaggtgcg gagaatctga cctgctggat tcatgacgtg gatttcttga gctgcagctg    720

ggcggtaggc ccgggggccc ccgcggacgt ccagtacgac ctgtacttga acgttgccaa    780

caggcgtcaa cagtacgagt gtcttcacta caaaacggat gctcagggaa cacgtatcgg    840

gtgtcgtttc gatgacatct ctcgactctc cagcggttct caaagttccc acatcctggt    900

gcggggcagg agcgcagcct tcggtatccc ctgcacagat aagtttgtcg tcttttcaca    960

gattgagata ttaactccac ccaacatgac tgcaaagtgt aataagacac attcctttat   1020

gcactggaaa atgagaagtc atttcaatcg caaatttcgc tatgagcttc agatacaaaa   1080

gagaatgcag cctgtaatca cagaacaggt cagagacaga acctccttcc agctactcaa   1140

tcctggaacg tacacagtac aaataagagc ccgggaaaga gtgtatgaat tcttgagcgc   1200

ctggagcacc ccccagcgct tcgagtgcga ccaggaggag ggcgcaaaca cacgtgcctg   1260

gcggacgtcg ctgctgatcg cgctggggac gctgctggcc ctggtctgtg tcttcgtgat   1320

ctgcagaagg tatctggtga tgcagagact ctttccccgc atccctcaca tgaaagaccc   1380

catcggtgac agcttccaaa acgacaagct ggtggtctgg gaggcgggca aagccggcct   1440

ggaggagtgt ctggtgactg aagtacaggt cgtgcagaaa acttgagact ggggttcagg   1500
```

-continued

```
gcttgtgggg gtctgcctca atctccctgg ccgggccagg cgcctgcaca gactggctgc   1560

tggacctgcg cacgcagccc aggaatggac attcctaacg ggtggtgggc atgggagatg   1620

cctgtgtaat ttcgtccgaa gctgccagga agaagaacag aactttgtgt gtttatttca   1680

tgataaagtg attttttttt ttttaaccca aaa                                1713


<210> SEQ ID NO 206
<211> LENGTH: 378
<212> TYPE: PRT
<213> ORGANISM: Homo sapiens

<400> SEQUENCE: 206

Met Val Leu Leu Trp Leu Thr Leu Leu Leu Ile Ala Leu Pro Cys Leu
1               5                   10                  15

Leu Gln Thr Lys Glu Asp Pro Asn Pro Pro Ile Thr Asn Leu Arg Met
            20                  25                  30

Lys Ala Lys Ala Gln Gln Leu Thr Trp Asp Leu Asn Arg Asn Val Thr
        35                  40                  45

Asp Ile Glu Cys Val Lys Asp Ala Asp Tyr Ser Met Pro Ala Val Asn
    50                  55                  60

Asn Ser Tyr Cys Gln Phe Gly Ala Ile Ser Leu Cys Glu Val Thr Asn
65                  70                  75                  80

Tyr Thr Val Arg Val Ala Asn Pro Pro Phe Ser Thr Trp Ile Leu Phe
                85                  90                  95

Pro Glu Asn Ser Gly Lys Pro Trp Ala Gly Ala Glu Asn Leu Thr Cys
            100                 105                 110

Trp Ile His Asp Val Asp Phe Leu Ser Cys Ser Trp Ala Val Gly Pro
        115                 120                 125

Gly Ala Pro Ala Asp Val Gln Tyr Asp Leu Tyr Leu Asn Val Ala Asn
    130                 135                 140

Arg Arg Gln Gln Tyr Glu Cys Leu His Tyr Lys Thr Asp Ala Gln Gly
145                 150                 155                 160

Thr Arg Ile Gly Cys Arg Phe Asp Asp Ile Ser Arg Leu Ser Ser Gly
                165                 170                 175

Ser Gln Ser Ser His Ile Leu Val Arg Gly Arg Ser Ala Ala Phe Gly
            180                 185                 190

Ile Pro Cys Thr Asp Lys Phe Val Val Phe Ser Gln Ile Glu Ile Leu
        195                 200                 205

Thr Pro Pro Asn Met Thr Ala Lys Cys Asn Lys Thr His Ser Phe Met
    210                 215                 220

His Trp Lys Met Arg Ser His Phe Asn Arg Lys Phe Arg Tyr Glu Leu
225                 230                 235                 240

Gln Ile Gln Lys Arg Met Gln Pro Val Ile Thr Glu Gln Val Arg Asp
                245                 250                 255

Arg Thr Ser Phe Gln Leu Leu Asn Pro Gly Thr Tyr Thr Val Gln Ile
            260                 265                 270

Arg Ala Arg Glu Arg Val Tyr Glu Phe Leu Ser Ala Trp Ser Thr Pro
        275                 280                 285

Gln Arg Phe Glu Cys Asp Gln Glu Glu Gly Ala Asn Thr Arg Ala Trp
    290                 295                 300

Arg Thr Ser Leu Leu Ile Ala Leu Gly Thr Leu Leu Ala Leu Val Cys
305                 310                 315                 320

Val Phe Val Ile Cys Arg Arg Tyr Leu Val Met Gln Arg Leu Phe Pro
                325                 330                 335
```

```
Arg Ile Pro His Met Lys Asp Pro Ile Gly Asp Ser Phe Gln Asn Asp
            340                 345                 350

Lys Leu Val Val Trp Glu Ala Gly Lys Ala Gly Leu Glu Glu Cys Leu
        355                 360                 365

Val Thr Glu Val Gln Val Val Gln Lys Thr
    370                 375


<210> SEQ ID NO 207
<211> LENGTH: 1479
<212> TYPE: DNA
<213> ORGANISM: Homo sapiens

<400> SEQUENCE: 207

gtcaggttca tggttacgaa gctgctgacc ccaggatccc agcccgtggg agagaagggg     60

gtctctgaca gcccccaccc ctccccactg ccagatcctt attgggtctg agtttcaggg    120

gtggggcccc agctggaggt tataaaacag ctcaatcggg gagtacaacc ttcggtttct    180

cttcggggaa agctgctttc agcgcacacg ggaagatatc agaaacatcc taggatcagg    240

acaccccaga tcttctcaac tggaaccacg aaggctgttt cttccacaca gtactttgat    300

ctccatttaa gcaggcacct ctgtcctgcg ttccggagct gcgttcccga tggtcctcct    360

ttggctcacg ctgctcctga tcgccctgcc ctgtctcctg caaacgaagg aaggtgggaa    420

gccttgggca ggtgcggaga atctgacctg ctggattcat gacgtggatt tcttgagctg    480

cagctgggcg gtaggcccgg gggcccccgc ggacgtccag tacgacctgt acttgaacgt    540

tgccaacagg cgtcaacagt acgagtgtct tcactacaaa acggatgctc agggaacacg    600

tatcgggtgt cgtttcgatg acatctctcg actctccagc ggttctcaaa gttcccacat    660

cctggtgcgg ggcaggagcg cagccttcgg tatcccctgc acagataagt ttgtcgtctt    720

ttcacagatt gagatattaa ctccacccaa catgactgca aagtgtaata agacacattc    780

ctttatgcac tggaaaatga gaagtcattt caatcgcaaa tttcgctatg agcttcagat    840

acaaaagaga atgcagcctg taatcacaga acaggtcaga gacagaacct ccttccagct    900

actcaatcct ggaacgtaca cagtacaaat aagagcccgg gaaagagtgt atgaattctt    960

gagcgcctgg agcacccccc agcgcttcga gtgcgaccag gaggagggcg caaacacacg   1020

tgcctggcgg acgtcgctgc tgatcgcgct ggggacgctg ctggccctgg tctgtgtctt   1080

cgtgatctgc agaaggtatc tggtgatgca gagactcttt ccccgcatcc ctcacatgaa   1140

agaccccatc ggtgacagct tccaaaacga caagctggtg gtctgggagg cgggcaaagc   1200

cggcctggag gagtgtctgg tgactgaagt acaggtcgtg cagaaaactt gagactgggg   1260

ttcagggctt gtgggggtct gcctcaatct ccctggccgg gccaggcgcc tgcacagact   1320

ggctgctgga cctgcgcacg cagcccagga atggacattc ctaacgggtg gtgggcatgg   1380

gagatgcctg tgtaatttcg tccgaagctg ccaggaagaa gaacagaact ttgtgtgttt   1440

atttcatgat aaagtgattt ttttttttt aacccaaaa                           1479


<210> SEQ ID NO 208
<211> LENGTH: 300
<212> TYPE: PRT
<213> ORGANISM: Homo sapiens
```

<400> SEQUENCE: 208

Met Val Leu Leu Trp Leu Thr Leu Leu Leu Ile Ala Leu Pro Cys Leu
1 5 10 15

Leu Gln Thr Lys Glu Gly Gly Lys Pro Trp Ala Gly Ala Glu Asn Leu
20 25 30

Thr Cys Trp Ile His Asp Val Asp Phe Leu Ser Cys Ser Trp Ala Val
35 40 45

Gly Pro Gly Ala Pro Ala Asp Val Gln Tyr Asp Leu Tyr Leu Asn Val
50 55 60

Ala Asn Arg Arg Gln Gln Tyr Glu Cys Leu His Tyr Lys Thr Asp Ala
65 70 75 80

Gln Gly Thr Arg Ile Gly Cys Arg Phe Asp Asp Ile Ser Arg Leu Ser
85 90 95

Ser Gly Ser Gln Ser Ser His Ile Leu Val Arg Gly Arg Ser Ala Ala
100 105 110

Phe Gly Ile Pro Cys Thr Asp Lys Phe Val Val Phe Ser Gln Ile Glu
115 120 125

Ile Leu Thr Pro Pro Asn Met Thr Ala Lys Cys Asn Lys Thr His Ser
130 135 140

Phe Met His Trp Lys Met Arg Ser His Phe Asn Arg Lys Phe Arg Tyr
145 150 155 160

Glu Leu Gln Ile Gln Lys Arg Met Gln Pro Val Ile Thr Glu Gln Val
165 170 175

Arg Asp Arg Thr Ser Phe Gln Leu Leu Asn Pro Gly Thr Tyr Thr Val
180 185 190

Gln Ile Arg Ala Arg Glu Arg Val Tyr Glu Phe Leu Ser Ala Trp Ser
195 200 205

Thr Pro Gln Arg Phe Glu Cys Asp Gln Glu Glu Gly Ala Asn Thr Arg
210 215 220

Ala Trp Arg Thr Ser Leu Leu Ile Ala Leu Gly Thr Leu Leu Ala Leu
225 230 235 240

Val Cys Val Phe Val Ile Cys Arg Arg Tyr Leu Val Met Gln Arg Leu
245 250 255

Phe Pro Arg Ile Pro His Met Lys Asp Pro Ile Gly Asp Ser Phe Gln
260 265 270

Asn Asp Lys Leu Val Val Trp Glu Ala Gly Lys Ala Gly Leu Glu Glu
275 280 285

Cys Leu Val Thr Glu Val Gln Val Val Gln Lys Thr
290 295 300

<210> SEQ ID NO 209
<211> LENGTH: 107
<212> TYPE: PRT
<213> ORGANISM: Artificial Sequence
<220> FEATURE:
<223> OTHER INFORMATION: CRIS-7 monoclonal antibody VL amino acid sequence

<400> SEQUENCE: 209

Gln Val Val Leu Thr Gln Ser Pro Ala Ile Met Ser Ala Phe Pro Gly
1 5 10 15

Glu Lys Val Thr Met Thr Cys Ser Ala Ser Ser Ser Val Ser Tyr Met
20 25 30

Asn Trp Tyr Gln Gln Lys Ser Gly Thr Ser Pro Lys Arg Trp Ile Tyr
35 40 45

Asp Ser Ser Lys Leu Ala Ser Gly Val Pro Ala Arg Phe Ser Gly Ser
50 55 60

Gly Ser Gly Thr Ser Tyr Ser Leu Thr Ile Ser Ser Met Glu Thr Glu
65 70 75 80

Asp Ala Ala Thr Tyr Tyr Cys Gln Gln Trp Ser Arg Asn Pro Pro Thr
85 90 95

Phe Gly Gly Gly Thr Lys Leu Gln Ile Thr Arg
100 105

<210> SEQ ID NO 210
<211> LENGTH: 121
<212> TYPE: PRT
<213> ORGANISM: Artificial Sequence
<220> FEATURE:
<223> OTHER INFORMATION: CRIS-7 monoclonal antibody VH amino acid sequence

<400> SEQUENCE: 210

Gln Val Gln Leu Gln Gln Ser Gly Ala Glu Leu Ala Arg Pro Gly Ala
1 5 10 15

Ser Val Lys Met Ser Cys Lys Ala Ser Gly Tyr Thr Phe Thr Arg Ser
20 25 30

Thr Met His Trp Val Lys Gln Arg Pro Gly Gln Gly Leu Glu Trp Ile
35 40 45

Gly Tyr Ile Asn Pro Ser Ser Ala Tyr Thr Asn Tyr Asn Gln Lys Phe
50 55 60

Lys Asp Lys Ala Thr Leu Thr Ala Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Ser Pro Gln Val His Tyr Asp Tyr Asn Gly Phe Pro Tyr Trp Gly
100 105 110

Gln Gly Thr Leu Val Thr Val Ser Ala
115 120

<210> SEQ ID NO 211
<211> LENGTH: 106
<212> TYPE: PRT
<213> ORGANISM: Artificial Sequence
<220> FEATURE:
<223> OTHER INFORMATION: HuM291 VL amino acid sequence

<400> SEQUENCE: 211

Asp Ile Gln Met Thr Gln Ser Pro Ser Ser Leu Ser Ala Ser Val Gly
1 5 10 15

Asp Arg Val Thr Ile Thr Cys Ser Ala Ser Ser Ser Val Ser Tyr Met
20 25 30

Asn Trp Tyr Gln Gln Lys Pro Gly Lys Ala Pro Lys Arg Leu Ile Tyr
35 40 45

Asp Thr Ser Lys Leu Ala Ser Gly Val Pro Ser Arg Phe Ser Gly Ser
50 55 60

Gly Ser Gly Thr Asp Phe Thr Leu Thr Ile Ser Ser Leu Gln Pro Glu
65 70 75 80

Asp Phe Ala Thr Tyr Tyr Cys Gln Gln Trp Ser Ser Asn Pro Pro Thr
85 90 95

Phe Gly Gly Gly Thr Lys Val Glu Ile Lys
100 105

```
<210> SEQ ID NO 212
<211> LENGTH: 120
<212> TYPE: PRT
<213> ORGANISM: Artificial Sequence
<220> FEATURE:
<223> OTHER INFORMATION: HuM291 VH amino acid sequence

<400> SEQUENCE: 212

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Thr Met His Trp Val Arg Gln Ala Pro Gly Gln Gly Leu Glu Trp Met
        35                  40                  45

Gly Tyr Ile Asn Pro Arg Ser Gly Tyr Thr His Tyr Asn Gln Lys Leu
    50                  55                  60

Lys Asp Lys Ala Thr Leu Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Tyr Tyr Asp Tyr Asp Gly Phe Ala Tyr Trp Gly Gln
            100                 105                 110

Gly Thr Leu Val Thr Val Ser Ser
        115                 120


<210> SEQ ID NO 213
<211> LENGTH: 15
<212> TYPE: PRT
<213> ORGANISM: Artificial Sequence
<220> FEATURE:
<223> OTHER INFORMATION: peptide linker

<400> SEQUENCE: 213

Gly Gly Gly Gly Ser Gly Gly Gly Gly Ser Gly Gly Gly Gly Ser
1               5                   10                  15


<210> SEQ ID NO 214
<211> LENGTH: 25
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(25)
<223> OTHER INFORMATION: Residues at positions 6-25 may be absent

<400> SEQUENCE: 214

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 215
<211> LENGTH: 15
<212> TYPE: PRT
<213> ORGANISM: Artificial Sequence
<220> FEATURE:
<223> OTHER INFORMATION: sss(s)-hIgG1 hinge

<400> SEQUENCE: 215

Glu Pro Lys Ser Ser Asp Lys Thr His Thr Ser Pro Pro Ser Ser
1               5                   10                  15
```

<210> SEQ ID NO 216
<211> LENGTH: 15
<212> TYPE: PRT
<213> ORGANISM: Artificial Sequence
<220> FEATURE:
<223> OTHER INFORMATION: csc(s)-hIgG1 hinge

<400> SEQUENCE: 216

Glu Pro Lys Ser Cys Asp Lys Thr His Thr Ser Pro Pro Cys Ser
1 5 10 15

<210> SEQ ID NO 217
<211> LENGTH: 15
<212> TYPE: PRT
<213> ORGANISM: Artificial Sequence
<220> FEATURE:
<223> OTHER INFORMATION: ssc(s)-hIgG1 hinge

<400> SEQUENCE: 217

Glu Pro Lys Ser Ser Asp Lys Thr His Thr Ser Pro Pro Cys Ser
1 5 10 15

<210> SEQ ID NO 218
<211> LENGTH: 15
<212> TYPE: PRT
<213> ORGANISM: Artificial Sequence
<220> FEATURE:
<223> OTHER INFORMATION: scc(s)-hIgG1 hinge

<400> SEQUENCE: 218

Glu Pro Lys Ser Ser Asp Lys Thr His Thr Cys Pro Pro Cys Ser
1 5 10 15

<210> SEQ ID NO 219
<211> LENGTH: 15
<212> TYPE: PRT
<213> ORGANISM: Artificial Sequence
<220> FEATURE:
<223> OTHER INFORMATION: css(s)-hIgG1 hinge

<400> SEQUENCE: 219

Glu Pro Lys Ser Cys Asp Lys Thr His Thr Ser Pro Pro Ser Ser
1 5 10 15

<210> SEQ ID NO 220
<211> LENGTH: 15
<212> TYPE: PRT
<213> ORGANISM: Artificial Sequence
<220> FEATURE:
<223> OTHER INFORMATION: scs(s)-hIgG1 hinge

<400> SEQUENCE: 220

Glu Pro Lys Ser Ser Asp Lys Thr His Thr Cys Pro Pro Ser Ser
1 5 10 15

<210> SEQ ID NO 221
<211> LENGTH: 15
<212> TYPE: PRT
<213> ORGANISM: Artificial Sequence
<220> FEATURE:
<223> OTHER INFORMATION: ccc(s)-hIgG1 hinge

<400> SEQUENCE: 221

Glu Pro Lys Ser Cys Asp Lys Thr His Thr Ser Pro Pro Cys Ser
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: ccc(p)-hIgG1 hinge

<400> SEQUENCE: 222

Glu Pro Lys Ser Cys Asp Lys Thr His Thr Ser Pro Pro Cys Pro
1 5 10 15

<210> SEQ ID NO 223
<211> LENGTH: 15
<212> TYPE: PRT
<213> ORGANISM: Artificial Sequence
<220> FEATURE:
<223> OTHER INFORMATION: sss(p)-hIgG1 hinge

<400> SEQUENCE: 223

Glu Pro Lys Ser Ser Asp Lys Thr His Thr Ser Pro Pro Ser Pro
1 5 10 15

<210> SEQ ID NO 224
<211> LENGTH: 15
<212> TYPE: PRT
<213> ORGANISM: Artificial Sequence
<220> FEATURE:
<223> OTHER INFORMATION: csc(p)-hIgG1 hinge

<400> SEQUENCE: 224

Glu Pro Lys Ser Cys Asp Lys Thr His Thr Ser Pro Pro Cys Pro
1 5 10 15

<210> SEQ ID NO 225
<211> LENGTH: 15
<212> TYPE: PRT
<213> ORGANISM: Artificial Sequence
<220> FEATURE:
<223> OTHER INFORMATION: ssc(p)-hIgG1 hinge

<400> SEQUENCE: 225

Glu Pro Lys Ser Ser Asp Lys Thr His Thr Ser Pro Pro Cys Pro
1 5 10 15

<210> SEQ ID NO 226
<211> LENGTH: 15
<212> TYPE: PRT
<213> ORGANISM: Artificial Sequence
<220> FEATURE:
<223> OTHER INFORMATION: scc(p)-hIgG1 hinge

<400> SEQUENCE: 226

Glu Pro Lys Ser Ser Asp Lys Thr His Thr Cys Pro Pro Cys Pro
1 5 10 15

<210> SEQ ID NO 227
<211> LENGTH: 15
<212> TYPE: PRT
<213> ORGANISM: Artificial Sequence
<220> FEATURE:
<223> OTHER INFORMATION: css(p)-hIgG1 hinge

<400> SEQUENCE: 227

Glu Pro Lys Ser Cys Asp Lys Thr His Thr Ser Pro Pro Ser Pro
1 5 10 15

```
<210> SEQ ID NO 228
<211> LENGTH: 15
<212> TYPE: PRT
<213> ORGANISM: Artificial Sequence
<220> FEATURE:
<223> OTHER INFORMATION: scs(p)-hIgG1 hinge

<400> SEQUENCE: 228

Glu Pro Lys Ser Ser Asp Lys Thr His Thr Cys Pro Pro Ser Pro
1               5                   10                  15


<210> SEQ ID NO 229
<211> LENGTH: 6
<212> TYPE: PRT
<213> ORGANISM: Artificial Sequence
<220> FEATURE:
<223> OTHER INFORMATION: Scppcp linker

<400> SEQUENCE: 229

Ser Cys Pro Pro Cys Pro
1               5


<210> SEQ ID NO 230
<211> LENGTH: 20
<212> TYPE: PRT
<213> ORGANISM: Artificial Sequence
<220> FEATURE:
<223> OTHER INFORMATION: STD1 linker

<400> SEQUENCE: 230

Asn Tyr Gly Gly Gly Gly Ser Gly Gly Gly Gly Ser Gly Gly Gly Gly
1               5                   10                  15

Ser Gly Asn Ser
            20


<210> SEQ ID NO 231
<211> LENGTH: 38
<212> TYPE: PRT
<213> ORGANISM: Artificial Sequence
<220> FEATURE:
<223> OTHER INFORMATION: STD2 linker

<400> SEQUENCE: 231

Asn Tyr Gly Gly Gly Gly Ser Gly Gly Gly Gly Ser Gly Gly Gly Gly
1               5                   10                  15

Ser Gly Asn Tyr Gly Gly Gly Gly Ser Gly Gly Gly Gly Ser Gly Gly
            20                  25                  30

Gly Gly Ser Gly Asn Ser
        35


<210> SEQ ID NO 232
<211> LENGTH: 2
<212> TYPE: PRT
<213> ORGANISM: Artificial Sequence
<220> FEATURE:
<223> OTHER INFORMATION: H1 linker

<400> SEQUENCE: 232

Asn Ser
1


<210> SEQ ID NO 233
<211> LENGTH: 8
<212> TYPE: PRT
<213> ORGANISM: Artificial Sequence
```

<220> FEATURE:
<223> OTHER INFORMATION: H2 linker

<400> SEQUENCE: 233

Gly Gly Gly Gly Ser Gly Asn Ser
1               5

<210> SEQ ID NO 234
<211> LENGTH: 10
<212> TYPE: PRT
<213> ORGANISM: Artificial Sequence
<220> FEATURE:
<223> OTHER INFORMATION: H3 linker

<400> SEQUENCE: 234

Asn Tyr Gly Gly Gly Gly Ser Gly Asn Ser
1               5                   10

<210> SEQ ID NO 235
<211> LENGTH: 13
<212> TYPE: PRT
<213> ORGANISM: Artificial Sequence
<220> FEATURE:
<223> OTHER INFORMATION: H4 linker

<400> SEQUENCE: 235

Gly Gly Gly Gly Ser Gly Gly Gly Gly Ser Gly Asn Ser
1               5                   10

<210> SEQ ID NO 236
<211> LENGTH: 15
<212> TYPE: PRT
<213> ORGANISM: Artificial Sequence
<220> FEATURE:
<223> OTHER INFORMATION: H5 linker

<400> SEQUENCE: 236

Asn Tyr Gly Gly Gly Gly Ser Gly Gly Gly Gly Ser Gly Asn Ser
1               5                   10                  15

<210> SEQ ID NO 237
<211> LENGTH: 18
<212> TYPE: PRT
<213> ORGANISM: Artificial Sequence
<220> FEATURE:
<223> OTHER INFORMATION: H6 linker

<400> SEQUENCE: 237

Gly Gly Gly Gly Ser Gly Gly Gly Gly Ser Gly Gly Gly Gly Ser Gly
1               5                   10                  15

Asn Ser

<210> SEQ ID NO 238
<211> LENGTH: 8
<212> TYPE: PRT
<213> ORGANISM: Artificial Sequence
<220> FEATURE:
<223> OTHER INFORMATION: H7 linker

<400> SEQUENCE: 238

Gly Cys Pro Pro Cys Pro Asn Ser
1               5

<210> SEQ ID NO 239
<211> LENGTH: 15
<212> TYPE: PRT

<213> ORGANISM: Artificial Sequence
<220> FEATURE:
<223> OTHER INFORMATION: (G4S)3 linker

<400> SEQUENCE: 239

Gly Gly Gly Gly Ser Gly Gly Gly Gly Ser Gly Gly Gly Gly Ser
1 5 10 15

<210> SEQ ID NO 240
<211> LENGTH: 16
<212> TYPE: PRT
<213> ORGANISM: Artificial Sequence
<220> FEATURE:
<223> OTHER INFORMATION: H105 linker

<400> SEQUENCE: 240

Ser Gly Gly Gly Gly Ser Gly Gly Gly Gly Ser Gly Gly Gly Gly Ser
1 5 10 15

<210> SEQ ID NO 241
<211> LENGTH: 20
<212> TYPE: PRT
<213> ORGANISM: Artificial Sequence
<220> FEATURE:
<223> OTHER INFORMATION: (G4S)4 linker

<400> SEQUENCE: 241

Gly Gly Gly Gly Ser Gly Gly Gly Gly Ser Gly Gly Gly Gly Ser Gly
1 5 10 15

Gly Gly Gly Ser
20

<210> SEQ ID NO 242
<211> LENGTH: 21
<212> TYPE: PRT
<213> ORGANISM: Artificial Sequence
<220> FEATURE:
<223> OTHER INFORMATION: H75 (NKG2A quadruple mutant) linker

<400> SEQUENCE: 242

Gln Arg His Asn Asn Ser Ser Leu Asn Thr Gly Thr Gln Met Ala Gly
1 5 10 15

His Ser Pro Asn Ser
20

<210> SEQ ID NO 243
<211> LENGTH: 16
<212> TYPE: PRT
<213> ORGANISM: Artificial Sequence
<220> FEATURE:
<223> OTHER INFORMATION: H83 (NKG2A derived) linker

<400> SEQUENCE: 243

Ser Ser Leu Asn Thr Gly Thr Gln Met Ala Gly His Ser Pro Asn Ser
1 5 10 15

<210> SEQ ID NO 244
<211> LENGTH: 18
<212> TYPE: PRT
<213> ORGANISM: Artificial Sequence
<220> FEATURE:
<223> OTHER INFORMATION: H106 (NKG2A derived) linker

<400> SEQUENCE: 244

Gln Arg His Asn Asn Ser Ser Leu Asn Thr Gly Thr Gln Met Ala Gly
1               5                   10                  15

His Ser

<210> SEQ ID NO 245
<211> LENGTH: 14
<212> TYPE: PRT
<213> ORGANISM: Artificial Sequence
<220> FEATURE:
<223> OTHER INFORMATION: H81 (NKG2D derived) linker

<400> SEQUENCE: 245

Glu Val Gln Ile Pro Leu Thr Glu Ser Tyr Ser Pro Asn Ser
1               5                   10

<210> SEQ ID NO 246
<211> LENGTH: 20
<212> TYPE: PRT
<213> ORGANISM: Artificial Sequence
<220> FEATURE:
<223> OTHER INFORMATION: H91 (NKG2D derived) linker

<400> SEQUENCE: 246

Asn Ser Leu Ala Asn Gln Glu Val Gln Ile Pro Leu Thr Glu Ser Tyr
1               5                   10                  15

Ser Pro Asn Ser
            20

<210> SEQ ID NO 247
<211> LENGTH: 19
<212> TYPE: PRT
<213> ORGANISM: Artificial Sequence
<220> FEATURE:
<223> OTHER INFORMATION: H94 linker

<400> SEQUENCE: 247

Ser Gly Gly Gly Gly Ser Gly Gly Gly Gly Ser Gly Gly Gly Gly Ser
1               5                   10                  15

Pro Asn Ser

<210> SEQ ID NO 248
<211> LENGTH: 19
<212> TYPE: PRT
<213> ORGANISM: Artificial Sequence
<220> FEATURE:
<223> OTHER INFORMATION: H111 linker

<400> SEQUENCE: 248

Ser Gly Gly Gly Gly Ser Gly Gly Gly Gly Ser Gly Gly Gly Gly Ser
1               5                   10                  15

Pro Gly Ser

<210> SEQ ID NO 249
<211> LENGTH: 15
<212> TYPE: PRT
<213> ORGANISM: Artificial Sequence
<220> FEATURE:
<223> OTHER INFORMATION: H16 linker

<400> SEQUENCE: 249

Leu Ser Val Lys Ala Asp Phe Leu Thr Pro Ser Ile Gly Asn Ser
1               5                   10                  15

<210> SEQ ID NO 250
<211> LENGTH: 20
<212> TYPE: PRT
<213> ORGANISM: Artificial Sequence
<220> FEATURE:
<223> OTHER INFORMATION: H17 linker

<400> SEQUENCE: 250

```
Leu Ser Val Lys Ala Asp Phe Leu Thr Pro Ser Ile Ser Cys Pro Pro
1               5                   10                  15

Cys Pro Asn Ser
            20
```

<210> SEQ ID NO 251
<211> LENGTH: 15
<212> TYPE: PRT
<213> ORGANISM: Artificial Sequence
<220> FEATURE:
<223> OTHER INFORMATION: H18 linker

<400> SEQUENCE: 251

```
Leu Ser Val Leu Ala Asn Phe Ser Gln Pro Glu Ile Gly Asn Ser
1               5                   10                  15
```

<210> SEQ ID NO 252
<211> LENGTH: 20
<212> TYPE: PRT
<213> ORGANISM: Artificial Sequence
<220> FEATURE:
<223> OTHER INFORMATION: H19 linker

<400> SEQUENCE: 252

```
Leu Ser Val Leu Ala Asn Phe Ser Gln Pro Glu Ile Ser Cys Pro Pro
1               5                   10                  15

Cys Pro Asn Ser
            20
```

<210> SEQ ID NO 253
<211> LENGTH: 15
<212> TYPE: PRT
<213> ORGANISM: Artificial Sequence
<220> FEATURE:
<223> OTHER INFORMATION: H20 linker

<400> SEQUENCE: 253

```
Leu Lys Ile Gln Glu Arg Val Ser Lys Pro Lys Ile Ser Asn Ser
1               5                   10                  15
```

<210> SEQ ID NO 254
<211> LENGTH: 20
<212> TYPE: PRT
<213> ORGANISM: Artificial Sequence
<220> FEATURE:
<223> OTHER INFORMATION: H21 linker

<400> SEQUENCE: 254

```
Leu Lys Ile Gln Glu Arg Val Ser Lys Pro Lys Ile Ser Cys Pro Pro
1               5                   10                  15

Cys Pro Asn Ser
            20
```

<210> SEQ ID NO 255
<211> LENGTH: 15
<212> TYPE: PRT
<213> ORGANISM: Artificial Sequence
<220> FEATURE:
<223> OTHER INFORMATION: H22 linker

<400> SEQUENCE: 255

Leu Asn Val Ser Glu Arg Pro Phe Pro Pro His Ile Gln Asn Ser
1 5 10 15

<210> SEQ ID NO 256
<211> LENGTH: 21
<212> TYPE: PRT
<213> ORGANISM: Artificial Sequence
<220> FEATURE:
<223> OTHER INFORMATION: H23 linker

<400> SEQUENCE: 256

Leu Asp Val Ser Glu Arg Pro Phe Pro Pro His Ile Gln Ser Cys Pro
1 5 10 15

Pro Cys Pro Asn Ser
20

<210> SEQ ID NO 257
<211> LENGTH: 15
<212> TYPE: PRT
<213> ORGANISM: Artificial Sequence
<220> FEATURE:
<223> OTHER INFORMATION: H24 linker

<400> SEQUENCE: 257

Arg Glu Gln Leu Ala Glu Val Thr Leu Ser Leu Lys Ala Asn Ser
1 5 10 15

<210> SEQ ID NO 258
<211> LENGTH: 20
<212> TYPE: PRT
<213> ORGANISM: Artificial Sequence
<220> FEATURE:
<223> OTHER INFORMATION: H25 linker

<400> SEQUENCE: 258

Arg Glu Gln Leu Ala Glu Val Thr Leu Ser Leu Lys Ala Cys Pro Pro
1 5 10 15

Cys Pro Asn Ser
20

<210> SEQ ID NO 259
<211> LENGTH: 15
<212> TYPE: PRT
<213> ORGANISM: Artificial Sequence
<220> FEATURE:
<223> OTHER INFORMATION: H26 linker

<400> SEQUENCE: 259

Arg Ile His Gln Met Asn Ser Glu Leu Ser Val Leu Ala Asn Ser
1 5 10 15

<210> SEQ ID NO 260
<211> LENGTH: 20
<212> TYPE: PRT
<213> ORGANISM: Artificial Sequence
<220> FEATURE:
<223> OTHER INFORMATION: H27 linker

<400> SEQUENCE: 260

Arg Ile His Gln Met Asn Ser Glu Leu Ser Val Leu Ala Cys Pro Pro
1 5 10 15

Cys Pro Asn Ser
20

<210> SEQ ID NO 261
<211> LENGTH: 15
<212> TYPE: PRT
<213> ORGANISM: Artificial Sequence
<220> FEATURE:
<223> OTHER INFORMATION: H28 linker

<400> SEQUENCE: 261

Asp Thr Lys Gly Lys Asn Val Leu Glu Lys Ile Phe Ser Asn Ser
1 5 10 15

<210> SEQ ID NO 262
<211> LENGTH: 15
<212> TYPE: PRT
<213> ORGANISM: Artificial Sequence
<220> FEATURE:
<223> OTHER INFORMATION: H30 linker

<400> SEQUENCE: 262

Leu Pro Pro Glu Thr Gln Glu Ser Gln Glu Val Thr Leu Asn Ser
1 5 10 15

<210> SEQ ID NO 263
<211> LENGTH: 15
<212> TYPE: PRT
<213> ORGANISM: Artificial Sequence
<220> FEATURE:
<223> OTHER INFORMATION: H32 linker

<400> SEQUENCE: 263

Arg Ile His Leu Asn Val Ser Glu Arg Pro Phe Pro Pro Asn Ser
1 5 10 15

<210> SEQ ID NO 264
<211> LENGTH: 20
<212> TYPE: PRT
<213> ORGANISM: Artificial Sequence
<220> FEATURE:
<223> OTHER INFORMATION: H33 linker

<400> SEQUENCE: 264

Arg Ile His Leu Asn Val Ser Glu Arg Pro Phe Pro Pro Cys Pro Pro
1 5 10 15

Cys Pro Asn Ser
20

<210> SEQ ID NO 265
<211> LENGTH: 13
<212> TYPE: PRT
<213> ORGANISM: Artificial Sequence
<220> FEATURE:
<223> OTHER INFORMATION: H36 linker

<400> SEQUENCE: 265

Gly Cys Pro Pro Cys Pro Gly Gly Gly Gly Ser Asn Ser
1 5 10

<210> SEQ ID NO 266
<211> LENGTH: 9

-continued

<212> TYPE: PRT
<213> ORGANISM: Artificial Sequence
<220> FEATURE:
<223> OTHER INFORMATION: H40 linker

<400> SEQUENCE: 266

Gly Cys Pro Pro Cys Pro Ala Asn Ser
1 5

<210> SEQ ID NO 267
<211> LENGTH: 9
<212> TYPE: PRT
<213> ORGANISM: Artificial Sequence
<220> FEATURE:
<223> OTHER INFORMATION: H41 linker

<400> SEQUENCE: 267

Gly Cys Pro Pro Cys Pro Ala Asn Ser
1 5

<210> SEQ ID NO 268
<211> LENGTH: 8
<212> TYPE: PRT
<213> ORGANISM: Artificial Sequence
<220> FEATURE:
<223> OTHER INFORMATION: H42 linker

<400> SEQUENCE: 268

Gly Cys Pro Pro Cys Pro Asn Ser
1 5

<210> SEQ ID NO 269
<211> LENGTH: 13
<212> TYPE: PRT
<213> ORGANISM: Artificial Sequence
<220> FEATURE:
<223> OTHER INFORMATION: H44 linker

<400> SEQUENCE: 269

Gly Gly Gly Ala Ser Cys Pro Pro Cys Pro Gly Asn Ser
1 5 10

<210> SEQ ID NO 270
<211> LENGTH: 13
<212> TYPE: PRT
<213> ORGANISM: Artificial Sequence
<220> FEATURE:
<223> OTHER INFORMATION: H45 linker

<400> SEQUENCE: 270

Gly Gly Gly Ala Ser Cys Pro Pro Cys Ala Gly Asn Ser
1 5 10

<210> SEQ ID NO 271
<211> LENGTH: 12
<212> TYPE: PRT
<213> ORGANISM: Artificial Sequence
<220> FEATURE:
<223> OTHER INFORMATION: H46 linker

<400> SEQUENCE: 271

Gly Gly Gly Ala Ser Cys Pro Pro Cys Ala Asn Ser
1 5 10

<210> SEQ ID NO 272
<211> LENGTH: 15
<212> TYPE: PRT

-continued

<213> ORGANISM: Artificial Sequence
<220> FEATURE:
<223> OTHER INFORMATION: H47 linker

<400> SEQUENCE: 272

Leu Ser Val Lys Ala Asp Phe Leu Thr Pro Ser Ile Gly Asn Ser
1 5 10 15

<210> SEQ ID NO 273
<211> LENGTH: 11
<212> TYPE: PRT
<213> ORGANISM: Artificial Sequence
<220> FEATURE:
<223> OTHER INFORMATION: H48 linker

<400> SEQUENCE: 273

Ala Asp Phe Leu Thr Pro Ser Ile Gly Asn Ser
1 5 10

<210> SEQ ID NO 274
<211> LENGTH: 15
<212> TYPE: PRT
<213> ORGANISM: Artificial Sequence
<220> FEATURE:
<223> OTHER INFORMATION: H50 linker

<400> SEQUENCE: 274

Leu Ser Val Leu Ala Asn Phe Ser Gln Pro Glu Ile Gly Asn Ser
1 5 10 15

<210> SEQ ID NO 275
<211> LENGTH: 15
<212> TYPE: PRT
<213> ORGANISM: Artificial Sequence
<220> FEATURE:
<223> OTHER INFORMATION: H51 linker

<400> SEQUENCE: 275

Leu Ser Val Leu Ala Asn Phe Ser Gln Pro Glu Ile Gly Asn Ser
1 5 10 15

<210> SEQ ID NO 276
<211> LENGTH: 11
<212> TYPE: PRT
<213> ORGANISM: Artificial Sequence
<220> FEATURE:
<223> OTHER INFORMATION: H52 linker

<400> SEQUENCE: 276

Ser Gln Pro Glu Ile Val Pro Ile Ser Asn Ser
1 5 10

<210> SEQ ID NO 277
<211> LENGTH: 16
<212> TYPE: PRT
<213> ORGANISM: Artificial Sequence
<220> FEATURE:
<223> OTHER INFORMATION: H53 linker

<400> SEQUENCE: 277

Ser Gln Pro Glu Ile Val Pro Ile Ser Cys Pro Pro Cys Pro Asn Ser
1 5 10 15

<210> SEQ ID NO 278
<211> LENGTH: 19
<212> TYPE: PRT
<213> ORGANISM: Artificial Sequence
<220> FEATURE:
<223> OTHER INFORMATION: H54 linker

<400> SEQUENCE: 278

Ser Val Leu Ala Asn Phe Ser Gln Pro Glu Ile Ser Cys Pro Pro Cys
1 5 10 15

Pro Asn Ser

<210> SEQ ID NO 279
<211> LENGTH: 15
<212> TYPE: PRT
<213> ORGANISM: Artificial Sequence
<220> FEATURE:
<223> OTHER INFORMATION: H55 linker

<400> SEQUENCE: 279

Arg Ile His Gln Met Asn Ser Glu Leu Ser Val Leu Ala Asn Ser
1 5 10 15

<210> SEQ ID NO 280
<211> LENGTH: 12
<212> TYPE: PRT
<213> ORGANISM: Artificial Sequence
<220> FEATURE:
<223> OTHER INFORMATION: H56 linker

<400> SEQUENCE: 280

Gln Met Asn Ser Glu Leu Ser Val Leu Ala Asn Ser
1 5 10

<210> SEQ ID NO 281
<211> LENGTH: 10
<212> TYPE: PRT
<213> ORGANISM: Artificial Sequence
<220> FEATURE:
<223> OTHER INFORMATION: H57 linker

<400> SEQUENCE: 281

Val Ser Glu Arg Pro Phe Pro Pro Asn Ser
1 5 10

<210> SEQ ID NO 282
<211> LENGTH: 15
<212> TYPE: PRT
<213> ORGANISM: Artificial Sequence
<220> FEATURE:
<223> OTHER INFORMATION: H58 linker

<400> SEQUENCE: 282

Lys Pro Phe Phe Thr Cys Gly Ser Ala Asp Thr Cys Pro Asn Ser
1 5 10 15

<210> SEQ ID NO 283
<211> LENGTH: 15
<212> TYPE: PRT
<213> ORGANISM: Artificial Sequence
<220> FEATURE:
<223> OTHER INFORMATION: H59 linker

<400> SEQUENCE: 283

Lys Pro Phe Phe Thr Cys Gly Ser Ala Asp Thr Cys Pro Asn Ser
1 5 10 15

<210> SEQ ID NO 284
<211> LENGTH: 15
<212> TYPE: PRT

<213> ORGANISM: Artificial Sequence
<220> FEATURE:
<223> OTHER INFORMATION: H60 linker

<400> SEQUENCE: 284

Gln Tyr Asn Cys Pro Gly Gln Tyr Thr Phe Ser Met Pro Asn Ser
1 5 10 15

<210> SEQ ID NO 285
<211> LENGTH: 21
<212> TYPE: PRT
<213> ORGANISM: Artificial Sequence
<220> FEATURE:
<223> OTHER INFORMATION: H61 linker

<400> SEQUENCE: 285

Glu Pro Ala Phe Thr Pro Gly Pro Asn Ile Glu Leu Gln Lys Asp Ser
1 5 10 15

Asp Cys Pro Asn Ser
20

<210> SEQ ID NO 286
<211> LENGTH: 21
<212> TYPE: PRT
<213> ORGANISM: Artificial Sequence
<220> FEATURE:
<223> OTHER INFORMATION: H62 linker

<400> SEQUENCE: 286

Gln Arg His Asn Asn Ser Ser Leu Asn Thr Arg Thr Gln Lys Ala Arg
1 5 10 15

His Cys Pro Asn Ser
20

<210> SEQ ID NO 287
<211> LENGTH: 20
<212> TYPE: PRT
<213> ORGANISM: Artificial Sequence
<220> FEATURE:
<223> OTHER INFORMATION: H63 linker

<400> SEQUENCE: 287

Asn Ser Leu Phe Asn Gln Glu Val Gln Ile Pro Leu Thr Glu Ser Tyr
1 5 10 15

Cys Pro Asn Ser
20

<210> SEQ ID NO 288
<211> LENGTH: 17
<212> TYPE: PRT
<213> ORGANISM: Artificial Sequence
<220> FEATURE:
<223> OTHER INFORMATION: H114 linker

<400> SEQUENCE: 288

Gly Gly Gly Gly Ser Gly Gly Gly Gly Ser Gly Gly Gly Gly Ser Pro
1 5 10 15

Ser

<210> SEQ ID NO 289
<211> LENGTH: 14
<212> TYPE: PRT
<213> ORGANISM: Artificial Sequence
<220> FEATURE:
<223> OTHER INFORMATION: CD3-binding domain LCDR1

-continued

<400> SEQUENCE: 289

Gly Ser Ser Thr Gly Ala Val Thr Ser Gly Tyr Tyr Pro Asn
1 5 10

<210> SEQ ID NO 290
<211> LENGTH: 14
<212> TYPE: PRT
<213> ORGANISM: Artificial Sequence
<220> FEATURE:
<223> OTHER INFORMATION: CD3-binding domain LCDR1

<400> SEQUENCE: 290

Arg Ser Ser Thr Gly Ala Val Thr Ser Gly Tyr Tyr Pro Asn
1 5 10

<210> SEQ ID NO 291
<211> LENGTH: 14
<212> TYPE: PRT
<213> ORGANISM: Artificial Sequence
<220> FEATURE:
<223> OTHER INFORMATION: CD3-binding domain LCDR1

<400> SEQUENCE: 291

Gly Ser Ser Thr Gly Ala Val Thr Ser Gly Asn Tyr Pro Asn
1 5 10

<210> SEQ ID NO 292
<211> LENGTH: 7
<212> TYPE: PRT
<213> ORGANISM: Artificial Sequence
<220> FEATURE:
<223> OTHER INFORMATION: CD3-binding domain LCDR2

<400> SEQUENCE: 292

Gly Thr Lys Phe Leu Ala Pro
1 5

<210> SEQ ID NO 293
<211> LENGTH: 7
<212> TYPE: PRT
<213> ORGANISM: Artificial Sequence
<220> FEATURE:
<223> OTHER INFORMATION: CD3-binding domain LCDR2

<400> SEQUENCE: 293

Ala Thr Asp Met Arg Pro Ser
1 5

<210> SEQ ID NO 294
<211> LENGTH: 7
<212> TYPE: PRT
<213> ORGANISM: Artificial Sequence
<220> FEATURE:
<223> OTHER INFORMATION: CD3-binding domain LCDR2

<400> SEQUENCE: 294

Gly Thr Lys Phe Leu Ala Pro
1 5

<210> SEQ ID NO 295
<211> LENGTH: 9
<212> TYPE: PRT
<213> ORGANISM: Artificial Sequence
<220> FEATURE:
<223> OTHER INFORMATION: CD3-binding domain LCDR3

<400> SEQUENCE: 295

Ala Leu Trp Tyr Ser Asn Arg Trp Val
1 5

<210> SEQ ID NO 296
<211> LENGTH: 9
<212> TYPE: PRT
<213> ORGANISM: Artificial Sequence
<220> FEATURE:
<223> OTHER INFORMATION: CD3-binding domain LCDR3

<400> SEQUENCE: 296

Ala Leu Trp Tyr Ser Asn Arg Trp Val
1 5

<210> SEQ ID NO 297
<211> LENGTH: 9
<212> TYPE: PRT
<213> ORGANISM: Artificial Sequence
<220> FEATURE:
<223> OTHER INFORMATION: CD3-binding domain LCDR3

<400> SEQUENCE: 297

Val Leu Trp Tyr Ser Asn Arg Trp Val
1 5

<210> SEQ ID NO 298
<211> LENGTH: 5
<212> TYPE: PRT
<213> ORGANISM: Artificial Sequence
<220> FEATURE:
<223> OTHER INFORMATION: CD3-binding domain HCDR1

<400> SEQUENCE: 298

Ile Tyr Ala Met Asn
1 5

<210> SEQ ID NO 299
<211> LENGTH: 5
<212> TYPE: PRT
<213> ORGANISM: Artificial Sequence
<220> FEATURE:
<223> OTHER INFORMATION: CD3-binding domain HCDR1

<400> SEQUENCE: 299

Lys Tyr Ala Met Asn
1 5

<210> SEQ ID NO 300
<211> LENGTH: 5
<212> TYPE: PRT
<213> ORGANISM: Artificial Sequence
<220> FEATURE:
<223> OTHER INFORMATION: CD3-binding domain HCDR1

<400> SEQUENCE: 300

Ser Tyr Ala Met Asn
1 5

<210> SEQ ID NO 301
<211> LENGTH: 19
<212> TYPE: PRT
<213> ORGANISM: Artificial Sequence
<220> FEATURE:
<223> OTHER INFORMATION: CD3-binding domain HCDR2

<400> SEQUENCE: 301

Arg Ile Arg Ser Lys Tyr Asn Asn Tyr Ala Thr Tyr Tyr Ala Asp Ser
1 5 10 15

Val Lys Ser

<210> SEQ ID NO 302
<211> LENGTH: 19
<212> TYPE: PRT
<213> ORGANISM: Artificial Sequence
<220> FEATURE:
<223> OTHER INFORMATION: CD3-binding domain HCDR2

<400> SEQUENCE: 302

Arg Ile Arg Ser Lys Tyr Asn Asn Tyr Ala Thr Tyr Tyr Ala Asp Ser
1 5 10 15

Val Lys Asp

<210> SEQ ID NO 303
<211> LENGTH: 19
<212> TYPE: PRT
<213> ORGANISM: Artificial Sequence
<220> FEATURE:
<223> OTHER INFORMATION: CD3-binding domain HCDR2

<400> SEQUENCE: 303

Arg Ile Arg Ser Lys Tyr Asn Asn Tyr Ala Thr Tyr Tyr Ala Asp Ser
1 5 10 15

Val Lys Gly

<210> SEQ ID NO 304
<211> LENGTH: 14
<212> TYPE: PRT
<213> ORGANISM: Artificial Sequence
<220> FEATURE:
<223> OTHER INFORMATION: CD3-binding domain HCDR3

<400> SEQUENCE: 304

His Gly Asn Phe Gly Asn Ser Tyr Val Ser Phe Phe Ala Tyr
1 5 10

<210> SEQ ID NO 305
<211> LENGTH: 14
<212> TYPE: PRT
<213> ORGANISM: Artificial Sequence
<220> FEATURE:
<223> OTHER INFORMATION: CD3-binding domain HCDR3

<400> SEQUENCE: 305

His Gly Asn Phe Gly Asn Ser Tyr Ile Ser Tyr Trp Ala Tyr
1 5 10

<210> SEQ ID NO 306
<211> LENGTH: 14
<212> TYPE: PRT
<213> ORGANISM: Artificial Sequence
<220> FEATURE:
<223> OTHER INFORMATION: CD3-binding domain HCDR3

<400> SEQUENCE: 306

His Gly Asn Phe Gly Asn Ser Tyr Leu Ser Phe Trp Ala Tyr
1 5 10

<210> SEQ ID NO 307
<211> LENGTH: 14

<212> TYPE: PRT
<213> ORGANISM: Artificial Sequence
<220> FEATURE:
<223> OTHER INFORMATION: I2C VL CDR1 (Kabat)

<400> SEQUENCE: 307

Gly Ser Ser Thr Gly Ala Val Thr Ser Gly Asn Tyr Pro Asn
1               5                   10

<210> SEQ ID NO 308
<211> LENGTH: 7
<212> TYPE: PRT
<213> ORGANISM: Artificial Sequence
<220> FEATURE:
<223> OTHER INFORMATION: I2C VL CDR2 (Kabat)

<400> SEQUENCE: 308

Gly Thr Lys Phe Leu Ala Pro
1               5

<210> SEQ ID NO 309
<211> LENGTH: 9
<212> TYPE: PRT
<213> ORGANISM: Artificial Sequence
<220> FEATURE:
<223> OTHER INFORMATION: I2C VL CDR3 (Kabat)

<400> SEQUENCE: 309

Val Leu Trp Tyr Ser Asn Arg Trp Val
1               5

<210> SEQ ID NO 310
<211> LENGTH: 9
<212> TYPE: PRT
<213> ORGANISM: Artificial Sequence
<220> FEATURE:
<223> OTHER INFORMATION: I2C VL CDR1 (IMGT)

<400> SEQUENCE: 310

Thr Gly Ala Val Thr Ser Gly Asn Tyr
1               5

<210> SEQ ID NO 311
<211> LENGTH: 251
<212> TYPE: PRT
<213> ORGANISM: Artificial Sequence
<220> FEATURE:
<223> OTHER INFORMATION: TSC455 (anti-CD3)  TSC394 F87Y scFv

<400> SEQUENCE: 311

Gln Val Gln Leu Val Gln Ser Gly Pro Glu Val Lys Lys Pro Gly Ser
1               5                   10                  15

Ser Val Lys Val Ser Cys Lys Ala Ser Gly Tyr Thr Phe Ser Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

```
Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Thr Leu Ser Ala Ser Val Gly Asp Arg Val
145                 150                 155                 160

Thr Met Thr Cys Ser Ala Ser Ser Ser Val Ser Tyr Met Asn Trp Tyr
                165                 170                 175

Gln Gln Lys Pro Gly Lys Ala Pro Lys Arg Trp Ile Tyr Asp Ser Ser
            180                 185                 190

Lys Leu Ala Ser Gly Val Pro Ser Arg Phe Ser Gly Ser Gly Ser Gly
        195                 200                 205

Thr Glu Tyr Thr Leu Thr Ile Ser Ser Leu Gln Pro Asp Asp Phe Ala
    210                 215                 220

Thr Tyr Tyr Cys Gln Gln Trp Ser Arg Asn Pro Pro Thr Phe Gly Gly
225                 230                 235                 240

Gly Thr Lys Val Glu Ile Lys Arg Ser Ser Ser
                245                 250


<210> SEQ ID NO 312
<211> LENGTH: 251
<212> TYPE: PRT
<213> ORGANISM: Artificial Sequence
<220> FEATURE:
<223> OTHER INFORMATION: TSC456 (anti-CD3)  TSC394 E86D F87Y scFv

<400> SEQUENCE: 312

Gln Val Gln Leu Val Gln Ser Gly Pro Glu Val Lys Lys Pro Gly Ser
1               5                   10                  15

Ser Val Lys Val Ser Cys Lys Ala Ser Gly Tyr Thr Phe Ser Arg Ser
            20                  25                  30

Thr Met His Trp Val Arg Gln Ala Pro Gly Gln Gly Leu Glu Trp Ile
        35                  40                  45

Gly Tyr Ile Asn Pro Ser Ser Ala Tyr Thr Asn Tyr Asn Gln Lys Phe
    50                  55                  60

Lys Asp Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gln Val His Tyr Asp Tyr Asn Gly Phe Pro Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gly Gly Gly Gly Ser Asp Ile Gln
    130                 135                 140

Met Thr Gln Ser Pro Ser Thr Leu Ser Ala Ser Val Gly Asp Arg Val
145                 150                 155                 160

Thr Met Thr Cys Ser Ala Ser Ser Ser Val Ser Tyr Met Asn Trp Tyr
                165                 170                 175

Gln Gln Lys Pro Gly Lys Ala Pro Lys Arg Trp Ile Tyr Asp Ser Ser
            180                 185                 190

Lys Leu Ala Ser Gly Val Pro Ser Arg Phe Ser Gly Ser Gly Ser Gly
        195                 200                 205

Thr Asp Tyr Thr Leu Thr Ile Ser Ser Leu Gln Pro Asp Asp Phe Ala
    210                 215                 220
```

Thr Tyr Tyr Cys Gln Gln Trp Ser Arg Asn Pro Pro Thr Phe Gly Gly
225 230 235 240

Gly Thr Lys Val Glu Ile Lys Arg Ser Ser Ser
245 250

<210> SEQ ID NO 313
<211> LENGTH: 247
<212> TYPE: PRT
<213> ORGANISM: Artificial Sequence
<220> FEATURE:
<223> OTHER INFORMATION: DRA222 (anti-CD3) scFv

<400> SEQUENCE: 313

Gln Val Gln Leu Val Glu Ser Gly Gly Gly Val Val Gln Pro Gly Arg
1 5 10 15

Ser Leu Arg Leu Ser Cys Lys Ala Ser Gly Tyr Thr Phe Thr Arg Ser
20 25 30

Thr Met His Trp Val Arg Gln Ala Pro Gly Gln Gly Leu Glu Trp Ile
35 40 45

Gly Tyr Ile Asn Pro Ser Ser Ala Tyr Thr Asn Tyr Asn Gln Lys Phe
50 55 60

Lys Asp Arg Phe Thr Ile Ser Ala Asp Lys Ser Lys Ser Thr Ala Phe
65 70 75 80

Leu Gln Met Asp Ser Leu Arg Pro Glu Asp Thr Gly Val Tyr Phe Cys
85 90 95

Ala Arg Pro Gln Val His Tyr Asp Tyr Asn Gly Phe Pro Tyr Trp Gly
100 105 110

Gln Gly Thr Pro Val Thr Val Ser Ser Gly Gly Gly Gly Ser Gly Gly
115 120 125

Gly Gly Ser Gly Gly Gly Gly Ser Ala Gln Asp Ile Gln Met Thr Gln
130 135 140

Ser Pro Ser Ser Leu Ser Ala Ser Val Gly Asp Arg Val Thr Met Thr
145 150 155 160

Cys Ser Ala Ser Ser Ser Val Ser Tyr Met Asn Trp Tyr Gln Gln Lys
165 170 175

Pro Gly Lys Ala Pro Lys Arg Trp Ile Tyr Asp Ser Ser Lys Leu Ala
180 185 190

Ser Gly Val Pro Ala Arg Phe Ser Gly Ser Gly Ser Gly Thr Asp Tyr
195 200 205

Thr Leu Thr Ile Ser Ser Leu Gln Pro Glu Asp Phe Ala Thr Tyr Tyr
210 215 220

Cys Gln Gln Trp Ser Arg Asn Pro Pro Thr Phe Gly Gly Gly Thr Lys
225 230 235 240

Leu Gln Ile Thr Ser Ser Ser
245

<210> SEQ ID NO 314
<211> LENGTH: 35
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (6)..(35)
<223> OTHER INFORMATION: Residues at positions 6-35 may be absent -continued

```
<400> SEQUENCE: 314

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35


<210> SEQ ID NO 315
<211> LENGTH: 5
<212> TYPE: PRT
<213> ORGANISM: Artificial Sequence
<220> FEATURE:
<223> OTHER INFORMATION: peptide linker

<400> SEQUENCE: 315

Gly Gly Gly Gly Ser
1               5


<210> SEQ ID NO 316
<211> LENGTH: 22
<212> TYPE: PRT
<213> ORGANISM: Artificial Sequence
<220> FEATURE:
<223> OTHER INFORMATION: peptide linker

<400> SEQUENCE: 316

Gly Gly Gly Gly Ser Gly Gly Gly Gly Ser Gly Gly Gly Gly Ser Gly
1               5                   10                  15

Gly Gly Gly Ser Pro Ser
            20
```

CD123 BINDING PROTEINS AND RELATED COMPOSITIONS AND METHODS

This application is a continuation application of U.S. application Ser. No. 16/335,561, filed Mar. 21, 2019 and issued as U.S. Pat. No. 11,242,400, which is a U.S. national stage application of International Application No. PCT/US2017/052808, filed Sep. 21, 2017, which claims priority to and benefit of U.S. Provisional Patent Application No. 62/397,736, filed on Sep. 21, 2016, and U.S. Provisional Patent Application No. 62/466,192, filed on Mar. 2, 2017. The contents of each of these applications are herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: APVO_054_06US_SeqList_ST25.txt; date recorded: Dec. 21, 2021; file size ~257,765 bytes).

FIELD OF THE DISCLOSURE

The present disclosure relates to molecules that specifically bind to CD123, which may have at least one humanized CD123-binding domain. These molecules are useful for the characterization or treatment of disorders characterized by overexpression of CD123, such as cancer. A protein therapeutic binding to CD123 may be a monospecific protein therapeutic or a multi-specific protein therapeutic. A multi-specific protein therapeutic may bind both CD123-expressing cells and the T-cell receptor complex on T-cells to induce target-dependent T-cell cytotoxicity, activation and proliferation.

BACKGROUND OF THE DISCLOSURE

CD123 is also known as the alpha chain of the human interleukin-3 (IL-3) receptor. CD123 is a type I transmembrane glycoprotein and is a member of the cytokine receptor superfamily. The interleukin-3 receptor is a heterodimer formed by CD123 and the beta chain (CD131). IL-3 binds to CD123, and signal transduction is provided by CD131. IL-3 regulates the function and production of hematopoietic and immune cells and stimulates endothelial cell proliferation (Testa et al., *Biomark Res.* 2:4 (2014)).

CD123 is overexpressed in many hematologic malignancies, including a subset of acute myeloid leukemia (AML), B-lymphoid leukemia, blastic plasmocytoid dendritic neoplasms (BPDCN) and hairy cell leukemia. Id. While most AML patients respond well to initial therapies, the majority of AML patients are ultimately diagnosed with relapsed or refractory disease (Ramos et al., *J. Clin. Med.* 4:665-695 (2015)). There is a need for molecules targeting CD123 with increased efficiency and potency and reduced adverse effects and that may be used to treat disorders associated with dysregulation of CD123.

SUMMARY OF THE DISCLOSURE

In some embodiments, the disclosure encompasses a recombinant polypeptide comprising a CD123-binding domain, wherein the CD123-binding domain comprises (i) an immunoglobulin light chain variable region comprising LCDR1, LCDR2, and LCDR3, and (ii) an immunoglobulin heavy chain variable region comprising HCDR1, HCDR2, and HCDR3, wherein the LCDR1 comprises an amino acid sequence as set forth in SEQ ID NO:6 or a sequence that differs from SEQ ID NO:6 by at least one amino acid substitution; the LCDR2 comprises an amino acid sequence as set forth in SEQ ID NO:8 or a sequence that differs from SEQ ID NO:8 by at least one amino acid substitution; the LCDR3 comprises an amino acid sequence as set forth in SEQ ID NO:10 or a sequence that differs from SEQ ID NO:10 by at least one amino acid substitution; the HCDR1 comprises an amino acid sequence as set forth in SEQ ID NO:12 or a sequence that differs from SEQ ID NO:12 by at least one amino acid substitution; the HCDR2 comprises an amino acid sequence as set forth in SEQ ID NO:14 or a sequence that differs from SEQ ID NO:14 by at least one amino acid substitution; and the HCDR3 comprises an amino acid sequence as set forth in SEQ ID NO:16 or a sequence that differs from SEQ ID NO:16 by at least one amino acid substitution. For instance, the disclosure encompasses a recombinant polypeptide comprising a CD123-binding domain, wherein the CD123-binding domain comprises (i) an immunoglobulin light chain variable region comprising LCDR1, LCDR2, and LCDR3, and (ii) an immunoglobulin heavy chain variable region comprising HCDR1, HCDR2, and HCDR3, wherein the LCDR1 comprises an amino acid sequence as set forth in SEQ ID NO:6 or a sequence that differs from SEQ ID NO:6 by one or two amino acid substitutions; the LCDR2 comprises an amino acid sequence as set forth in SEQ ID NO:8 or a sequence that differs from SEQ ID NO:8 by one or two amino acid substitutions; the LCDR3 comprises an amino acid sequence as set forth in SEQ ID NO:10 or a sequence that differs from SEQ ID NO:10 by one or two amino acid substitutions; the HCDR1 comprises an amino acid sequence as set forth in SEQ ID NO:12 or a sequence that differs from SEQ ID NO:12 by one or two amino acid substitutions; the HCDR2 comprises an amino acid sequence as set forth in SEQ ID NO:14 or a sequence that differs from SEQ ID NO:14 by one or two amino acid substitutions; and the HCDR3 comprises an amino acid sequence as set forth in SEQ ID NO:16 or a sequence that differs from SEQ ID NO:16 by one or two amino acid substitutions. The invention includes a recombinant polypeptide with a CD-123 binding domain that comprises (a) the LCDR1 amino acid sequence as set forth in SEQ ID NO:6; (b) the LCDR2 amino acid sequence as set forth in SEQ ID NO:8; (c) the LCDR3 amino acid sequence as set forth in SEQ ID NO:10; (d) the HCDR1 amino acid sequence as set forth in SEQ ID NO:12; (e) the HCDR2 amino acid sequence as set forth in SEQ ID NO:14; and (f) the HCDR3 amino acid sequence as set forth in SEQ ID NO:16. A recombinant polypeptide that binds CD123 may comprises (i) an immunoglobulin light chain variable region comprising an amino acid sequence that is at least 88%, at least 90%, at least 92%, at least 95%, at least 97%, at least 98% or at least 99% identical to the amino acid sequence set forth in SEQ ID NO:2; and (ii) an immunoglobulin heavy chain variable region comprising an amino acid sequence that is at least 85%, at least 90%, at least 92%, at least 95%, at least 97%, at least 98% or at least 99% identical to the amino acid sequence set forth in SEQ ID NO:4. For instance, the invention includes a recombinant polypeptide of claim 1, wherein the CD123-binding domain comprises: (i) the immunoglobulin light chain variable region comprising the amino acid sequence of SEQ ID NO:2; and (ii) the immunoglobulin heavy chain variable region comprising the amino acid sequence of SEQ ID NO:4.

In another embodiment, the invention includes a recombinant CD123-binding polypeptide comprising a CD123-binding domain, wherein the binding domain comprises an immunoglobulin light chain variable region comprising LCDR1, LCDR2, LCDR3 and an immunoglobulin heavy chain variable region comprising HCDR1, HCDR2 and HCDR3, and wherein (i) (a) the HCDR1 comprises an amino acid sequence as set forth in SEQ ID NO:28 or a sequence that differs from SEQ ID NO:28 by at least one amino acid substitution; (b) the HCDR2 comprises an amino acid sequence as set forth in SEQ ID NO:30 or a sequence that differs from SEQ ID NO:30 by at least one amino acid substitution; and (c) the HCDR3 comprises an amino acid sequence as set forth in SEQ ID NO:32 or a sequence that differs from SEQ ID NO:32 by at least one amino acid substitution; or (ii) (a) the HCDR1 comprises an amino acid sequence as set forth in SEQ ID NO:36 or a sequence that differs from SEQ ID NO:36 by at least one amino acid substitution; (b) the HCDR2 comprises an amino acid sequence as set forth in SEQ ID NO:38 or a sequence that differs from SEQ ID NO:38 by at least one amino acid substitution; and (c) the HCDR3 comprises an amino acid sequence as set forth in SEQ ID NO:40 or a sequence that differs from SEQ ID NO:40 by at least one amino acid substitution; or (iii)(a) the HCDR1 comprises an amino acid sequence as set forth in SEQ ID NO:44 or a sequence that differs from SEQ ID NO:44 by at least one amino acid substitution; (b) the HCDR2 comprises an amino acid sequence as set forth in SEQ ID NO:46 or a sequence that differs from SEQ ID NO:46 by at least one amino acid substitution; and (c) the HCDR3 comprises an amino acid sequence as set forth in SEQ ID NO:48 or a sequence that differs from SEQ ID NO:48 by at least one amino acid substitution; or (iv) (a) the HCDR1 comprises an amino acid sequence as set forth in SEQ ID NO:100 or a sequence that differs from SEQ ID NO:100 by at least one amino acid substitution; (b) the HCDR2 comprises an amino acid sequence as set forth in SEQ ID NO:102 or a sequence that differs from SEQ ID NO:102 by at least one amino acid substitution; and (c) the HCDR3 comprises an amino acid sequence as set forth in SEQ ID NO:104 or a sequence that differs from SEQ ID NO:104 by at least one amino acid substitution; or (v)(a) the HCDR1 comprises an amino acid sequence as set forth in SEQ ID NO:108 or a sequence that differs from SEQ ID NO:108 by at least one amino acid substitution; (b) the HCDR2 comprises an amino acid sequence as set forth in SEQ ID NO: 110 or a sequence that differs from SEQ ID NO: 110 by at least one amino acid substitution; and (c) the HCDR3 comprises an amino acid sequence as set forth in SEQ ID NO: 112 or a sequence that differs from SEQ ID NO: 112 by at least one amino acid substitution; or (vi)(a) the HCDR1 comprises an amino acid sequence as set forth in SEQ ID NO: 116 or a sequence that differs from SEQ ID NO: 116 by at least one amino acid substitution; (b) the HCDR2 comprises an amino acid sequence as set forth in SEQ ID NO:118 or a sequence that differs from SEQ ID NO:118 by at least one amino acid substitution; and (c) the HCDR3 comprises an amino acid sequence as set forth in SEQ ID NO:120 or a sequence that differs from SEQ ID NO:120 by at least one amino acid substitution; or (vii)(a) the HCDR1 comprises an amino acid sequence as set forth in SEQ ID NO:124 or a sequence that differs from SEQ ID NO:124 by at least one amino acid substitution; (b) the HCDR2 comprises an amino acid sequence as set forth in SEQ ID NO:126 or a sequence that differs from SEQ ID NO:126 by at least one amino acid substitution; and (c) the HCDR3 comprises an amino acid sequence as set forth in SEQ ID NO:128 or a sequence that differs from SEQ ID NO:128 by at least one amino acid substitution. The invention includes recombinant polypeptides comprising a heavy chain variable region as defined by (i)-(vii) and a light chain variable region comprising (a) the LCDR1 comprises an amino acid sequence as set forth in SEQ ID NO:22 or a sequence that differs from SEQ ID NO:22 by at least one amino acid substitution; (b) the LCDR2 comprises an amino acid sequence as set forth in SEQ ID NO:24 or a sequence that differs from SEQ ID NO:24 by at least one amino acid substitution; and (c) the LCDR3 comprises an amino acid sequence as set forth in SEQ ID NO:26 or a sequence that differs from SEQ ID NO:26 by at least one amino acid substitution. For instance, the invention includes a recombinant polypeptide comprising a light chain variable region comprises an amino acid sequence that is at least 88%, at least 90%, at least 92%, at least 95%, at least 97%, at least 98% or at least 99% identical to the amino acid sequence set forth in SEQ ID NO:18, and a heavy chain variable region comprises an amino acid sequence that is at least 85%, at least 90%, at least 92%, at least 95%, at least 97%, at least 98% or at least 99% identical to the amino acid sequence set forth in SEQ ID NO:20, 34, 42, 98, 106, 114, or 122.

In certain embodiments, a recombinant CD123-binding polypeptide comprises (a) the LCDR1 has an amino acid sequence set forth in SEQ ID NO:54 or a sequence that differs from SEQ ID NO:54 by at least one amino acid substitution; (b) the LCDR2 has an amino acid sequence set forth in SEQ ID NO:56 or a sequence that differs from SEQ ID NO:56 by at least one amino acid substitution; (c) the LCDR3 has an amino acid sequence set forth in SEQ ID NO:58 or a sequence that differs from SEQ ID NO:58 by at least one amino acid substitution; (d) the HCDR1 has an amino acid sequence set forth in SEQ ID NO:60 or a sequence that differs from SEQ ID NO:60 by at least one amino acid substitution; (e) the HCDR2 has an amino acid sequence set forth in SEQ ID NO:61 or a sequence that differs from SEQ ID NO:61 by at least one amino acid substitution; and (f) the HCDR3 has an amino acid sequence set forth in SEQ ID NO:62 or a sequence that differs from SEQ ID NO:62 by at least one amino acid substitution. For instance, the invention includes a recombinant polypeptide comprising a CD123-binding domain, wherein (i) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:50; and (ii) the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:52.

In another embodiment, the recombinant polypeptide comprising a CD123-binding domain, comprises (a) the LCDR1 comprises an amino acid sequence as set forth in SEQ ID NO:70 or a sequence that differs from SEQ ID NO:70 by at least one amino acid substitution; (b) the LCDR2 comprises an amino acid sequence as set forth in SEQ ID NO:72 or a sequence that differs from SEQ ID NO:72 by at least one amino acid substitution; (c) the LCDR3 comprises an amino acid sequence as set forth in SEQ ID NO:74 or a sequence that differs from SEQ ID NO:74 by at least one amino acid substitution; (d) the HCDR1 comprises an amino acid sequence as set forth in SEQ ID NO:76 or a sequence that differs from SEQ ID NO:76 by at least one amino acid substitution; (e) the HCDR2 comprises an amino acid sequence as set forth in SEQ ID NO:78 or a sequence that differs from SEQ ID NO:78 by at least one amino acid substitution; and (f) the HCDR3 comprises an amino acid sequence as set forth in SEQ ID NO:80 or a sequence that differs from SEQ ID NO:80 by at least one amino acid substitution. For instance, the invention includes a recombinant polypeptide comprising the variable regions set forth in SEQ ID Nos: 66 and 68.

In certain embodiments, the recombinant polypeptide comprises (a) the LCDR1 comprises an amino acid sequence as set forth in SEQ ID NO:86 or a sequence that differs from SEQ ID NO:86 by at least one amino acid substitution; (b) the LCDR2 comprises an amino acid sequence as set forth in SEQ ID NO:88 or a sequence that differs from SEQ ID NO:88 by at least one amino acid substitution; (c) the LCDR3 comprises an amino acid sequence as set forth in SEQ ID NO:90 or a sequence that differs from SEQ ID NO:90 by at least one amino acid substitution; (d) the HCDR1 comprises an amino acid sequence as set forth in SEQ ID NO:92 or a sequence that differs from SEQ ID NO:92 by at least one amino acid substitution; (e) the HCDR2 comprises an amino acid sequence as set forth in SEQ ID NO:94 or a sequence that differs from SEQ ID NO:94 by at least one amino acid substitution; and (f) the HCDR3 comprises an amino acid sequence as set forth in SEQ ID NO:96 or a sequence that differs from SEQ ID NO:96 by at least one amino acid substitution. For instance, the invention includes a polypeptide comprising the variable domains as set forth in SEQ ID NO:82 and 84.

(ii) the immunoglobulin heavy chain variable region comprising an amino acid sequence that is at least 85%, at least 90%, at least 92%, at least 95%, at least 97%, at least 98% or at least 99% identical to the amino acid sequence set forth in SEQ ID NO:84.

The polypeptides of the invention bind to human CD123 with specificity. In certain embodiments, the polypeptides bind to non-human primate CD123. In further embodiments, the polypeptides bind to cynomolgous monkey CD123. The invention includes a CD123-binding polypeptide comprising a human CD123-binding domain and a CD123-binding polypeptide comprising a humanized CD123-binding domain. In one embodiment, the CD123-binding domain is a single chain variable fragment (scFv).

The recombinant polypeptides of the invention include bi-specific polypeptides comprising a second binding domain. In one embodiment, the second binding domain binds a T-cell, CD3, CD3ε or a T-cell receptor (TCR) complex or a component of a T-cell receptor complex with specificity. For instance, the invention includes recombinant CD123-binding polypeptides comprising a CD3 binding scFv. The invention includes combining any one of the CD123-binding scFvs disclosed with a disclosed CD3 binding scFv. In one embodiment, the polypeptide comprises, from (i) the CD123-binding domain, (ii) a hinge region, (iii) an immunoglobulin constant region, (iv) a carboxyl-terminus linker, and (v) the second binding domain. For instance, the invention includes a recombinant polypeptide comprising, in order from amino to carboxyl terminus, (i) the CD123-binding domain, (ii) the hinge region, (iii) the immunoglobulin constant region, (iv) the carboxyl-terminus linker, and (v) the second binding domain.

In one embodiment of the invention, the bi-specific polypeptides comprising a CD123 binding domain and a CD3 binding domain comprise a modified immunoglobulin constant region engineered to exhibit no to minimal antibody-dependent cell-mediated cytotoxicity (ADCC) activity and/or complement-dependent cytotoxicity (CDC) activity. In one embodiment of the invention, the CD3 binding domain is derived from a monoclonal antibody selected from CRIS-7, HuM291 and I2C.

In certain embodiments of the invention, the CD123-binding polypeptide comprises (i) an amino acid sequence at least about 93% identical, at least about 95% identical, at least about 97% identical, at least about 98% identical or at least about 99% identical to the amino acid sequence of SEQ ID NO:130; (ii) an amino acid sequence at least about 93% identical, at least about 95% identical, at least about 97% identical, at least about 98% identical or at least about 99% identical to the amino acid sequence of SEQ ID NO:132; (iii) an amino acid sequence at least about 93% identical, at least about 95% identical, at least about 97% identical, at least about 98% identical or at least about 99% identical to the amino acid sequence of SEQ ID NO:134; (iv) an amino acid sequence at least about 93% identical, at least about 95% identical, at least about 97% identical, at least about 98% identical or at least about 99% identical to the amino acid sequence of SEQ ID NO:136; (v) an amino acid sequence at least about 93% identical, at least about 95% identical, at least about 97% identical, at least about 98% identical or at least about 99% identical to the amino acid sequence of SEQ ID NO:138; (vi) an amino acid sequence at least about 93% identical, at least about 95% identical, at least about 97% identical, at least about 98% identical or at least about 99% identical to the amino acid sequence of SEQ ID NO:140; (vii) an amino acid sequence at least about 93% identical, at least about 95% identical, at least about 97% identical, at least about 98% identical or at least about 99% identical to the amino acid sequence of SEQ ID NO:142; (viii) an amino acid sequence at least about 93% identical, at least about 95% identical, at least about 97% identical, at least about 98% identical or at least about 99% identical to the amino acid sequence of SEQ ID NO:144; (iv) an amino acid sequence at least about 93% identical, at least about 95% identical, at least about 97% identical, at least about 98% identical or at least about 99% identical to the amino acid sequence of SEQ ID NO:146; (x) amino acid sequence at least about 93% identical, at least about 95% identical, at least about 97% identical, at least about 98% identical or at least about 99% identical to the amino acid sequence of SEQ ID NO:148; (xi) an amino acid sequence at least about 93% identical, at least about 95% identical, at least about 97% identical, at least about 98% identical or at least about 99% identical to the amino acid sequence of SEQ ID NO:150; (xii) an amino acid sequence at least about 93% identical, at least about 95% identical, at least about 97% identical, at least about 98% identical or at least about 99% identical to the amino acid sequence of SEQ ID NO:152; (xiii) an amino acid sequence at least about 93% identical, at least about 95% identical, at least about 97% identical, at least about 98% identical or at least about 99% identical to the amino acid sequence of SEQ ID NO:154; or (xiv) an amino acid sequence at least about 93% identical, at least about 95% identical, at least about 97% identical, at least about 98% identical or at least about 99% identical to the amino acid sequence of SEQ ID NO:156.

In one embodiment of the invention, the recombinant polypeptide induces redirected T-cell cytotoxicity (RTCC). In certain embodiments, the recombinant polypeptide induces T-cell activation or T-cell proliferation. In certain embodiments, the polypeptide induces T-cell-dependent lysis of CD123-expressing cells.

In certain embodiments of the invention, the bi-specific polypeptide comprising a CD123-binding domain and a CD3-binding domain when bound to a CD3 protein on a T cell induces reduced cytokine release from said T cell as compared to an OKT3 antibody control. In certain embodiments of the invention, the bi-specific polypeptide comprising a CD123-binding domain and a CRIS-7 derived CD3-binding domain induces reduced cytokine release from said T cell as compared to a bi-specific comprising an CD3-binding domain derived from OKT3 or I2C. In certain embodiments of the invention, the bi-specific polypeptide comprising a CD123-binding domain (e.g., a CD123-binding domain comprising an amino acid sequence at least 93%, at least 95%, at least 96%, at least 97%, at least 98%, at least 99% or 100% identical to SEQ ID NO: 2 and/or SEQ ID NO:4) and a CRIS-7 derived CD3-binding domain and in the scFv-Fc-scFv format induces reduced cytokine release in a non-human primate or human as compared to a bi-specific polypeptide comprising a CD123-binding domain and I2C derived CD3-binding domain in an scFv-scFv or diabody format.

In certain embodiments of the invention, the bispecific polypeptide comprising a CD123-binding domain and a CD3-binding domain (for instance, a recombinant polypeptide comprising an amino acid sequence at least 93%, at least 95%, at least 96%, at least 97%, at least 98%, at least 99% or 100% identical to SEQ ID NO:130 or SEQ ID NO:132) induces reduced cytokine release in a non-human primate or human as compared to MGD006 or TRI168. In one embodiment of the invention, a recombinant polypeptide comprising an amino acid sequence at least 93%, at least 95%, at least 96%, at least 97%, at least 98%, at least 99% or 100% identical to SEQ ID NO:130 or SEQ ID NO:132 induces reduced levels of IFNγ, IL-2, TNFα and/or IL-10 as compared to MGD006 or TRI168.

The disclosure encompasses an isolated nucleic acid molecule encoding a CD123-binding polypeptide described herein or a portion of said CD123-binding polypeptide. The isolated nucleic acid molecule may comprise a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

The disclosure relates to an expression vector comprising a nucleic acid segment encoding a CD123-binding polypeptide described herein, wherein the nucleic acid segment is operatively linked to regulatory sequences suitable for expression of the nucleic acid segment in a host cell. The nucleic acid segment of the expression vector may comprise a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

The disclosure includes a recombinant host cell comprising an expression vector described herein.

The disclosure relates to a method for producing a CD123-binding polypeptide, the method comprising culturing a recombinant host cell comprising an expression vector described herein under conditions whereby the nucleic acid segment of the vector is expressed, thereby producing the CD123-binding polypeptide. The method may further comprise recovering the CD123-binding polypeptide.

In some embodiments, the disclosure relates to a pharmaceutical composition comprising a CD123-binding polypeptide described herein and a pharmaceutically acceptable carrier, diluent, or excipient. The pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The pharmaceutical composition formulated as an oral unit dosage form may be selected from the group consisting of: tablets, pills, pellets, capsules, powders, lozenges, granules, solutions, suspensions, emulsions, syrups, elixirs, sustained-release formulations, aerosols, and sprays.

The disclosure also relates to a method for inducing redirected T-cell cytotoxicity (RTCC) against a cell expressing CD123, the method comprising: contacting said CD123-expressing cell with a CD123-binding polypeptide described herein, wherein the second binding domain specifically binds a T-cell, CD3, CD3ε or a T-cell receptor (TCR) complex or a component of a T-cell receptor complex; and wherein said contacting is under conditions whereby RTCC against the CD123-expressing cell is induced.

The disclosure encompasses a method for inducing T-cell dependent lysis of a cell expressing CD123, the method comprising: contacting said CD123-expressing cell with a CD123-binding polypeptide or CD123-binding protein described herein, wherein the second binding domain specifically binds a T-cell, CD3, CD3ε or a T-cell receptor (TCR) complex or a component of a T-cell receptor complex; and wherein said contacting is under conditions whereby T-cell dependent lysis of the CD123-expressing cell is induced.

The disclosure encompasses a method for treating a disorder (e.g., cancer) in a subject, wherein said disorder is characterized by overexpression of CD123, the method comprising administering to the subject a therapeutically effective amount of a CD123-binding polypeptide described herein. The disclosure also relates to a CD123-binding polypeptide described herein for the manufacture of a medicament for treatment of a disorder (e.g., cancer) in a subject, wherein said disorder is characterized by overexpression of CD123. The disclosure includes a CD123-binding polypeptide described herein for use in treating a disorder (e.g., cancer) in a subject, wherein said disorder is characterized by overexpression of CD123. The cancer treated by the CD123-binding polypeptides described herein may be acute myeloid leukemia (AML), B-lymphoid leukemia, blastic plasmocytoid dendritic neoplasm (BPDCN), or hairy cell leukemia.

These and other embodiments and/or other aspects of the disclosure will become evident upon reference to the following detailed description of the disclosure and the attached drawings.

BRIEF DESCRIPTION OF THE DRAWINGS

FIG. 13 shows the WinNonlin® non-compartmental (NCA) estimates and fit of half-life (HL) for treatment groups of cynomolgus monkeys treated with TRI130, as described in Example 14.

FIG. 14 shows a graph depicting the change in lymphocyte population over time in cynomolgus monkeys treated with TRI130, as described in Example 14.

FIG. 15 shows a graph depicting the change in basophil population over time in cynomolgus monkeys treated with TRI130, as described in Example 14.

FIG. 16 shows a graph depicting the tumor burden as measured by bioluminescence levels over time in a disseminated xenograft mouse model of acute myeloid leukemia (AML), as described in Example 15.

FIG. 17 shows bioluminescent images of tumor burden in mice at day 14.

FIG. 18 shows the results of assays measuring TRI130- and TRI168-induced T-cell activation with $CD123^+$ Molm-13 target cells, as described in Example 17.

FIG. 19 shows the results of assays measuring TRI130- and TRI168-induced T-cell cytotoxicity of $CD123^+$ Molm-13 target cells, as described in Example 17.

FIG. 20 shows the results of assays measuring TRI130- and TRI168-induced T-cell cytokine release with $CD123^+$ Molm-13 target cells, as described in Example 17.

FIG. 21 shows the results of assays measuring TRI130- and TRI168-induced T-cell cytokine release in peripheral blood mononuclear cells (PBMC) cultures, as described in Example 17.

FIG. 22 shows the results of assays measuring cytotoxicity of TRI130 incubated with AML cell samples from AML subjects, as described in Example 18.

DETAILED DESCRIPTION OF THE DISCLOSURE

Figure 1A:
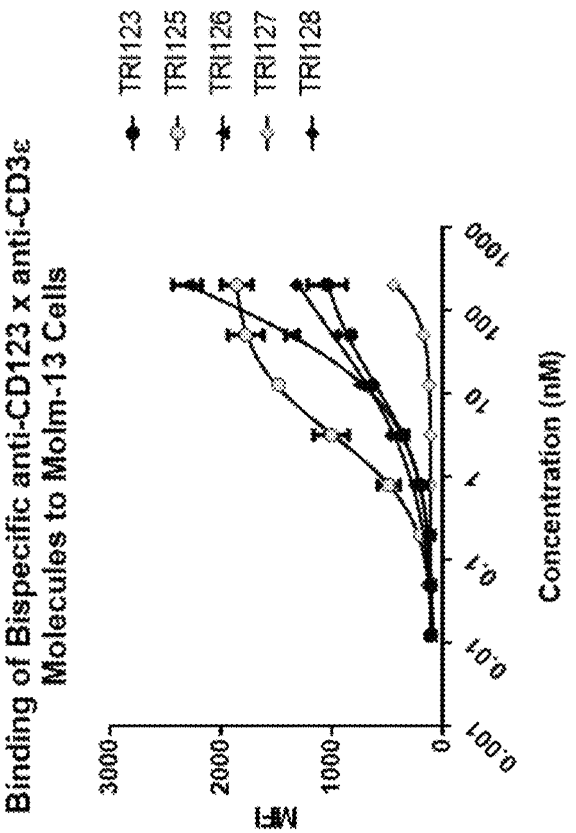
FIG. 1A-FIG. 1D show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in three independent experiments to the CD123 (+) Molm-13 human tumor cell line.
Figure 1B:
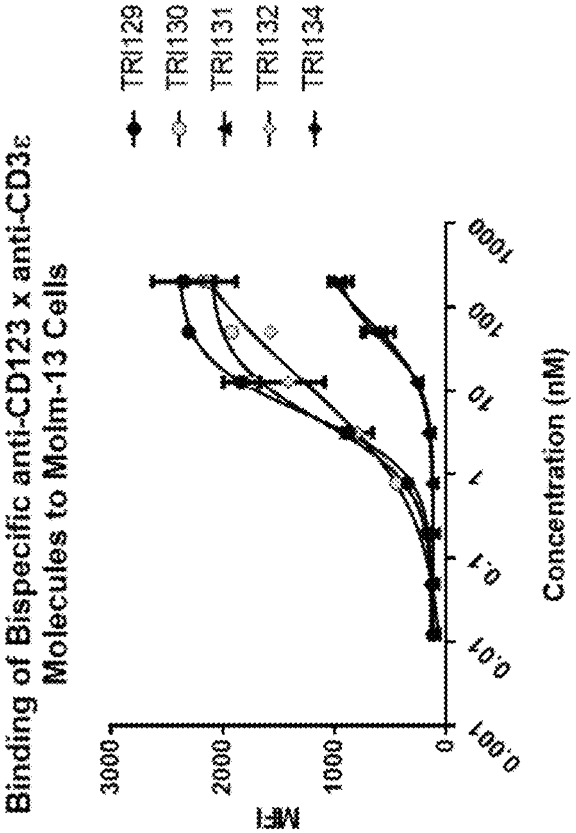
Figure 1C:
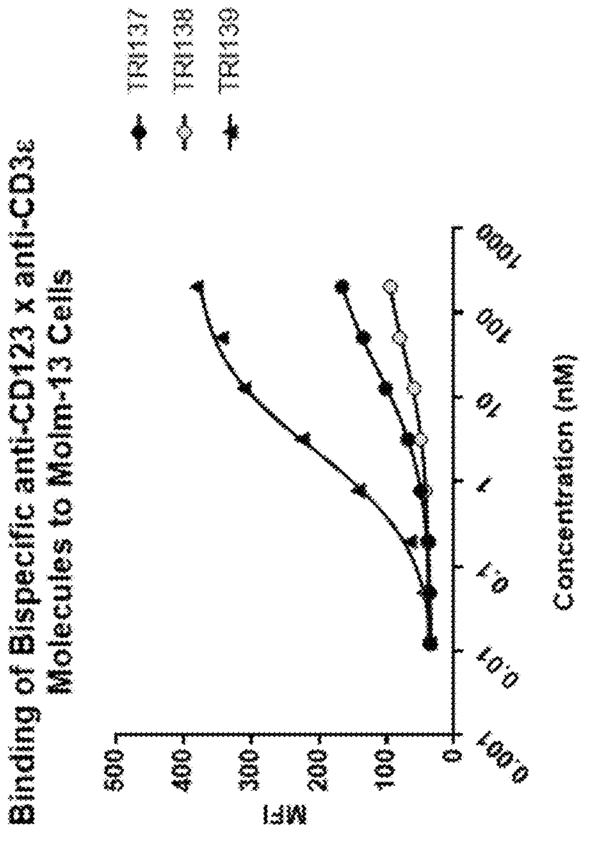
Figure 1D:
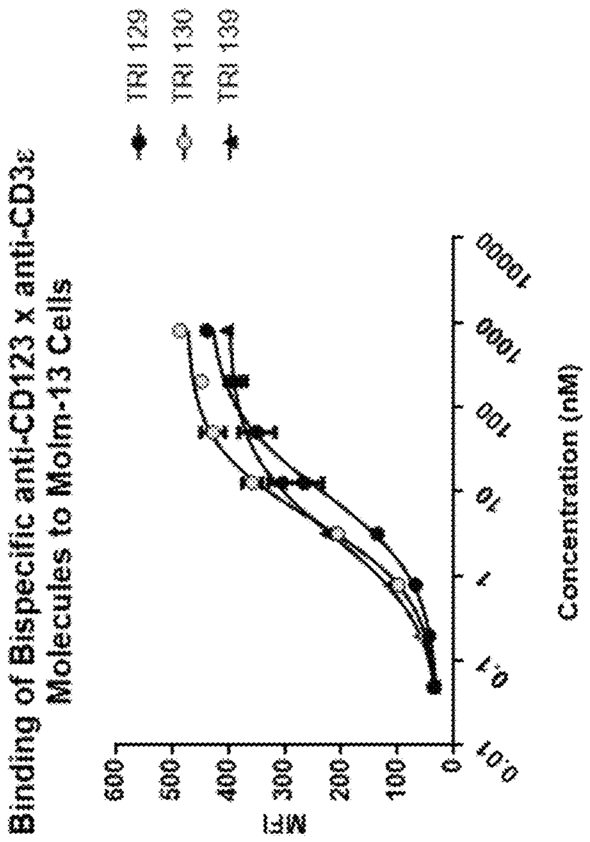

The disclosure provides binding domains that specifically bind to CD123 (also known as interleukin-3 receptor alpha chain) and binding molecules (e.g. polypeptides and proteins) that specifically bind to CD123. These binding molecules may bind specifically to CD123 and to another target. Administration of a therapeutically effective amount of a CD123-binding polypeptide or protein to a patient in need thereof is useful for treatment of certain disorders associated with the over-expression of CD123, including certain cancers. In one embodiment, a CD123-binding polypeptide or protein binds both a target cell over-expressing CD123 and a T-cell, thereby "cross-linking" the target cell over-expressing CD123 and the T-cell. The binding of both domains to their targets elicits potent target-dependent redirected T-cell cytotoxicity (RTCC) (e.g., induces target-dependent T-cell cytotoxicity, T-cell activation and/or T-cell proliferation). The CD123-binding therapeutics of the disclosure offer various advantages in treating patients, for example, effective binding to CD123, efficient induction of RTCC activity, reduced levels of cytokine release and/or a lower risk of adverse events (e.g., toxicity). In certain aspects, the CD123-binding proteins bind to CD123 more effectively in certain formats (e.g., scFv compared to parent antibody) and/or certain orientations (e.g., VL-VH compared to VH-VL), leading to higher potency and improved utility in treating disorders associated with over-expression of CD123.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

In the present description, any concentration range, percentage range, ratio range, or integer range is to be understood to include the value of any integer within the recited range and, when appropriate, fractions thereof (such as one tenth and one hundredth of an integer), unless otherwise indicated. It should be understood that the terms "a" and "an" as used herein refer to "one or more" of the enumerated components unless otherwise indicated. The use of the alternative (e.g., "or") should be understood to mean either one, both, or any combination thereof of the alternatives. As used herein, the terms "include" and "comprise" are used synonymously. In addition, it should be understood that the polypeptides comprising the various combinations of the components (e.g., domains or regions) and substituents described herein, are disclosed by the present application to the same extent as if each polypeptide was set forth individually. Thus, selection of particular components of individual polypeptides is within the scope of the present disclosure.

As used herein, the term "binding domain" or "binding region" refers to the domain, region, portion, or site of a protein, polypeptide, oligopeptide, or peptide or antibody or binding domain derived from an antibody that possesses the ability to specifically recognize and bind to a target molecule, such as an antigen, ligand, receptor, substrate, or inhibitor (e.g., CD123, CD3). Exemplary binding domains include single-chain antibody variable regions (e.g., domain antibodies, sFv, scFv, scFab), receptor ectodomains, and ligands (e.g., cytokines, chemokines). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions). A variety of assays are known for identifying binding domains of the present disclosure that specifically bind a particular target, including Western blot, ELISA, phage display library screening, and BIACORE® interaction analysis. As used herein, a CD123-binding polypeptide can have a "first binding domain" and, optionally, a "second binding domain." In certain embodiments, the "first binding domain" is a CD123-binding domain and the format is an antibody or antibody-like protein or domain. In certain embodiments comprising both the first and second binding domains, the second binding domain is a T-cell binding domain such as a scFv derived from a mouse monoclonal antibody (e.g., CRIS-7) or phage display (e.g., I2C) that binds to a T-cell surface antigen (e.g., CD3). In other embodiments, the second binding domain is a second CD123-binding domain. In yet other embodiments, the second binding domain is a binding domain other than a CD123-binding domain or a T-cell binding domain.

"Cytokine release" or "cytokine storm" or "infusion reaction" refers to the release of cytokines from T-cells. When cytokines are released into the circulation, systemic symptoms such as fever, nausea, chills, hypotension, tachycardia, asthenia, headache, rash, scratchy throat, and dyspnea can result. Some patients may experience severe, life-threatening reactions that result from massive release of cytokines. "Reduced" cytokine release refers to the to the reduction in the release of at least one cytokine (e.g., IFNγ, IL-2, TNFα and/or IL-10) following administration of a recombinant polypeptide of the invention as compared to the OKT-3 antibody or other CD3 binding bispecific molecule. Reduced cytokine release can be measured using in vitro assays or in vivo.

A binding domain or protein "specifically binds" a target if it binds the target with an affinity or $K_a$ (i.e., an equilibrium association constant of a particular binding interaction with units of 1/M) equal to or greater than $10^5$ $M^{-1}$, while not significantly binding other components present in a test sample. Binding domains can be classified as "high affinity" binding domains and "low affinity" binding domains. "High affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. "Low affinity" binding domains refer to those binding domains with a $K_a$ of up to $10^7$ $M^{-1}$, up to $10^6$ $M^{-1}$, up to $10^5$ $M^{-1}$. Alternatively, affinity can be defined as an equilibrium dissociation constant ($K_d$) of a particular binding interaction with units of M (e.g., $10^{-5}$ M to $10^{-13}$ M). Affinities of binding domain polypeptides and single chain polypeptides according to the present disclosure can be readily determined using conventional techniques (see, e.g., Scatchard et al. (1949) Ann. N.Y. Acad. Sci. 51:660; and U.S. Pat. Nos. 5,283,173, 5,468,614, or the equivalent).

"CD3" is known in the art as a multi-protein complex of six chains (see, e.g., Abbas and Lichtman, 2003; Janeway et al., p. 172 and 178, 1999), which are subunits of the T-cell receptor complex. In mammals, the CD3 subunits of the T-cell receptor complex are a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T-cell receptor chains. The intracellular tails of the CD3γ, CD3δ, and CD3ε chains each contain a single conserved motif known as an immunoreceptor tyrosine-based activation motif or ITAM, whereas each CD3ζ chain has three. It is believed the ITAMs are important for the signaling capacity of a TCR complex. CD3 as used in the present disclosure can be from various animal species, including human, monkey, mouse, rat, or other mammals.

As used herein, a "conservative substitution" is recognized in the art as a substitution of one amino acid for another amino acid that has similar properties. Exemplary conservative substitutions are well-known in the art (see, e.g., WO 97/09433, page 10, published Mar. 13, 1997; Lehninger, Biochemistry, Second Edition; Worth Publishers, Inc. NY: NY (1975), pp. 71-77; Lewin, Genes IV, Oxford University Press, NY and Cell Press, Cambridge, MA (1990), p. 8). In certain embodiments, a conservative substitution includes a leucine to serine substitution.

As used herein, the term "derivative" refers to a modification of one or more amino acid residues of a peptide by chemical or biological means, either with or without an enzyme, e.g., by glycosylation, alkylation, acylation, ester formation, or amide formation.

As used herein, a polypeptide or amino acid sequence "derived from" a designated polypeptide or protein refers to the origin of the polypeptide. In certain embodiments, the polypeptide or amino acid sequence which is derived from a particular sequence (sometimes referred to as the "starting" or "parent" or "parental" sequence) has an amino acid sequence that is essentially identical to the starting sequence or a portion thereof, wherein the portion consists of at least 10-20 amino acids, at least 20-30 amino acids, or at least 30-50 amino acids, or at least 50-150 amino acids, or which is otherwise identifiable to one of ordinary skill in the art as having its origin in the starting sequence. For example, a binding domain can be derived from an antibody, e.g., a Fab, F(ab')2, Fab', scFv, single domain antibody (sdAb), etc.

Polypeptides derived from another polypeptide can have one or more mutations relative to the starting polypeptide, e.g., one or more amino acid residues which have been substituted with another amino acid residue or which has one or more amino acid residue insertions or deletions. The polypeptide can comprise an amino acid sequence which is not naturally occurring. Such variations necessarily have less than 100% sequence identity or similarity with the starting polypeptide. In one embodiment, the variant will have an amino acid sequence from about 60% to less than 100% amino acid sequence identity or similarity with the amino acid sequence of the starting polypeptide. In another embodiment, the variant will have an amino acid sequence from about 75% to less than 100%, from about 80% to less than 100%, from about 85% to less than 100%, from about 90% to less than 100%, from about 95% to less than 100% amino acid sequence identity or similarity with the amino acid sequence of the starting polypeptide.

As used herein, unless otherwise provided, a position of an amino acid residue in a variable region of an immunoglobulin molecule is numbered according to the IMGT numbering convention (Brochet, X, et al, Nucl. Acids Res. (2008) 36, W503-508) and a position of an amino acid residue in a constant region of an immunoglobulin molecule is numbered according to EU nomenclature (Ward et al., 1995 Therap. *Immunol.* 2:77-94). Other numbering conventions are known in the art (e.g., the Kabat numbering convention (Kabat, Sequences of Proteins of Immunological Interest, $5^{th}$ ed. Bethesda, MD: Public Health Service, National Institutes of Health (1991)).

As used herein, the term "dimer" refers to a biological entity that consists of two subunits associated with each other via one or more forms of intramolecular forces, including covalent bonds (e.g., disulfide bonds) and other interactions (e.g., electrostatic interactions, salt bridges, hydrogen bonding, and hydrophobic interactions), and is stable under appropriate conditions (e.g., under physiological conditions, in an aqueous solution suitable for expressing, purifying, and/or storing recombinant proteins, or under conditions for non-denaturing and/or non-reducing electrophoresis). A "heterodimer" or "heterodimeric protein," as used herein, refers to a dimer formed from two different polypeptides. A heterodimer does not include an antibody formed from four polypeptides (i.e., two light chains and two heavy chains). A "homodimer" or "homodimeric protein," as used herein, refers to a dimer formed from two identical polypeptides. The recombinant polypeptides of the invention exist primarily in a dimerized form. All disclosure of the polypeptide, including characteristics and activities (such as binding and RTCC) should be understood to include the polypeptide in its dimer form as well as other multimeric forms.

In some embodiments, a CD123-binding polypeptide comprises, in order from amino-terminus to carboxyl-terminus or in order from carboxyl-terminus to amino-terminus, (i) the CD123-binding domain, (ii) a hinge region, (iii) an immunoglobulin constant region, (iv) a carboxyl-terminus linker (or an amino-terminus linker), and (v) a second binding domain. As used herein and depending on context, a "hinge region" or a "hinge" refers to a polypeptide region between a binding domain (e.g., a CD123-binding domain) and an immunoglobulin constant region. As used herein and depending on context, a "linker" may refer to (1) a polypeptide region between $V_H$ and $V_L$ regions in a single-chain Fv (scFv) or (2) a polypeptide region between an immunoglobulin constant region and a second binding domain in a CD123-binding polypeptide comprising two binding domains. A polypeptide region between an immunoglobulin constant region and a second binding domain in a CD123-binding polypeptide comprising two binding domains may also be referred to as a "carboxyl-terminus linker" or an "amino-terminus linker." Non-limiting examples of carboxyl-terminus and amino-terminus linkers include flexible linkers comprising glycine-serine (e.g., $(Gly_4Ser)$) repeats (SEQ ID NO: 315), and linkers derived from (a) an interdomain region of a transmembrane protein (e.g., a type I transmembrane protein); (b) a stalk region of a type II C-lectin; or (c) an immunoglobulin hinge. Non-limiting examples of hinges and linkers are provided in Tables 1 and 2. In some embodiments, a "linker" provides a spacer function compatible with interaction of the two sub-binding domains so that the resulting polypeptide retains a specific binding affinity to the same target molecule as an antibody that comprises the same light and heavy chain variable regions. In certain embodiments, a linker is comprised of five to about 35 amino acids, for instance, about 15 to about 25 amino acids. In some embodiments, a linker is comprised of at least 5 amino acids, at least 7 amino acids or at least 9 amino acids.

A "wild-type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody. In certain embodiments, a wild type immunoglobulin hinge region sequence is human, and can comprise a human IgG hinge region.

An "altered wild-type immunoglobulin hinge region" or "altered immunoglobulin hinge region" refers to (a) a wild type immunoglobulin hinge region with up to 30% amino acid changes (e.g., up to 25%, 20%, 15%, 10%, or 5% amino acid substitutions or deletions), or (b) a portion of a wild type immunoglobulin hinge region that has a length of about 5 amino acids (e.g., about 5, 6, 7, 8, 9, 10, 11, 12, 13, 14, 15, 16, 17, 18, 19, or 20 amino acids) up to about 120 amino acids (for instance, having a length of about 10 to about 40 amino acids or about 15 to about 30 amino acids or about 15 to about 20 amino acids or about 20 to about 25 amino acids), has up to about 30% amino acid changes (e.g., up to about 25%, 20%, 15%, 10%, 5%, 4%, 3%, 2%, or 1% amino acid substitutions or deletions or a combination thereof), and has an IgG core hinge region as disclosed in US 2013/0129723 and US 2013/0095097.

As used herein, the term "humanized" refers to a process of making an antibody or immunoglobulin binding proteins and polypeptides derived from a non-human species (e.g., mouse or rat) less immunogenic to humans, while still retaining antigen-binding properties of the original antibody, using genetic engineering techniques. In some embodiments, the binding domain(s) of an antibody or immunoglobulin binding proteins and polypeptides (e.g., light and heavy chain variable regions, Fab, scFv) are humanized. Non-human binding domains can be humanized using techniques known as CDR grafting (Jones et al., *Nature* 321:522 (1986)) and variants thereof, including "reshaping" (Verhoeyen, et al., 1988 *Science* 239:1534-1536; Riechmann, et al., 1988 *Nature* 332:323-337; Tempest, et al., *Bio/Technol* 1991 9:266-271), "hyperchimerization" (Queen, et al., 1989 *Proc Natl Acad Sci USA* 86:10029-10033; Co, et al., 1991 *Proc Natl Acad Sci USA* 88:2869-2873; Co, et al., 1992 *J Immunol* 148:1149-1154), and "veneering" (Mark, et al., "Derivation of therapeutically active humanized and veneered anti-CD18 antibodies." In: Metcalf B W, Dalton B J, eds. Cellular adhesion: molecular definition to therapeutic potential. New York: Plenum Press, 1994: 291-312). If derived from a non-human source, other regions of the antibody or immunoglobulin binding proteins and polypeptides, such as the hinge region and constant region domains, can also be humanized.

An "immunoglobulin dimerization domain" or "immunoglobulin heterodimerization domain", as used herein, refers to an immunoglobulin domain of a polypeptide chain that preferentially interacts or associates with a different immunoglobulin domain of a second polypeptide chain, wherein the interaction of the different immunoglobulin heterodimerization domains substantially contributes to or efficiently promotes heterodimerization of the first and second polypeptide chains (i.e., the formation of a dimer between two different polypeptide chains, which is also referred to as a "heterodimer"). The interactions between immunoglobulin heterodimerization domains "substantially contributes to or efficiently promotes" the heterodimerization of first and second polypeptide chains if there is a statistically significant reduction in the dimerization between the first and second polypeptide chains in the absence of the immunoglobulin heterodimerization domain of the first polypeptide chain and/or the immunoglobulin heterodimerization domain of the second polypeptide chain. In certain embodiments, when the first and second polypeptide chains are co-expressed, at least 60%, at least about 60% to about 70%, at least about 70% to about 80%, at least 80% to about 90%, 91%, 92%, 93%, 94%, 95%, 96%, 97%, 98%, or 99% of the first and second polypeptide chains form heterodimers with each other. Representative immunoglobulin heterodimerization domains include an immunoglobulin CH1 domain, an immunoglobulin CL domain (e.g., CK or CA isotypes), or derivatives thereof, including wild type immunoglobulin CH1 and CL domains and altered (or mutated) immunoglobulin CH1 and CL domains, as provided therein.

An "immunoglobulin constant region" or "constant region" is a term defined herein to refer to a peptide or polypeptide sequence that corresponds to or is derived from part or all of one or more constant region domains. In certain embodiments, the immunoglobulin constant region corresponds to or is derived from part or all of one or more constant region domains, but not all constant region domains of a source antibody. In certain embodiments, the constant region comprises IgG CH2 and CH3 domains, e.g., IgG1 CH2 and CH3 domains. In certain embodiments, the constant region does not comprise a CH1 domain. In certain embodiments, the constant region domains making up the constant region are human. In some embodiments (for example, in certain variations of a CD123-binding polypeptide or protein comprising a second binding domain that specifically binds CD3 or another T-cell surface antigen), the constant region domains of a fusion protein of this disclosure lack or have minimal effector functions of antibody-dependent cell-mediated cytotoxicity (ADCC) and complement activation and complement-dependent cytotoxicity (CDC), while retaining the ability to bind some $F_C$ receptors (such as $F_C$Rn, the neonatal Fc receptor) and retaining a relatively long half-life in vivo. In other variations, a fusion protein of this disclosure includes constant domains that retain such effector function of one or both of ADCC and CDC. In certain embodiments, a binding domain of this disclosure is fused to a human IgG1 constant region, wherein the IgG1 constant region has one or more of the following amino acids mutated: leucine at position 234 (L234), leucine at position 235 (L235), glycine at position 237 (G237), glutamate at position 318 (E318), lysine at position 320 (K320), lysine at position 322 (K322), or any combination thereof (numbering according to EU). For example, any one or more of these amino acids can be changed to alanine. In a further embodiment, an IgG1 Fc domain has each of L234, L235, G237, E318, K320, and K322 (according to EU numbering) mutated to an alanine (i.e., L234A, L235A, G237A, E318A, K320A, and K322A, respectively), and optionally an N297A mutation as well (i.e., essentially eliminating glycosylation of the CH2 domain). In another embodiment, the IgG1 Fc domain has each of L234A, L235A, G237A and K322A mutations. For instance, the invention includes a recombinant polypeptide comprising a CD123 binding domain or scFv with an amino acid sequence at least 93%, at least 95%, at least 97%, at least 98%, at least 99% or 100% identical to SEQ ID NO:130; an IgG1 domain comprising the mutations L234A, L235A, G237A and K322A; and a CD3 binding domain. The invention includes a recombinant polypeptide comprising a CD123 binding domain comprising an amino acid sequence at least 93%, at least 95%, at least 97%, at least 98%, at least 99% or 100% identical to SEQ ID NO:130; an IgG1 domain comprising the mutations L234A, L235A, G237A and K322A; and a CD3 binding domain comprising an amino acid sequence at least 93%, at least 95%, at least 97%, at least 98%, at least 99% or 100% identical to SEQ ID NO:192 or SEQ ID NO:193.

"Fc region" or "Fc domain" refers to a polypeptide sequence corresponding to or derived from the portion of a source antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. However, more recently the term has been applied to a single chain consisting of CH3, CH2, and at least a portion of the hinge sufficient to form a disulfide-linked dimer with a second such chain. For a review of immunoglobulin structure and function, see Putnam, *The Plasma Proteins*, Vol. V (Academic Press, Inc., 1987), pp. 49-140; and Padlan, *Mol. Immunol.* 31:169-217, 1994. As used herein, the term Fc includes variants of naturally occurring sequences.

In some embodiments, a CD123-binding protein comprises a protein scaffold as generally disclosed in, for example, in US Patent Application Publication Nos. 2003/0133939, 2003/0118592, and 2005/0136049. A CD123-binding protein may comprise, in order from amino-terminus to carboxyl-terminus: a first binding domain, a hinge region, and an immunoglobulin constant region. In other embodiments, a CD123-binding protein comprises a protein scaffold as generally disclosed in, for example, in US Patent Application Publication No. 2009/0148447. A CD123-binding protein may comprise, in order from amino-terminus to carboxyl-terminus: an immunoglobulin constant region, a hinge region and a first binding domain.

CD123-binding polypeptides and proteins disclosed herein may incorporate a multi-specific binding protein scaffold. Multi-specific binding proteins and polypeptides using scaffolds are disclosed, for instance, in PCT Application Publication No. WO 2007/146968, U.S. Patent Application Publication No. 2006/0051844, PCT Application Publication No. WO 2010/040105, PCT Application Publication No. WO 2010/003108, U.S. Pat. Nos. 7,166,707 and 8,409,577, which are each incorporated herein by reference in their entirety. A CD123-binding protein may comprise two binding domains (the domains can be designed to specifically bind the same or different targets), a hinge region, a linker (e.g., a carboxyl-terminus or an amino-terminus linker), and an immunoglobulin constant region. A CD123-binding protein may be a homodimeric protein comprising two identical, disulfide-bonded polypeptides.

Figure 11:
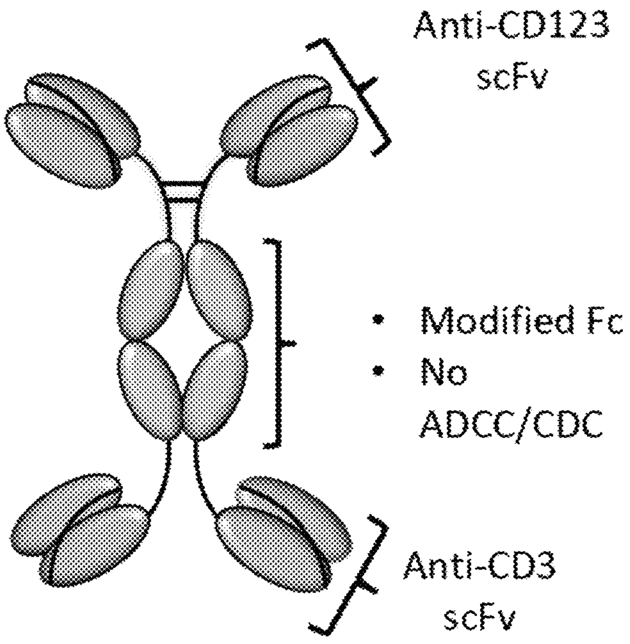
FIG. 11 is an illustration of a recombinant CD123-binding polypeptide capable of RTCC in the CD123-binding domain-hinge domain-immunoglobulin constant domain-CD3 binding domain configuration.

In one embodiment of the invention, the CD123-binding protein comprises, in order from amino-terminus to carboxyl terminus, a first binding domain, a hinge region, an immunoglobulin constant region and a second binding domain. FIG. 11 illustrates a CD123-binding protein in this configuration.

As used herein, the term "junction amino acids" or "junction amino acid residues" refers to one or more (e.g., about 2-10) amino acid residues between two adjacent regions or domains of a polypeptide, such as between a hinge and an adjacent immunoglobulin constant region or between a hinge and an adjacent binding domain or between a peptide linker and an adjacent immunoglobulin variable domain or an adjacent immunoglobulin constant region. Junction amino acids can result from the construct design of a polypeptide (e.g., amino acid residues resulting from the use of a restriction enzyme site during the construction of a nucleic acid molecule encoding a polypeptide).

As used herein, the term "patient in need" or "subject in need" refers to a patient at risk of, or suffering from, a disease, disorder or condition that is amenable to treatment or amelioration with a CD123-binding protein or polypeptide or a composition thereof provided herein. A patient in need may, for instance, be a patient diagnosed with a disease associated with the expression of CD123 such as acute myeloid leukemia (AML), B-lymphoid leukemia, blastic plasmocytoid dendritic neoplasms (BPDCN), hairy cell leukemia (HCL), myelodysplastic syndrome (MDS), acute lymphoblastic leukemia (ALL), refractory anemia with excess blasts (RAEB), chronic myeloid leukemia and Hodgkin's lymphoma.

As used herein, the term "pharmaceutically acceptable" refers to molecular entities and compositions that do not generally produce allergic or other serious adverse reactions when administered using routes well known in the art. Molecular entities and compositions approved by a regulatory agency of the Federal or a state government or listed in the U.S. Pharmacopeia or other generally recognized pharmacopeia for use in animals, and more particularly in humans are considered to be "pharmaceutically acceptable."

As used herein, the term "promoter" refers to a region of DNA involved in binding RNA polymerase to initiate transcription.

As used herein, the terms "nucleic acid," "nucleic acid molecule," or "polynucleotide" refer to deoxyribonucleotides or ribonucleotides and polymers thereof in either single- or double-stranded form. Unless specifically limited, the terms encompass nucleic acids containing analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions can be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J. Biol. Chem.* 260:2605-2608; Cassol et al. (1992); Rossolini et al. (1994) *Mol. Cell. Probes* 8:91-98). The term nucleic acid is used interchangeably with gene, cDNA, and mRNA encoded by a gene. As used herein, the terms "nucleic acid," "nucleic acid molecule," or "polynucleotide" are intended to include DNA molecules (e.g., cDNA or genomic DNA), RNA molecules (e.g., mRNA), analogs of the DNA or RNA generated using nucleotide analogs, and derivatives, fragments and homologs thereof.

The term "expression" refers to the biosynthesis of a product encoded by a nucleic acid. For example, in the case of nucleic acid segment encoding a polypeptide of interest, expression involves transcription of the nucleic acid segment into mRNA and the translation of mRNA into one or more polypeptides.

The terms "expression unit" and "expression cassette" are used interchangeably herein and denote a nucleic acid segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. In addition to a transcriptional promoter and terminator, an expression unit can further include other nucleic acid segments such as, e.g., an enhancer or a polyadenylation signal.

The term "expression vector," as used herein, refers to a nucleic acid molecule, linear or circular, comprising one or more expression units. In addition to one or more expression units, an expression vector can also include additional nucleic acid segments such as, for example, one or more origins of replication or one or more selectable markers. Expression vectors are generally derived from plasmid or viral DNA, or can contain elements of both.

As used herein, the term "sequence identity" refers to a relationship between two or more polynucleotide sequences or between two or more polypeptide sequences. When a position in one sequence is occupied by the same nucleic acid base or amino acid residue in the corresponding position of the comparator sequence, the sequences are said to be "identical" at that position. The percentage "sequence identity" is calculated by determining the number of positions at which the identical nucleic acid base or amino acid residue occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window. The comparison window for nucleic acid sequences can be, for instance, at least 20, 30, 40, 50, 60, 70, 80, 90, 100, 110, 120, 130, 140, 150, 160, 170, 180, 190, 200, 300, 400, 500, 600, 700, 800, 900 or 1000 or more nucleic acids in length. The comparison window for polypeptide sequences can be, for instance, at least 20, 30, 40, 50, 60, 70, 80, 90, 100, 110, 120, 130, 140, 150, 160, 170, 180, 190, 200, 300 or more amino acids in length. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which was available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (Proc. Natl. Acad. Sci. USA 90(12):5873-5877, 1993). When utilizing "BLAST 2 Sequences," parameters that were default parameters as of Sep. 1, 2004, can be used for word size (3), open gap penalty (11), extension gap penalty (1), gap dropoff (50), expect value (10) and any other required parameter including but not limited to matrix option. Two nucleotide or amino acid sequences are considered to have "substantially similar sequence identity" or "substantial sequence identity" if the two sequences have at least 80%, at least 85%, at least 90%, at least 95%, at least 96%, at least 97%, at least 98%, or at least 99% sequence identity relative to each other.

As used herein, a "polypeptide" or "polypeptide chain" is a single, linear and contiguous arrangement of covalently linked amino acids. Polypeptides can have or form one or more intrachain disulfide bonds. With regard to polypeptides as described herein, reference to amino acid residues corresponding to those specified by SEQ ID NO includes post-translational modifications of such residues.

As used herein, "CD123-binding protein" may be used interchangeably with "CD123-binding polypeptide," "polypeptide," and "recombinant polypeptide." Such molecules specifically bind to CD123 (e.g., human CD123), also known as Cluster of Differentiation 123, Interleukin-3 receptor alpha chain, and IL3RA. CD123 is a type I transmembrane glycoprotein, with an extracellular domain comprising a predicted Ig-like domain and two FnIII domains. The CD123-binding proteins of the disclosure bind to the extracellular domain of CD123. The term "CD123" may refer to any isoform of CD123. Exemplary human CD123 nucleotide and amino acid sequences are provided in SEQ ID NOs:205 and 206 and SEQ ID NOs:207 and 208, respectively. CD123 associates with the beta chain of the interleukin-3 receptor to form the receptor.

A "protein" is a macromolecule comprising one or more polypeptide chains. A protein can also comprise non-peptidic components, such as carbohydrate groups. Carbohydrates and other non-peptidic substituents can be added to a protein by the cell in which the protein is produced, and will vary with the type of cell. Proteins are defined herein in terms of their amino acid backbone structures; substituents such as carbohydrate groups are generally not specified, but may be present nonetheless. A protein may be an antibody or an antigen-binding fragment of an antibody. In some embodiments, a protein may also be an scFv-Fc-scFv molecule, scFv-scFv dimer, or a diabody.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl-terminus of the reference sequence, but is not necessarily at the carboxyl-terminus of the complete polypeptide.

"T-cell receptor" (TCR) is a molecule found on the surface of T-cells that, along with CD3, is generally responsible for recognizing antigens bound to major histocompatibility complex (MHC) molecules. It consists of a disulfide-linked heterodimer of the highly variable α and β chains in most T-cells. In other T-cells, an alternative receptor made up of variable γ and δ chains is expressed. Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Abbas and Lichtman, *Cellular and Molecular Immunology* (5th Ed.), Editor: Saunders, Philadelphia, 2003; Janeway et al., *Immunobiology: The Immune System in Health and Disease,* 4$^{th}$ Ed., Current Biology Publications, p148, 149, and 172, 1999). TCR as used in the present disclosure can be from various animal species, including human, mouse, rat, or other mammals.

"TCR complex," as used herein, refers to a complex formed by the association of CD3 chains with other TCR chains. For example, a TCR complex can be composed of a CD3γ chain, a CD3δ chain, two CD3ε chains, a homodimer of CD3ζ chains, a TCRα chain, and a TCRβ chain. Alternatively, a TCR complex can be composed of a CD3γ chain, a CD3δ chain, two CD3ε chains, a homodimer of CD3ζ chains, a TCRγ chain, and a TCRδ chain.

"A component of a TCR complex," as used herein, refers to a TCR chain (i.e., TCRα, TCRβ, TCRγ or TCRδ), a CD3 chain (i.e., CD3γ, CD3δ, CD3ε or CD3ζ), or a complex formed by two or more TCR chains or CD3 chains (e.g., a complex of TCRα and TCRβ, a complex of TCRγ and TCRδ, a complex of CD3ε and CD3δ, a complex of CD3γ and CD3ε, or a sub-TCR complex of TCRα, TCRβ, CD3γ, CD3δ, and two CD3ε chains).

"Antibody-dependent cell-mediated cytotoxicity" and "ADCC," as used herein, refer to a cell-mediated process in which nonspecific cytotoxic cells that express FcγRs (e.g., monocytic cells such as Natural Killer (NK) cells and macrophages) recognize bound antibody (or other protein capable of binding FcγRs) on a target cell and subsequently cause lysis of the target cell. In principle, any effector cell with an activating FcγR can be triggered to mediate ADCC. The primary cells for mediating ADCC are NK cells, which express only FcγRIII, whereas monocytes, depending on their state of activation, localization, or differentiation, can express FcγRI, FcγRII, and FcγRIII. For a review of FcγR expression on hematopoietic cells, see, e.g., Ravetch et al., 1991, Annu. Rev. Immunol., 9:457-92.

The term "having ADCC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)), is capable of mediating antibody-dependent cell-mediated cytotoxicity (ADCC) through binding of a cytolytic Fc receptor (e.g., FcγRIII) on a cytolytic immune effector cell expressing the Fc receptor (e.g., an NK cell).

"Complement-dependent cytotoxicity" and "CDC," as used herein, refer to a process in which components in normal serum ("complement"), together with an antibody or other C1q-complement-binding protein bound to a target antigen, exhibit lysis of a target cell expressing the target antigen. Complement consists of a group of serum proteins that act in concert and in an orderly sequence to exert their effect.

The terms "classical complement pathway" and "classical complement system," as used herein, are synonymous and refer to a particular pathway for the activation of complement. The classical pathway requires antigen-antibody complexes for initiation and involves the activation, in an orderly fashion, of nine major protein components designated C1 through C9. For several steps in the activation process, the product is an enzyme that catalyzes the subsequent step. This cascade provides amplification and activation of large amounts of complement by a relatively small initial signal.

The term "having CDC activity," as used herein in reference to a polypeptide or protein, means that the polypeptide or protein (for example, one comprising an immunoglobulin hinge region and an immunoglobulin constant region having CH2 and CH3 domains, such as derived from IgG (e.g., IgG1)) is capable of mediating complement-dependent cytotoxicity (CDC) through binding of C1q complement protein and activation of the classical complement system. In one embodiment of the invention, the recombinant polypeptide has been modified to abate CDC activity.

"Redirected T-cell cytotoxicity" and "RTCC," as used herein, refer to a T-cell-mediated process in which a cytotoxic T-cell is recruited to a target cell using a multi-specific protein that is capable of specifically binding both the cytotoxic T-cell and the target cell, and whereby a target-dependent cytotoxic T-cell response is elicited against the target cell. Polypeptides and proteins comprising anti-CD123 and anti-CD3 binding domains, as disclosed herein, are capable of RTCC.

As used herein, the term "treatment," "treating," or "ameliorating" refers to either a therapeutic treatment or prophylactic/preventative treatment. A treatment is therapeutic if at least one symptom of disease in an individual receiving treatment improves or a treatment can delay worsening of a progressive disease in an individual, or prevent onset of additional associated diseases.

As used herein, the term "therapeutically effective amount (or dose)" or "effective amount (or dose)" of a specific binding molecule or compound refers to that amount of the compound sufficient to result in amelioration of one or more symptoms of the disease being treated in a statistically significant manner or a statistically significant improvement in organ function. When referring to an individual active ingredient, administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or concurrently in separate formulations).

As used herein, the term "transformation," "transfection," and "transduction" refer to the transfer of nucleic acid (i.e., a nucleotide polymer) into a cell. As used herein, the term "genetic transformation" refers to the transfer and incorporation of DNA, especially recombinant DNA, into a cell. The transferred nucleic acid can be introduced into a cell via an expression vector.

As used herein, the term "variant" or "variants" refers to a nucleic acid or polypeptide differing from a reference nucleic acid or polypeptide, but retaining essential properties thereof. Generally, variants are overall closely similar, and, in many regions, identical to the reference nucleic acid or polypeptide. For instance, a variant may exhibit at least about 70%, at least about 80%, at least about 90%, at least about 95%, at least about 96%, at least about 97%, at least about 98% or at least about 99% sequence identity compared to the active portion or full length reference nucleic acid or polypeptide.

The terms "light chain variable region" (also referred to as "light chain variable domain" or "VL" or $V_L$) and "heavy chain variable region" (also referred to as "heavy chain variable domain" or "VH" or $V_H$) refer to the variable binding region from an antibody light and heavy chain, respectively. The variable binding regions are made up of discrete, well-defined sub-regions known as "complementarity determining regions" (CDRs) and "framework regions" (FRs), generally comprising in order FR1-CDR1-FR2-CDR2-FR3-CDR3-FR4 from amino-terminus to carboxyl-terminus. In one embodiment, the FRs are humanized. The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM). A "Fab" (fragment antigen binding) is the part of an antibody that binds to antigens and includes the variable region and CH1 domain of the heavy chain linked to the light chain via an inter-chain disulfide bond.

The present disclosure describes binding domains that specifically bind CD123 (e.g., human CD123), as well as polypeptides and proteins comprising these binding domains. In some embodiments, the CD123-binding proteins and polypeptides comprise a second binding domain, which may bind to CD123 or to a different target. The polypeptides and proteins comprising binding domains of this disclosure can further comprise immunoglobulin constant regions, linker peptides, hinge regions, immunoglobulin dimerization/heterodimerization domains, junctional amino acids, tags, etc. These components of the disclosed polypeptides and proteins are described in further detail below.

Additionally, the CD123-binding polypeptides and proteins disclosed herein can be in the form of an antibody or a fusion protein of any of a variety of different formats (e.g., the fusion protein can be in the form of a CD123-binding bispecific or multi-specific molecule). Non-limiting examples of bispecific molecules include a scFv-Fc-scFv molecule. Some bispecific molecules comprise or consist of an anti-CD123 scFv linked to a second binding domain scFv and do not include other sequences such as an immunoglobulin constant region. In other embodiments, a CD123-binding protein is a diabody.

A CD123-binding protein in accordance with the present disclosure generally includes at least one CD123-binding polypeptide chain comprising (a) a CD123-binding domain as set forth herein. In certain variations, the CD123-binding polypeptide further includes (b) a hinge region carboxyl-terminal to the CD123-binding domain, and (c) an immunoglobulin constant region. In further variations, the CD123-binding polypeptide further includes (d) a carboxyl-terminus linker carboxyl-terminal to the immunoglobulin constant region, and (e) a second binding domain carboxyl-terminal to the carboxyl-terminus linker.

In yet other variations, the CD123-binding polypeptide comprises (b) a hinge region amino-terminal to the CD123-binding domain, and (c) an immunoglobulin sub-region amino-terminal to the hinge region.

In some embodiments, recombinant polypeptides are capable of homodimerization, typically through disulfide bonding, via the immunoglobulin constant region and/or hinge region (e.g., via an immunoglobulin constant region comprising IgG CH2 and CH3 domains and an IgG hinge region). Thus, in certain embodiments of the present disclosure, two identical single chain CD123-binding polypeptides homodimerize to form a dimeric CD123-binding protein. An example of a homodimer of the invention is provided in FIG. 11.

In other embodiments, a CD123-binding polypeptide includes a heterodimerization domain that is capable of heterodimerization with a different heterodimerization domain in a second, non-identical polypeptide chain. In certain variations, the second polypeptide chain for heterodimerization includes a second binding domain. Accordingly, in certain embodiments of the present disclosure, two non-identical polypeptide chains, one comprising the CD123-binding domain and the second optionally comprising a second binding domain, dimerize to form a heterodimeric CD123-binding protein. Examples of types of heterodimers include those described in U.S. Patent Application Publication No. 2013/0095097 and US 2013/0129723.

In some embodiments, a CD123-binding domain, protein or polypeptide is conjugated to a drug or a toxic moiety.

CD123-binding polypeptides, proteins, and their various components used in the therapeutics of the present disclosure are further described below.

As indicated above, the disclosure relates to binding domains that specifically bind CD123. In some variations, the CD123-binding domain is capable of competing for binding to CD123 with an antibody having $V_L$ and $V_H$ regions having amino acid sequences as shown in SEQ ID NO:194 and SEQ ID NO:196, respectively (e.g., 12F1). The murine anti-CD123 antibody 12F1 is described in, for example, U.S. Patent Application Publication No. 2013/041739 and Kuo et al, (2012) *Protein Eng Design Select*, p 1-9.

The CD123-binding domain may comprise sequences shown in Table 3, and some relevant SEQ ID NOs are summarized in Table 6. In certain embodiments, the CD123-binding domain comprises (i) an immunoglobulin light chain variable region (VL) comprising CDRs LCDR1, LCDR2, and LCDR3, and (ii) an immunoglobulin heavy chain variable region (VH) comprising CDRs HCDR1, HCDR2, and HCDR3 with HCDR1 comprising an amino acid sequence as set forth in SEQ ID NO:12, with HCDR2 comprising an amino acid sequence as set forth in SEQ ID NO:14 and with HCDR3 comprising an amino acid sequence as set forth in SEQ ID NO:16. In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:6 or a sequence that differs from SEQ ID NO:6 by at least one amino acid substitution; (ii) the LCDR2 has an amino acid sequence set forth in SEQ ID NO:8 or a sequence that differs from SEQ ID NO:8 by at least one amino acid substitution; (iii) the LCDR3 has an amino acid sequence set forth in SEQ ID NO:10 or a sequence that differs from SEQ ID NO:10 by at least one amino acid substitution; (iv) the HCDR1 has an amino acid sequence set forth in SEQ ID NO:12 or a sequence that differs from SEQ ID NO:12 by at least one amino acid substitution; (v) the HCDR2 has an amino acid sequence set forth in SEQ ID NO:14 or a sequence that differs from SEQ ID NO:14 by at least one amino acid substitution; and (vi) the HCDR3 has an amino acid sequence set forth in SEQ ID NO:16 or a sequence that differs from SEQ ID NO:16 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody. For instance, the invention includes a recombinant polypeptide comprising (i) the LCDR1 has an amino acid sequence set forth in SEQ ID NO:6 or a sequence that differs from SEQ ID NO:6 by one or two amino acid substitutions; (ii) the LCDR2 has an amino acid sequence set forth in SEQ ID NO:8 or a sequence that differs from SEQ ID NO:8 by one or two amino acid substitutions; (iii) the LCDR3 has an amino acid sequence set forth in SEQ ID NO:10 or a sequence that differs from SEQ ID NO:10 by one or two amino acid substitutions; (iv) the HCDR1 has an amino acid sequence set forth in SEQ ID NO:12 or a sequence that differs from SEQ ID NO:12 by one or two amino acid substitutions; (v) the HCDR2 has an amino acid sequence set forth in SEQ ID NO:14 or a sequence that differs from SEQ ID NO:14 by one or two amino acid substitutions; and (vi) the HCDR3 has an amino acid sequence set forth in SEQ ID NO:16 or a sequence that differs from SEQ ID NO:16 by one or two amino acid substitutions. The amino acid substitution described above may be a conservative or a non-conservative amino acid substitution.

In related embodiments, a recombinant polypeptide of the invention comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:2) or to a heavy chain variable region ($V_H$) (e.g., SEQ ID NO:4), or both. In one embodiment, the CD123-binding domain of the recombinant polypeptide is an scfv comprising a variable heavy chain comprising SEQ ID NO:4 and a variable light chain comprising SEQ ID NO:2 in the VHVL orientation. In another embodiment, the CD123-binding domain of the recombinant polypeptide is an scFv comprising a variable light chain comprising SEQ ID NO:2 and a variable heavy chain comprising SEQ ID NO:4 in the VLVH orientation. For instance, in certain embodiments, the polypeptide of the invention comprises an amino acid sequence of SEQ ID NO:130 or SEQ ID NO:132. The invention includes a recombinant polypeptide that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of SEQ ID NO:130 or SEQ ID NO:132.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:28 or a sequence that differs from SEQ ID NO:28 by at least one amino acid substitution; (v) the HCDR2 has an amino acid sequence set forth in SEQ ID NO:30 or a sequence that differs from SEQ ID NO:30 by at least one amino acid substitution; and (vi) the HCDR3 has an amino acid sequence set forth in SEQ ID NO:32 or a sequence that differs from SEQ ID NO:32 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:20), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:36 or a sequence that differs from SEQ ID NO:36 by at least one amino acid substitution; (v) the HCDR2 has an amino acid sequence set forth in SEQ ID NO:38 or a sequence that differs from SEQ ID NO:38 by at least one amino acid substitution; and (vi) the HCDR3 has an amino acid sequence set forth in SEQ ID NO:40 or a sequence that differs from SEQ ID NO:40 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:34), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:44 or a sequence that differs from SEQ ID NO:44 by at least one amino acid substitution; (v) the HCDR2 has an amino acid sequence set forth in SEQ ID NO:46 or a sequence that differs from SEQ ID NO:46 by at least one amino acid substitution; and (vi) the HCDR3 has an amino acid sequence set forth in SEQ ID NO:48 or a sequence that differs from SEQ ID NO:48 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:42), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:100 or a sequence that differs from SEQ ID NO:100 by at least one amino acid substitution; (v) the HCDR2 has an amino acid sequence set forth in SEQ ID NO:102 or a sequence that differs from SEQ ID NO:102 by at least one amino acid substitution; and (vi) the HCDR3 has an amino acid sequence set forth in SEQ ID NO:104 or a sequence that differs from SEQ ID NO:104 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:98), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO: 116 or a sequence that differs from SEQ ID NO: 116 by at least one amino acid substitution; (v) the HCDR2 has an amino acid sequence set forth in SEQ ID NO:118 or a sequence that differs from SEQ ID NO:118 by at least one amino acid substitution; and (vi) the HCDR3 has an amino acid sequence set forth in SEQ ID NO:120 or a sequence that differs from SEQ ID NO:120 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:114), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:22 or a sequence that differs from SEQ ID NO:22 by at least one amino acid substitution; (ii) the LCDR2 has an amino acid sequence set forth in SEQ ID NO:24 or a sequence that differs from SEQ ID NO:24 by at least one amino acid substitution; (iii) the LCDR3 has an amino acid sequence set forth in SEQ ID NO:26 or a sequence that differs from SEQ ID NO:26 by at least one amino acid substitution; (iv) the HCDR1 has an amino acid sequence set forth in SEQ ID NO:124 or a sequence that differs from SEQ ID NO:124 by at least one amino acid substitution; (v) the HCDR2 has an amino acid sequence set forth in SEQ ID NO:126 or a sequence that differs from SEQ ID NO:126 by at least one amino acid substitution; and (vi) the HCDR3 has an amino acid sequence set forth in SEQ ID NO:128 or a sequence that differs from SEQ ID NO:128 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:18) or to a heavy chain variable region ($V_H$) (e.g., SEQ ID NO:122), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:54 or a sequence that differs from SEQ ID NO:54 by at least one amino acid substitution; (ii) the LCDR2 has an amino acid sequence set forth in SEQ ID NO:56 or a sequence that differs from SEQ ID NO:56 by at least one amino acid substitution; (iii) the LCDR3 has an amino acid sequence set forth in SEQ ID NO:58 or a sequence that differs from SEQ ID NO:58 by at least one amino acid substitution; (iv) the HCDR1 has an amino acid sequence set forth in SEQ ID NO:60 or a sequence that differs from SEQ ID NO:60 by at least one amino acid substitution; (v) the HCDR2 has an amino acid sequence set forth in SEQ ID NO:62 or a sequence that differs from SEQ ID NO:62 by at least one amino acid substitution; and (vi) the HCDR3 has an amino acid sequence set forth in SEQ ID NO:64 or a sequence that differs from SEQ ID NO:64 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:50) or to a heavy chain variable region ($V_H$) (e.g., SEQ ID NO:52), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:70 or a sequence that differs from SEQ ID NO:70 by at least one amino acid substitution; (ii) the LCDR2 has an amino acid sequence set forth in SEQ ID NO:72 or a sequence that differs from SEQ ID NO:72 by at least one amino acid substitution; (iii) the LCDR3 has an amino acid sequence set forth in SEQ ID NO:74 or a sequence that differs from SEQ ID NO:74 by at least one amino acid substitution; (iv) the HCDR1 has an amino acid sequence set forth in SEQ ID NO:76 or a sequence that differs from SEQ ID NO:76 by at least one amino acid substitution; (v) the HCDR2 has an amino acid sequence set forth in SEQ ID NO:78 or a sequence that differs from SEQ ID NO:78 by at least one amino acid substitution; and (vi) the HCDR3 has an amino acid sequence set forth in SEQ ID NO:80 or a sequence that differs from SEQ ID NO:80 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:66) or to a heavy chain variable region ($V_H$) (e.g., SEQ ID NO:68), or both.

In certain embodiments, the CD123-binding domain comprises (i) an immunoglobulin light chain variable region ($V_L$) comprising CDRs LCDR1, LCDR2, and LCDR3, and (ii) an immunoglobulin heavy chain variable region ($V_H$) comprising CDRs HCDR1, HCDR2, and HCDR3. In some such embodiments, (i) the LCDR1 has an amino acid sequence set forth in SEQ ID NO:86 or a sequence that differs from SEQ ID NO:86 by at least one amino acid substitution; (ii) the LCDR2 has an amino acid sequence set forth in SEQ ID NO:88 or a sequence that differs from SEQ ID NO:88 by at least one amino acid substitution; (iii) the LCDR3 has an amino acid sequence set forth in SEQ ID NO:90 or a sequence that differs from SEQ ID NO:90 by at least one amino acid substitution; (iv) the HCDR1 has an amino acid sequence set forth in SEQ ID NO:92 or a sequence that differs from SEQ ID NO:92 by at least one amino acid substitution; (v) the HCDR2 has an amino acid sequence set forth in SEQ ID NO:94 or a sequence that differs from SEQ ID NO:94 by at least one amino acid substitution; and (vi) the HCDR3 has an amino acid sequence set forth in SEQ ID NO:96 or a sequence that differs from SEQ ID NO:96 by at least one amino acid substitution. The amino acid substitution described above may be a conservative or a non-conservative amino acid substitution. In some embodiments, an LCDR1, LCDR2, LCDR3, HCDR1, HCDR2, and/or HCDR3 differs from a recited sequence by 1, 2, 3, 4, 5, 6, 7, 8, 9, or 10 amino acids. In certain embodiments, a CDR of the present disclosure contains about one or more (e.g., about 2, 3, 4, 5, 6, 7, 8, 9, 10) insertions, about one or more (e.g., about 2, 3, 4, 5, 6, 7, 8, 9, 10) deletions, about one or more (e.g., about 2, 3, 4, 5, 6, 7, 8, 9, 10) amino acid substitutions (e.g., conservative amino acid substitutions or non-conservative amino acid substitutions), or a combination of the above-noted changes, when compared to the CDR sequence of a known monoclonal antibody.

In related embodiments, a CD123-binding domain comprises or is a sequence that is at least about 80%, at least about 85%, at least about 88%, at least about 90%, at least about 91%, at least about 92%, at least about 93%, at least about 94%, at least about 95%, at least about 96%, at least about 97%, at least about 98%, at least about 99%, at least about 99.5%, or 100% identical to an amino acid sequence of a light chain variable region ($V_L$) (e.g., SEQ ID NO:82) or to a heavy chain variable region ($V_H$) (e.g., SEQ ID NO:84), or both.

In certain embodiments, a CD123-binding domain comprises humanized immunoglobulin $V_L$ and/or $V_H$ regions. Techniques for humanizing immunoglobulin $V_L$ and $V_H$ regions are known in the art and are discussed, for example, in U.S. Patent Application Publication No. 2006/0153837. In certain embodiments, a CD123-binding domain comprises human immunoglobulin $V_L$ and/or $V_H$ regions.

"Humanization" is expected to result in an antibody that is less immunogenic, with complete retention of the antigen-binding properties of the original molecule. In order to retain all of the antigen-binding properties of the original antibody, the structure of its antigen binding site should be reproduced in the "humanized" version. This can be achieved by grafting only the nonhuman CDRs onto human variable framework domains and constant regions, with or without retention of critical framework residues (Jones et al., *Nature* 321:522 (1986); Verhoeyen et al., *Science* 239:1539 (1988)) or by recombining the entire nonhuman variable domains (to preserve ligand-binding properties), but "cloaking" them with a human-like surface through judicious replacement of exposed residues (to reduce antigenicity) (Padlan, *Molec. Immunol.* 28:489 (1991)).

Essentially, humanization by CDR grafting involves recombining only the CDRs of a non-human antibody onto a human variable region framework and a human constant region. Theoretically, this should substantially reduce or eliminate immunogenicity (except if allotypic or idiotypic differences exist). However, it has been reported that some framework residues of the original antibody also may need to be preserved (Reichmann et al., *Nature,* 332:323 (1988); Queen et al., *Proc. Natl. Acad. Sci. USA,* 86:10,029 (1989)).

The framework residues that need to be preserved are amenable to identification through computer modeling. Alternatively, critical framework residues can potentially be identified by comparing known antigen-binding site structures (Padlan, *Molec. Immunol.,* 31(3):169-217 (1994), incorporated herein by reference).

The residues that potentially affect antigen binding fall into several groups. The first group comprises residues that are contiguous with the antigen site surface, which could therefore make direct contact with antigens. These residues include the amino-terminal residues and those adjacent to the CDRs. The second group includes residues that could alter the structure or relative alignment of the CDRs, either by contacting the CDRs or another peptide chain in the antibody. The third group comprises amino acids with buried side chains that could influence the structural integrity of the variable domains. The residues in these groups are usually found in the same positions (Padlan, 1994, supra) although their positions as identified may differ depending on the numbering system (see Kabat et al., "Sequences of proteins of immunological interest, 5th ed., Pub. No. 91-3242, U.S. Dept. Health & Human Services, NIH, Bethesda, Md., 1991).

Knowledge about humanized antibodies in the art is applicable to the polypeptides according to the disclosure, even if these polypeptides are not antibodies.

In some embodiments, the disclosure relates to CD123-binding domains wherein (i) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:2 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:4; (ii) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:20; (iii) the immunoglobulin light chain variable region comprises an amino acid sequence that is at least 88%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:34; (iv) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:42; (v) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:50 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:52; (vi) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:66 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:68; (vii) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:82 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:84; (viii) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:122; (ix) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:98; (x) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO:106; or (xi) the immunoglobulin light chain variable region comprises an amino acid sequence that is at least 85%, at least 90%, at least 92%, at least 95%, at least 97%, at least 98% or at least 99% identical to the amino acid sequence set forth in SEQ ID NO:18 and the immunoglobulin heavy chain variable region comprises an amino acid sequence that is at least 85%, at least 90%, at least 92%, at least 95%, at least 97%, at least 98% or at least 99% identical to the amino acid sequence set forth in SEQ ID NO: 114.

In further embodiments, each CDR comprises no more than one, two, or three substitutions, insertions or deletions, as compared to that from a monoclonal antibody or fragment or derivative thereof that specifically binds to a target of interest (e.g., CD123).

In certain embodiments, a CD123-binding protein can comprise one or more additional binding domains (e.g., second binding domain) that bind a target other than CD123. These other binding domains can comprise, for example, a particular cytokine or a molecule that targets the binding domain polypeptide to a particular cell type, a toxin, an additional cell receptor, an antibody, etc.

In certain embodiments, a CD123-binding molecule or protein can comprise a T-cell binding domain for recruitment of T-cells to target cells expressing CD123. In certain embodiments, a CD123-binding protein as described herein can comprise (i) a binding domain that specifically binds a TCR complex or a component thereof (e.g., TCRα, TCRβ, CD3γ, CD3δ, and CD3ε) and (ii) another binding domain that specifically binds to CD123. A CD123-binding protein can utilize essentially any binding domain that binds a T-cell, e.g., an antibody derived binding domain. Exemplary anti-CD3 antibodies from which the CD3 binding domain can be derived include the CRIS-7 monoclonal antibody (Reinherz, E. L. et al. (eds.), *Leukocyte typing II.*, Springer Verlag, New York, (1986); $V_L$ and $V_H$ amino acid sequences respectively shown in SEQ ID NO:209 (QVVLTQSPAIMSAFPGEKVTMTCSASSSVSYMNWYQQKSGTSPKRWIYDSSKLASGVPARFS GSGSGTSYSLTISSMETEDAATYYCQQWSRNPPTFGGGTKLQITR) and SEQ ID NO:210 (QVQLQQSGAELARPGASVKMSCKASGYTFTRSTMHWVKQRPGQGLEWIGYINP SSAYTNYNQKFKDKATLTADKSSSTAYMQLSSLTSEDSAVYYCASPQVHYDYNGFPYWGQGT LVTVSA)); HuM291 (Chau et al. (2001) *Transplantation* 71:941-950; $V_L$ and $V_H$ amino acid sequences respectively shown in SEQ ID NO:211 (DIQMTQSPSSLSASVGDRVTITCSASSSVSYMNWYQQKPGKAPKRLIYDTSKLASGVP SRFSGSGSGTDFTLTISSLQPEDFATYYCQQWSSNPPTFGGGTKVEIK) and SEQ ID NO:212 (QVQLVQSGAEVKKPGASVKVSCKASGYTFISYTMHWVRQAPGQGLEWMGYINPRSGYTHYN QKLKDKATLTADKSASTAYMELSSLRSEDTAVYYCARSAYYDYDGFAYWGQGTLVTVSS)); BC3 monoclonal antibody (Anasetti et al. (1990) *J. Exp. Med.* 172:1691); OKT3 monoclonal antibody (Ortho multicenter Transplant Study Group (1985) *N. Engl. J. Med.* 313:337) and derivatives thereof such as OKT3 ala-ala (also referred to as OKT3 AA-FL or OKT3 FL), a humanized, Fc variant with alanine substitutions at positions 234 and 235 (Herold et al. (2003) *J. Clin. Invest.* 11:409); visilizumab (Carpenter et al. (2002) *Blood* 99:2712), G19-4 monoclonal antibody (Ledbetter et al., 1986, *J. Immunol.* 136:3945), 145-2C11 monoclonal antibody (Hirsch et al. (1988) *J. Immunol.* 140: 3766) and I2C monoclonal antibody (see, e.g., US 2011/0293619 and US20120244162). For example, a CD3 binding domain may comprise a CD3 binding domain disclosed in U.S. Patent Application Publication No. 2012/0244162, including a CD3 binding domain comprising a VL region selected from SEQ ID NO: 17, 21, 35, 39, 53, 57, 71, 75, 89, 83, 107, 111, 125, 129, 143, 147, 161, 165, 179 and 183 of US 2012/0244162 and/or a VH region selected from SEQ ID NO:15, 19, 33, 37, 51, 55, 69, 73, 87, 91. 105, 109, 123, 127, 141, 145, 159, 163, 177 and 181 of US 2012/0244162. In some embodiments, a CD3 binding domain comprises an amino acid sequence selected from SEQ ID NO: 23, 25, 41, 43, 59, 61, 77, 79, 95, 97, 113, 115, 131, 133, 149, 151, 167, 169, 185, and 187 of US 2012/0244162. In some embodiments, a CD3 binding domain is one described in WO2004/106380, WO2005/040220A1, US 2014/0099318 or derived from a CD3 binding domain thereof. An exemplary anti-TCR antibody is the BMA031 monoclonal antibody (Borst et al. (1990) *Human Immunology* 29:175-188). The CD3 binding domain may be derived from any of the antibodies or sequences described in WO 2013/158856 (incorporated herein by reference in its entirety). In certain variations, the second binding domain of a CD123-binding polypeptide described herein comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 has the amino acid sequences set forth in SEQ ID NOs:162, 163 and 164, respectively, and the HCDR1, HCDR2, and HCDR3 has the amino acid sequences set forth in SEQ ID NOs: 165, 166 and 167, respectively; or (b) the LCDR1, LCDR2 and LCDR3 has the amino acid sequences set forth in SEQ ID NO:168, SEQ ID NO:169, and SEQ ID NO:170, respectively, and the HCDR1, HCDR2, and HCDR3 has the amino acid sequences set forth in SEQ ID NO: 171, SEQ ID NO:172, and SEQ ID NO:173, respectively. In other aspects, the second binding domain of a CD123-binding polypeptide described herein comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 has the amino acid sequences set forth in SEQ ID NOs: 171, 172 and 173, respectively, and the HCDR1, HCDR2, and HCDR3 has the amino acid sequences set forth in SEQ ID NOs: 174, 175 and 176, respectively; or (b) the LCDR1, LCDR2 and LCDR3 has the amino acid sequences set forth in SEQ ID NOs: 176, 177 and 178, respectively, and the HCDR1, HCDR2, and HCDR3 has the amino acid sequences set forth in SEQ ID NOs: 179, 180 and 181, respectively. In certain embodiments, the second binding domain of a CD123-binding polypeptide described herein comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 has the amino acid sequences set forth in SEQ ID NOs: 182, 183 and 184, respectively, and the HCDR1, HCDR2, and HCDR3 has the amino acid sequences set forth in SEQ ID NOs: 185, 186 and 187, respectively; or (b) the LCDR1, LCDR2 and LCDR3 has the amino acid sequences set forth in SEQ ID NOs: 188, 189 and 190, respectively, and the HCDR1, HCDR2, and HCDR3 has the amino acid sequences set forth in SEQ ID NOs: 191, 192 and 193, respectively. In some aspects, the second binding domains comprising the CDR sequences recited in this paragraph are humanized.

In some embodiments of a CD123-binding protein comprising a second binding domain that specifically binds CD3ε, the second binding domain competes for binding to CD3ε with the CRIS-7, HuM291 or I2C monoclonal antibody. In certain variations, the CD3-binding domain comprises an immunoglobulin light chain variable region ($V_L$) and an immunoglobulin heavy chain variable region ($V_H$) derived from the CRIS-7, HuM291 or I2C monoclonal antibody (e.g., the $V_L$ and $V_H$ of the second binding domain can be humanized variable regions comprising, respectively, the light chain CDRs and the heavy chain CDRs of the monoclonal antibody). A second binding domain may comprise the light chain variable region, the heavy chain variable region, or both, of the DRA222, TSC455, or TSC456 CD3-binding domains. The amino acid sequences of DRA222, TSC455, and TSC456 are provided in Table 3. The DRA222 binding domains are also described in WO 2013/158856. TSC455 may also be referred to as TSC394 F87Y. TSC455 may also be referred to as TSC394 E86D F87Y or TSC394 DY. In some embodiments, the second binding domain specifically binds CD3 and comprises an immunoglobulin light chain variable region and an immunoglobulin heavy chain variable region; wherein the immunoglobulin light chain variable region comprises an amino acid sequence that is at least about 93% identical, at least about 95% identical, at least about 97% identical, at least about 98% identical or at least about 99% identical to the amino acid sequence in SEQ ID NO:157; or at least about 94% identical, at least about 95% identical, at least about 97% identical, at least about 98% identical or at least about 99% identical to the amino acid sequence in SEQ ID NO:158; and wherein the immunoglobulin heavy chain variable region comprises an amino acid sequence that is at least about 82% identical, at least about 85% identical, at least about 87% identical, at least about 90% identical, at least about 92% identical, at least about 95% identical, at least about 97% identical, at least about 98% identical or at least about 99% identical to the amino acid sequence in SEQ ID NO:159. In some embodiments, a CD123-binding polypeptide or protein further comprising a CD3-binding domain may have a low level of high molecular weight aggregates produced during recombinant expression of the polypeptide or protein. A CD123-binding polypeptide or protein further comprising a CD3-binding domain may exhibit a relatively long stability in human serum, depending on the CD3-binding domain present in the polypeptide or protein.

In certain variations, the second binding domain of a CD123-binding polypeptide described herein is a CD3-binding domain and comprises one or more of the CD3-binding sequences (e.g., CDRs or variable regions) disclosed in US 2013/0129730, US 2011/0293619, U.S. Pat. No. 7,635,472, WO 2010/037836, WO 2004/106381, or WO 2011/121110; each incorporated herein by reference in its entirety. In some embodiments, a CD3-binding domain comprises one or more of the following sequences:

| LCDR1 | LCDR2 | LCDR3 |
|---|---|---|
| GSSTGAV TSGYYPN (SEQ ID NO: 289) | GTKFLAP (SEQ ID NO: 292) | ALWYSNR VW (SEQ ID NO: 295) |
| RSSTGAV TSGYYPN (SEQ ID NO: 290) | ATDMRPS (SEQ ID NO: 293) | ALWYSNR WW (SEQ ID NO: 296) |
| GSSTGAV TSGNYPN (SEQ ID NO: 291) | GTKFLAP (SEQ ID NO: 294) | VLWYSNR WV (SEQ ID NO: 297) |

In various embodiments, a CD3-binding domain comprises one or more of the following sequences:

| HCDR1 | HCDR2 | HCDR3 |
|---|---|---|
| IYAMN (SEQ ID NO: 298) | RIRSKYN NYATYYA DSVKS (SEQ ID NO: 301) | HGNFGNS YVSFFAY (SEQ ID NO: 304) |
| KYAMN (SEQ ID NO: 299) | RIRSKYN NYATYYA DSVKD (SEQ ID NO: 302) | HGNFGNS YISYWAY (SEQ ID NO: 305) |
| SYAMN (SEQ ID NO: 300) | RIRSKYN NYATYYA DSVKG (SEQ ID NO: 303) | HGNFGNS YLSFWAY (SEQ ID NO: 306) |

In certain embodiments, the CD123-binding polypeptide used in the methods and compositions described herein is a bispecific single chain molecule comprising a CD123 binding domain and a CD3 binding domain. In some embodiments, a CD123- and/or a CD3-binding domain is derived from an antibody and comprises a variable heavy chain (VH) and a variable light chain (VL). For example, an scFv comprises a VH and VL. These binding domains and variable chains may be arranged in any order that still retains some binding to the target(s). For example, the variable domains may be arranged in the order such as VH CD123-VL CD123-VH CD3-VL CD3; VL CD123-VH CD123-VH CD3-VL CD3; VH CD123-VL CD123-VL CD3-VH CD3; VL CD123-VH CD123-VL CD3-VH CD3; VH CD3-VL CD3-VH CD123-VL CD123; VL CD3-VH CD3-VL CD123-VH CD123; VH CD3-VL CD3-VL CD123-VH CD123; or VL CD3-VH CD3-VH CD123-VL CD123. The pairs of VH regions and VL regions in the binding domain binding to CD3 may be in the format of a single chain antibody (scFv). The VH and VL regions may be arranged in the order VH-VL or VL-VH. In some embodiments, the scFv may bind to CD123 more effectively than the antibody comprising the same VH and VL region sequences in the same orientation. In certain embodiments, the scFv may bind more effectively to CD123 in the VL-VH orientation than in the VH-VL orientation, or vice versa (see, e.g., Example 2). The VH-region may be positioned N-terminally to a linker sequence. The VL region may be positioned C-terminally to the linker sequence. The domain arrangement in the CD3 binding domain of the bispecific single chain molecule may be VH-VL, with said CD3 binding domain located C-terminally to the CD123-binding domain. A bispecific molecule may comprise an scFv binding to CD123 linked to an scFv binding to CD3. These scFvs may be linked with a short peptide. In some embodiments, bispecific single chain molecules do not comprise a hinge region or a constant region (see, for example, US 2013/0295121, WO 2010/037836, WO 2004/106381 and WO 2011/121110; each incorporated herein by reference in its entirety).

In some embodiments, a binding domain is a single-chain Fv fragment (scFv) that comprises $V_H$ and $V_L$ regions specific for a target of interest. In certain embodiments, the $V_H$ and $V_L$ regions are human or humanized.

In some variations, a binding domain is a single-chain Fv (scFv) comprising immunoglobulin $V_L$ and $V_H$ regions joined by a peptide linker. The use of peptide linkers for joining $V_L$ and $V_H$ regions is well-known in the art, and a large number of publications exist within this particular field. In some embodiments, a peptide linker is a 15mer consisting of three repeats of a Gly-Gly-Gly-Gly-Ser amino acid sequence ($(Gly_4Ser)_3$) (SEQ ID NO:213). Other linkers have been used, and phage display technology, as well as selective infective phage technology, has been used to diversify and select appropriate linker sequences (Tang et al., *J. Biol. Chem.* 271, 15682-15686, 1996; Hennecke et al., *Protein Eng.* 11, 405-410, 1998). In certain embodiments, the $V_L$ and $V_H$ regions are joined by a peptide linker having an amino acid sequence comprising the formula $(Gly_4Ser)_n$, wherein n=1-5 (SEQ ID NO:214). Other suitable linkers can be obtained by optimizing a simple linker (e.g., $(Gly_4Ser)_n$) (SEQ ID NO: 315) through random mutagenesis.

In some embodiments, a CD123-binding polypeptide comprises, in order from amino-terminus to carboxyl-terminus (or in order from carboxyl-terminus to amino-terminus), (i) the CD123-binding domain, (ii) a hinge region, (iii) an immunoglobulin constant region, (iv) a carboxyl-terminus linker (or an amino-terminus linker), and (v) the second binding domain. As used herein in the context of a polypeptide construct comprising a first binding domain and a second binding domain, a "hinge region" or a "hinge" refers to a polypeptide region between the first binding domain and the Fc region. A "carboxyl-terminus linker" or "an amino-terminus linker" refers to a polypeptide region between the Fc region and the second binding domain. In some embodiments, a carboxyl-terminus (or an amino-terminus linker) linker comprises or consists of SEQ ID NO:248. In certain embodiments, a hinge is a wild-type human immunoglobulin hinge region. In certain other embodiments, one or more amino acid residues can be added at the amino- or carboxyl-terminus of a wild type immunoglobulin hinge region as part of a fusion protein construct design. For example, additional junction amino acid residues at the hinge amino-terminus can be "RT," "RSS," "TG," or "T," or at the hinge carboxyl-terminus can be "SG", or a hinge deletion can be combined with an addition, such as AP with "SG" added at the carboxyl-terminus.

In certain embodiments, a hinge, a carboxyl-terminus linker, or an amino-terminus linker is an altered immunoglobulin hinge in which one or more cysteine residues in a wild type immunoglobulin hinge region is substituted with one or more other amino acid residues (e.g., serine or alanine).

Exemplary altered immunoglobulin hinges, carboxyl-terminus linkers, and amino-terminus linkers include an immunoglobulin human IgG1 hinge region having one, two or three cysteine residues found in a wild type human IgG1 hinge substituted by one, two or three different amino acid residues (e.g., serine or alanine). An altered immunoglobulin hinge can additionally have a proline substituted with another amino acid (e.g., serine or alanine). For example, the above-described altered human IgG1 hinge can additionally have a proline located carboxyl-terminal to the three cysteines of wild type human IgG1 hinge region substituted by another amino acid residue (e.g., serine, alanine). In one embodiment, the prolines of the core hinge region are not substituted.

In certain embodiments, a hinge, a carboxyl-terminus linker, or an amino-terminus linker polypeptide comprises or is a sequence that is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a wild type immunoglobulin hinge region, such as a wild type human IgG1 hinge, a wild type human IgG2 hinge, or a wild type human IgG4 hinge.

In further embodiments, a hinge, a carboxyl-terminus linker, or an amino-terminus linker present in a CD123-binding polypeptide can be a hinge that is not based on or derived from an immunoglobulin hinge (i.e., not a wild-type immunoglobulin hinge or an altered immunoglobulin hinge). Examples for such hinges and carboxyl-terminus linkers include peptides of about five to about 150 amino acids derived from an interdomain region of a transmembrane protein or stalk region of a type II C-lectin, for instance, peptides of about eight to 25 amino acids and peptides of about seven to 18 amino acids. In another embodiment, a carboxyl-terminus linker or amino-terminus linker comprises a $(Gly_4Ser)$ repeat (SEQ ID NO: 315) such as $(Gly_4Ser)_3PS$ (SEQ ID NO: 316).

In certain embodiments, hinge, carboxyl-terminus linker, and amino-terminal linker sequences have about 5 to 150 amino acids, 5 to 10 amino acids, 10 to 20 amino acids, 20 to 30 amino acids, 30 to 40 amino acids, 40 to 50 amino acids, 50 to 60 amino acids, 5 to 60 amino acids, 5 to 40 amino acids, 8 to 20 amino acids, or 10 to 15 amino acids. The hinge or linker can be primarily flexible, but can also provide more rigid characteristics or can contain primarily α-helical structure with minimal β-sheet structure. The lengths or the sequences of the hinges and linkers can affect the binding affinities of the binding domains to which the hinges are directly or indirectly (via another region or domain, such as an heterodimerization domain) connected as well as one or more activities of the Fc region portions to which the hinges or linkers are directly or indirectly connected.

In certain embodiments, hinge, carboxyl-terminus linker, and amino-terminal linker sequences are stable in plasma and serum and are resistant to proteolytic cleavage. The first lysine in the IgG1 upper hinge region can be mutated to minimize proteolytic cleavage, for instance, the lysine can be substituted with methionine, threonine, alanine or glycine, or is deleted.

In some embodiments of the disclosure, a CD123-binding polypeptide is capable of forming a heterodimer with a second polypeptide chain and comprises a hinge region (a) immediately amino-terminal to an immunoglobulin constant region (e.g., amino-terminal to a CH2 domain wherein the immunoglobulin constant region includes CH2 and CH3 domains, or amino-terminal to a CH3 domain wherein the immunoglobulin sub-regions includes CH3 and CH4 domains), (b) interposed between and connecting a binding domain (e.g., scFv) and a immunoglobulin heterodimerization domain, (c) interposed between and connecting a immunoglobulin heterodimerization domain and an immunoglobulin constant region (e.g., wherein the immunoglobulin constant region includes CH2 and CH3 domains or CH3 and CH4 domains), (d) interposed between and connecting an immunoglobulin constant region and a binding domain, (e) at the amino-terminus of a polypeptide chain, or (f) at the carboxyl-terminus of a polypeptide chain. A polypeptide chain comprising a hinge region as described herein will be capable of associating with a different polypeptide chain to form a heterodimeric protein provided herein, and the heterodimer formed will contain a binding domain that retains its target specificity or its specific target binding affinity.

Some exemplary hinge, carboxyl-terminus linker, and amino-terminus linker sequences suitable for use in accordance with the present disclosure are shown in the Tables 1 and 2 below. Additional exemplary hinge and linker regions are set forth in SEQ ID NOs: 241-244, 601, 78, 763-791, 228, 379-434, 618-749 of US 2013/0129723 (said sequences incorporated by reference herein).

TABLE 1

Exemplary hinges and linkers

| Name | Amino Acid Sequence | SEQ ID NO |
|---|---|---|
| sss(s)-hIgG1 hinge | EPKSSDKTHTSPPSS | SEQ ID NO: 215 |
| csc(s)-hIgG1 hinge | EPKSCDKTHTSPPCS | SEQ ID NO: 216 |
| ssc(s)-hIgG1 hinge | EPKSSDKTHTSPPCS | SEQ ID NO: 217 |
| scc(s)-hIgG1 hinge | EPKSSDKTHTCPPCS | SEQ ID NO: 218 |
| css(s)-hIgG1 hinge | EPKSCDKTHTSPPSS | SEQ ID NO: 219 |
| scs(s)-hIgG1 hinge | EPKSSDKTHTCPPSS | SEQ ID NO: 220 |
| ccc(s)-hIgG1 hinge | EPKSCDKTHTSPPCS | SEQ ID NO: 221 |
| ccc(p)-hIgG1 hinge | EPKSCDKTHTSPPCP | SEQ ID NO: 222 |
| sss(p)-hIgG1 hinge | EPKSSDKTHTSPPSP | SEQ ID NO: 223 |
| csc(p)-hIgG1 hinge | EPKSCDKTHTSPPCP | SEQ ID NO: 224 |
| ssc(p)-hIgG1 hinge | EPKSSDKTHTSPPCP | SEQ ID NO: 225 |
| scc(p)-hIgG1 hinge | EPKSSDKTHTCPPCP | SEQ ID NO: 226 |
| css(p)-hIgG1 hinge | EPKSCDKTHTSPPSP | SEQ ID NO: 227 |
| scs(p)-hIgG1 hinge | EPKSSDKTHTCPPSP | SEQ ID NO: 228 |
| Scppcp | SCPPCP | SEQ ID NO: 229 |
| STD1 | NYGGGGSGGGGSGGGGSGNS | SEQ ID NO: 230 |
| STD2 | NYGGGGSGGGGSGGGGSGNYGGGGSGGGGSGGGGSGNS | SEQ ID NO: 231 |
| H1 | NS | SEQ ID NO: 232 |
| H2 | GGGGSGNS | SEQ ID NO: 233 |
| H3 | NYGGGGSGNS | SEQ ID NO: 234 |
| H4 | GGGGSGGGGSGNS | SEQ ID NO: 235 |
| H5 | NYGGGGSGGGGSGNS | SEQ ID NO: 236 |
| H6 | GGGGSGGGGSGGGGSGNS | SEQ ID NO: 237 |
| H7 | GCPPCPNS | SEQ ID NO: 238 |
| $(G_4S)_3$ | GGGGSGGGGSGGGGS | SEQ ID NO: 239 |
| H105 | SGGGGSGGGGSGGGGS | SEQ ID NO: 240 |
| $(G_4S)_4$ | GGGGSGGGGSGGGGSGGGGS | SEQ ID NO: 241 |
| H75(NKG2A quadruple mutant) | QRHNNSSLNTGTQMAGHSPNS | SEQ ID NO: 242 |
| H83(NKG2A derived) | SSLNTGTQMAGHSPNS | SEQ ID NO: 243 |
| H106(NKG2A derived) | QRHNNSSLNTGTQMAGHS | SEQ ID NO: 244 |
| H81 (NKG2D derived) | EVQIPLTESYSPNS | SEQ ID NO: 245 |
| H91 (NKG2D derived) | NSLANQEVQIPLTESYSPNS | SEQ ID NO: 246 |
| H94 | SGGGGSGGGGSGGGGSPNS | SEQ ID NO: 247 |
| H111 | SGGGGSGGGGSGGGGSPGS | SEQ ID NO: 248 |
| H114 | GGGGSGGGGSGGGGSPS | SEQ ID NO: 288 |

TABLE 2

Exemplary hinges and linkers (derived from H7 hinge, stalk region of a type II C-lectin, or interdomain region of a type 1 transmembrane protein)

| Name | Amino Acid Sequence | Molecule and/or hinge from which derived | SEQ ID NO |
|---|---|---|---|
| H16 | LSVKADFLTPSIGNS | CD80 | SEQ ID NO: 249 |
| H17 | LSVKADFLTPSISCPPCPNS | CD80 + H7 | SEQ ID NO: 250 |
| H18 | LSVLANFSQPEIGNS | CD86 | SEQ ID NO: 251 |

TABLE 2 -continued

Exemplary hinges and linkers (derived from H7 hinge, stalk region of a type II C-lectin, or interdomain region of a type 1 transmembrane protein)

| Name | Amino Acid Sequence | Molecule and/or hinge from which derived | SEQ ID NO |
|---|---|---|---|
| H19 | LSVLANFSQPEISCPPCPNS | CD86 + H7 | SEQ ID NO: 252 |
| H20 | LKIQERVSKPKISNS | CD2 | SEQ ID NO: 253 |
| H21 | LKIQERVSKPKISCPPCPNS | CD2 + H7 | SEQ ID NO: 254 |
| H22 | LNVSERPFPPHIQNS | CD22 | SEQ ID NO: 255 |
| H23 | LDVSERPFPPHIQSCPPCPNS | CD22 + H7 | SEQ ID NO: 256 |
| H24 | REQLAEVTLSLKANS | CD80 | SEQ ID NO: 257 |
| H25 | REQLAEVTLSLKACPPCPNS | CD80 + H7 | SEQ ID NO: 258 |
| H26 | RIHQMNSELSVLANS | CD86 | SEQ ID NO: 259 |
| H27 | RIHQMNSELSVLACPPCPNS | CD86 + H7 | SEQ ID NO: 260 |
| H28 | DTKGKNVLEKIFSNS | CD2 | SEQ ID NO: 261 |
| H30 | LPPETQESQEVTLNS | CD22 | SEQ ID NO: 262 |
| H32 | RIHLNVSERPFPPNS | CD22 | SEQ ID NO: 263 |
| H33 | RIHLNVSERPFPPCPPCPNS | CD22 + H7 | SEQ ID NO: 264 |
| H36 | GCPPCPGGGGSNS | H7 | SEQ ID NO: 265 |
| H40 | GCPPCPANS | H7 | SEQ ID NO: 266 |
| H41 | GCPPCPANS | H7 | SEQ ID NO: 267 |
| H42 | GCPPCPNS | H7 | SEQ ID NO: 268 |
| H44 | GGGASCPPCPGNS | H7 | SEQ ID NO: 269 |
| H45 | GGGASCPPCAGNS | H7 | SEQ ID NO: 270 |
| H46 | GGGASCPPCANS | H7 | SEQ ID NO: 271 |
| H47 | LSVKADFLTPSIGNS | CD80 | SEQ ID NO: 272 |
| H48 | ADFLTPSIGNS | CD80 | SEQ ID NO: 273 |
| H50 | LSVLANFSQPEIGNS | CD86 | SEQ ID NO: 274 |

TABLE 2 -continued

Exemplary hinges and linkers (derived from H7 hinge, stalk region of a type II C-lectin, or interdomain region of a type 1 transmembrane protein)

| Name | Amino Acid Sequence | Molecule and/or hinge from which derived | SEQ ID NO |
|---|---|---|---|
| H51 | LSVLANFSQPEIGNS | CD86 | SEQ ID NO: 275 |
| H52 | SQPEIVPISNS | CD86 | SEQ ID NO: 276 |
| H53 | SQPEIVPISCPPCPNS | CD86 + H7 | SEQ ID NO: 277 |
| H54 | SVLANFSQPEISCPPCPNS | CD86 + H7 | SEQ ID NO: 278 |
| H55 | RIHQMNSELSVLANS | CD86 | SEQ ID NO: 279 |
| H56 | QMNSELSVLANS | CD86 | SEQ ID NO: 280 |
| H57 | VSERPFPPNS | CD22 | SEQ ID NO: 281 |
| H58 | KPFFTCGSADTCPNS | CD72 | SEQ ID NO: 282 |
| H59 | KPFFTCGSADTCPNS | CD72 | SEQ ID NO: 283 |
| H60 | QYNCPGQYTFSMPNS | CD69 | SEQ ID NO: 284 |
| H61 | EPAFTPGPNIELQKDSDCPNS | CD94 | SEQ ID NO: 285 |
| H62 | QRHNNSSLNTRTQKARHCPNS | NKG2A | SEQ ID NO: 286 |
| H63 | NSLFNQEVQIPLTESYCPNS | NKG2D | SEQ ID NO: 287 |

As indicated herein, in certain embodiments, polypeptides of the present disclosure comprise an immunoglobulin constant region (also referred to as a constant region) in a polypeptide chain. The inclusion of an immunoglobulin constant region slows clearance of the homodimeric and heterodimeric proteins formed from two CD123-binding polypeptide chains from circulation after administration to a subject. By mutations or other alterations, an immunoglobulin constant region further enables relatively easy modulation of dimeric polypeptide effector functions (e.g., ADCC, ADCP, CDC, complement fixation, and binding to Fc receptors), which can either be increased or decreased depending on the disease being treated, as known in the art and described herein. In certain embodiments, an immunoglobulin constant region of one or both of the polypeptide chains of the polypeptide homodimers and heterodimers of the present disclosure will be capable of mediating one or more of these effector functions In other embodiments, one or more of these effector functions are reduced or absent in an immunoglobulin constant region of one or both of the polypeptide chains of the polypeptide homodimers and heterodimers of the present disclosure, as compared to a corresponding wild-type immunoglobulin constant region. For example, for dimeric CD123-binding polypeptides designed to elicit RTCC, such as, e.g., via the inclusion of a CD3-binding domain, an immunoglobulin constant region may have reduced or no effector function relative to a corresponding wild-type immunoglobulin constant region.

An immunoglobulin constant region present in polypeptides of the present disclosure can comprise or is derived from part or all of: a CH2 domain, a CH3 domain, a CH4 domain, or any combination thereof. For example, an immunoglobulin constant region can comprise a CH2 domain, a CH3 domain, both CH2 and CH3 domains, both CH3 and CH4 domains, two CH3 domains, a CH4 domain, two CH4 domains, and a CH2 domain and part of a CH3 domain.

A CH2 domain that can form an immunoglobulin constant region of a polypeptide of the present disclosure can be a wild type immunoglobulin CH2 domain or an altered immunoglobulin CH2 domain thereof from certain immunoglobulin classes or subclasses (e.g., IgG1, IgG2, IgG3, IgG4, IgA1, IgA2, or IgD) and from various species (including human, mouse, rat, and other mammals).

In certain embodiments, a CH2 domain is a wild type human immunoglobulin CH2 domain, such as wild type CH2 domains of human IgG1, IgG2, IgG3, IgG4, IgA1, IgA2, or IgD, as set forth in SEQ ID NOS: 115, 199-201 and 195-197, respectively, of US 2013/0129723 (said sequences incorporated by reference herein). In certain embodiments, the CH2 domain is a wild type human IgG1 CH2 domain as set forth in SEQ ID NO:115 of US 2013/0129723 (said sequence incorporated by reference herein).

In certain embodiments, a CH2 domain is an altered immunoglobulin CH2 region (e.g., an altered human IgG1 CH2 domain) that comprises an amino acid substitution at the asparagine of position 297 (e.g., asparagine to alanine). Such an amino acid substitution reduces or eliminates glycosylation at this site and abrogates efficient Fc binding to FcγR and C1q. The sequence of an altered human IgG1 CH2 domain with an Asn to Ala substitution at position 297 is set forth in SEQ ID NO:324 of US 2013/0129723 (said sequence incorporated by reference herein).

In certain embodiments, a CH2 domain is an altered immunoglobulin CH2 region (e.g., an altered human IgG1 CH2 domain) that comprises at least one substitution or deletion at positions 234 to 238. For example, an immunoglobulin CH2 region can comprise a substitution at position 234, 235, 236, 237 or 238, positions 234 and 235, positions 234 and 236, positions 234 and 237, positions 234 and 238, positions 234-236, positions 234, 235 and 237, positions 234, 236 and 238, positions 234, 235, 237, and 238, positions 236-238, or any other combination of two, three, four, or five amino acids at positions 234-238. In addition or alternatively, an altered CH2 region can comprise one or more (e.g., two, three, four or five) amino acid deletions at positions 234-238, for instance, at one of position 236 or position 237 while the other position is substituted. The above-noted mutation(s) decrease or eliminate the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 has been replaced with one or more alanine residues. In further embodiments, only one of the amino acid residues at positions 234-238 have been deleted while one or more of the remaining amino acids at positions 234-238 can be substituted with another amino acid (e.g., alanine or serine).

In certain other embodiments, a CH2 domain is an altered immunoglobulin CH2 region (e.g., an altered human IgG1 CH2 domain) that comprises one or more amino acid substitutions at positions 253, 310, 318, 320, 322, and 331. For example, an immunoglobulin CH2 region can comprise a substitution at position 253, 310, 318, 320, 322, or 331, positions 318 and 320, positions 318 and 322, positions 318, 320 and 322, or any other combination of two, three, four, five or six amino acids at positions 253, 310, 318, 320, 322, and 331. The above-noted mutation(s) decrease or eliminate the complement-dependent cytotoxicity (CDC) of a polypeptide heterodimer that comprises the altered CH2 domain.

In certain other embodiments, in addition to the amino acid substitution at position 297, an altered CH2 region (e.g., an altered human IgG1 CH2 domain) can further comprise one or more (e.g., two, three, four, or five) additional substitutions at positions 234-238. For example, an immunoglobulin CH2 region can comprise a substitution at positions 234 and 297, positions 234, 235, and 297, positions 234, 236 and 297, positions 234-236 and 297, positions 234, 235, 237 and 297, positions 234, 236, 238 and 297, positions 234, 235, 237, 238 and 297, positions 236-238 and 297, or any combination of two, three, four, or five amino acids at positions 234-238 in addition to position 297. In addition or alternatively, an altered CH2 region can comprise one or more (e.g., two, three, four or five) amino acid deletions at positions 234-238, such as at position 236 or position 237. The additional mutation(s) decreases or eliminates the antibody-dependent cell-mediated cytotoxicity (ADCC) activity or Fc receptor-binding capability of a polypeptide heterodimer that comprises the altered CH2 domain. In certain embodiments, the amino acid residues at one or more of positions 234-238 have been replaced with one or more alanine residues. In further embodiments, only one of the amino acid residues at positions 234-238 has been deleted while one or more of the remaining amino acids at positions 234-238 can be substituted with another amino acid (e.g., alanine or serine).

In certain embodiments, in addition to one or more (e.g., 2, 3, 4, or 5) amino acid substitutions at positions 234-238, a mutated CH2 region (e.g., an altered human IgG1 CH2 domain) in a fusion protein of the present disclosure can contain one or more (e.g., 2, 3, 4, 5, or 6) additional amino acid substitutions (e.g., substituted with alanine) at one or more positions involved in complement fixation (e.g., at positions 1253, H310, E318, K320, K322, or P331). Examples of mutated immunoglobulin CH2 regions include human IgG1, IgG2, IgG4 and mouse IgG2a CH2 regions with alanine substitutions at positions 234, 235, 237 (if present), 318, 320 and 322. An exemplary mutated immunoglobulin CH2 region is mouse IGHG2c CH2 region with alanine substitutions at L234, L235, G237, E318, K320, and K322.

In still further embodiments, in addition to the amino acid substitution at position 297 and the additional deletion(s) or substitution(s) at positions 234-238, an altered CH2 region (e.g., an altered human IgG1 CH2 domain) can further comprise one or more (e.g., two, three, four, five, or six) additional substitutions at positions 253, 310, 318, 320, 322, and 331. For example, an immunoglobulin CH2 region can comprise a (1) substitution at position 297, (2) one or more substitutions or deletions or a combination thereof at positions 234-238, and one or more (e.g., 2, 3, 4, 5, or 6) amino acid substitutions at positions 1253, H310, E318, K320, K322, and P331, such as one, two, three substitutions at positions E318, K320 and K322. The amino acids at the above-noted positions can be substituted by alanine or serine.

In certain embodiments, an immunoglobulin CH2 region polypeptide comprises: (i) an amino acid substitution at the asparagines of position 297 and one amino acid substitution at position 234, 235, 236 or 237; (ii) an amino acid substitution at the asparagine of position 297 and amino acid substitutions at two of positions 234-237; (iii) an amino acid substitution at the asparagine of position 297 and amino acid substitutions at three of positions 234-237; (iv) an amino acid substitution at the asparagine of position 297, amino acid substitutions at positions 234, 235 and 237, and an amino acid deletion at position 236; (v) amino acid substitutions at three of positions 234-237 and amino acid substitutions at positions 318, 320 and 322; or (vi) amino acid substitutions at three of positions 234-237, an amino acid deletion at position 236, and amino acid substitutions at positions 318, 320 and 322.

Exemplary altered immunoglobulin CH2 regions with amino acid substitutions at the asparagine of position 297 include: human IgG1 CH2 region with alanine substitutions at L234, L235, G237 and N297 and a deletion at G236 (SEQ ID NO:325 of US 2013/0129723, said sequence incorporated by reference herein), human IgG2 CH2 region with alanine substitutions at V234, G236, and N297 (SEQ ID NO:326 of US 2013/0129723, said sequence incorporated by reference herein), human IgG4 CH2 region with alanine substitutions at F234, L235, G237 and N297 and a deletion of G236 (SEQ ID NO:322 of US 2013/0129723, said sequence incorporated by reference herein), human IgG4 CH2 region with alanine substitutions at F234 and N297 (SEQ ID NO:343 of US 2013/0129723, said sequence incorporated by reference herein), human IgG4 CH2 region with alanine substitutions at L235 and N297 (SEQ ID NO:344 of US 2013/0129723, said sequence incorporated by reference herein), human IgG4 CH2 region with alanine substitutions at G236 and N297 (SEQ ID NO:345 of US 2013/0129723, said sequence incorporated by reference herein), and human IgG4 CH2 region with alanine substitutions at G237 and N297 (SEQ ID NO:346 of US 2013/0129723, said sequence incorporated by reference herein).

In certain embodiments, in addition to the amino acid substitutions described above, an altered CH2 region (e.g., an altered human IgG1 CH2 domain) can contain one or more additional amino acid substitutions at one or more positions other than the above-noted positions. Such amino acid substitutions can be conservative or non-conservative amino acid substitutions. For example, in certain embodiments, P233 can be changed to E233 in an altered IgG2 CH2 region (see, e.g., SEQ ID NO:326 of US 2013/0129723, said sequence incorporated by reference herein). In addition or alternatively, in certain embodiments, the altered CH2 region can contain one or more amino acid insertions, deletions, or both. The insertion(s), deletion(s) or substitution(s) can be anywhere in an immunoglobulin CH2 region, such as at the N- or C-terminus of a wild type immunoglobulin CH2 region resulting from linking the CH2 region with another region (e.g., a binding domain or an immunoglobulin heterodimerization domain) via a hinge.

In certain embodiments, an altered CH2 region in a polypeptide of the present disclosure comprises or is a sequence that is at least 90%, at least 91%, at least 92%, at least 93%, at least 94%, at least 95%, at least 96%, at least 97%, at least 98%, at least 99% identical to a wild type immunoglobulin CH2 region, such as the CH2 region of wild type human IgG1, IgG2, or IgG4, or mouse IgG2a (e.g., IGHG2c).

An altered immunoglobulin CH2 region in a CD123-binding polypeptide of the present disclosure can be derived from a CH2 region of various immunoglobulin isotypes, such as IgG1, IgG2, IgG3, IgG4, IgA1, IgA2, and IgD, from various species (including human, mouse, rat, and other mammals). In certain embodiments, an altered immunoglobulin CH2 region in a fusion protein of the present disclosure can be derived from a CH2 region of human IgG1, IgG2 or IgG4, or mouse IgG2a (e.g., IGHG2c), whose sequences are set forth in SEQ ID NOS:115, 199, 201, and 320 of US 2013/0129723 (said sequences incorporated by reference herein).

In certain embodiments, an altered CH2 domain is a human IgG1 CH2 domain with alanine substitutions at positions 235, 318, 320, and 322 (i.e., a human IgG1 CH2 domain with L235A, E318A, K320A and K322A substitutions) (SEQ ID NO:595 of US 2013/0129723, said sequence incorporated by reference herein), and optionally an N297 mutation (e.g., to alanine). In certain other embodiments, an altered CH2 domain is a human IgG1 CH2 domain with alanine substitutions at positions 234, 235, 237, 318, 320 and 322 (i.e., a human IgG1 CH2 domain with L234A, L235A, G237A, E318A, K320A and K322A substitutions) (SEQ ID NO:596 of US 2013/0129723, said sequence incorporated by reference herein), and optionally an N297 mutation (e.g., to alanine).

In certain embodiments, an altered CH2 domain is an altered human IgG1 CH2 domain with mutations known in the art that enhance immunological activities such as ADCC, ADCP, CDC, complement fixation, Fc receptor binding, or any combination thereof.

The CH3 domain that can form an immunoglobulin constant region of a polypeptide of the present disclosure can be a wild type immunoglobulin CH3 domain or an altered immunoglobulin CH3 domain thereof from certain immunoglobulin classes or subclasses (e.g., IgG1, IgG2, IgG3, IgG4, IgA1, IgA2, IgD, IgE, IgM) of various species (including human, mouse, rat, and other mammals). In certain embodiments, a CH3 domain is a wild type human immunoglobulin CH3 domain, such as wild type CH3 domains of human IgG1, IgG2, IgG3, IgG4, IgA1, IgA2, IgD, IgE, or IgM as set forth in SEQ ID NOS:116, 208-210, 204-207, and 212, respectively of US 2013/0129723 (said sequences incorporated by reference herein). In certain embodiments, the CH3 domain is a wild type human IgG1 CH3 domain as set forth in SEQ ID NO:116 of US 2013/0129723 (said sequence incorporated by reference herein). In certain embodiments, a CH3 domain is an altered human immunoglobulin CH3 domain, such as an altered CH3 domain based on or derived from a wild-type CH3 domain of human IgG1, IgG2, IgG3, IgG4, IgA1, IgA2, IgD, IgE, or IgM antibodies. For example, an altered CH3 domain can be a human IgG1 CH3 domain with one or two mutations at positions H433 and N434 (positions are numbered according to EU numbering). The mutations in such positions can be involved in complement fixation. In certain other embodiments, an altered CH3 domain can be a human IgG1 CH3 domain but with one or two amino acid substitutions at position F405 or Y407. The amino acids at such positions are involved in interacting with another CH3 domain. In certain embodiments, an altered CH3 domain can be an altered human IgG1 CH3 domain with its last lysine deleted. The sequence of this altered CH3 domain is set forth in SEQ ID NO:761 of US 2013/0129723 (said sequence incorporated by reference herein).

In certain embodiments, CD123-binding polypeptides forming a polypeptide heterodimer comprise a CH3 pair that comprises so called "knobs-into-holes" mutations (see, Marvin and Zhu, Acta Pharmacologica Sinica 26:649-58, 2005; Ridgway et al., Protein Engineering 9:617-21, 1996). More specifically, mutations can be introduced into each of the two CH3 domains of each polypeptide chain so that the steric complementarity required for CH3/CH3 association obligates these two CH3 domains to pair with each other. For example, a CH3 domain in one single chain polypeptide of a polypeptide heterodimer can contain a T366W mutation (a "knob" mutation, which substitutes a small amino acid with a larger one), and a CH3 domain in the other single chain polypeptide of the polypeptide heterodimer can contain a Y407A mutation (a "hole" mutation, which substitutes a large amino acid with a smaller one). Other exemplary knobs-into-holes mutations include (1) a T366Y mutation in one CH3 domain and a Y407T in the other CH3 domain, and (2) a T366W mutation in one CH3 domain and T366S, L368A and Y407V mutations in the other CH3 domain.

The CH4 domain that can form an immunoglobulin constant region of CD123-binding polypeptides of the present disclosure can be a wild type immunoglobulin CH4 domain or an altered immunoglobulin CH4 domain thereof from IgE or IgM molecules. In certain embodiments, the CH4 domain is a wild type human immunoglobulin CH4 domain, such as wild type CH4 domains of human IgE and IgM molecules as set forth in SEQ ID NOS:213 and 214, respectively, of US 2013/0129723 (said sequences incorporated by reference herein). In certain embodiments, a CH4 domain is an altered human immunoglobulin CH4 domain, such as an altered CH4 domain based on or derived from a CH4 domain of human IgE or IgM molecules, which have mutations that increase or decrease an immunological activity known to be associated with an IgE or IgM Fc region.

In certain embodiments, an immunoglobulin constant region of CD123-binding polypeptides of the present disclosure comprises a combination of CH2, CH3 or CH4 domains (i.e., more than one constant region domain selected from CH2, CH3 and CH4). For example, the immunoglobulin constant region can comprise CH2 and CH3 domains or CH3 and CH4 domains. In certain other embodiments, the immunoglobulin constant region can comprise two CH3 domains and no CH2 or CH4 domains (i.e., only two or more CH3). The multiple constant region domains that form an immunoglobulin constant region can be based on or derived from the same immunoglobulin molecule, or the same class or subclass immunoglobulin molecules. In certain embodiments, the immunoglobulin constant region is an IgG CH2CH3 (e.g., IgG1 CH2CH3, IgG2 CH2CH3, and IgG4 CH2CH3) and can be a human (e.g., human IgG1, IgG2, and IgG4) CH2CH3. For example, in certain embodiments, the immunoglobulin constant region comprises (1) wild type human IgG1 CH2 and CH3 domains, (2) human IgG1 CH2 with N297A substitution (i.e., CH2(N297A)) and wild type human IgG1 CH3, or (3) human IgG1 CH2(N297A) and an altered human IgG1 CH3 with the last lysine deleted.

Alternatively, the multiple constant region domains can be based on or derived from different immunoglobulin molecules, or different classes or subclasses immunoglobulin molecules. For example, in certain embodiments, an immunoglobulin constant region comprises both human IgM CH3 domain and human IgG1 CH3 domain. The multiple constant region domains that form an immunoglobulin constant region can be directly linked together or can be linked to each other via one or more (e.g., about 2-10) amino acids.

Exemplary immunoglobulin constant regions are set forth in SEQ ID NOS:305-309, 321, 323, 341, 342, and 762 of US 2013/0129723 (said sequences incorporated by reference herein).

In certain embodiments, the immunoglobulin constant regions of both CD123-binding polypeptides of a polypeptide dimer are identical to each other. In certain other embodiments, the immunoglobulin constant region of one polypeptide chain of a dimeric protein is different from the immunoglobulin constant region of the other polypeptide chain of the dimer. For example, one immunoglobulin constant region of a heterodimeric protein can contain a CH3 domain with a "knob" mutation, whereas the other immunoglobulin constant region of the heterodimeric protein can contain a CH3 domain with a "hole" mutation.

The disclosure relates to CD123-binding proteins and polypeptides that may comprise any of the sequences shown in Table 3. In some embodiments, CD123-binding proteins and polypeptides may comprise a signal sequence. Sequences for various cloned sequences and components are also presented in Table 3. Amino acid sequences given for polypeptide constructs do not include the human or rabbit immunoglobulin leader sequences. CDR sequences and amino acid substitution positions shown are those defined using the IMGT criteria (Brochet, X, et al, Nucl. Acids Res. (2008) 36, W503-508). Thus, the first residue in FR1 of a heavy or light chain variable domain or region is considered to be position 1.

TABLE 3

Binding Polypeptide Sequences and Components

| Name | Nucleotide Sequence | Amino Acid Sequence | SEQ ID NOs: nucleotide (amino acid) |
|---|---|---|---|
| OMT1 variable light chain domain | gacatcgtgatgacccagtctccagactccctggctgtgtctctg ggcgagagggccaccatcaactgcaagtccagccacagtgtttta tacagctccaacaataagaactacttagcttggtaccagcagaaa ccaggacagcctcctaagctgctcatttactgggcatctacccgg gaatccggggtccctgaccgattcagtggcagcgggtctgggaca gatttcactctcaccatcagcagcctgcaggctgaagatgtggca gtttattactgtcagcaatattatagtactcctccgaccactttc ggcggagggaccaaggtggagatcaaa | divmtqspdslavslg eratincksshsvlys snnknylawyqqkpgq ppklliywastresgv pdrfsgsgsgtdftlt isslqaedvavyycqq yystppttfgggtkve ik | SEQ ID NO: 1 (SEQ ID NO: 2) |
| OMT1 variable heavy chain domain | gaggtgcagctgttggagtctgggggaggcttggtacagcctggg gggtccctgagactctcctgtgcagcctctggattcacctttagc agctatggcatgagctgggtccgccaggctccagggaaggggctg gagggggtctcagctattagtggtagtggtggtagcacatactac gcagactccgtgaagggccggttcaccatctccagagacaattcc aagaacacgctgtatctgcaaatgaacagcctgagagccgaggac acggccgtatattactgtgcgaaagaaaagttacgatattttgac tggttatccgatgcttttgatatctggggccaagggacaatggtc accgtctcttca | evqllesggglvqpgg slrlscaasgftfssy gmswvrqapgkglegv saisgsggstyyadsv kgrftisrdnskntly lqmnslraedtavyyc akeklryfdwlsdafd iwgqgtmvtvss | SEQ ID NO: 3 (SEQ ID NO: 4) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| OMT1 CDR L1 | cacagtgttttatacagctccaacaataagaactac | HSVLYSSNNKNY | SEQ ID NO: 5 (SEQ ID NO: 6) |
| OMT1 CDR L2 | tgggcatct | WAS | SEQ ID NO: 7 (SEQ ID NO: 8) |
| OMT1 CDR L3 | cagcaatattatagtactcctccgaccact | QQYYSTPPTT | SEQ ID NO: 9 (SEQ ID NO: 10) |
| OMT1 CDR H1 | ggattcacctttagcagctatggc | GFTFSSYG | SEQ ID NO: 11 (SEQ ID NO: 12) |
| OMT1 CDR H2 | attagtggtagtggtggtagcaca | ISGSGGST | SEQ ID NO: 13 (SEQ ID NO: 14) |
| OMT1 CDR H3 | gcgaaagaaaagttacgatattttgactggttatccgatgcttttgatatc | AKEKLRYFDWLSDAFDI | SEQ ID NO: 15 (SEQ ID NO: 16) |
| DB8 variable light chain domain | gacatccagatgacccagtctccatcctccctgtctgcatctgtaggagacagagtcaccatcacttgccgggcaagtcagagcattagcagctatctgaattggtatcagcagaaaccagggaaagcccctaagctcctgatctatgctgcatccagtttgcaaagtggggtcccatcaaggttcagtggcagtggatctgggacagatttcactctcaccatcagcagtctgcaacctgaagattttgcaacttactactgtcaacagagttacagtacccctctcactttcggcggaggtaccaaggtggagatcaaa | diqmtqspsslsasvgdrvtitcrasqsissylnwyqqkpgkapklliyaasslqsgvpsrfsgsgsgtdftltisslqpedfatyycqqsystpltfgggtkveik | SEQ ID NO: 17 (SEQ ID NO: 18) |
| DB8 variable heavy chain domain | caggtgcagctggtgcagtctggggctgaggtgaagaagcctggggcctcagtgaaggtttcctgcaaggcatctggatacatcttcaccgactactatatgcactgggtgcgtcaggcccctggacaagggcttgagtggatgggatggatgagccctaacagtggtaacacaggctatgcacagaagttccagggccgtgtcaccatgacccgcgacacgtccacgagcacagtctacatggagctgagcagcctgcgttctgaggacacggccgtgtattactgtgcgagagatgcggcggattacggtgactacgttgcttttgatatctggggccaagggacaatggtcaccgtctcttca | qvqlvqsgaevkkpgasvkvsckasgyiftdyymhwvrqapgqglewmgwmspnsgntgyaqkfqgrvtmtrdtststvymelssirsedtavyycardaadygdyvafdiwgqgtmvtvss | SEQ ID NO: 19 (SEQ ID NO: 20) |
| DB8 CDR L1 | cagagcattagcagctat | QSISSY | SEQ ID NO: 21 (SEQ ID NO: 22) |
| DB8 CDR L2 | gctgcatcc | AAS | SEQ ID NO: 23 (SEQ ID NO: 24) |
| DB8 CDR L3 | caacagagttacagtacccctctcact | QQSYSTPLT | SEQ ID NO: 25 (SEQ ID NO: 26) |
| DB8 CDR H1 | ggatacatcttcaccgactactat | GYIFTDYY | SEQ ID NO: 27 (SEQ ID NO: 28) |
| DB8 CDR H2 | atgagccctaacagtggtaacaca | MSPNSGNT | SEQ ID NO: 29 (SEQ ID NO: 30) |
| DB8 CDR H3 | gcgagagatgcggcggattacggtgactacgttgcttttgatatc | ARDAADYGDYVAFDI | SEQ ID NO: 31 (SEQ ID NO: 32) |
| DB60 variable light chain domain | gacatccagatgacccagtctccatcctccctgtctgcatctgtaggagacagagtcaccatcacttgccgggcaagtcagagcattagcagctatctgaattggtatcagcagaaaccagggaaagcccctaagctcctgatctatgctgcatccagtttgcaaagtggggtcccatcaaggttcagtggcagtggatctgggacagatttcactctcaccatcagcagtctgcaacctgaagattttgcaacttactactgtcaacagagttacagtacccctctcactttcggcggaggtaccaaggtggagatcaaa | diqmtqspsslsasvgdrvtitcrasqsissylnwyqqkpgkapklliyaasslqsgvpsrfsgsgsgtdftltisslqpedfatyycqqsystpltfgggtkveik | SEQ ID NO: 17 (SEQ ID NO: 18) |
| DB60 variable heavy chain domain | caggtgcagctggtgcagtctggggctgaggtgaagaagcctggggcctc agtgaaggtttcctgcaaggcatctggatacaccttcaccagctactatat gcactgggtgcgtcaggcccctggacaagggcttgagtggatgggtgg atcaaccctaacagtggtgacacaagctatgcacagaagttccagggcc gtgtcaccatgacccgcgacacgtccacgagcacagtctacatggagctg | qvqlvqsgaevkkpgas vkvsckasgytftsyym hwvrqapgqglewmg winpnsgdtsyaqkfqg rvtmtrdtststvymels | SEQ ID NO: 33 (SEQ ID NO: 34) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | agcagcctgcgttctgaggacacggccgtgtattactgtgcgcag gatag tagtggttccggggcttttgatatctggggccaagggacaatggt caccgt ctcttca | slrsedtavyycaqds sg sgafdiwgqgtmvtvs s | |
| DB60 CDR L1 | cagagcattagcagctat | QSISSY | SEQ ID NO: 21 (SEQ ID NO: 22) |
| DB60 CDR L2 | gctgcatcc | AAS | SEQ ID NO: 23 (SEQ ID NO: 24) |
| DB60 CDR L3 | caacagagttacagtacccctctcact | QQSYSTPLT | SEQ ID NO: 25 (SEQ ID NO: 26) |
| DB60 CDR H1 | ggatacaccttcaccagctactat | GYTFTSYY | SEQ ID NO: 35 (SEQ ID NO: 36) |
| DB60 CDR H2 | atcaaccctaacagtggtgacaca | INPNSGDT | SEQ ID NO: 37 (SEQ ID NO: 38) |
| DB60 CDR H3 | gcgcaggatagtagtggttccggggcttttgatatc | AQDSSGSGAFDI | SEQ ID NO: 39 (SEQ ID NO: 40) |
| DB65 variable light chain domain | gacatccagatgacccagtctccatcctccctgtctgcatctgta ggagacagagtcaccatcacttgccgggcaagtcagagcattagc agctatctgaattggtatcagcagaaaccagggaaagcccctaag ctcctgatctatgctgcatccagtttgcaaagtggggtcccatca aggttcagtggcagtggatctgggacagatttcactctcaccatc agcagtctgcaacctgaagattttgcaacttactactgtcaacag agttacagtacccctctcactttcggcggaggtaccaaggtggag atcaaa | diqmtqspsslsasvg drvtitcrasqsissy lnwyqqkpgkapklli yaasslqsgvpsrfsg sgsgtdftltisslqp edfatyycqqsystpl tfgggtkveik | SEQ ID NO: 17 (SEQ ID NO: 18) |
| DB65 variable heavy chain domain | caggtgcagctggtgcagtctggggctgaggtgaagaagcctggg gcctcagtgaaggtttcctgcaaggcatctggatacaccttcacc ggctactatatgcactgggtgcgtcaggcccctggacaagggctt gagtggatgggatggatgaaccctaacagtggtaacacaggctat gcacagaagttccagggccgtgtcaccatgacccgcgacacgtcc acgagcacagtctacatggagctgagcagcctgcgttctgaggac acggccgtgtattactgtgcgaaagaggaaccgatttttggagtg gttatggatgcttttgatatctggggccaagggacaatggtcacc gtctcctca | qvqlvqsgaevkkpga svkvsckasgytftgy ymhwvrqapgqglewm gwmnpnsgntgyaqkf qgrvtmtrdtststvy melsslrsedtavyyc akeepifgvvmdafdi wgqgtmvtvss | SEQ ID NO: 41 (SEQ ID NO: 42) |
| DB65 CDR L1 | cagagcattagcagctat | QSISSY | SEQ ID NO: 21 (SEQ ID NO: 22) |
| DB65 CDR L2 | gctgcatcc | AAS | SEQ ID NO: 23 (SEQ ID NO: 24) |
| DB65 CDR L3 | caacagagttacagtacccctctcact | QQSYSTPLT | SEQ ID NO: 25 (SEQ ID NO: 26) |
| DB65 CDR H1 | ggatacaccttcaccggctactat | GYTFTGYY | SEQ ID NO: 43 (SEQ ID NO: 44) |
| DB65 CDR H2 | atgaaccctaacagtggtaacaca | MNPNSGNT | SEQ ID NO: 45 (SEQ ID NO: 46) |
| DB65 CDR H3 | gcgaaagaggaaccgatttttggagtggttatggatgcttttgat atc | AKEEPIFGVVMDAFDI | SEQ ID NO: 47 (SEQ ID NO: 48) |
| DB82 variable light chain domain | gacatccagatgacccagtctccatcctccctgtctgcatctgta ggagaccgcgtcaccatcacttgccgggcaagtcagaccataaac aactatttgaactggtatcagcagaaaccagggaaagcccctaag ctcctgatctattctgcatctactttgcaaagtggggtcccatca cgtttcagtggcagtggatctgggacagatttcactctcaccatc agcagtctgcaacctgaagattttgcaacttactactgtcaccag agttacacttcacctctcactttcggcggaggtaccaaggtggag atcaaa | diqmtqspsslsasvg drvtitcrasqtinny lnwyqqkpgkapklli ysastlqsgvpsrfsg sgsgtdftltisslqp edfatyychqsytspl tfgggtkveik | SEQ ID NO: 49 (SEQ ID NO: 50) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| DB82 variable heavy chain domain | gaggtgcagctggtggagtctgggggaggcttggtacagcctggg gggtccctgcgcctctcctgtgcagcctctggattcacctttagc agctatgccatgagctgggtccgccaggctccagggaaggggctg gagtgggtctcagttattagtgccaatagtgctggtctaggccat gcggactctgtgaagggccggttcaccatctcccgcgacaattcc aagaacacgctgtatctgcaaatgaacagcctgcgcgccgaggac acggccgtatattactgtgcgagagtgggctatagcagctcggct gatgcttttgatatctggggccaagggacaatggtcaccgtctcc tcg | evqlvesggglvqpgg slriscaasgftfssy amswvrqapgkglewv svisansaglghadsv kgrftisrdnskntly lqmnslraedtavyyc arvgysssadafdiwg qgtmvtvss | SEQ ID NO: 51 (SEQ ID NO: 52) |
| DB82 CDR L1 | cagaccataaacaactat | QTINNY | SEQ ID NO: 53 (SEQ ID NO: 54) |
| DB82 CDR L2 | tctgcatct | SAS | SEQ ID NO: 55 (SEQ ID NO: 56) |
| DB82 CDR L3 | caccagagttacacttcacctctcact | HQSYTSPLT | SEQ ID NO: 57 (SEQ ID NO: 58) |
| DB82 CDR H1 | ggattcacctttagcagctatgcc | GFTFSSYA | SEQ ID NO: 59 (SEQ ID NO: 60) |
| DB82 CDR H2 | attagtgccaatagtgctggtcta | ISANSAGL | SEQ ID NO: 61 (SEQ ID NO: 62) |
| DB82 CDR H3 | gcgagagtgggctatagcagctcggctgatgcttttgatatc | ARVGYSSSADAFDI | SEQ ID NO: 63 (SEQ ID NO: 64) |
| DB83 variable light chain domain | gatgttgtgatgactcagtctccactctccctgcccgtcacccct ggagagccggcctccatctcctgcaggtctagtcagagcctcctg catagtaatggagacaactatttggattggtacctgcagaagcca gggcagtctccacagctcctgatctatttgggttctaatcgggcc tccggggtccctgaccgtttcagtggcagtggatcaggcacagat tttacactgaaaatcagccgtgtggaggctgaggatgttggggtt tattactgcatgcaagctacacactggccactcactttcggccct ggtaccaaagtggatatcaaa | dvvmtqsplslpvtpg epasiscrssqsllhs ngdnyldwylqkpgqs pqlliylgsnrasgvp drfsgsgsgtdftlki srveaedvgvyycmqa thwpltfgpgtkvdik | SEQ ID NO: 65 (SEQ ID NO: 66) |
| DB83 variable heavy chain domain | caggtgcagctggtgcagtctggggctgaggtgaagaagcctggg gcctcagtgaaggtttcctgcaaggcatctggatacaccttcact agctatgctatgcattgggtgcgtcaggcccctggacaagggctt gagtggatgggacttgttgatcctgaagatggtgaaacaatatat gcagagaagttccagggccgtgtcaccatgacccgcgacacgtcc acgagcacagtctacatggagctgagcagcctgcgttctgaggac acggccgtgtattactgtgcgagacgaacgtattactatgatagt agtggttcccgttatgcttttgatatctggggccaagggaccacg gtcaccgtctcttca | qvqlvqsgaevkkpga svkvsckasgytftsy amhwvrqapgqglewm glvdpedgetiyaekf qgrvtmtrdtststvy melsslrsedtavyyc arrtyyydssgsryaf diwgqgttv tvss | SEQ ID NO: 67 (SEQ ID NO: 68) |
| DB83 CDR L1 | cagagcctcctgcatagtaatggagacaactat | QSLLHSNGDNY | SEQ ID NO: 69 (SEQ ID NO: 70) |
| DB83 CDR L2 | ttgggttct | LGS | SEQ ID NO: 71 (SEQ ID NO: 72) |
| DB83 CDR L3 | atgcaagctacacactggccactcact | MQATHWPLT | SEQ ID NO: 73 (SEQ ID NO: 74) |
| DB83 CDR H1 | ggatacaccttcactagctatgct | GYTFTSYA | SEQ ID NO: 75 (SEQ ID NO: 76) |
| DB83 CDR H2 | gttgatcctgaagatggtgaaaca | VDPEDGET | SEQ ID NO: 77 (SEQ ID NO: 78) |
| DB83 CDR H3 | gcgagacgaacgtattactatgatagtagtggttcccgttatgct tttgatatc | ARRTYYYDSSGSRYAF DI | SEQ ID NO: 79 (SEQ ID NO: 80) |
| DB86 variable light chain domain | gacatccagatgacccagtctccatcctccctgtctgcatctgta ggagaccgcgtcaccatcacttgccgggcaagtcagggcatcaga aatgatttaggttggtatcagcagaaaccagggaaagcccctaag ctcctgatctatgctgcatccactttgcaatcaggggtcccatca cgtttcagtggcagtggatctgggacagatttcactctcaccatc agcagtctgcaacctgaagattttgcaacttactactgtcaacag agttacggtgccccccctcactttcggcggaggtaccaaggtggag atcaaa | diqmtqspsslsasvg drvtitcrasqgirnd lgwyqqkpgkapklli yaastlqsgvpsrfsg sgsgtdftltisslqp edfatyycqqsygapl tfgggtkveik | SEQ ID NO: 81 (SEQ ID NO: 82) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| DB86 variable heavy chain domain | caggtgcagctggtgcagtctggggctgaggtgaagaagcctggg gcctcagtgaaggtttcctgcaaggcatctggatatatgttcagt ggccattctgcacactgggtgcgtcaggcccctggacaagggctt gagtggatgggatggatgaaccctaacagtggtaacacaggctat gcacagaagttccagggccgtgtcaccatgacccgcgacacgtcc acgagcacagtctacatggagctgagcagcctgcgttctgaggac acggccgtgtattactgtgcgagagatagcagtggctggtacgat gtctttgactactggggccaggggaccctggtcaccgtctcctca | qvqlvqsgaevkkpga svkvsckasgymfsgh sahwvrqapgqglewm gwmnpnsgntgyaqkf qgrvtmtrdtststvy melsslrsedtavyyc ardssgwydvfdywgq gtlvtvss | SEQ ID NO: 83 (SEQ ID NO: 84) |
| DB86 CDR L1 | cagggcatcagaaatgat | QGIRND | SEQ ID NO: 85 (SEQ ID NO: 86) |
| DB86 CDR L2 | gctgcatcc | AAS | SEQ ID NO: 87 (SEQ ID NO: 88) |
| DB86 CDR L3 | caacagagttacggtgccccctc | QQSYGAPLT | SEQ ID NO: 89 (SEQ ID NO: 90) |
| DB86 CDR H1 | ggatatatgttcagtggccattct | GYMFSGHS | SEQ ID NO: 91 (SEQ ID NO: 92) |
| DB86 CDR H2 | atgaaccctaacagtggtaacaca | MNPNSGNT | SEQ ID NO: 93 (SEQ ID NO: 94) |
| DB86 CDR H3 | gcgagagatagcagtggctggtacgatgtctttgactac | ARDSSGWYDVFDY | SEQ ID NO: 95 (SEQ ID NO: 96) |
| DB280 variable light chain domain | gacatccagatgacccagtctccatcctccctgtctgcatctgta ggagacagagtcaccatcacttgccgggcaagtcagagcattagc agctatctgaattggtatcagcagaaaccagggaaagcccctaag ctcctgatctatgctgcatccagtttgcaaagtggggtcccatca aggttcagtggcagtggatctgggacagatttcactctcaccatc agcagtctgcaacctgaagattttgcaacttactactgtcaacag agttacagtacccctctcactttcggcggaggtaccaaggtggag atcaaa | diqmtqspsslsasvg drvtitcrasqsissy lnwyqqkpgkapklli yaasslqsgvpsrfsg sgsgtdftltisslqp edfatyycqqsystpl tfgggtkveik | SEQ ID NO: 17 (SEQ ID NO: 18) |
| DB280 variable heavy chain domain | caggtgcagctggtgcagtctggggctgaggtgaagaagcctggg gcctcagtgaaggtttcctgcaaggcatctggatacagcctcaac ttatactatatgcactgggtgcgtcaggcccctggacaagggctt gagtggatgggatggatgaaccctaacagtggtaacacaggctat gcacagaagttccagggccgtgtcaccatgacccgcgacacgtcc acgagcacagtctacatggagctgagcagcctgcgttctgaggac acggccgtgtattactgtgcgagcctcgattgtagtggtggtagc tgctactccgaatatgatgcttttgatatctggggccaagggacc acggtcaccgtctcctca | qvqlvqsgaevkkpga svkvsckasgyslnly ymhwvrqapgqglewm gwmnpnsgntgyaqkf qgrvtmtrdtststvy melsslrsedtavyyc asldcsggscyseyda fdiwgqgttvtvss | SEQ ID NO: 97 (SEQ ID NO: 98) |
| DB280 CDR L1 | cagagcattagcagctat | QSISSY | SEQ ID NO: 21 (SEQ ID NO: 22) |
| DB280 CDR L2 | gctgcatcc | AAS | SEQ ID NO: 23 (SEQ ID NO: 24) |
| DB280 CDR L3 | caacagagttacagtacccctctcact | QQSYSTPLT | SEQ ID NO: 25 (SEQ ID NO: 26) |
| DB280 CDR H1 | ggatacagcctcaacttatactat | GYSLNLYY | SEQ ID NO: 99 (SEQ ID NO: 100) |
| DB280 CDR H2 | atgaaccctaacagtggtaacaca | MNPNSGNT | SEQ ID NO: 101 (SEQ ID NO: 102) |
| DB280 CDR H3 | gcgagcctcgattgtagtggtggtagctgctactccgaatatgat gcttttgatatc | ASLDCSGGSCYSEYDA FDI | SEQ ID NO: 103 (SEQ ID NO: 104) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| DB331 variable light chain domain | gacatccagatgacccagtctccatcctccctgtctgcatctgta ggagacagagtcaccatcacttgccgggcaagtcagagcattagc agctatctgaattggtatcagcagaaaccagggaaagcccctaag ctcctgatctatgctgcatccagtttgcaaagtggggtcccatca aggttcagtggcagtggatctgggacagatttcactctcaccatc agcagtctgcaacctgaagattttgcaacttactactgtcaacag agttacagtacccctctcactttcggcggaggtaccaaggtggag atcaaa | diqmtqspsslsasvg drvtitcrasqsissy lnwyqqkpgkapklli yaasslqsgvpsrfsg sgsgtdftltisslqp edfatyycqqsystpl tfgggtkveik | SEQ ID NO: 17 (SEQ ID NO: 18) |
| DB331 variable heavy chain domain | caggtgcagctggtgcagtctggggctgaggtgaagaagcctggg gcctcagtgaaggtttcctgcaaggcatctggatacaccttcacc agctactatatgcactgggtgcgtcaggcccctggacaagggctt gagtggatgggatggatgaaccctaacagtggtaacacaggctat gcacagaagttccagggccgtgtcaccatgacccgcgacacgtcc acgagcacagtctacatggagctgagcagcctgcgttctgaggac acggccgtgtattactgtgcaacagatctcgcgggggaagccttg ttcgaccccctggggccagggcaccctggtcaccgtctcctca | qvqlvqsgaevkkpga svkvsckasgytftsy ymhwvrqapgqglewm gwmnpnsgntgyaqkf qgrvtmtrdtststvy melsslrsedtavyyc atdlageaifdpwgqg tlvtvss | SEQ ID NO: 105 (SEQ ID NO: 106) |
| DB331 CDR L1 | cagagcattagcagctat | QSISSY | SEQ ID NO: 21 (SEQ ID NO: 22) |
| DB331 CDR L2 | gctgcatcc | AAS | SEQ ID NO: 23 (SEQ ID NO: 24) |
| DB331 CDR L3 | caacagagttacagtacccctctcact | QQSYSTPLT | SEQ ID NO: 25 (SEQ ID NO: 26) |
| DB331 CDR H1 | ggatacaccttcaccagctactat | GYTFTSYY | SEQ ID NO: 107 (SEQ ID NO: 108) |
| DB331 CDR H2 | atgaaccctaacagtggtaacaca | MNPNSGNT | SEQ ID NO: 109 (SEQ ID NO: 110) |
| DB331 CDR H3 | gcaacagatctcgcgggggaagccttgttcgacccc | ATDLAGEALFDP | SEQ ID NO: 111 (SEQ ID NO: 112) |
| DB415 variable light chain domain | gacatccagatgacccagtctccatcctccctgtctgcatctgta ggagacagagtcaccatcacttgccgggcaagtcagagcattagc agctatctgaattggtatcagcagaaaccagggaaagcccctaag ctcctgatctatgctgcatccagtttgcaaagtggggtcccatca aggttcagtggcagtggatctgggacagatttcactctcaccatc agcagtctgcaacctgaagattttgcaacttactactgtcaacag agttacagtacccctctcactttcggcggaggtaccaaggtggag atcaaa | diqmtqspsslsasvg drvtitcrasqsissy lnwyqqkpgkapklli yaasslqsgvpsrfsg sgsgtdftltisslqp edfatyycqqsystpl tfgggtkveik | SEQ ID NO: 17 (SEQ ID NO: 18) |
| DB415 variable heavy chain domain | gaggtgcagctggtggagtctgggggaggcttggtacagcctggg gggtccctgcgcctctcctgtgcagcctctggaatcaccttcagt agttatggcatgcattgggtccgccaggctccagggaaggggctg gagtgggtctcaggtattagttggaatagtggtaacagagtctat gtggactctgtgaagggccggttcaccatctcccgcgacaattcc aagaacacgctgtatctgcaaatgaacagcctgcgcgccgaggac acggccgtatattactgtgcgagagatactaatgatgcttttgat atctggggccaagggaccacggtcaccgtctcctca | evqlvesggglvqpgg slrlscaasgitfssy gmhwvrqapgkglewv sgiswnsgnrvyvdsv kgrftisrdnskntly lqmnslraedtavyyc ardtndafdiwgqgtt vtvss | SEQ ID NO: 113 (SEQ ID NO: 114) |
| DB415 CDR L1 | cagagcattagcagctat | QSISSY | SEQ ID NO: 21 (SEQ ID NO: 22) |
| DB415 CDR L2 | gctgcatcc | AAS | SEQ ID NO: 23 (SEQ ID NO: 24) |
| DB415 CDR L3 | caacagagttacagtacccctctcact | QQSYSTPLT | SEQ ID NO: 25 (SEQ ID NO: 26) |
| DB415 CDR H1 | ggaatcaccttcagtagttatggc | GITFSSYG | SEQ ID NO: 115 (SEQ ID NO: 116) |
| DB415 CDR H2 | attagttggaatagtggtaacaga | ISWNSGNR | SEQ ID NO: 117 (SEQ ID NO: 118) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| DB415 CDR H3 | gcgagagatactaatgatgcttttgatatc | ARDTNDAFDI | SEQ ID NO: 119 (SEQ ID NO: 120) |
| DB435 variable light chain domain | gacatccagatgacccagtctccatcctccctgtctgcatctgta ggagacagagtcaccatcacttgccgggcaagtcagagcattagc agctatctgaattggtatcagcagaaaccagggaaagcccctaag ctcctgatctatgctgcatccagtttgcaaagtggggtcccatca aggttcagtggcagtggatctgggacagatttcactctcaccatc agcagtctgcaacctgaagattttgcaacttactactgtcaacag agttacagtacccctctcactttcggcggaggtaccaaggtggag atcaaa | diqmtqspsslsasvg drvtitcrasqsissy lnwyqqkpgkapklli yaasslqsgvpsrfsg sgsgtdftltisslqp edfatyycqqsystpl tfgggtkveik | SEQ ID NO: 17 (SEQ ID NO: 18) |
| DB435 variable heavy chain domain | caggtgcagctggtgcagtctggggctgaggtgaagaagcctggg gcctcagtgaaggtttcctgcaaggcatctggaggcaccttcagc agctatgctatcagctgggtgcgtcaggcccctggacaagggctt gagtggatgggctggatcacccctcacaatggtaacataaagtat gcacgggagttccagggccgtgtcaccatgacccgcgacacgtcc acgagcacagtctacatggagctgagcagcctgcgttctgaggac acggccgtgtattactgtgcgaaagatctgaactggaacgcagcc tttgactactggggccaggggaccctggtcaccgtctcctca | qvqlvqsgaevkkpga svkvsckasggtfssy aiswvrqapgqglewm gwitphngnikyaref qgrvtmtrdtststvy melsslrsedtavyyc akdlnwnaafdywgqg tlvtvss | SEQ ID NO: 121 (SEQ ID NO: 122) |
| DB435 CDR L1 | cagagcattagcagctat | QSISSY | SEQ ID NO: 21 (SEQ ID NO: 22) |
| DB435 CDR L2 | gctgcatcc | AAS | SEQ ID NO: 233 (SEQ ID NO: 24) |
| DB435 CDR L3 | caacagagttacagtacccctctcact | QQSYSTPLT | SEQ ID NO: 25 (SEQ ID NO: 26) |
| DB435 CDR H1 | ggaggcaccttcagcagctatgct | GGTFSSYA | SEQ ID NO: 123 (SEQ ID NO: 124) |
| DB435 CDR H2 | atcacccctcacaatggtaacata | ITPHNGNI | SEQ ID NO: 125 (SEQ ID NO: 126) |
| DB435 CDR H3 | gcgaaagatctgaactggaacgcagcctttgactac | AKDLNWNAAFDY | SEQ ID NO: 127 (SEQ ID NO: 128) |
| OMT1 VHVL x TSC456 scFv-Fc-scFv TRI129 | atggaagcaccagcgcagcttctcttcctcctgctactctggctc ccagataccaccggtgaggtgcagctgttggagtctgggggaggc ttggtacagcctggggggtccctgagactctcctgtgcagcctct ggattcacctttagcagctatggcatgagctgggtccgccaggct ccagggaaggggctggagggggtctcagctattagtggtagtggt ggtagcacatactacgcagactccgtgaagggccggttcaccatc tccagagacaattccaagaacacgctgtatctgcaaatgaacagc ctgagagccgaggacacggccgtatattactgtgcgaaagaaaag ttacgatattttgactggttatccgatgcttttgatatctggggc caagggacaatggtcaccgtctcttcaggtggaggcggttcaggc ggaggtggatccggcggtggcggctccggtggcggcggatctgac atcgtgatgacccagtctccagactccctggctgtgtctctgggc gagagggccaccatcaactgcaagtccagccacagtgttttatac agctccaacaataagaactacttagcttggtaccagcagaaacca ggacagcctcctaagctgctcatttactgggcatctacccgggaa tccggggtccctgaccgattcagtggcagcgggtctgggacagat ttcactctcaccatcagcagcctgcaggctgaagatgtggcagtt tattactgtcagcaatattatagtactcctccgaccactttcggc ggagggaccaaggtggagatcaaatcctcgagtgagcccaaatct tctgacaaaactcacacatgcccaccgtgcccagcacctgaagcc gcgggtgcaccgtcagtcttcctcttccccccaaaacccaaggac accctcatgatctcccggacccctgaggtcacatgcgtggtggtg gacgtgagccacgaagaccctgaggtcaagttcaactggtacgtg gacggcgtggaggtgcataatgccaagacaaagccgcgggaggag cagtacaacagcacgtaccgtgtggtcagcgtcctcaccgtcctg caccaggactggctgaatggcaaggaatacaagtgcgcggtctcc aacaaagccctcccagcccccatcgagaaaaccatctccaaagcc aaagggcagccccgagaaccacaggtgtacaccctgcccccatcc cgggatgagctgaccaagaaccaggtcagcctgacctgcctggtc aaaggcttctatccaagcgacatcgccgtggagtgggagagcaat gggcagccggagaacaactacaagaccacgcctcccgtgctggac | evqllesggglvqpgg slrlscaasgftfssy gmswvrqapgkglegv saisgsggstyyadsv kgrftisrdnskntly lqmnslraedtavyyc akeklryfdwlsdafd iwgqgtmvtvssgggg sggggsggggsggggs divmtqspdslavslg eratincksshsvlys snnknylawyqqkpgq ppklliywastresgv pdrfsgsgsgtdftlt isslqaedvavyycqq yystppttfgggtkve iksssepkssdkthtc ppcpapeaagapsvfl fppkpkdtlmisrtpe vtcvvvdvshedpevk fnwyvdgvevhnaktk preeqynstyrvvsvl tvlhqdwingkeykca vsnkalpapiektisk akgqprepqvytipps rdeltknqvsltclvk gfypsdiavewesngq pennykttppvldsdg sfflyskltvdksrwq qgnvfscsvmhealhn hytqkslslspgsggg | SEQ ID NO: 129 (SEQ ID NO: 130) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | tccgacggctccttcttcctctacagcaagctcaccgtggacaag<br>agcaggtggcagcaggggaacgtcttctcatgctccgtgatgcat<br>gaggctctgcacaaccactacacgcagaagagcctctccctgtct<br>ccgggttccggaggagggggttcaggtgggggaggttctggcggc<br>gggggaagcccttcacaggtgcaactggtgcagagtggacccgag<br>gttaaaaaaccagggtcctccgttaaggttagctgcaaagcctct<br>ggctacacattttccaggagtacaatgcactgggtgaggcaggct<br>cctggacagggactcgagtggatcgggtatatcaacccatctagc<br>gcctataccaattacaaccaaaagtttaaggaccgagttaccatt<br>accgctgacaaatccaccagtacagcttatatggagctgtcatct<br>cttaggtccgaggacactgctgtttattactgcgctcgtcctcag<br>gttcactatgactataatggttttccctactggggtcagggaacc<br>ctggtgactgtctcttctggcggtggaggcagcggtgggggtggg<br>tctggaggcggtggcagtggcggcggaggctctgatattcagatg<br>actcagtctcctagcactctcagcgccagcgtgggggatcgtgtg<br>acaatgacttgctccgctagcagtagtgtgtcttacatgaattgg<br>tatcagcagaagcccgggaaagcacctaagcgctggatctatgac<br>tcttccaagctggcaagtggtgtcccctcacggttctctggctca<br>ggttctggtactgactatactttgactatctcctccctccagccc<br>gatgatttcgctacctattattgtcagcagtggagccgtaaccca<br>cccactttcggaggcggtaccaaagtggagatcaagaggtcataa | gsggggsggggspsqv<br>qlvqsgpevkkpgssv<br>kvsckasgytfsrstm<br>hwvrqapgqglewigy<br>inpssaytnynqkfkd<br>rvtitadkststayme<br>lsslrsedtavyycar<br>pqvhydyngfpywgqg<br>tlvtvssggggsgggg<br>sggggsggggsdiqmt<br>qspstlsasvgdrvtm<br>tcsasssvsymnwyqq<br>kpgkapkrwiydsskl<br>asgvpsrfsgsgsgtd<br>ytltisslqpddfaty<br>ycqqwsrnpptfgggt<br>kveikrs | |
| OMT1<br>VLVH x<br>TSC456<br>scFv-<br>Fc-<br>scFv<br>TRI130 | atggaagcaccagcgcagcttctcttcctcctgctactctggctc<br>ccagataccaccggtgacatcgtgatgacccagtctccagactcc<br>ctggctgtgtctctgggcgagagggccaccatcaactgcaagtcc<br>agccacagtgttttatacagctccaacaataagaactacttagct<br>tggtaccagcagaaaccaggacagcctcctaagctgctcatttac<br>tgggcatctacccgggaatccggggtccctgaccgattcagtggc<br>agcgggtctgggacagatttcactctcaccatcagcagcctgcag<br>gctgaagatgtggcagtttattactgtcagcaatattatagtact<br>cctccgaccactttcggcggagggaccaaggtggagatcaaaggt<br>ggaggcggttcaggcggaggtggatccggcggtggcggctccggt<br>ggcggcggatctgaggtgcagctgttggagtctgggggaggcttg<br>gtacagcctggggggtccctgagactctcctgtgcagcctctgga<br>ttcacctttagcagctatggcatgagctgggtccgccaggctcca<br>gggaaggggctggagggggtctcagctattagtggtagtggtggt<br>agcacatactacgcagactccgtgaagggccggttcaccatctcc<br>agagacaattccaagaacacgctgtatctgcaaatgaacagcctg<br>agagccgaggacacggccgtatattactgtgcgaaagaaaagtta<br>cgatattttgactggttatccgatgcttttgatatctggggccaa<br>gggacaatggtcaccgtctcctcgagtgagcccaaatcttctgac<br>aaaactcacacatgcccaccgtgcccagcacctgaagccgcgggt<br>gcaccgtcagtcttcctcttccccccaaaacccaaggacaccctc<br>atgatctcccggacccctgaggtcacatgcgtggtggtggacgtg<br>agccacgaagaccctgaggtcaagttcaactggtacgtggacggc<br>gtggaggtgcataatgccaagacaaagccgcgggaggagcagtac<br>aacagcacgtaccgtgtggtcagcgtcctcaccgtcctgcaccag<br>gactggctgaatggcaaggaatacaagtgcgcggtctccaacaaa<br>gccctcccagcccccatcgagaaaaccatctccaaagccaaaggg<br>cagccccgagaaccacaggtgtacaccctgcccccatcccgggat<br>gagctgaccaagaaccaggtcagcctgacctgcctggtcaaaggc<br>ttctatccaagcgacatcgccgtggagtgggagagcaatgggcag<br>ccggagaacaactacaagaccacgcctcccgtgctggactccgac<br>ggctccttcttcctctacagcaagctcaccgtggacaagagcagg<br>tggcagcaggggaacgtcttctcatgctccgtgatgcatgaggct<br>ctgcacaaccactacacgcagaagagcctctccctgtctccgggt<br>tccggaggagggggttcaggtgggggaggttctggcggcgggggga<br>agcccttcacaggtgcaactggtgcagagtggacccgaggttaaa<br>aaaccagggtcctccgttaaggttagctgcaaagcctctggctac<br>acattttccaggagtacaatgcactgggtgaggcaggctcctgga<br>cagggactcgagtggatcgggtatatcaacccatctagcgcctat<br>accaattacaaccaaaagtttaaggaccgagttaccattaccgct<br>gacaaatccaccagtacagcttatatggagctgtcatctcttagg<br>tccgaggacactgctgtttattactgcgctcgtcctcaggttcac<br>tatgactataatggttttccctactggggtcagggaaccctggtg<br>actgtctcttctggcggtggaggcagcggtgggggtgggtctgga<br>ggcggtggcagtggcggcggaggctctgatattcagatgactcag<br>tctcctagcactctcagcgccagcgtgggggatcgtgtgacaatg<br>acttgctccgctagcagtagtgtgtcttacatgaattggtatcag<br>cagaagcccgggaaagcacctaagcgctggatctatgactcttcc<br>aagctggcaagtggtgtcccctcacggttctctggctcaggttct<br>ggtactgactatactttgactatctcctccctccagcccgatgat<br>ttcgctacctattattgtcagcagtggagccgtaacccacccact<br>ttcggaggcggtaccaaagtggagatcaagaggtcataa | divmtqspdslavslg<br>er<br>atincksshsvlyssn<br>nk<br>nylawyqqkpgqppkl<br>l<br>iywastresgvpdrfs<br>gs<br>gsgtdftltisslqae<br>dva<br>vyycqqyystppttfg<br>gg<br>tkveikggggsggggs<br>gg<br>ggsggggsevqllesg<br>gg<br>lvqpggslrlscaasg<br>ftfs<br>sygmswvrqapgkgle<br>gvsaisgsggstyyad<br>sv<br>kgrftisrdnskntly<br>lqm<br>nslraedtavyycake<br>kl<br>ryfdwlsdafdiwgqg<br>t<br>mvtvsssepkssdkth<br>t<br>cppcpapeaagapsvf<br>l<br>fppkpkdtlmisrtpe<br>vt<br>cvvvdvshedpevkfn<br>wyvdgvevhnaktkpr<br>eeqynstyrwsvltvl<br>h<br>qdwingkeykcavsnk<br>alpapiektiskakgq<br>pr<br>epqvytippsrdeltk<br>nq<br>vsltclvkgfypsdia<br>ve<br>wesngqpennykttpp<br>vldsdgsfflyskltv<br>dksr<br>wqqgnvfscsvmheal<br>hnhytqkslslspgsg<br>gg<br>gsggggsggggspsqv<br>q | SEQ ID NO: 131<br>(SEQ ID<br>NO: 132) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | | lvqsgpevkkpgssvk<br>v<br>sckasgytfsrstmhw<br>v<br>rqapgqglewigyinp<br>s<br>saytnynqkfkdrvti<br>ta<br>dkststaymelsslrs<br>ed<br>tavyycarpqvhydyn<br>g<br>fpywgqgtlvtvssgg<br>g<br>gsggggsggggsgggg<br>s<br>diqmtqspstlsasvg<br>dr<br>vtmtcsasssvsymnw<br>yqqkpgkapkrwiyds<br>sklasgvpsrfsgsgs<br>gtd<br>ytltisslqpddfaty<br>ycq<br>qwsrnpptfgggtkve<br>ikrs | |
| DB8 VHVL x TSC456 scFv-Fc-scFv TRI123 | atggaagcaccagcgcagcttctcttcctcctgctactctggctc<br>ccagataccaccggtcaggtgcagctggtgcagtctggggctgag<br>gtgaagaagcctggggcctcagtgaaggtttcctgcaaggcatct<br>ggatacatcttcaccgactactatatgcactgggtgcgtcaggcc<br>cctggacaagggcttgagtggatgggatggatgagccctaacagt<br>ggtaacacaggctatgcacagaagttccagggccgtgtcaccatg<br>acccgcgacacgtccacgagcacagtctacatggagctgagcagc<br>ctgcgttctgaggacacggccgtgtattactgtgcgagagatgcg<br>gcggattacggtgactacgttgcttttgatatctggggccaaggg<br>acaatggtcaccgtctcttcaggcggcggcggcagcggcggcggc<br>ggcagcggcggcggaggctccggcggcggcggcagcgacatccag<br>atgacccagtctccatcctccctgtctgcatctgtaggagacaga<br>gtcaccatcacttgccgggcaagtcagagcattagcagctatctg<br>aattggtatcagcagaaaccagggaaagcccctaagctcctgatc<br>tatgctgcatccagtttgcaaagtggggtcccatcaaggttcagt<br>ggcagtggatctgggacagatttcactctcaccatcagcagtctg<br>caacctgaagattttgcaacttactactgtcaacagagttacagt<br>acccctctcactttcggcggaggtaccaaggtggagatcaaatcc<br>tcgagtgagcccaaatcttctgacaaaactcacacatgcccaccg<br>tgcccagcacctgaagccgcgggtgcaccgtcagtcttcctcttc<br>cccccaaaacccaaggacaccctcatgatctcccggacccctgag<br>gtcacatgcgtggtggtggacgtgagccacgaagaccctgaggtc<br>aagttcaactggtacgtggacggcgtggaggtgcataatgccaag<br>acaaagccgcgggaggagcagtacaacagcacgtaccgtgtggtc<br>agcgtcctcaccgtcctgcaccaggactggctgaatggcaaggaa<br>tacaagtgcgcggtctccaacaaagccctcccagcccccatcgag<br>aaaaccatctccaaagccaaagggcagccccgagaaccacaggtg<br>tacaccctgcccccatcccgggatgagctgaccaagaaccaggtc<br>agcctgacctgcctggtcaaaggcttctatccaagcgacatcgcc<br>gtggagtgggagagcaatgggcagccggagaacaactacaagacc<br>acgcctcccgtgctggactccgacggctccttcttcctctacagc<br>aagctcaccgtggacaagagcaggtggcagcaggggaacgtcttc<br>tcatgctccgtgatgcatgaggctctgcacaaccactacacgcag<br>aagagcctctccctgtctccgggttccggaggagggggttcaggt<br>gggggaggttctggcggcgggggaagcccttcacaggtgcaactg<br>gtgcagagtggacccgaggttaaaaaaccagggtcctccgttaag<br>gttagctgcaaagcctctggctacacattttccaggagtacaatg<br>cactgggtgaggcaggctcctggacagggactcgagtggatcggg<br>tatatcaacccatctagcgcctataccaattacaaccaaaagttt<br>aaggaccgagttaccattaccgctgacaaatccaccagtacagct<br>tatatggagctgtcatctcttaggtccgaggacactgctgtttat<br>tactgcgctcgtcctcaggttcactatgactataatggttttccc<br>tactggggtcagggaaccctggtgactgtctcttctggcggtgga<br>ggcagcggtgggggtgggtctggaggcggtggcagtggcggcgga<br>ggctctgatattcagatgactcagtctcctagcactctcagcgcc<br>agcgtgggggatcgtgtgacaatgacttgctccgctagcagtagt<br>gtgtcttacatgaattggtatcagcagaagcccgggaaagcacct | qvqlvqsgaevkkpga<br>svkvsckasgyiftdy<br>ymhwvrqapgqglewm<br>gwmspnsgntgyaqkf<br>qgrvtmtrdtststvy<br>melssirsedtavyyc<br>ardaadygdyvafdiw<br>gqgtmvtvssggggsg<br>gggsggggsggggsdi<br>qmtqspsslsasvgdr<br>vtitcrasqsissyln<br>wyqqkpgkapklliya<br>asslqsgvpsrfsgsg<br>sgtdftltisslqped<br>fatyycqqsystpltf<br>gggtkveiksssepks<br>sdkthtcppcpapeaa<br>gapsvflfppkpkdtl<br>misrtpevtcvvvdvsh<br>edpevkfnwyvdgvev<br>hnaktkpreeqynsty<br>rvvsvltvlhqdwlng<br>keykcavsnkalpapi<br>ektiskakgqprepqv<br>ytlppsrdeltknqvs<br>ltclvkgfypsdiave<br>wesngqpennykttpp<br>vldsdgsfflyskltv<br>dksrwqqgnvfscsvm<br>healhnhytqkslsls<br>pgsggggsggggsggg<br>gspsqvqlvqsgpevk<br>kpgssvkvsckasgyt<br>fsrstmhwvrqapgqg<br>lewigyinpssaytny<br>nqkfkdrvtitadkst<br>staymelsslrsedta<br>vyycarpqvhydyngf<br>pywgqgtlvtvssggg<br>gsggggsggggsgggg<br>sdiqmtqspstlsasv<br>gdrvtmtcsasssvsy<br>mnwyqqkpgkapkrwi<br>ydssklasgvpsrfsg<br>sgsgtdytltisslqp<br>ddfatyycqqwsrnpp<br>tfgggtkveikrs | SEQ ID NO: 133<br>(SEQ ID<br>NO: 134) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | aagcgctggatctatgactcttccaagctggcaagtggtgtcccc<br>tcacggttctctggctcaggttctggtactgactatactttgact<br>atctcctccctccagcccgatgatttcgctacctattattgtcag<br>cagtggagccgtaacccacccactttcggaggcggtaccaaagtg<br>gagatcaagaggtcataa | | |
| DB8 VLVH x TSC456 scFv-Fc-scFv TRI124 | atggaagcaccagcgcagcttctcttcctcctgctactctggctc<br>ccagataccaccggtgacatccagatgacccagtctccatcctcc<br>ctgtctgcatctgtaggagacagagtcaccatcacttgccgggca<br>agtcagagcattagcagctatctgaattggtatcagcagaaacca<br>gggaaagcccctaagctcctgatctatgctgcatccagtttgcaa<br>agtggggtcccatcaaggttcagtggcagtggatctgggacagat<br>ttcactctcaccatcagcagtctgcaacctgaagattttgcaact<br>tactactgtcaacagagttacagtacccctctcactttcggcgga<br>ggtaccaaggtggagatcaaaggcggcggcggcagcggcggcggc<br>ggcagcggcggcggaggctccggcggcggcggcagccaggtgcag<br>ctggtgcagtctggggctgaggtgaagaagcctggggcctcagtg<br>aaggtttcctgcaaggcatctggatacatcttcaccgactactat<br>atgcactgggtgcgtcaggcccctggacaagggcttgagtggatg<br>ggatggatgagccctaacagtggtaacacaggctatgcacagaag<br>ttccagggccgtgtcaccatgacccgcgacacgtccacgagcaca<br>gtctacatggagctgagcagcctgcgttctgaggacacggccgtg<br>tattactgtgcgagagatgcggcggattacggtgactacgttgct<br>tttgatatctggggccaagggacaatggtcaccgtctcctcgagt<br>gagcccaaatcttctgacaaaactcacacatgcccaccgtgccca<br>gcacctgaagccgcgggtgcaccgtcagtcttcctcttcccccca<br>aaacccaaggacaccctcatgatctcccggacccctgaggtcaca<br>tgcgtggtggtggacgtgagccacgaagaccctgaggtcaagttc<br>aactggtacgtggacggcgtggaggtgcataatgccaagacaaag<br>ccgcgggaggagcagtacaacagcacgtaccgtgtggtcagcgtc<br>ctcaccgtcctgcaccaggactggctgaatggcaaggaatacaag<br>tgcgcggtctccaacaaagccctcccagcccccatcgagaaaacc<br>atctccaaagccaaagggcagccccgagaaccacaggtgtacacc<br>ctgcccccatcccgggatgagctgaccaagaaccaggtcagcctg<br>acctgcctggtcaaaggcttctatccaagcgacatcgccgtggag<br>tgggagagcaatgggcagccggagaacaactacaagaccacgcct<br>cccgtgctggactccgacggctccttcttcctctacagcaagctc<br>accgtggacaagagcaggtggcagcaggggaacgtcttctcatgc<br>tccgtgatgcatgaggctctgcacaaccactacacgcagaagagc<br>ctctccctgtctccgggttccggaggagggggttcaggtgggggga<br>ggttctggcggcgggggaagcccttcacaggtgcaactggtgcag<br>agtggacccgaggttaaaaaaccagggtcctccgttaaggttagc<br>tgcaaagcctctggctacacattttccaggagtacaatgcactgg<br>gtgaggcaggctcctggacagggactcgagtggatcgggtatatc<br>aacccatctagcgcctataccaattacaaccaaaagtttaaggac<br>cgagttaccattaccgctgacaaatccaccagtacagcttatatg<br>gagctgtcatctcttaggtccgaggacactgctgtttattactgc<br>gctcgtcctcaggttcactatgactataatggttttccctactgg<br>ggtcagggaaccctggtgactgtctcttctggcggtggaggcagc<br>ggtgggggtgggtctggaggcggtggcagtggcggcggaggctct<br>gatattcagatgactcagtctcctagcactctcagcgccagcgtg<br>gggatcgtgtgacaatgacttgctccgctagcagtagtgtgtct<br>tacatgaattggtatcagcagaagcccgggaaagcacctaagcgc<br>tggatctatgactcttccaagctggcaagtggtgtcccctcacgg<br>ttctctggctcaggttctggtactgactatactttgactatctcc<br>tccctccagcccgatgatttcgctacctattattgtcagcagtgg<br>agccgtaa | diqmtqspsslsasvg<br>drvtitcrasqsissy<br>lnwyqqkpgkapklli<br>yaasslqsgvpsrfsg<br>sgsgtdftltisslqp<br>edfatyycqqsystpl<br>tfgggtkveikggggs<br>ggggsggggsggggsq<br>vqlvqsgaevkkpgas<br>vkvsckasgyiftdyy<br>mhwvrqapgqglewmg<br>wmspnsgntgyaqkfq<br>grvtmtrdtststvym<br>elssirsedtavyyca<br>rdaadygdyvafdiwg<br>qgtmvtvsssepkssd<br>kthtcppcpapeaaga<br>psvflfppkpkdtlmi<br>srtpevtcvwdvshed<br>pevkfnwyvdgvevhn<br>aktkpreeqynstyrv<br>vsvltvlhqdwlngke<br>ykcavsnkalpapiek<br>tiskakgqprepqvyt<br>ippsrdeltknqvslt<br>clvkgfypsdiavewe<br>sngqpennykttppvl<br>dsdgsfflyskltvdk<br>srwqqgnvfscsvmhe<br>alhnhytqkslslspg<br>sggggsggggsggggs<br>psqvqlvqsgpevkkp<br>gssvkvsckasgytfs<br>rstmhwvrqapgqgle<br>wigyinpssaytnynq<br>kfkdrvtitadkstst<br>aymelsslrsedtavy<br>ycarpqvhydyngfpy<br>wgqgtlvtvssggggs<br>ggggsggggsggggsd<br>iqmtqspstlsasvgd<br>rvtmtcsasssvsymn<br>wyqqkpgkapkrwiyd<br>ssklasgvpsrfsgsg<br>sgtdytltisslqpdd<br>fatyycqqwsrnpptf<br>gggtkveikrs | SEQ ID NO: 135 (SEQ ID NO: 136) |
| DB8 VHVL x TSC456 scFv-Fc-scFv TRI137 | cccacccactttcggaggcggtaccaaagtggagatcaagaggtc<br>ataaatggaagcaccagcgcagcttctcttcctcctgctactctg<br>gctcccagataccaccggtcaggtgcagctggtgcagtctggggc<br>tgaggtgaagaagcctggggcctcagtgaaggtttcctgcaaggc<br>atctggatacatcttcaccgactactatatgcactgggtgcgtca<br>ggcccctggacaagggcttgagtggatgggatggatgagccctaa<br>cagtggtaacacaggctatgcacagaagttccagggccgtgtcac<br>catgacccgcgacacgtccacgagcacagtctacatggagctgag<br>cagcctgcgttctgaggacacggccgtgtattactgtgcgagaga<br>tgcggcggattacggtgactacgttgcttttgatatctggggcca<br>agggacaatggtcaccgtctcttcaggtggaggcggttcaggcgg<br>aggtggatccggcggtggcggctccggtggcggcggatctgacat<br>ccagatgacccagtctccatcctccctgtctgcatctgtaggaga<br>cagagtcaccatcacttgccgggcaagtcagagcattagcagcta<br>tctgaattggtatcagcagaaaccagggaaagcccctaagctcct<br>gatctatgctgcatccagtttgcaaagtggggtcccatcaaggtt | qvqlvqsgaevkkpga<br>svkvsckasgyiftdy<br>ymhwvrqapgqglewm<br>gwmspnsgntgyaqkf<br>qgrvtmtrdtststvy<br>melssirsedtavyyc<br>ardaadygdyvafdiw<br>gqgtmvtvssggggsg<br>gggsggggsggggsdi<br>qmtqspsslsasvgdr<br>vtitcrasqsissyln<br>wyqqkpgkapklliya<br>asslqsgvpsrfsgsg<br>sgtdftltisslqped<br>fatyycqqsystpltf<br>gggtkveiksssepks | SEQ ID NO: 137 (SEQ ID NO: 138) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | cagtggcagtggatctgggacagatttcactctcaccatcagcag<br>tctgcaacctgaagattttgcaacttactactgtcaacagagtta<br>cagtacccctctcactttcggcggaggtaccaaggtggagatcaa<br>atcctcgagtgagcccaaatcttctgacaaaactcacacatgccc<br>accgtgcccagcacctgaagccgcgggtgcaccgtcagtcttcct<br>cttccccccaaaacccaaggacaccctcatgatctcccggacccc<br>tgaggtcacatgcgtggtggtggacgtgagccacgaagaccctga<br>ggtcaagttcaactggtacgtggacggcgtggaggtgcataatgc<br>caagacaaagccgcgggaggagcagtacaacagcacgtaccgtgt<br>ggtcagcgtcctcaccgtcctgcaccaggactggctgaatggcaa<br>ggaatacaagtgcgcggtctccaacaaagccctcccagcccccat<br>cgagaaaaccatctccaaagccaaagggcagccccgagaaccaca<br>ggtgtacaccctgcccccatcccgggatgagctgaccaagaacca<br>ggtcagcctgacctgcctggtcaaaggcttctatccaagcgacat<br>cgccgtggagtgggagagcaatgggcagccggagaacaactacaa<br>gaccacgcctcccgtgctggactccgacggctccttcttcctcta<br>cagcaagctcaccgtggacaagagcaggtggcagcaggggaacgt<br>cttctcatgctccgtgatgcatgaggctctgcacaaccactacac<br>gcagaagagcctctccctgtctccgggttccggaggagggggttc<br>aggtgggggaggttctggcggcgggggaagcccttcacaggtgca<br>actggtgcagagtggacccgaggttaaaaaaccagggtcctccgt<br>taaggttagctgcaaagcctctggctacacattttccaggagtac<br>aatgcactgggtgaggcaggctcctggacagggactcgagtggat<br>cgggtatatcaacccatctagcgcctataccaattacaaccaaaa<br>gtttaaggaccgagttaccattaccgctgacaaatccaccagtac<br>agcttatatggagctgtcatctcttaggtccgaggacactgctgt<br>ttattactgcgctcgtcctcaggttcactatgactataatggttt<br>tccctactggggtcagggaaccctggtgactgtctcttctggcgg<br>tggaggcagcggtgggggtgggtctggaggcggtggcagtggcgg<br>cggaggctctgatattcagatgactcagtctcctagcactctcag<br>cgccagcgtgggggatcgtgtgacaatgacttgctccgctagcag<br>tagtgtgtcttacatgaattggtatcagcagaagcccgggaaagc<br>acctaagcgctggatctatgactcttccaagctggcaagtggtgt<br>cccctcacggttctctggctcaggttctggtactgactatacttt<br>gactatctcctccctccagcccgatgatttcgctacctattattg<br>tcagcagtggagccgtaacccacccactttcggaggcggtaccaa<br>agtggagatcaagaggtcatga | sdkthtcppcpapeaa<br>gapsvflfppkpkdtl<br>misrtpevtcvvvdvs<br>hedpevkfnwyvdgve<br>vhnaktkpreeqynst<br>yrvvsvltvlhqdwin<br>gkeykcavsnkalpap<br>iektiskakgqprepq<br>vytippsrdeltknqv<br>sltclvkgfypsdiav<br>ewesngqpennykttp<br>pvldsdgsfflysklt<br>vdksrwqqgnvfscsv<br>mhealhnhytqkslsl<br>spgsggggsggggsgg<br>ggspsqvqlvqsgpev<br>kkpgssvkvsckasgy<br>tfsrstmhwvrqapgq<br>glewigyinpssaytn<br>ynqkfkdrvtitadks<br>tstaymelsslrsedt<br>avyycarpqvhydyng<br>fpywgqgtlvtvssgg<br>ggsggggsggggsggg<br>gsdiqmtqspstlsas<br>vgdrvtmtcsasssvs<br>ymnwyqqkpgkapkrw<br>iydssklasgvpsrfs<br>gsgsgtdytltisslq<br>pddfatyycqqwsrnp<br>ptfgggtkveikrs | |
| DB60 VHVL x TSC456 scFv-Fc-scFv TRI125 | atggaagcaccagcgcagcttctcttcctcctgctactctggctc<br>ccagataccaccggtcaggtgcagctggtgcagtctggggctgag<br>gtgaagaagcctggggcctcagtgaaggtttcctgcaaggcatct<br>ggatacaccttcaccagctactatatgcactgggtgcgtcaggcc<br>cctggacaagggcttgagtggatggggtggatcaaccctaacagt<br>ggtgacacaagctatgcacagaagttccagggccgtgtcaccatg<br>acccgcgacacgtccacgagcacagtctacatggagctgagcagc<br>ctgcgttctgaggacacggccgtgtattactgtgcgcaggatagt<br>agtggttccggggcttttgatatctggggccaagggacaatggtc<br>accgtctcttcaggcggcggcggcagcggcggcggcggcagcggc<br>ggcggaggctccggcggcggcggcagcgacatccagatgacccag<br>tctccatcctccctgtctgcatctgtaggagacagagtcaccatc<br>acttgccgggcaagtcagagcattagcagctatctgaattggtat<br>cagcagaaaccagggaaagcccctaagctcctgatctatgctgca<br>tccagtttgcaaagtggggtcccatcaaggttcagtggcagtgga<br>tctgggacagatttcactctcaccatcagcagtctgcaacctgaa<br>gattttgcaacttactactgtcaacagagttacagtacccctctc<br>actttcggcggaggtaccaaggtggagatcaaatcctcgagtgag<br>cccaaatcttctgacaaaactcacacatgcccaccgtgcccagca<br>cctgaagccgcgggtgcaccgtcagtcttcctcttccccccaaaa<br>cccaaggacaccctcatgatctcccggacccctgaggtcacatgc<br>gtggtggtggacgtgagccacgaagaccctgaggtcaagttcaac<br>tggtacgtggacggcgtggaggtgcataatgccaagacaaagccg<br>cgggaggagcagtacaacagcacgtaccgtgtggtcagcgtcctc<br>accgtcctgcaccaggactggctgaatggcaaggaatacaagtgc<br>gcggtctccaacaaagccctcccagcccccatcgagaaaaccatc<br>tccaaagccaaagggcagccccgagaaccacaggtgtacaccctg<br>cccccatcccgggatgagctgaccaagaaccaggtcagcctgacc<br>tgcctggtcaaaggcttctatccaagcgacatcgccgtggagtgg<br>gagagcaatgggcagccggagaacaactacaagaccacgcctccc<br>gtgctggactccgacggctccttcttcctctacagcaagctcacc<br>gtggacaagagcaggtggcagcaggggaacgtcttctcatgctcc<br>gtgatgcatgaggctctgcacaaccactacacgcagaagagcctc<br>tccctgtctccgggttccggaggagggggttcaggtgggggaggt<br>tctggcggcgggggaagcccttcacaggtgcaactggtgcagagt<br>ggacccgaggttaaaaaaccagggtcctccgttaaggttagctgc | qvqlvqsgaevkkpga<br>svkvsckasgytftsy<br>ymhwvrqapgqglewm<br>gwinpnsgdtsyaqkf<br>qgrvtmtrdtststvy<br>melsslrsedtavyyc<br>aqdssgsgafdiwgqg<br>tmvtvssggggsgggg<br>sggggsggggsdiqmt<br>qspsslsasvgdrvti<br>tcrasqsissylnwyq<br>qkpgkapklliyaass<br>lqsgvpsrfsgsgsgt<br>dftltisslqpedfat<br>yycqqsystpltfggg<br>tkveiksssepkssdk<br>thtcppcpapeaagap<br>svfifppkpkdtlmis<br>rtpevtcvvvdvshed<br>pevkfnwyvdgevhn<br>aktkpreeqynstyrv<br>vsvltvlhqdwlngke<br>ykcavsnkalpapiek<br>tiskakgqprepqvyt<br>lppsrdeltknqvslt<br>clvkgfypsdiavewe<br>sngqpennykttppvl<br>dsdgsfflyskltvdk<br>srwqqgnvfscsvmhe<br>alhnhytqkslslspg<br>sggggsggggsggggs<br>psqvqlvqsgpevkkp<br>gssvkvsckasgytfs<br>rstmhwvrqapgqgle<br>wigyinpssaytnynq<br>kfkdrvtitadkstst | SEQ ID NO: 139 (SEQ ID NO: 140) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | aaagcctctggctacacattttccaggagtacaatgcactgggtg<br>aggcaggctcctggacagggactcgagtggatcgggtatatcaac<br>ccatctagcgcctataccaattacaaccaaaagtttaaggaccga<br>gttaccattaccgctgacaaatccaccagtacagcttatatggag<br>ctgtcatctcttaggtccgaggacactgctgtttattactgcgct<br>cgtcctcaggttcactatgactataatggttttccctactggggt<br>cagggaaccctggtgactgtctcttctggcggtggaggcagcggt<br>gggggtgggtctggaggcggtggcagtggcggcggaggctctgat<br>attcagatgactcagtctcctagcactctcagcgccagcgtgggg<br>gatcgtgtgacaatgacttgctccgctagcagtagtgtgtcttac<br>atgaattggtatcagcagaagcccgggaaagcacctaagcgctgg<br>atctatgactcttccaagctggcaagtggtgtcccctcacggttc<br>tctggctcaggttctggtactgactatactttgactatctcctcc<br>ctccagcccgatgatttcgctacctattattgtcagcagtggagc<br>cgtaacccacccactttcggaggcggtaccaaagtggagatcaag<br>aggtcataa | aymelsslrsedtavy<br>ycarpqvhydyngfpy<br>wgqgtlvtvssggggs<br>ggggsggggsggggsd<br>iqmtqspstlsasvgd<br>rvtmtcsasssvsymn<br>wyqqkpgkapkrwiyd<br>ssklasgvpsrfsgsg<br>sgtdytltisslqpdd<br>fatyycqqwsrnpptf<br>gggtkveikrs | |
| DB65 VHVL<br>x TSC456<br>scFv-Fc-<br>scFv<br>TRI126 | atggaagcaccagcgcagcttctcttcctcctgctactctggctc<br>ccagataccaccggtcaggtgcagctggtgcagtctggggctgag<br>gtgaagaagcctggggcctcagtgaaggtttcctgcaaggcatct<br>ggatacaccttcaccggctactatatgcactgggtgcgtcaggcc<br>cctggacaagggcttgagtggatgggatggatgaaccctaacagt<br>ggtaacacaggctatgcacagaagttccagggccgtgtcaccatg<br>acccgcgacacgtccacgagcacagtctacatggagctgagcagc<br>ctgcgttctgaggacacggccgtgtattactgtgcgaaagaggaa<br>ccgatttttggagtggttatggatgcttttgatatctggggccaa<br>gggacaatggtcaccgtctcctcaggcggcggcggcagcggcggc<br>ggcggcagcggcggcggaggctccggcggcggcggcagcgacatc<br>cagatgacccagtctccatcctccctgtctgcatctgtaggagac<br>agagtcaccatcacttgccgggcaagtcagagcattagcagctat<br>ctgaattggtatcagcagaaaccagggaaagcccctaagctcctg<br>atctatgctgcatccagtttgcaaagtggggtcccatcaaggttc<br>agtggcagtggatctgggacagatttcactctcaccatcagcagt<br>ctgcaacctgaagattttgcaacttactactgtcaacagagttac<br>agtacccctctcactttcggcggaggtaccaaggtggagatcaaa<br>tcctcgagtgagcccaaatcttctgacaaaactcacacatgccca<br>ccgtgcccagcacctgaagccgcgggtgcaccgtcagtcttcctc<br>ttccccccaaaacccaaggacaccctcatgatctcccggacccct<br>gaggtcacatgcgtggtggtggacgtgagccacgaagaccctgag<br>gtcaagttcaactggtacgtggacggcgtggaggtgcataatgcc<br>aagacaaagccgcgggaggagcagtacaacagcacgtaccgtgtg<br>gtcagcgtcctcaccgtcctgcaccaggactggctgaatggcaag<br>gaatacaagtgcgcggtctccaacaaagccctcccagcccccatc<br>gagaaaaccatctccaaagccaaagggcagccccgagaaccacag<br>gtgtacaccctgcccccatcccgggatgagctgaccaagaaccag<br>gtcagcctgacctgcctggtcaaaggcttctatccaagcgacatc<br>gccgtggagtgggagagcaatgggcagccggagaacaactacaag<br>accacgcctcccgtgctggactccgacggctccttcttcctctac<br>agcaagctcaccgtggacaagagcaggtggcagcaggggaacgtc<br>ttctcatgctccgtgatgcatgaggctctgcacaaccactacacg<br>cagaagagcctctccctgtctccgggttccggaggagggggttca<br>ggtgggggaggttctggcggcgggggaagcccttcacaggtgcaa<br>ctggtgcagagtggacccgaggttaaaaaaccagggtcctccgtt<br>aaggttagctgcaaagcctctggctacacattttccaggagtaca<br>atgcactgggtgaggcaggctcctggacagggactcgagtggatc<br>gggtatatcaacccatctagcgcctataccaattacaaccaaaag<br>tttaaggaccgagttaccattaccgctgacaaatccaccagtaca<br>gcttatatggagctgtcatctcttaggtccgaggacactgctgtt<br>tattactgcgctcgtcctcaggttcactatgactataatggtttt<br>ccctactggggtcagggaaccctggtgactgtctcttctggcggt<br>ggaggcagcggtgggggtgggtctggaggcggtggcagtggcggc<br>ggaggctctgatattcagatgactcagtctcctagcactctcagc<br>gccagcgtgggggatcgtgtgacaatgacttgctccgctagcagt<br>agtgtgtcttacatgaattggtatcagcagaagcccgggaaagca<br>cctaagcgctggatctatgactcttccaagctggcaagtggtgtc<br>ccctcacggttctctggctcaggttctggtactgactatactttg<br>actatctcctccctccagcccgatgatttcgctacctattattgt<br>cagcagtggagccgtaacccacccactttcggaggcggtaccaaa<br>gtggagatcaagaggtcataa | qvqlvqsgaevkkpga<br>svkvsckasgytftgy<br>ymhwvrqapgqglewm<br>gwmnpnsgntgyaqkf<br>qgrvtmtrdtststvy<br>melsslrsedtavyyc<br>akeepifgvvmdafdi<br>wgqgtmvtvssggggs<br>ggggsggggsggggsd<br>iqmtqspsslsasvgd<br>rvtitcrasqsissyl<br>nwyqqkpgkapklliy<br>aasslqsgvpsrfsgs<br>gsgtdftltisslqpe<br>dfatyycqqsystplt<br>fgggtkveiksssepk<br>ssdkthtcppcpapea<br>agapsvflfppkpkdt<br>lmisrtpevtcvvvdv<br>shedpevkfnwyvdgv<br>evhnaktkpreeqyns<br>tyrvvsvltvlhqdwi<br>ngkeykcavsnkalpa<br>piektiskakgqprep<br>qvytlppsrdeltknq<br>vsltclvkgfypsdia<br>vewesngqpennyktt<br>ppvldsdgsfflyskl<br>tvdksrwqqgnvfscs<br>vmhealhnhytqksls<br>lspgsggggsggggsg<br>gggspsqvqlvqsgpe<br>vkkpgssvkvsckasg<br>ytfsrstmhwvrqapg<br>qglewigyinpssayt<br>nynqkfkdrvtitadk<br>ststaymelsslrsed<br>tavyycarpqvhydyn<br>gfpywgqgtlvtvssg<br>gggsggggsggggsgg<br>ggsdiqmtqspstlsa<br>svgdrvtmtcsasssv<br>symnwyqqkpgkapkr<br>wiydssklasgvpsrf<br>sgsgsgtdytltissl<br>qpddfatyycqqwsrn<br>pptfgggtkveikrs | SEQ ID NO: 141<br>(SEQ ID<br>NO: 142) |
| DB82 VLVH<br>x TSC456<br>scFv-Fc-<br>scFv | atggaagcaccagcgcagcttctcttcctcctgctactctggctc<br>ccagataccaccggtgacatccagatgacccagtctccatcctcc<br>ctgtctgcatctgtaggagaccgcgtcaccatcacttgccgggca<br>agtcagaccataaacaactatttgaactggtatcagcagaaacca | diqmtqspsslsasvg<br>drvtitcrasqtinny<br>lnwyqqkpgkaplli<br>ysastlqsgvpsrfsg | SEQ ID NO: 143<br>(SEQ ID<br>NO: 144) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| TRI127 | gggaaagcccctaagctcctgatctattctgcatctactttgcaa | sgsgtdftltisslqp | |
| | agtggggtcccatcacgtttcagtggcagtggatctgggacagat | edfatyychqsytspl | |
| | ttcactctcaccatcagcagtctgcaacctgaagattttgcaact | tfgggtkveikggggs | |
| | tactactgtcaccagagttacacttcacctctcactttcggcgga | ggggsggggsggggse | |
| | ggtaccaaggtggagatcaaaggcggcggcggcagcggcggcggc | vqlvesggglvqpggs | |
| | ggcagcggcggcggaggctccggcggcggcggcagcgaggtgcag | lrlscaasgftfssya | |
| | ctggtggagtctgggggaggcttggtacagcctggggggtccctg | mswvrqapgkglewvs | |
| | cgcctctcctgtgcagcctctggattcacctttagcagctatgcc | visansaglghadsvk | |
| | atgagctgggtccgccaggctccagggaaggggctggagtgggtc | grftisrdnskntlyl | |
| | tcagttattagtgccaatagtgctggtctaggccatgcggactct | qmnslraedtavyyca | |
| | gtgaagggccggttcaccatctcccgcgacaattccaagaacacg | rvgysssadafdiwgq | |
| | ctgtatctgcaaatgaacagcctgcgcgccgaggacacggccgta | gtmvtvsssepkssdk | |
| | tattactgtgcgagagtgggctatagcagctcggctgatgctttt | thtcppcpapeaagap | |
| | gatatctggggccaagggacaatggtcaccgtctcctcgagtgag | svfifppkpkdtlmis | |
| | cccaaatcttctgacaaaactcacacatgcccaccgtgcccagca | rtpevtcvvvdvshed | |
| | cctgaagccgcgggtgcaccgtcagtcttcctcttccccccaaaa | pevkfnwyvdgvevhn | |
| | cccaaggacaccctcatgatctcccggacccctgaggtcacatgc | aktkpreeqynstyrv | |
| | gtggtggtggacgtgagccacgaagaccctgaggtcaagttcaac | vsvltvlhqdwlngke | |
| | tggtacgtggacggcgtggaggtgcataatgccaagacaaagccg | ykcavsnkalpapiek | |
| | cgggaggagcagtacaacagcacgtaccgtgtggtcagcgtcctc | tiskakgqprepqvyt | |
| | accgtcctgcaccaggactggctgaatggcaaggaatacaagtgc | lppsrdeltknqvslt | |
| | gcggtctccaacaaagccctcccagcccccatcgagaaaaccatc | clvkgfypsdiavewe | |
| | tccaaagccaaagggcagccccgagaaccacaggtgtacaccctg | sngqpennykttppvl | |
| | cccccatcccgggatgagctgaccaagaaccaggtcagcctgacc | dsdgsfflyskltvdk | |
| | tgcctggtcaaaggcttctatccaagcgacatcgccgtggagtgg | srwqqgnvfscsvmhe | |
| | gagagcaatgggcagccggagaacaactacaagaccacgcctccc | alhnhytqkslslspg | |
| | gtgctggactccgacggctccttcttcctctacagcaagctcacc | sggggsggggsggggs | |
| | gtggacaagagcaggtggcagcaggggaacgtcttctcatgctcc | psqvqlvqsgpevkkp | |
| | gtgatgcatgaggctctgcacaaccactacacgcagaagagcctc | gssvkvsckasgytfs | |
| | tccctgtctccgggttccggaggagggggttcaggtgggggaggt | rstmhwvrqapgqgle | |
| | tctggcggcgggggaagcccttcacaggtgcaactggtgcagagt | wigyinpssaytnynq | |
| | ggacccgaggttaaaaaaccagggtcctccgttaaggttagctgc | kfkdrvtitadkstst | |
| | aaagcctctggctacacatttccaggagtacaatgcactgggtg | aymelsslrsedtavy | |
| | aggcaggctcctggacagggactcgagtggatcgggtatatcaac | ycarpqvhydyngfpy | |
| | ccatctagcgcctataccaattacaaccaaaagtttaaggaccga | wgqgtlvtvssggggs | |
| | gttaccattaccgctgacaaatccaccagtacagcttatatggag | ggggsggggsggggsd | |
| | ctgtcatctcttaggtccgaggacactgctgtttattactgcgct | iqmtqspstlsasvgd | |
| | cgtcctcaggttcactatgactataatggttttccctactggggt | rvtmtcsasssvsymn | |
| | cagggaaccctggtgactgtctcttctggcggtggaggcagcggt | wyqqkpgkapkrwiyd | |
| | gggggtgggtctggaggcggtggcagtggcggcggaggctctgat | ssklasgvpsrfsgsg | |
| | attcagatgactcagtctcctagcactctcagcgccagcgtgggg | sgtdytltisslqpdd | |
| | gatcgtgtgacaatgacttgctccgctagcagtagtgtgtcttac | fatyycqqwsrnpptf | |
| | atgaattggtatcagcagaagcccgggaaagcacctaagcgctgg | gggtkveikrs | |
| | atctatgactcttccaagctggcaagtggtgtcccctcacggttc | | |
| | tctggctcaggttctggtactgactatactttgactatctcctcc | | |
| | ctccagcccgatgatttcgctacctattattgtcagcagtggagc | | |
| | cgtaacccacccactttcggaggcggtaccaaagtggagatcaag | | |
| | aggtcataa | | |
| DB83 VHVL | atggaagcaccagcgcagcttctcttcctcctgctactctggctc | qvqlvqsgaevkkpga | SEQ ID NO: 145 |
| x TSC456 | ccagataccaccggtcaggtgcagctggtgcagtctggggctgag | svkvsckasgytftsy | (SEQ ID |
| scFv-Fc- | gtgaagaagcctggggcctcagtgaaggtttcctgcaaggcatct | amhwvrqapgqglewm | NO: 146) |
| scFv | ggatacaccttcactagctatgctatgcattgggtgcgtcaggcc | glvdpedgetiyaekf | |
| TRI134 | cctggacaagggcttgagtggatgggacttgttgatcctgaagat | qgrvtmtrdtststvy | |
| | ggtgaaacaatatatgcagagaagttccagggccgtgtcaccatg | melsslrsedtavyyc | |
| | acccgcgacacgtccacgagcacagtctacatggagctgagcagc | arrtyyydssgsryaf | |
| | ctgcgttctgaggacacggccgtgtattactgtgcgagacgaacg | diwgqgttvtvssggg | |
| | tattactatgatagtagtggttcccgttatgcttttgatatctgg | gsggggsggggsgggg | |
| | ggccaagggaccacggtcaccgtctcttcaggcggcggcggcagc | sdwmtqsplslpvtpg | |
| | ggcggcggcggcagcggcggcggaggctccggcggcggcggcagc | epasiscrssqsllhs | |
| | gatgttgtgatgactcagtctccactctccctgcccgtcacccct | ngdnyldwylqkpgqs | |
| | ggagagccggcctccatctcctgcaggtctagtcagagcctcctg | pqlliylgsnrasgvp | |
| | catagtaatggagacaactatttggattggtacctgcagaagcca | drfsgsgsgtdftlki | |
| | gggcagtctccacagctcctgatctatttgggttctaatcgggcc | srveaedvgvyycmqa | |
| | tccggggtccctgaccgtttcagtggcagtggatcaggcacagat | thwpltfgpgtkvdik | |
| | tttacactgaaaatcagccgtgtggaggctgaggatgttggggtt | sssepkssdkthtcpp | |
| | tattactgcatgcaagctacacactggccactcactttcggccct | cpapeaagapsvflfp | |
| | ggtaccaaagtggatatcaaatcctcgagtgagcccaaatcttct | pkpkdtlmisrtpevt | |
| | gacaaaactcacacatgcccaccgtgcccagcacctgaagccgcg | cvvvdvshedpevkfn | |
| | ggtgcaccgtcagtcttcctcttccccccaaaacccaaggacacc | wyvdgvevhnaktkpr | |
| | ctcatgatctcccggacccctgaggtcacatgcgtggtggtggac | eeqynstyrvvsvltv | |
| | gtgagccacgaagaccctgaggtcaagttcaactggtacgtggac | lhqdwlngkeykcavs | |
| | ggcgtggaggtgcataatgccaagacaaagccgcgggaggagcag | nkalpapiektiskak | |
| | tacaacagcacgtaccgtgtggtcagcgtcctcaccgtcctgcac | gqprepqvytlppsrd | |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| | caggactggctgaatggcaaggaatacaagtgcgcggtctccaac<br>aaagccctcccagcccccatcgagaaaaccatctccaaagccaaa<br>gggcagccccgagaaccacaggtgtacaccctgcccccatcccgg<br>gatgagctgaccaagaaccaggtcagcctgacctgcctggtcaaa<br>ggcttctatccaagcgacatcgccgtggagtgggagagcaatggg<br>cagccggagaacaactacaagaccacgcctcccgtgctggactcc<br>gacggctccttcttcctctacagcaagctcaccgtggacaagagc<br>aggtggcagcaggggaacgtcttctcatgctccgtgatgcatgag<br>gctctgcacaaccactacacgcagaagagcctctccctgtctccg<br>ggttccggaggagggggttcaggtgggggaggttctggcggcggg<br>ggaagcccttcacaggtgcaactggtgcagagtggacccgaggtt<br>aaaaaaccagggtcctccgttaaggttagctgcaaagcctctggc<br>tacacattttccaggagtacaatgcactgggtgaggcaggctcct<br>ggacagggactcgagtggatcgggtatatcaacccatctagcgcc<br>tataccaattacaaccaaaagtttaaggaccgagttaccattacc<br>gctgacaaatccaccagtacagcttatatggagctgtcatctctt<br>aggtccgaggacactgctgtttattactgcgctcgtcctcaggtt<br>cactatgactataatggttttccctactggggtcagggaaccctg<br>gtgactgtctcttctggcggtggaggcagcggtgggggtgggtct<br>ggaggcggtggcagtggcggcggaggctctgatattcagatgact<br>cagtctcctagcactctcagcgccagcgtgggggatcgtgtgaca<br>atgacttgctccgctagcagtagtgtgtcttacatgaattggtat<br>cagcagaagcccgggaaagcacctaagcgctggatctatgactct<br>tccaagctggcaagtggtgtcccctcacggttctctggctcaggt<br>tctggtactgactatactttgactatctcctccctccagcccgat<br>gatttcgctacctattattgtcagcagtggagccgtaacccaccc<br>actttcggaggcggtaccaaagtggagatcaagaggtcataa | eltknqvsltclvkgf<br>ypsdiavewesngqpe<br>nnykttppvldsdgsf<br>flyskltvdksrwqqg<br>nvfscsvmhealhnhy<br>tqkslslspgsggggs<br>ggggsggggspsqvql<br>vqsgpevkkpgssvkv<br>sckasgytfsrstmhw<br>vrqapgqglewigyin<br>pssaytnynqkfkdrv<br>titadkststaymels<br>slrsedtavyycarpq<br>vhydyngfpywgqgtl<br>vtvssggggsggggsg<br>gggsggggsdiqmtqs<br>pstlsasvgdrvtmtc<br>sasssvsymnwyqqkp<br>gkapkrwiydssklas<br>gvpsrfsgsgsgtdyt<br>ltisslqpddfatyyc<br>qqwsrnpptfgggtkv<br>eikrs | |
| DB86 VHVL x TSC456 scFv-Fc-scFv TRI128 | atggaagcaccagcgcagcttctcttcctcctgctactctggctc<br>ccagataccaccggtcaggtgcagctggtgcagtctggggctgag<br>gtgaagaagcctggggcctcagtgaaggtttcctgcaaggcatct<br>ggatatatgttcagtggccattctgcacactgggtgcgtcaggcc<br>cctggacaagggcttgagtggatgggatggatgaaccctaacagt<br>ggtaacacaggctatgcacagaagttccagggccgtgtcaccatg<br>acccgcgacacgtccacgagcacagtctacatggagctgagcagc<br>ctgcgttctgaggacacggccgtgtattactgtgcgagagatagc<br>agtggctggtacgatgtctttgactactggggccaggggaccctg<br>gtcaccgtctcctcaggtggaggcggttcaggcggaggtggatcc<br>ggcggtggcggctccggtggcggcggatctgacatccagatgacc<br>cagtctccatcctccctgtctgcatctgtaggagaccgcgtcacc<br>atcacttgccgggcaagtcagggcatcagaaatgatttaggttgg<br>tatcagcagaaaccagggaaagcccctaagctcctgatctatgct<br>gcatccactttgcaatcaggggtcccatcacgtttcagtggcagt<br>ggatctgggacagatttcactctcaccatcagcagtctgcaacct<br>gaagattttgcaacttactactgtcaacagagttacggtgccccc<br>ctcactttcggcggaggtaccaaggtggagatcaaatcctcgagt<br>gagcccaaatcttctgacaaaactcacacatgcccaccgtgccca<br>gcacctgaagccgcgggtgcaccgtcagtcttcctcttcccccca<br>aaacccaaggacaccctcatgatctcccggacccctgaggtcaca<br>tgcgtggtggtggacgtgagccacgaagaccctgaggtcaagttc<br>aactggtacgtggacggcgtggaggtgcataatgccaagacaaag<br>ccgcgggaggagcagtacaacagcacgtaccgtgtggtcagcgtc<br>ctcaccgtcctgcaccaggactggctgaatggcaaggaatacaag<br>tgcgcggtctccaacaaagccctcccagcccccatcgagaaaacc<br>atctccaaagccaaagggcagccccgagaaccacaggtgtacacc<br>ctgcccccatcccgggatgagctgaccaagaaccaggtcagcctg<br>acctgcctggtcaaaggcttctatccaagcgacatcgccgtggag<br>tgggagagcaatgggcagccggagaacaactacaagaccacgcct<br>cccgtgctggactccgacggctccttcttcctctacagcaagctc<br>accgtggacaagagcaggtggcagcaggggaacgtcttctcatgc<br>tccgtgatgcatgaggctctgcacaaccactacacgcagaagagc<br>ctctccctgtctccgggttccggaggagggggttcaggtggggga<br>ggttctggcggcgggggaagcccttcacaggtgcaactggtgcag<br>agtggacccgaggttaaaaaaccagggtcctccgttaaggttagc<br>tgcaaagcctctggctacacattttccaggagtacaatgcactgg<br>gtgaggcaggctcctggacagggactcgagtggatcgggtatatc<br>aacccatctagcgcctataccaattacaaccaaaagtttaaggac<br>cgagttaccattaccgctgacaaatccaccagtacagcttatatg<br>gagctgtcatctcttaggtccgaggacactgctgtttattactgc<br>gctcgtcctcaggttcactatgactataatggttttccctactgg<br>ggtcagggaaccctggtgactgtctcttctggcggtggaggcagc<br>ggtgggggtgggtctggaggcggtggcagtggcggcggaggctct<br>gatattcagatgactcagtctcctagcactctcagcgccagcgtg | qvqlvqsgaevkkpga<br>svkvsckasgymfsgh<br>sahwvrqapgqglewm<br>gwmnpnsgntgyaqkf<br>qgrvtmtrdtststvy<br>melsslrsedtavyyc<br>ardssgwydvfdywgq<br>gtlvtvssggggsggg<br>gsggggsggggsdiqm<br>tqspsslsasvgdrvt<br>itcrasqgirndlgwy<br>qqkpgkaplliyaas<br>tlqsgvpsrfsgsgsg<br>tdftltisslqpedfa<br>tyycqqsygapltfgg<br>gtkveiksssepkssd<br>kthtcppcpapeaaga<br>psvflfppkpkdtlmi<br>srtpevtcvvvdvshe<br>dpevkfnwyvdgvevh<br>naktkpreeqynstyr<br>vvsvltvlhqdwlngk<br>eykcavsnkalpapie<br>ktiskakgqprepqvy<br>tlppsrdeltknqvsl<br>tcivkgfypsdiavew<br>esngqpennykttppv<br>ldsdgsfflyskltvd<br>ksrwqqgnvfscsvmh<br>ealhnhytqkslslsp<br>gsggggsggggsgggg<br>spsqvqlvqsgpevkk<br>pgssvkvsckasgytf<br>srstmhwvrqapgqgl<br>ewigyinpssaytnyn<br>qkfkdrvtitadksts<br>taymelsslrsedtav<br>yycarpqvhydyngfp<br>ywgqgtlvtvssgggg<br>sggggsggggsggggs<br>diqmtqspstlsasvg<br>drvtmtcsasssvsym<br>nwyqqkpgkapkrwiy<br>dssklasgvpsrfsgs<br>gsgtdytltisslqpd | SEQ ID NO: 147 (SEQ ID NO: 148) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | ggggatcgtgtgacaatgacttgctccgctagcagtagtgtgtct<br>tacatgaattggtatcagcagaagcccgggaaagcacctaagcgc<br>tggatctatgactcttccaagctggcaagtggtgtcccctcacgg<br>ttctctggctcaggttctggtactgactatactttgactatctcc<br>tccctccagcccgatgatttcgctacctattattgtcagcagtgg<br>agccgtaacccacccactttcggaggcggtaccaaagtggagatc<br>aagaggtcataa | dfatyycqqwsrnppt<br>fgggtkveikrs | |
| DB280<br>VHVL x<br>TSC456<br>scFv-Fc-<br>scFv<br>TRI131 | atggaagcaccagcgcagcttctcttcctcctgctactctggctc<br>ccagataccaccggtcaggtgcagctggtgcagtctggggctgag<br>gtgaagaagcctggggcctcagtgaaggtttcctgcaaggcatct<br>ggatacagcctcaacttatactatatgcactgggtgcgtcaggcc<br>cctggacaagggcttgagtggatgggatggatgaaccctaacagt<br>ggtaacacaggctatgcacagaagttccagggccgtgtcaccatg<br>acccgcgacacgtccacgagcacagtctacatggagctgagcagc<br>ctgcgttctgaggacacggccgtgtattactgtgcgagcctcgat<br>tgtagtggtggtagctgctactccgaatatgatgcttttgatatc<br>tggggccaagggaccacggtcaccgtctcctcaggcggcggcggc<br>agcggcggcggcggcagcggcggcggaggctccggcggcggcggc<br>agcgacatccagatgacccagtctccatcctccctgtctgcatct<br>gtaggagacagagtcaccatcacttgccgggcaagtcagagcatt<br>agcagctatctgaattggtatcagcagaaaccagggaaagcccct<br>aagctcctgatctatgctgcatccagtttgcaaagtggggtccca<br>tcaaggttcagtggcagtggatctgggacagatttcactctcacc<br>atcagcagtctgcaacctgaagattttgcaacttactactgtcaa<br>cagagttacagtacccctctcactttcggcggaggtaccaaggtg<br>gagatcaaatcctcgagtgagcccaaatcttctgacaaaactcac<br>acatgcccaccgtgcccagcacctgaagccgcgggtgcaccgtca<br>gtcttcctcttccccccaaaacccaaggacaccctcatgatctcc<br>cggacccctgaggtcacatgcgtggtggtggacgtgagccacgaa<br>gaccctgaggtcaagttcaactggtacgtggacggcgtggaggtg<br>cataatgccaagacaaagccgcgggaggagcagtacaacagcacg<br>taccgtgtggtcagcgtcctcaccgtcctgcaccaggactggctg<br>aatggcaaggaatacaagtgcgcggtctccaacaaagccctccca<br>gcccccatcgagaaaaccatctccaaagccaaagggcagccccga<br>gaaccacaggtgtacaccctgcccccatcccgggatgagctgacc<br>aagaaccaggtcagcctgacctgcctggtcaaaggcttctatcca<br>agcgacatcgccgtggagtgggagagcaatgggcagccggagaac<br>aactacaagaccacgcctcccgtgctggactccgacggctccttc<br>ttcctctacagcaagctcaccgtggacaagagcaggtggcagcag<br>gggaacgtcttctcatgctccgtgatgcatgaggctctgcacaac<br>cactacacgcagaagagcctctccctgtctccgggttccggagga<br>gggggttcaggtgggggaggttctggcggcgggggaagcccttca<br>caggtgcaactggtgcagagtggacccgaggttaaaaaaccaggg<br>tcctccgttaaggttagctgcaaagcctctggctacacatttcc<br>aggagtacaatgcactgggtgaggcaggctcctggacagggactc<br>gagtggatcgggtatatcaacccatctagcgcctataccaattac<br>aaccaaaagtttaaggaccgagttaccattaccgctgacaaatcc<br>accagtacagcttatatggagctgtcatctcttaggtccgaggac<br>actgctgtttattactgcgctcgtcctcaggttcactatgactat<br>aatggttttccctactggggtcagggaaccctggtgactgtctct<br>tctggcggtggaggcagcggtgggggtgggtctggaggcggtggc<br>agtggcggcggaggctctgatattcagatgactcagtctcctagc<br>actctcagcgccagcgtgggggatcgtgtgacaatgacttgctcc<br>gctagcagtagtgtgtcttacatgaattggtatcagcagaagccc<br>gggaaagcacctaagcgctggatctatgactcttccaagctggca<br>agtggtgtcccctcacggttctctggctcaggttctggtactgac<br>tatactttgactatctcctccctccagcccgatgatttcgctacc<br>tattattgtcagcagtggagccgtaacccacccactttcggaggc<br>ggtaccaaagtggagatcaagaggtcataa | qvqlvqsgaevkkpga<br>svkvsckasgyslnly<br>ymhwvrqapgqglewm<br>gwmnpnsgntgyaqkf<br>qgrvtmtrdtststvy<br>melsslrsedtavyyc<br>asldcsggscyseyda<br>fdiwgqgttvtvssgg<br>ggsggggsggggsggg<br>gsdiqmtqspsslsas<br>vgdrvtitcrasqsis<br>sylnwyqqkpgkapkl<br>liyaasslqsgvpsrf<br>sgsgsgtdftltissl<br>qpedfatyycqqsyst<br>pltfgggtkveiksss<br>epkssdkthtcppcpa<br>peaagapsvflfppkp<br>kdtlmisrtpevtcvv<br>vdvshedpevkfnwyv<br>dgvevhnaktkpreeq<br>ynstyrvvsvltvlhq<br>dwingkeykcavsnka<br>lpapiektiskakgqp<br>repqvytlppsrdelt<br>knqvsltclvkgfyps<br>diavewesngqpenny<br>kttppvldsdgsffly<br>skltvdksrwqqgnvf<br>scsvmhealhnhytqk<br>slslspgsggggsggg<br>gsggggspsqvqlvqs<br>gpevkkpgssvkvsck<br>asgytfsrstmhwvrq<br>apgqglewigyinpss<br>aytnynqkfkdrvtit<br>adkststaymelsslr<br>sedtavyycarpqvhy<br>dyngfpywgqgtlvtv<br>ssggggsggggsgggg<br>sggggsdiqmtqspst<br>lsasvgdrvtmtcsas<br>ssvsymnwyqqkpgka<br>pkrwiydssklasgvp<br>srfsgsgsgtdytlti<br>sslqpddfatyycqqw<br>srnpptfgggtkveik<br>rs | SEQ ID NO: 149<br>(SEQ ID<br>NO: 150) |
| DB331<br>VHVL x<br>TSC456<br>scFv-Fc-<br>scFv<br>TRI132 | atggaagcaccagcgcagcttctcttcctcctgctactctggctc<br>ccagataccaccggtcaggtgcagctggtgcagtctggggctgag<br>gtgaagaagcctggggcctcagtgaaggtttcctgcaaggcatct<br>ggatacaccttcaccagctactatatgcactgggtgcgtcaggcc<br>cctggacaagggcttgagtggatgggatggatgaaccctaacagt<br>ggtaacacaggctatgcacagaagttccagggccgtgtcaccatg<br>acccgcgacacgtccacgagcacagtctacatggagctgagcagc<br>ctgcgttctgaggacacggccgtgtattactgtgcaacagatctc<br>gcgggggaagccttgttcgacccctggggccagggcaccctggtc<br>accgtctcctcaggcggcggcggcagcggcggcggcggcagcggc<br>ggcggaggctccggcggcggcggcagcgacatccagatgacccag<br>tctccatcctccctgtctgcatctgtaggagacagagtcaccatc<br>acttgccgggcaagtcagagcattagcagctatctgaattggtat | qvqlvqsgaevkkpga<br>svkvsckasgytftsy<br>ymhwvrqapgqglewm<br>gwmnpnsgntgyaqkf<br>qgrvtmtrdtststvy<br>melsslrsedtavyyc<br>atdlagealfdpwgqg<br>tlvtvssggggsgggg<br>sggggsggggsdiqmt<br>qspsslsasvgdrvti<br>tcrasqsissylnwyq<br>qkpgkapklliyaass<br>lqsgvpsrfsgsgsgt | SEQ ID NO: 151<br>(SEQ ID<br>NO: 152) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| | cagcagaaaccagggaaagcccctaagctcctgatctatgctgca | dftltisslqpedfat | |
| | tccagtttgcaaagtggggtcccatcaaggttcagtggcagtgga | yycqqsystpltfggg | |
| | tctgggacagatttcactctcaccatcagcagtctgcaacctgaa | tkveiksssepkssdk | |
| | gattttgcaacttactactgtcaacagagttacagtacccctctc | thtcppcpapeaagap | |
| | actttcggcggaggtaccaaggtggagatcaaatcctcgagtgag | svflfppkpkdtlmis | |
| | cccaaatcttctgacaaaactcacacatgcccaccgtgcccagca | rtpevtcvvvdvshed | |
| | cctgaagccgcgggtgcaccgtcagtcttcctcttccccccaaaa | pevkfnwyvdgvevhn | |
| | cccaaggacaccctcatgatctcccggacccctgaggtcacatgc | aktkpreeqynstyrv | |
| | gtggtggtggacgtgagccacgaagaccctgaggtcaagttcaac | vsvltvlhqdwlngke | |
| | tggtacgtggacggcgtggaggtgcataatgccaagacaaagccg | ykcavsnkalpapiek | |
| | cgggaggagcagtacaacagcacgtaccgtgtggtcagcgtcctc | tiskakgqprepqvyt | |
| | accgtcctgcaccaggactggctgaatggcaaggaatacaagtgc | lppsrdeltknqvslt | |
| | gcggtctccaacaaagccctcccagcccccatcgagaaaaccatc | clvkgfypsdiavewe | |
| | tccaaagccaaagggcagccccgagaaccacaggtgtacaccctg | sngqpennykttppvl | |
| | cccccatcccgggatgagctgaccaagaaccaggtcagcctgacc | dsdgsfflyskltvdk | |
| | tgcctggtcaaaggcttctatccaagcgacatcgccgtggagtgg | srwqqgnvfscsvmhe | |
| | gagagcaatgggcagccggagaacaactacaagaccacgcctccc | alhnhytqkslslspg | |
| | gtgctggactccgacggctccttcttcctctacagcaagctcacc | sggggsggggsggggs | |
| | gtggacaagagcaggtggcagcaggggaacgtcttctcatgctcc | psqvqlvqsgpevkkp | |
| | gtgatgcatgaggctctgcacaaccactacacgcagaagagcctc | gssvkvsckasgytfs | |
| | tccctgtctccgggttccggaggagggggttcaggtggggggaggt | rstmhwvrqapgqgle | |
| | tctggcggcgggggaagcccttcacaggtgcaactggtgcagagt | wigyinpssaytnynq | |
| | ggacccgaggttaaaaaaccagggtcctccgttaaggttagctgc | kfkdrvtitadkstst | |
| | aaagcctctggctacacatttccaggagtacaatgcactgggtg | aymelsslrsedtavy | |
| | aggcaggctcctggacagggactcgagtggatcgggtatatcaac | ycarpqvhydyngfpy | |
| | ccatctagcgcctataccaattacaaccaaaagtttaaggaccga | wgqgtlvtvssggggs | |
| | gttaccattaccgctgacaaatccaccagtacagcttatatggag | ggggsggggsggggsd | |
| | ctgtcatctcttaggtccgaggacactgctgtttattactgcgct | iqmtqspstlsasvgd | |
| | cgtcctcaggttcactatgactataatggttttccctactggggt | rvtmtcsasssvsymn | |
| | cagggaaccctggtgactgtctcttctggcggtggaggcagcggt | wyqqkpgkapkrwiyd | |
| | gggggtgggtctggaggcggtggcagtggcggcggaggctctgat | ssklasgvpsrfsgsg | |
| | attcagatgactcagtctcctagcactctcagcgccagcgtgggg | sgtdytltisslqpdd | |
| | gatcgtgtgacaatgacttgctccgctagcagtagtgtgtcttac | fatyycqqwsrnpptf | |
| | atgaattggtatcagcagaagcccgggaaagcacctaagcgctgg | gggtkveikrs | |
| | atctatgactcttccaagctggcaagtggtgtcccctcacggttc | | |
| | tctggctcaggttctggtactgactatactttgactatctcctcc | | |
| | ctccagcccgatgatttcgctacctattattgtcagcagtggagc | | |
| | cgtaacccacccactttcggaggcggtaccaaagtggagatcaag | | |
| | aggtcataa | | |
| DB415 | atggaagcaccagcgcagcttctcttcctcctgctactctggctc | evqlvesggglvqpgg | SEQ ID NO: 153 |
| VHVL x | ccagataccaccggtgaggtgcagctggtggagtctgggggaggc | slriscaasgitfssy | (SEQ ID |
| TSC456 | ttggtacagcctggggggtccctgcgcctctcctgtgcagcctct | gmhwvrqapgkglewv | NO: 154) |
| scFv-Fc- | ggaatcaccttcagtagttatggcatgcattgggtccgccaggct | sgiswnsgnrvyvdsv | |
| scFv | ccagggaaggggctggagtgggtctcaggtattagttggaatagt | kgrftisrdnskntly | |
| TRI138 | ggtaacagagtctatgtggactctgtgaagggccggttcaccatc | lqmnslraedtavyyc | |
| | tcccgcgacaattccaagaacacgctgtatctgcaaatgaacagc | ardtndafdiwgqgtt | |
| | ctgcgcgccgaggacacggccgtatattactgtgcgagagatact | vtvssggggsggggsg | |
| | aatgatgcttttgatatctggggccaagggaccacggtcaccgtc | gggsggggsdiqmtqs | |
| | tcctcaggtggaggcggttcaggcggaggtggatccggcggtggc | psslsasvgdrvtitc | |
| | ggctccggtggcggcggatctgacatccagatgacccagtctcca | rasqsissylnwyqqk | |
| | tcctccctgtctgcatctgtaggagacagagtcaccatcacttgc | pgkapklliyaasslq | |
| | cgggcaagtcagagcattagcagctatctgaattggtatcagcag | sgvpsrfsgsgsgtdf | |
| | aaaccagggaaagcccctaagctcctgatctatgctgcatccagt | tltisslqpedfatyy | |
| | ttgcaaagtggggtcccatcaaggttcagtggcagtggatctggg | cqqsystpltfgggtk | |
| | acagatttcactctcaccatcagcagtctgcaacctgaagatttt | veiksssepkssdkth | |
| | gcaacttactactgtcaacagagttacagtacccctctcactttc | tcppcpapeaagapsv | |
| | ggcggaggtaccaaggtggagatcaaatcctcgagtgagcccaaa | flfppkpkdtlmisrt | |
| | tcttctgacaaaactcacacatgcccaccgtgcccagcacctgaa | pevtcvvvdvshedpe | |
| | gccgcgggtgcaccgtcagtcttcctcttccccccaaaacccaag | vkfnwyvdgvevhnak | |
| | gacaccctcatgatctcccggacccctgaggtcacatgcgtggtg | tkpreeqynstyrvvs | |
| | gtggacgtgagccacgaagaccctgaggtcaagttcaactggtac | vltvlhqdwlngkeyk | |
| | gtggacggcgtggaggtgcataatgccaagacaaagccgcgggag | cavsnkalpapiekti | |
| | gagcagtacaacagcacgtaccgtgtggtcagcgtcctcaccgtc | skakgqprepqvytlp | |
| | ctgcaccaggactggctgaatggcaaggaatacaagtgcgcggtc | psrdeltknqvsltcl | |
| | tccaacaaagccctcccagcccccatcgagaaaaccatctccaaa | vkgfypsdiavewesn | |
| | gccaaagggcagccccgagaaccacaggtgtacaccctgcccca | gqpennykttppvlds | |
| | tcccgggatgagctgaccaagaaccaggtcagcctgacctgcctg | dgsfflyskltvdksr | |
| | gtcaaaggcttctatccaagcgacatcgccgtggagtgggagagc | wqqgnvfscsvmheal | |
| | aatgggcagccggagaacaactacaagaccacgcctcccgtgctg | hnhytqkslslspgsg | |
| | gactccgacggctccttcttcctctacagcaagctcaccgtggac | gggsggggsggggsps | |
| | aagagcaggtggcagcaggggaacgtcttctcatgctccgtgatg | qvqlvqsgpevkkpgs | |
| | catgaggctctgcacaaccactacacgcagaagagcctctccctg | svkvsckasgytfsrs | |
| | tctccgggttccggaggagggggttcaggtggggggaggttctggc | tmhwvrqapgqglewi | |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| | ggcgggggaagcccttcacaggtgcaactggtgcagagtggaccc | gyinpssaytnynqkf | |
| | gaggttaaaaaaccagggtcctccgttaaggttagctgcaaagcc | kdrvtitadkststay | |
| | tctggctacacattttccaggagtacaatgcactgggtgaggcag | melsslrsedtavyyc | |
| | gctcctggacagggactggagtggatcgggtatatcaacccatct | arpqvhydyngfpywg | |
| | agcgcctataccaattacaaccaaaagtttaaggaccgagttacc | qgtlvtvssggggsgg | |
| | attaccgctgacaaatccaccagtacagcttatatggagctgtca | ggsggggsggggsdiq | |
| | tctcttaggtccgaggacactgctgtttattactgcgctcgtcct | mtqspstlsasvgdrv | |
| | caggttcactatgactataatggttttccctactggggtcaggga | tmtcsasssvsymnwy | |
| | accctggtgactgtctcttctggcggtggaggcagcggtgggggt | qqkpgkapkrwiydss | |
| | gggtctggaggcggtggcagtggcggcggaggctctgatattcag | klasgvpsrfsgsgsg | |
| | atgactcagtctcctagcactctcagcgccagcgtgggggatcgt | tdytltisslqpddfa | |
| | gtgacaatgacttgctccgctagcagtagtgtgtcttacatgaat | tyycqqwsrnpptfgg | |
| | tggtatcagcagaagcccgggaaagcacctaagcgctggatctat | gtkveikrs | |
| | gactcttccaagctggcaagtggtgtcccctcacggttctctggc | | |
| | tcaggttctggtactgactatactttgactatctcctccctccag | | |
| | cccgatgatttcgctacctattattgtcagcagtggagccgtaac | | |
| | ccacccactttcggaggcggtaccaaagtggagatcaagaggtca | | |
| | tga | | |
| DB435 | atggaagcaccagcgcagcttctcttcctcctgctactctggctc | qvqlvqsgaevkkpga | SEQ ID NO: 155 |
| VHVL x | ccagataccaccggtcaggtgcagctggtgcagtctggggctgag | svkvsckasggtfssy | (SEQ ID |
| TSC456 | gtgaagaagcctggggcctcagtgaaggtttcctgcaaggcatct | aiswvrqapgqglewm | NO: 156) |
| scFv-Fc- | ggaggcaccttcagcagctatgctatcagctgggtgcgtcaggcc | gwitphngnikyaref | |
| scFv | cctggacaagggcttgagtggatgggctggatcacccctcacaat | qgrvtmtrdtststvy | |
| TRI139 | ggtaacataaagtatgcacgggagttccagggccgtgtcaccatg | melsslrsedtavyyc | |
| | acccgcgacacgtccacgagcacagtctacatggagctgagcagc | akdlnwnaafdywgqg | |
| | ctgcgttctgaggacacggccgtgtattactgtgcgaaagatctg | tlvtvssggggsgggg | |
| | aactggaacgcagcctttgactactggggccaggggaccctggtc | sggggsggggsdiqmt | |
| | accgtctcctcaggtggaggcggttcaggcggaggtggatccggc | qspsslsasvgdrvti | |
| | ggtggcggctccggtggcggcggatctgacatccagatgacccag | tcrasqsissylnwyq | |
| | tctccatcctccctgtctgcatctgtaggagacagagtcaccatc | qkpgkapklliyaass | |
| | acttgccgggcaagtcagagcattagcagctatctgaattggtat | lqsgvpsrfsgsgsgt | |
| | cagcagaaaccagggaaagcccctaagctcctgatctatgctgca | dftltisslqpedfat | |
| | tccagtttgcaaagtggggtcccatcaaggttcagtggcagtgga | yycqqsystpltfggg | |
| | tctgggacagatttcactctcaccatcagcagtctgcaacctgaa | tkveiksssepkssdk | |
| | gattttgcaacttactactgtcaacagagttacagtacccctctc | thtcppcpapeaagap | |
| | actttcggcggaggtaccaaggtggagatcaaatcctcgagtgag | svfifppkpkdtlmis | |
| | cccaaatcttctgacaaaactcacacatgcccaccgtgcccagca | rtpevtcvvvdvshed | |
| | cctgaagccgcgggtgcaccgtcagtcttcctcttccccccaaaa | pevkfnwyvdgvevhn | |
| | cccaaggacaccctcatgatctcccggacccctgaggtcacatgc | aktkpreeqynstyrv | |
| | gtggtggtggacgtgagccacgaagaccctgaggtcaagttcaac | vsvltvlhqdwlngke | |
| | tggtacgtggacggcgtggaggtgcataatgccaagacaaagccg | ykcavsnkalpapiek | |
| | cgggaggagcagtacaacagcacgtaccgtgtggtcagcgtcctc | tiskakgqprepqvyt | |
| | accgtcctgcaccaggactggctgaatggcaaggaatacaagtgc | lppsrdeltknqvslt | |
| | gcggtctccaacaaagccctcccagcccccatcgagaaaaccatc | clvkgfypsdiavewe | |
| | tccaaagccaaagggcagccccgagaaccacaggtgtacaccctg | sngqpennykttppvl | |
| | cccccatcccgggatgagctgaccaagaaccaggtcagcctgacc | dsdgsfflyskltvdk | |
| | tgcctggtcaaaggcttctatccaagcgacatcgccgtggagtgg | srwqqgnvfscsvmhe | |
| | gagagcaatgggcagccggagaacaactacaagaccacgcctccc | alhnhytqkslslspg | |
| | gtgctggactccgacggctccttcttcctctacagcaagctcacc | sggggsggggsggggs | |
| | gtggacaagagcaggtggcagcaggggaacgtcttctcatgctcc | psqvqlvqsgpevkkp | |
| | gtgatgcatgaggctctgcacaaccactacacgcagaagagcctc | gssvkvsckasgytfs | |
| | tccctgtctccgggttccggaggagggggttcaggtgggggaggt | rstmhwvrqapgqgle | |
| | tctggcggcgggggaagcccttcacaggtgcaactggtgcagagt | wigyinpssaytnynq | |
| | ggacccgaggttaaaaaaccagggtcctccgttaaggttagctgc | kfkdrvtitadkstst | |
| | aaagcctctggctacacattttccaggagtacaatgcactgggtg | aymelsslrsedtavy | |
| | aggcaggctcctggacagggactggagtggatcgggtatatcaac | ycarpqvhydyngfpy | |
| | ccatctagcgcctataccaattacaaccaaaagtttaaggaccga | wgqgtlvtvssggggs | |
| | gttaccattaccgctgacaaatccaccagtacagcttatatggag | ggggsggggsggggsd | |
| | ctgtcatctcttaggtccgaggacactgctgtttattactgcgct | iqmtqspstlsasvgd | |
| | cgtcctcaggttcactatgactataatggttttccctactggggt | rvtmtcsasssvsymn | |
| | cagggaaccctggtgactgtctcttctggcggtggaggcagcggt | wyqqkpgkapkrwiyd | |
| | gggggtgggtctggaggcggtggcagtggcggcggaggctctgat | ssklasgvpsrfsgsg | |
| | attcagatgactcagtctcctagcactctcagcgccagcgtgggg | sgtdytltisslqpdd | |
| | gatcgtgtgacaatgacttgctccgctagcagtagtgtgtcttac | fatyycqqwsrnpptf | |
| | atgaattggtatcagcagaagcccgggaaagcacctaagcgctgg | gggtkveikrs | |
| | atctatgactcttccaagctggcaagtggtgtcccctcacggttc | | |
| | tctggctcaggttctggtactgactatactttgactatctcctcc | | |
| | ctccagcccgatgatttcgctacctattattgtcagcagtggagc | | |
| | cgtaacc | | |

TABLE 3-continued

Binding Polypeptide Sequences and Components

| Name | Nucleotide Sequence | Amino Acid Sequence | SEQ ID NOs: nucleotide (amino acid) |
|---|---|---|---|
| Cris7 and DRA222 VH CDR1 (Kabat) | cacccactttcggaggcggtacca aagtggagatcaagaggtcatga | RSTMH | (SEQ ID NO: 165) |
| Cris7 and DRA222 VH CDR2 (Kabat) | | YINPSSAYTNYNQKF K | (SEQ ID NO: 166) |
| Cris7 and DRA222 VH CDR3 (Kabat) | | QVHYDYNGFPY | (SEQ ID NO: 167) |
| Cris7 and DRA222 VL CDR1 (Kabat) | | SASSSVSYMN | (SEQ ID NO: 162) |
| Cris7 and DRA222 VL CDR2 (Kabat) | | DSSKLAS | (SEQ ID NO: 163) |
| Cris7 and DRA222 VL CDR3 (Kabat) | | QQWSRNPPT | (SEQ ID NO: 164) |
| Cris7 and DRA222 VH CDR1 (IMGT) | | GYTFTRST | (SEQ ID NO: 171) |
| Cris7 and DRA222 VH CDR2 (IMGT) | | INPSSAYT | (SEQ ID NO: 172) |
| Cris7 and DRA222 VH CDR3 (IMGT) | | QQWSRNPPT | (SEQ ID NO: 173) |
| Cris7 and DRA222 VL CDR1 (IMGT) | | ASSSVSY | (SEQ ID NO: 168) |
| Cris7 and DRA222 VL CDR2 (IMGT) | | DSS | (SEQ ID NO: 169) |
| Cris7 and DRA222 VL CDR3 (IMGT) | | QQWSRNPPT | (SEQ ID NO: 170) |
| I2CVH CDR1 (Kabat) | | KYAMN | (SEQ ID NO: 174) |
| I2CVH CDR2 (Kabat) | | RIRSKYNNYATYYAD SVKD | (SEQ ID NO: 175) |
| I2CVH CDR3 (Kabat) | | HGNFGNSYISYWAY | (SEQ ID NO: 176) |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| I2CVL CDR1 (Kabat) | | GSSTGAVTSGNYPN | (SEQ ID NO: 307) |
| I2CVL CDR2 (Kabat) | | GTKFLAP | (SEQ ID NO: 308) |
| I2CVL CDR3 (Kabat) | | VLWYSNRWV | (SEQ ID NO: 309) |
| I2CVH CDR1 (IMGT) | | GFTFNKYA | (SEQ ID NO: 179) |
| I2CVH CDR2 (IMGT) | | IRSKYNNYAT | (SEQ ID NO: 180) |
| I2CVH CDR3 (IMGT) | | VRHGNFGNSYISYW AY | (SEQ ID NO: 181) |
| I2CVL CDR1 (IMGT) | | TGAVTSGNY | (SEQ ID NO: 310) |
| I2CVL CDR2 (IMGT) | | GTK | (SEQ ID NO: 177) |
| I2CVL CDR3 (IMGT) | | VLWYSNRWV | (SEQ ID NO: 178) |
| HuM291 VH CDR1 (Kabat) | | SYTMH | (SEQ ID NO: 185) |
| HuM291 VH CDR2 (Kabat) | | YINPRSGYTHYNQKL KD | (SEQ ID NO: 186) |
| HuM291 VH CDR3 (Kabat) | | SAYYDYDGFAY | (SEQ ID NO: 187) |
| HuM291 VL CDR1 (Kabat) | | SASSSVSYMN | (SEQ ID NO: 182) |
| HuM291 VL CDR2 (Kabat) | | DTSKLAS | (SEQ ID NO: 183) |
| HuM291 VL CDR3 (Kabat) | | QQWSSNPPT | (SEQ ID NO: 184) |
| HuM291 VH CDR1 (IMGT) | | GYTFISYT | (SEQ ID NO: 191) |
| HuM291 VH CDR2 (IMGT) | | INPRSGYT | (SEQ ID NO: 192) |
| HuM291 VH CDR3 (IMGT) | | ARSAYYDYDGFAY | (SEQ ID NO: 193) |

TABLE 3-continued

| Binding Polypeptide Sequences and Components | | | |
|---|---|---|---|
| Name | Nucleotide Sequence | Amino Acid Sequence | SEQ ID NOs: nucleotide (amino acid) |
| HuM291 VL CDR1 (IMGT) | | ASSSVSY | (SEQ ID NO: 188) |
| HuM291 VL CDR2 (IMGT) | | DTS | (SEQ ID NO: 189) |
| HuM291 VL CDR3 (IMGT) | | QQWSSNPPT | (SEQ ID NO: 190) |
| TSC455 (anti-CD3) TSC394 F87YscFv | | QVQLVQSGPEVKKP GSSVKVSCKASGYTF SRSTMHWVRQAPG QGLEWIGYINPSSAY TNYNQKFKDRVTIT ADKSTSTAYMELSSL RSEDTAVYYCARPQ VHYDYNGFPYWGQ GTLVTVSSGGGGSG GGGSGGGGSGGGG SDIQMTQSPSTLSAS VGDRVTMTCSASSS VSYMNWYQQKPG KAPKRWIYDSSKLAS GVPSRFSGSGSGTEY TLTISSLQPDDFATYY CQQWSRNPPTFGG GTKVEIKRSSS | (SEQ ID NO: 311) |
| TSC456 (anti-CD3) TSC394 E86D F87Y scFv | | QVQLVQSGPEVKKP GSSVKVSCKASGYTF SRSTMHWVRQAPG QGLEWIGYINPSSAY TNYNQKFKDRVTIT ADKSTSTAYMELSSL RSEDTAVYYCARPQ VHYDYNGFPYWGQ GTLVTVSSGGGGSG GGGSGGGGSGGGG SDIQMTQSPSTLSAS VGDRVTMTCSASSS VSYMNWYQQKPG KAPKRWIYDSSKLAS GVPSRFSGSGSGTD YTLTISSLQPDDFATY YCQQWSRNPPTFG GGTKVEIKRSSS | (SEQ ID NO: 312) |
| TSC455 and TSC456 variable heavy domain | | QVQLVQSGPEVKKP GSSVKVSCKASGYTF SRSTMHWVRQAPG QGLEWIGYINPSSAY TNYNQKFKDRVTIT ADKSTSTAYMELSSL RSEDTAVYYCARPQ VHYDYNGFPYWGQ GTLVTVSS | (SEQ ID NO: 159) |
| TSC455 variable light domain | | DIQMTQSPSTLSAS VGDRVTMTCSASSS VSYMNWYQQKPG KAPKRWIYDSSKLAS GVPSRFSGSGSGTEY TLTISSLQPDDFATYY CQQWSRNPPTFGG GTKVEIKRS | (SEQ ID NO: 157) |

TABLE 3-continued

Binding Polypeptide Sequences and Components

| Name | Nucleotide Sequence | Amino Acid Sequence | SEQ ID NOs: nucleotide (amino acid) |
|---|---|---|---|
| TSC456 variable light domain | | DIQMTQSPSTLSAS VGDRVTMTCSASSS VSYMNWYQQKPG KAPKRWIYDSSKLAS GVPSRFSGSGSGTD YTLTISSLQPDDFATY YCQQWSRNPPTFG GGTKVEIKRS | (SEQ ID NO: 158) |
| DRA222 (anti-CD3) scFv | | QVQLVESGGGVVQ PGRSLRLSCKASGYT FTRSTMHWVRQAP GQGLEWIGYINPSS AYTNYNQKFKDRFTI SADKSKSTAFLQMD SLRPEDTGVYFCARP QVHYDYNGFPYWG QGTPVTVSSGGGGS GGGGSGGGGSAQD IQMTQSPSSLSASV GDRVTMTCSASSSV SYMNWYQQKPGK APKRWIYDSSKLAS GVPARFSGSGSGTD YTLTISSLQPEDFATY YCQQWSRNPPTFG GGTKLQITSSS | (SEQ ID NO: 313) |
| DRA222 variable heavy domain | | QVQLVESGGGVVQ PGRSLRLSCKASGYT FTRSTMHWVRQAP GQGLEWIGYINPSS AYTNYNQKFKDRFTI SADKSKSTAFLQMD SLRPEDTGVYFCARP QVHYDYNGFPYWG QGTPVTVSS | (SEQ ID NO: 161) |
| DRA222 variable light domain | | DIQMTQSPSSLSAS VGDRVTMTCSASSS VSYMNWYQQKPG KAPKRWIYDSSKLAS GVPARFSGSGSGTD YTLTISSLQPEDFATY YCQQWSRNPPTFG GGTKLQITS | (SEQ ID NO: 160) |

CD123-binding proteins may comprise any of the CD123-binding domains described above. In some aspects, CD123-binding proteins comprise humanized $V_H$ or $V_L$ amino acid sequences, or both.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:2 or SEQ ID NO:4. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:2 and SEQ ID NO:4. The polypeptides may comprise an amino acid sequence that is at least about 95%, at least about 97% identical, at least about 99% or 100% identical to the amino acid sequence set forth in SEQ ID NO:2 or SEQ ID NO:4. In some embodiments, the polypeptide comprises an amino acid sequence that is that is at least about 95%, at least about 97% identical, or at least about 99% identical to the amino acid sequence set forth in SEQ ID NO:130 or SEQ ID NO:132. In some embodiments, the polypeptide comprises an amino acid sequence that is that is at least about 95%, at least about 97% identical, or at least about 99% identical to the scFv portion of the amino acid sequence set forth in SEQ ID NO:130 or SEQ ID NO:132. In certain embodiments, the polypeptide comprises or consists of an amino acid sequence set forth in SEQ ID NO:2, SEQ ID NO:4, SEQ ID NO:130, or SEQ ID NO:132.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:20. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:20. The polypeptides may comprise an amino acid sequence that is at least about 95%, at least about 97% identical, at least about 99% or 100% identical to the amino acid sequence set forth in SEQ ID NO:18 or SEQ ID NO:20. In some embodiments, the polypeptide comprises an amino acid sequence that is that is at least about 95%, at least about 97% identical, or at least about 99% identical to the amino acid sequence set forth in SEQ ID NO:134, SEQ ID NO:136, or SEQ ID NO:138. In some embodiments, the polypeptide comprises an amino acid sequence that is that is at least about 95%, at least about 97% identical, or at least about 99% identical to the scFv portion of the amino acid sequence set forth in SEQ ID NO:134, SEQ ID NO:136, or SEQ ID NO:138. In certain embodiments, the polypeptide comprises or consists of an amino acid sequence set forth in SEQ ID NO:18, SEQ ID NO:20, SEQ ID NO:134, SEQ ID NO:136, or SEQ ID NO:138.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:34. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:34. The polypeptides may comprise an amino acid sequence that is at least about 95%, at least about 97% identical, at least about 99% or 100% identical to the amino acid sequence set forth in SEQ ID NO:18 or SEQ ID NO:34. In some embodiments, the polypeptide comprises an amino acid sequence that is that is at least about 95%, at least about 97% identical, or at least about 99% identical to the amino acid sequence set forth in SEQ ID NO:140. In some embodiments, the polypeptide comprises an amino acid sequence that is that is at least about 95%, at least about 97% identical, or at least about 99% identical to the scFv portion of the amino acid sequence set forth in SEQ ID NO:140. In certain embodiments, the polypeptide comprises or consists of an amino acid sequence set forth in SEQ ID NO:18, SEQ ID NO:34, or SEQ ID NO:140.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:42. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:42. The polypeptides may comprise an amino acid sequence that is at least about 95%, at least about 97% identical, at least about 99% or 100% identical to the amino acid sequence set forth in SEQ ID NO:18 or SEQ ID NO:42. In some embodiments, the polypeptide comprises an amino acid sequence that is that is at least about 95%, at least about 97% identical, or at least about 99% identical to the amino acid sequence set forth in SEQ ID NO:142. In some embodiments, the polypeptide comprises an amino acid sequence that is that is at least about 95%, at least about 97% identical, or at least about 99% identical to the scFv portion of the amino acid sequence set forth in SEQ ID NO:142. In certain embodiments, the polypeptide comprises or consists of an amino acid sequence set forth in SEQ ID NO:18, SEQ ID NO:42, or SEQ ID NO:142.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:50 or SEQ ID NO:52. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:50 and SEQ ID NO:52. The polypeptides may comprise an amino acid sequence that is at least about 95%, at least about 97% identical, at least about 99% or 100% identical to the amino acid sequence set forth in SEQ ID NO:50 or SEQ ID NO:52. In some embodiments, the polypeptide comprises an amino acid sequence that is that is at least about 95%, at least about 97% identical, or at least about 99% identical to the amino acid sequence set forth in SEQ ID NO:144. In some embodiments, the polypeptide comprises an amino acid sequence that is that is at least about 95%, at least about 97% identical, or at least about 99% identical to the scFv portion of the amino acid sequence set forth in SEQ ID NO:144. In certain embodiments, the polypeptide comprises or consists of an amino acid sequence set forth in SEQ ID NO:50, SEQ ID NO:52, or SEQ ID NO:144.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:66 or SEQ ID NO:68. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:66 and SEQ ID NO:68. The polypeptides may comprise an amino acid sequence that is at least about 95%, at least about 97% identical, at least about 99% or 100% identical to the amino acid sequence set forth in SEQ ID NO:66 or SEQ ID NO:68. In some embodiments, the polypeptide comprises an amino acid sequence that is that is at least about 95%, at least about 97% identical, or at least about 99% identical to the amino acid sequence set forth in SEQ ID NO:146. In some embodiments, the polypeptide comprises an amino acid sequence that is that is at least about 95%, at least about 97% identical, or at least about 99% identical to the scFv portion of the amino acid sequence set forth in SEQ ID NO:146. In certain embodiments, the polypeptide comprises or consists of an amino acid sequence set forth in SEQ ID NO:66, SEQ ID NO:68, or SEQ ID NO:146.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:82 or SEQ ID NO:84. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:82 and SEQ ID NO:84. The polypeptides may comprise an amino acid sequence that is at least about 95%, at least about 97% identical, at least about 99% or 100% identical to the amino acid sequence set forth in SEQ ID NO:82 or SEQ ID NO:84. In some embodiments, the polypeptide comprises an amino acid sequence that is that is at least about 95%, at least about 97% identical, or at least about 99% identical to the amino acid sequence set forth in SEQ ID NO:148. In some embodiments, the polypeptide comprises an amino acid sequence that is that is at least about 95%, at least about 97% identical, or at least about 99% identical to the scFv portion of the amino acid sequence set forth in SEQ ID NO:148. In certain embodiments, the polypeptide comprises or consists of an amino acid sequence set forth in SEQ ID NO:82, SEQ ID NO:84, or SEQ ID NO:148.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:98. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:98. The polypeptides may comprise an amino acid sequence that is at least about 95%, at least about 97% identical, at least about 99% or 100% identical to the amino acid sequence set forth in SEQ ID NO:18 or SEQ ID NO:150. In some embodiments, the polypeptide comprises an amino acid sequence that is that is at least about 95%, at least about 97% identical, or at least about 99% identical to the amino acid sequence set forth in SEQ ID NO:150. In some embodiments, the polypeptide comprises an amino acid sequence that is that is at least about 95%, at least about 97% identical, or at least about 99% identical to the scFv portion of the amino acid sequence set forth in SEQ ID NO:140. In certain embodiments, the polypeptide comprises or consists of an amino acid sequence set forth in SEQ ID NO:18, SEQ ID NO:98, or SEQ ID NO:150.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:106. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:106. The polypeptides may comprise an amino acid sequence that is at least about 95%, at least about 97% identical, at least about 99% or 100% identical to the amino acid sequence set forth in SEQ ID NO:18 or SEQ ID NO:106. In some embodiments, the polypeptide comprises an amino acid sequence that is that is at least about 95%, at least about 97% identical, or at least about 99% identical to the amino acid sequence set forth in SEQ ID NO:152. In some embodiments, the polypeptide comprises an amino acid sequence that is that is at least about 95%, at least about 97% identical, or at least about 99% identical to the scFv portion of the amino acid sequence set forth in SEQ ID NO:152. In certain embodiments, the polypeptide comprises or consists of an amino acid sequence set forth in SEQ ID NO:18, SEQ ID NO:106, or SEQ ID NO:152.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:114. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:114. The polypeptides may comprise an amino acid sequence that is at least about 95%, at least about 97% identical, at least about 99% or 100% identical to the amino acid sequence set forth in SEQ ID NO:18 or SEQ ID NO: 114. In some embodiments, the polypeptide comprises an amino acid sequence that is that is at least about 95%, at least about 97% identical, or at least about 99% identical to the amino acid sequence set forth in SEQ ID NO:154. In some embodiments, the polypeptide comprises an amino acid sequence that is that is at least about 95%, at least about 97% identical, or at least about 99% identical to the scFv portion of the amino acid sequence set forth in SEQ ID NO:154. In certain embodiments, the polypeptide comprises or consists of an amino acid sequence set forth in SEQ ID NO:18, SEQ ID NO:114, or SEQ ID NO:154.

The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 or SEQ ID NO:122. The polypeptides may comprise an amino acid sequence that is at least 88% identical, at least 89% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence as set forth in SEQ ID NO:18 and SEQ ID NO:122. The polypeptides may comprise an amino acid sequence that is at least about 95%, at least about 97% identical, at least about 99% or 100% identical to the amino acid sequence set forth in SEQ ID NO:18 or SEQ ID NO:122. In some embodiments, the polypeptide comprises an amino acid sequence that is that is at least about 95%, at least about 97% identical, or at least about 99% identical to the amino acid sequence set forth in SEQ ID NO:156. In some embodiments, the polypeptide comprises an amino acid sequence that is that is at least about 95%, at least about 97% identical, or at least about 99% identical to the scFv portion of the amino acid sequence set forth in SEQ ID NO:156. In certain embodiments, the polypeptide comprises or consists of an amino acid sequence set forth in SEQ ID NO:18, SEQ ID NO:122, or SEQ ID NO:156.

The polypeptides disclosed herein may have improved characteristics compared to other CD123-binding domains or polypeptides. For example, a CD123-binding domain or polypeptide may exhibit a reduced isoelectric point compared to the isoelectric point of a different CD123-binding domain or polypeptide. "Isoelectric point" or "pI" is the pH at which net charge is zero. The isoelectric point of a protein may be measured by any suitable method, e.g., analytical capillary isoelectric focusing chromatography.

A CD123-binding domain or protein disclosed herein may bind to CD123 (e.g., human CD123) with a higher affinity than the parent antibody.

In one embodiment of the invention, the recombinant polypeptide comprises, in order from amino to carboxyl terminus, (i) a human or humanized CD123-binding domain, (ii) a hinge region, (iii) an immunoglobulin constant region, (iv) a carboxyl-terminus linker, and (v) a human or humanized second binding domain that specifically binds a T-cell, CD3, CD3ε or a T-cell receptor (TCR) complex or a component of a T-cell receptor complex, wherein the human or humanized CD123-binding domain comprises an amino acid sequence at least about 80%, at least about 90%, at least about 95%, at least about 96%, at least about 97%, at least about 98%, at least about 99% or at least about 99.5% identical to SEQ ID NO:2 and SEQ ID NO:4 and wherein the human or humanized second binding domain that specifically binds a T-cell, CD3, CD3ε or a T-cell receptor (TCR) complex or a component of a T-cell receptor complex comprises an amino acid sequence at least about 80%, at least about 90%, at least about 95%, at least about 96%, at least about 97%, at least about 98%, at least about 99% or at least about 99.5% identical to SEQ ID NO:311 or SEQ ID NO:312.

In one embodiment of the invention, the recombinant polypeptide does not contain a CD123-binding domain derived from murine antibody 12F1 (SEQ ID Nos:195 and 197). For instance, in one embodiment, the CD123-binding domain does not comprise a heavy chain or light chain variable domain that is significantly identical to a heavy chain or light chain variable domain of 12F1 (e.g., is not 95% identical or greater to 12F1 heavy and light chain variable domains) or does not contain all six CDRs as contained in murine 12F1. In one embodiment of the invention, the CD123-binding domain does not compete for binding to CD123 with murine antibody 12F1 (SEQ ID NOs:195 and 197). In one embodiment of the invention, the recombinant polypeptide is cross-reactive to cynomolgous CD123 whereas antibody 12F1 (and humanized derivatives thereof) is not cross-reactive to cynomolgous CD123.

TABLE 4

12F1 Murine Antibody Sequences

| Name | Nucleotide Sequence | Amino Acid Sequence | SEQ ID Nos: nucleotide (amino acid) |
|---|---|---|---|
| 12F1 murine variable light chain domain | gacatcatgatgtcccagtccccctcctccctg gccgtgtccgtgggcgagaagttcaccatgac ctgcaagtcctcccagtccctgttcttcggctcc acccagaagaactacctggcctggtaccagca gaagcccggccagtcccccaagctgctgatct actgggcctccacccgggagtccggcgtgccc gaccggttcaccggctccggctccggcaccga cttcaccctggccatctcctccgtgatgcccga ggacctggccgtgtactactgccagcagtacta caactacccctggaccttcggcggcggcacca agctggagatcaag | dimmsqspsslavsvgekftmtckssqs lffgstqknylawyqqkpgqspklliywa stresgvpdrftgsgsgtdftlaissvmpe dlavyycqqyynypwtfgggtkleik | SEQ ID NO: 194 (SEQ ID NO: 195) |
| 12F1 murine variable heavy chain domain | cagctgcaggagtccggccccggcct ggtgaagccctcccagtccctgtccctg acctgctccgtgaccgactactccatca cctccggctactactggaactggattcg gcagttccccggcaacaagctggagtg gatgggctacatctcctacgacggctcc aacaactacaaccccctccctgaagaac cggatctccatcacccgggacacctcc aagaaccagttcttcctgaagctgtcctc cgtgaccaccgaggacaccgccacct actactgctcccggggcgagggcttct acttcgactcctggggccagggcacca ccctgaccgtgtcctcg | vqlqesgpglvkpsqslsltcsvtd ysitsgyywnwirqfpgnklew mgyisydgsnnynpslknrisitr dtsknqfflklssvttedtatyycsr gegfyfdswgqgttltvss | SEQ ID NO: 196 (SEQ ID NO: 197) |

In one embodiment, the polypeptide of the invention (including in dimer form) binds to human CD123 and non-human primate (NHP) CD123 with specificity. In another embodiment of the invention, the polypeptide binds to cynomolgus monkey CD123.

The disclosure also includes nucleic acids (e.g., DNA or RNA) encoding CD123-binding domains and polypeptides described herein. Nucleic acids of the disclosure include nucleic acids having a region that is substantially identical to a polynucleotide as listed in Table 3, infra. In certain embodiments, a nucleic acid in accordance with the present disclosure has at least 80%, typically at least about 90%, and more typically at least about 95% or at least about 98% identity to a polypeptide-encoding polynucleotide as listed in Table 3. Nucleic acids of the disclosure also include complementary nucleic acids. In some instances, the sequences will be fully complementary (no mismatches) when aligned. In other instances, there can be up to about a 20% mismatch in the sequences. In some embodiments of the disclosure are provided nucleic acids encoding both first and second polypeptide chains of a heterodimeric CD123-binding protein of the disclosure. The nucleic acid sequences provided herein can be exploited using codon optimization, degenerate sequence, silent mutations, and other DNA techniques to optimize expression in a particular host, and the present disclosure encompasses such sequence modifications.

The invention includes a recombinant polypeptide encoded by a nucleic acid comprising at nucleic acid sequence at least about 80%, at least about 85%, at least about 90%, at least about 95%, at least about 96%, at least about 97%, at least about 98%, at least about 99% and at least 100% identical to the nucleic acid sequence of SEQ ID NO:1 and/or SEQ ID NO:3. The invention includes a recombinant polypeptide encoded by a nucleic acid comprising at nucleic acid sequence at least about 80%, at least about 85%, at least about 90%, at least about 95%, at least about 96%, at least about 97%, at least about 98%, at least about 99% and at least 100% identical to the nucleic acid sequence of SEQ ID NO:131.

The disclosure relates to an isolated nucleic acid molecule encoding CD123-binding domains, proteins and polypeptides (or portions thereof) described herein, wherein said nucleic acid molecule comprises a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

Polynucleotide molecules comprising a desired polynucleotide sequence are propagated by placing the molecule in a vector. Viral and non-viral vectors can be used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. The partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

For expression, an expression cassette or system may be employed. To express a nucleic acid encoding a polypeptide disclosed herein, a nucleic acid molecule encoding the polypeptide, operably linked to regulatory sequences that control transcriptional expression in an expression vector, is introduced into a host cell. In addition to transcriptional regulatory sequences, such as promoters and enhancers, expression vectors can include translational regulatory sequences and a marker gene which is suitable for selection of cells that carry the expression vector. The gene product encoded by a polynucleotide of the disclosure is expressed in any convenient expression system, including, for example, bacterial, yeast, insect, amphibian and mammalian systems. In the expression vector, the polypeptide-encoding polynucleotide is linked to a regulatory sequence as appropriate to obtain the desired expression properties. These can include promoters, enhancers, terminators, operators, repressors, and inducers. The promoters can be regulated (e.g., the promoter from the steroid inducible pIND vector (Invitrogen)) or constitutive (e.g., promoters from CMV, SV40, Elongation Factor, or LTR sequences). These are linked to the desired nucleotide sequence using the techniques described above for linkage to vectors. Any techniques known in the art can be used. Accordingly, the expression vector will generally provide a transcriptional and translational initiation region, which can be inducible or constitutive, where the coding region is operably linked under the transcriptional control of the transcriptional initiation region, and a transcriptional and translational termination region.

An expression cassette ("expression unit") can be introduced into a variety of vectors, e.g., plasmid, BAC, YAC, bacteriophage such as lambda, P1, M13, etc., plant or animal viral vectors (e.g., retroviral-based vectors, adenovirus vectors), and the like, where the vectors are normally characterized by the ability to provide selection of cells comprising the expression vectors. The vectors can provide for extrachromosomal maintenance, particularly as plasmids or viruses, or for integration into the host chromosome. Where extrachromosomal maintenance is desired, an origin sequence is provided for the replication of the plasmid, which can be low- or high copy-number. A wide variety of markers are available for selection, particularly those which protect against toxins, more particularly against antibiotics. The particular marker that is chosen is selected in accordance with the nature of the host, where, in some cases, complementation can be employed with auxotrophic hosts. Introduction of the DNA construct can use any convenient method, including, e.g., conjugation, bacterial transformation, calcium-precipitated DNA, electroporation, fusion, transfection, infection with viral vectors, biolistics, and the like. The disclosure relates to an expression vector comprising a nucleic acid segment, wherein said nucleic acid segment may comprise a nucleotide sequence set forth in SEQ ID NO:1, SEQ ID NO:3, SEQ ID NO:17, SEQ ID NO:19, SEQ ID NO:33, SEQ ID NO:41, SEQ ID NO:49, SEQ ID NO:51, SEQ ID NO:65, SEQ ID NO:67, SEQ ID NO:81, SEQ ID NO:83, SEQ ID NO:97, SEQ ID NO:105, SEQ ID NO:113, SEQ ID NO:121, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, or SEQ ID NO:155.

Accordingly, proteins for use within the present disclosure can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms), particularly cultured mammalian cells. Techniques for manipulating cloned DNA molecules and introducing exogenous DNA into a variety of host cells are disclosed by Sambrook and Russell, *Molecular Cloning: A Laboratory Manual* (3rd ed., Cold Spring Harbor Laboratory Press, Cold Spring Harbor, NY, 2001), and Ausubel et al., *Short Protocols in Molecular Biology* (4th ed., John Wiley & Sons, 1999). For instance, the recombinant polypeptides of the invention can be expressed from CHO and HEK293 cells.

For example, for recombinant expression of a homodimeric CD123-binding protein comprising two identical CD123-binding polypeptides as described herein, an expression vector will generally include a nucleic acid segment encoding the CD123-binding polypeptide, operably linked to a promoter. For recombinant expression of a heterodimeric CD123-binding protein, comprising different first and second polypeptide chains, the first and second polypeptide chains can be co-expressed from separate vectors in the host cell for expression of the entire heterodimeric protein. Alternatively, for the expression of heterodimeric CD123-binding proteins, the first and second polypeptide chains are co-expressed from separate expression units in the same vector in the host cell for expression of the entire heterodimeric protein. The expression vector(s) are transferred to a host cell by conventional techniques, and the transfected cells are then cultured by conventional techniques to produce the encoded polypeptide(s) to produce the corresponding CD123-binding protein.

To direct a recombinant protein into the secretory pathway of a host cell, a secretory signal sequence (also known as a leader sequence) is provided in the expression vector. The secretory signal sequence can be that of the native form of the recombinant protein, or can be derived from another secreted protein or synthesized de novo. The secretory signal sequence is operably linked to the polypeptide-encoding DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences can be positioned elsewhere in the DNA sequence of interest (see, e.g., Welch et al., U.S. Pat. No. 5,037,743; Holland et al., U.S. Pat. No. 5,143,830). In certain variations, a secretory signal sequence for use in accordance with the present disclosure has the amino acid sequence MEAPAQLLFLLLLWLPDTTG (SEQ ID NO:198).

Cultured mammalian cells are suitable hosts for production of recombinant proteins for use within the present disclosure. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, Virology 52:456, 1973), electroporation (Neumann et al., *EMBO J.* 1:841-845, 1982), DEAE-dextran mediated transfection (Ausubel et al., supra), and liposome-mediated transfection (Hawley-Nelson et al., *Focus* 15:73, 1993; Ciccarone et al., *Focus* 15:80, 1993). The production of recombinant polypeptides in cultured mammalian cells is disclosed by, for example, Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44; CHO DXB11 (Hyclone, Logan, UT); see also, e.g., Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658). Additional suitable cell lines are known in the art and available from public depositories such as the American Type Culture Collection, Manassas, Virginia Strong transcription promoters can be used, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants." Cells that have been cultured in the presence of the selective agent and are able to pass the gene of interest to their progeny are referred to as "stable transfectants." Exemplary selectable markers include a gene encoding resistance to the antibiotic neomycin, which allows selection to be carried out in the presence of a neomycin-type drug, such as G-418 or the like; the gpt gene for xanthine-guanine phosphoribosyl transferase, which permits host cell growth in the presence of mycophenolic acid/xanthine; and markers that provide resistance to zeocin, bleomycin, blastocidin, and hygromycin (see, e.g., Gatignol et al., *Mol. Gen. Genet.* 207:342, 1987; Drocourt et al., *Nucl. Acids Res.* 18:4009, 1990). Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. An exemplary amplifiable selectable marker is dihydrofolate reductase, which confers resistance to methotrexate. Other drug resistance genes (e.g., hygromycin resistance, multi-drug resistance, puromycin acetyltransferase) can also be used.

Other higher eukaryotic cells can also be used as hosts, including insect cells, plant cells and avian cells. The use of *Agrobacterium rhizogenes* as a vector for expressing genes in plant cells has been reviewed by Sinkar et al., *J. Biosci.* (Bangalore) 11:47-58, 1987. Transformation of insect cells and production of foreign polypeptides therein is disclosed by Guarino et al., U.S. Pat. No. 5,162,222 and WO 94/06463.

Insect cells can be infected with recombinant baculovirus, commonly derived from *Autographa californica* nuclear polyhedrosis virus (AcNPV). See King and Possee, *The Baculovirus Expression System: A Laboratory Guide* (Chapman & Hall, London); O'Reilly et al., *Baculovirus Expression Vectors: A Laboratory Manual* (Oxford University Press, New York 1994); and *Baculovirus Expression Protocols. Methods in Molecular Biology* (Richardson ed., Humana Press, Totowa, NJ, 1995). Recombinant baculovirus can also be produced through the use of a transposon-based system described by Luckow et al. (*J. Virol.* 67:4566-4579, 1993). This system, which utilizes transfer vectors, is commercially available in kit form (BAC-TO-BAC kit; Life Technologies, Gaithersburg, MD). The transfer vector (e.g., PFASTBAC1; Life Technologies) contains a Tn7 transposon to move the DNA encoding the protein of interest into a baculovirus genome maintained in *E. coli* as a large plasmid called a "bacmid." See Hill-Perkins and Possee, *J. Gen. Virol.* 71:971-976, 1990; Bonning et al., *J. Gen. Virol.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a protein-encoding DNA sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses the protein or interest is subsequently produced. Recombinant viral stocks are made by methods commonly used in the art.

For protein production, a recombinant virus can be used to infect host cells, typically a cell line derived from the fall armyworm, *Spodoptera frugiperda* (e.g., Sf9 or Sf21 cells) or *Trichoplusia ni* (e.g., HIGH FIVE cells; Invitrogen, Carlsbad, CA). See generally Glick and Pasternak, *Molecular Biotechnology, Principles & Applications of Recombinant DNA* (ASM Press, Washington, D.C., 1994). See also U.S. Pat. No. 5,300,435. Serum-free media are used to grow and maintain the cells. Suitable media formulations are known in the art and can be obtained from commercial suppliers. The cells are grown up from an inoculation density of approximately $2\text{-}5\times10^5$ cells to a density of $1\text{-}2\times10^6$ cells, at which time a recombinant viral stock is added at a multiplicity of infection (MOI) of 0.1 to 10, more typically near 3. Procedures used are generally described in available laboratory manuals (see, e.g., King and Possee, supra; O'Reilly et al., supra; Richardson, supra).

Fungal cells, including yeast cells, can also be used within the present disclosure. Yeast species of in this regard include, e.g., *Saccharomyces cerevisiae, Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). An exemplary vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936; and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii*, and *Candida maltosa* are known in the art. See, e.g., Gleeson et al., *J. Gen. Microbiol.* 132:3459-3465, 1986; Cregg, U.S. Pat. No. 4,882,279; and Raymond et al., *Yeast* 14:11-23, 1998. *Aspergillus* cells can be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808; 5,736,383; 5,854,039; and 5,888,768.

Prokaryotic host cells, including strains of the bacteria *Escherichia coli, Bacillus*, and other genera are also useful host cells within the present disclosure. Techniques for transforming these hosts and expressing foreign DNA sequences cloned therein are well-known in the art (see, e.g., Sambrook and Russell, supra). When expressing a recombinant protein in bacteria such as *E. coli*, the protein can be retained in the cytoplasm, typically as insoluble granules, or can be directed to the periplasmic space by a bacterial secretion sequence. In the former case, the cells are lysed, and the granules are recovered and denatured using, for example, guanidine isothiocyanate or urea. The denatured protein can then be refolded and dimerized by diluting the denaturant, such as by dialysis against a solution of urea and a combination of reduced and oxidized glutathione, followed by dialysis against a buffered saline solution. In the alternative, the protein can be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted proteins can be recovered from the periplasmic space in a soluble and functional form by disrupting the cells (by, for example, sonication or osmotic shock) to release the contents of the periplasmic space and recovering the protein, thereby obviating the need for denaturation and refolding. Antibodies, including single-chain antibodies, can be produced in bacterial host cells according to known methods. See, e.g., Bird et al., *Science* 242:423-426, 1988; Huston et al., *Proc. Natl. Acad. Sci. USA* 85:5879-5883, 1988; and Pantoliano et al., *Biochem.* 30:10117-10125, 1991.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media can also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

CD123-binding proteins may be purified by conventional protein purification methods, typically by a combination of chromatographic techniques. See generally *Affinity Chromatography: Principles & Methods* (Pharmacia LKB Biotechnology, Uppsala, Sweden, 1988); Scopes, *Protein Purifica-*

*tion: Principles and Practice* (Springer-Verlag, New York 1994). Proteins comprising an immunoglobulin Fc region can be purified by affinity chromatography on immobilized protein A or protein G. Additional purification steps, such as gel filtration, can be used to obtain the desired level of purity or to provide for desalting, buffer exchange, and the like.

The present disclosure provides methods for treating a subject with a disorder characterized by over-expression of CD123. Generally, such methods include administering to a subject in need of such treatment the polypeptide or CD123-binding protein as described herein. In some embodiments, the CD123-binding protein comprises at least one effector function selected from antibody-dependent cell-mediated cytotoxicity (ADCC) and complement-dependent cytotoxicity (CDC), such that the CD123-binding protein induces ADCC and/or CDC against CD123-expressing cells in the subject.

In other embodiments, where the polypeptide comprises a second binding domain that specifically binds a T-cell (e.g., to a TCR complex or component thereof, such as CD3ε), the polypeptide or CD123-binding protein induces redirected T-cell cytotoxicity (RTCC) against CD123-expressing cells in the subject. In some embodiments, RTCC polypeptides (e.g., polypeptides that induce RTCC) comprise a modified constant domain to reduce or remove ADCC and/or CDC activity.

In certain variations of the method, the disorder is a cancer. Exemplary cancers amenable to treatment in accordance with the present disclosure include, for example, acute myeloid leukemia (AML), B-lymphoid leukemia, blastic plasmocytoid dendritic neoplasm (BPDCN), hairy cell leukemia, myelodysplastic syndrome, acute lymphoblastic leukemia, refractory anemia with excess blasts, chronic myeloid leukemia and Hodgkin's lymphoma.

The disclosure also encompasses a use of a CD123-binding polypeptide for the manufacture of a medicament for treatment of a disorder (e.g., cancer) characterized by over-expression of CD123. In one embodiment, the CD123-binding polypeptide has RTCC activity, e.g., it comprises an anti-CD123 and anti-CD3 binding domain. In one embodiment, the disclosure includes a CD123-binding polypeptide for use in treating a disorder (e.g., cancer) characterized by over-expression of CD123.

In one embodiment, the disclosure provides a method of treating a patient diagnosed with acute myeloid leukemia, B-lymphoid leukemia, blastic plasmocytoid dendritic neoplasms, hairy cell leukemia, myelodysplastic syndrome, acute lymphoblastic leukemia, refractory anemia with excess blasts, chronic myeloid leukemia, Hodgkin's lymphoma or other cancer associated with the expression of CD123 by administering a therapeutically effective amount of a pharmaceutical composition comprising a recombinant polypeptide at least about 80%, at least about 85%, at least about 90%, at least about 95%, at least about 96%, at least about 97%, at least about 98%, at least about 99% or at least about 100% identical to the amino acid sequence of SEQ ID NO:130 or 132.

In some embodiments, the disclosure provides a method of treating a patient with a cancer, comprising administering to the patient a CD123-binding polypeptide comprising the amino acid sequence set forth in SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, or SEQ ID NO:156.

In some embodiments, for treatment methods and uses described herein, a polypeptide of the invention is delivered in a manner consistent with conventional methodologies associated with management of the disease or disorder for which treatment is sought. In accordance with the disclosure herein, a therapeutically effective amount of the polypeptide or CD123-binding protein in dimer form is administered to a subject in need of such treatment for a time and under conditions sufficient to prevent or treat the disease or disorder.

Subjects for administration of polypeptides as described herein include patients at high risk for developing a particular disorder characterized by CD123 over-expression as well as patients presenting with an existing such disorder. Typically, the subject has been diagnosed as having the disorder for which treatment is sought. Further, subjects can be monitored during the course of treatment for any change in the disorder (e.g., for an increase or decrease in clinical symptoms of the disorder). Also, in some variations, the subject does not suffer from another disorder requiring treatment that involves targeting CD123-expressing cells.

In prophylactic applications, pharmaceutical compositions or medicants are administered to a patient susceptible to, or otherwise at risk of, a particular disorder in an amount sufficient to eliminate or reduce the risk or delay the onset of the disorder. In therapeutic applications, compositions or medicants are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

To identify subject patients for treatment according to the methods of the disclosure, accepted screening methods can be employed to determine risk factors associated with specific disorders or to determine the status of an existing disorder identified in a subject. Such methods can include, for example, determining whether an individual has relatives who have been diagnosed with a particular disorder. Screening methods can also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T-cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, CD123-expressing cells can be implemented as an independent treatment program or as a follow-up, adjunct, or coordinate treatment regimen to other treatments.

For administration, the polypeptide of the invention (e.g., in dimer form) may be formulated as a pharmaceutical composition. A pharmaceutical composition may comprise: (i) a CD123-binding polypeptide; and (ii) a pharmaceutically acceptable carrier, diluent or excipient. A pharmaceutical composition comprising a CD123-binding protein can be formulated according to known methods to prepare pharmaceutically useful compositions, whereby the therapeutic molecule is combined in a mixture with a pharmaceutically acceptable carrier, diluent or excipient. A carrier is said to be a "pharmaceutically acceptable carrier" if its administration can be tolerated by a recipient patient. Sterile phosphate-buffered saline is one example of a pharmaceutically acceptable carrier. Other suitable carriers, diluents or excipients are well-known to those in the art. (See, e.g., Gennaro (ed.), *Remington's Pharmaceutical Sciences* (Mack Publishing Company, 19th ed. 1995).) Formulations can further include one or more excipients, preservatives, solubilizers, buffering agents, albumin to prevent protein loss on vial surfaces, etc.

A pharmaceutical composition may be formulated in a dosage form selected from the group consisting of: an oral unit dosage form, an intravenous unit dosage form, an intranasal unit dosage form, a suppository unit dosage form, an intradermal unit dosage form, an intramuscular unit dosage form, an intraperitoneal unit dosage form, a subcutaneous unit dosage form, an epidural unit dosage form, a sublingual unit dosage form, and an intracerebral unit dosage form. The oral unit dosage form may be selected from the group consisting of: tablets, pills, pellets, capsules, powders, lozenges, granules, solutions, suspensions, emulsions, syrups, elixirs, sustained-release formulations, aerosols, and sprays.

A pharmaceutical composition comprising a polypeptide of the invention may be administered to a subject in a therapeutically effective amount. According to the methods of the present disclosure, a CD123-binding protein can be administered to subjects by a variety of administration modes, including, for example, by intramuscular, subcutaneous, intravenous, intra-atrial, intra-articular, parenteral, intranasal, intrapulmonary, transdermal, intrapleural, intrathecal, and oral routes of administration.

Determination of effective dosages in this context is typically based on animal model studies followed up by human clinical trials and is guided by determining effective dosages and administration protocols that significantly reduce the occurrence or severity of the subject disorder in model subjects. Effective doses of the compositions of the present disclosure vary depending upon many different factors, including means of administration, target site, physiological state of the patient, whether the patient is human or an animal, other medications administered, whether treatment is prophylactic or therapeutic, as well as the specific activity of the composition itself and its ability to elicit the desired response in the individual. Usually, the patient is a human, but in some diseases, the patient can be a nonhuman mammal. Typically, dosage regimens are adjusted to provide an optimum therapeutic response, i.e., to optimize safety and efficacy. Accordingly, a therapeutically effective amount is also one in which any undesired collateral effects are outweighed by the beneficial effects of administering a CD123-binding protein as described herein. For administration of the CD123-binding protein, a dosage may range from, for instance, about 0.1 μg to 100 mg/kg or 1 μg/kg to about 50 mg/kg, or 10 μg to 5 mg/kg of the subject's body weight.

Dosage of the pharmaceutical composition can be varied by the attending clinician to maintain a desired concentration at a target site.

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measureable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, MD.)

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

The disclosure will be further clarified by the following examples, which are intended to be purely exemplary of the disclosure and in no way limiting.

EXAMPLES

Example 1: Generation of Humanized Variants of Anti-CD123 Antibodies and Construction of Monospecific and Bispecific CD123-Binding Molecules

Isolation of Monospecific CD123-Binding Molecules by Phage Display anti-CD123-specific scFv binding molecules were isolated from SuperHuman library, Distributed Bio Inc. (South San Francisco, CA), using soluble phage display panning technique against biotinylated recombinant CD123 protein (SEQ ID NO:200) following Distributed Bio protocols and as described previously by Ayriss, J et al, (2007) *J Proteome Res*., p 1072-82. Binding specificity of clones was characterized by ELISA using CD123 and unrelated recombinant protein with identical purification tag. Flow cytometry using HEK293 cells transfected with human and cynomolgus monkey variants of CD123, SEQ ID NO: 201 and SEQ ID NO:203, respectively, was used to identify clones binding to CD123 in the context of cell surface. Nucleotide and amino acid sequences of binding molecules referred to in these Examples can be found in Table 5.

Isolation of Monospecific CD123-Binding Molecules by Hybridoma Generation

Anti-CD123-specific antibodies were isolated from a hybridoma library generated after immunizing OmniMice (Ligand Inc, San Diego, CA) with recombinant human CD123 ectodomain (SEQ ID NO:200). Binding specificity of individual clones was confirmed by testing binding using flow cytometry on HEK293 cells transfected with human and cynomolgus monkey variants of CD123, SEQ ID NO:201 and 203, respectively, and further confirmed by lack of binding to parental HEK293 cells. Sequences were obtained by RT-PCR using the OneStep RT-PCR Kit (QIAGEN Inc., Valencia, CA), following a modified version of the manufacturer's protocol. Briefly, cells from each clone were scraped from frozen cell bank vials and resuspended in RNase-free water. This cell suspension was then used as template in a RT-PCR reaction using sets of gene-specific primers that flank the heavy, kappa or lambda variable domains. Sequencing was performed using a reverse primer in the constant domains for each of these fragments. Sequences were then converted to scFv format by amplifying the variable domains using primers that contain overlapping sequences and were assembled into a mammalian expression vector using NEBuilder® HiF DNA Assembly Cloning Kit (New England Biolabs, Beverly, MA).

TABLE 5

CD123 sequences used for immunization and screening

| Name | Nucleotide Sequence | Amino Acid Sequence | SEQ ID NOs: nucleotide (amino acid) |
|---|---|---|---|
| human CD123 ectodomain, with Avi-3xFLAG-His affinity tag TRI032 | atggaagcaccagcgcagcttctcttcctcctgctactctggctcccagat<br>accaccggtaaggaggaccccaacccccccatcaccaacctgaggatga<br>aggccaaggcccagcagctgacctgggacctgaacaggaacgtgacag<br>acatcgaatgcgtgaaggatgccgactacagcatgcccgccgtgaacaa<br>ctcctactgccagttcggcgccatcagcctgtgcgaggtgacaaactaca<br>ccgtgagagtggccaaccccccttcagcacctggatcctgtttcccgaga<br>acagcggcaaaccctgggctggcgctgagaacctgacctgctggatccac<br>gacgtggactttctgtcctgcagctgggctgtgggacccggagctcctgcc<br>gatgtgcagtacgacctgtacctgaatgtggccaacagaagacagcagt<br>acgagtgcctgcattacaagaccgacgcccagggaaccaggatcggctg<br>caggtttgatgacatcagcaggctgtcctccggcagccagtccagccaca<br>tcctggtgagaggcagatccgccgccttcggcattccctgcacagacaag<br>ttcgtcgtcttcagccagatcgagattctgacccccccaacatgaccgcc<br>aagtgtaacaagacccacagcttcatgcactggaagatgaggagccact<br>tcaacaggaagttcaggtacgagctccagatccagaagaggatgcagcc<br>cgtgatcaccgagcaggtgagggacaggacatccttccagctgctgaatc<br>ccggcacatacaccgtgcagatcagggccagggaaagggtgtacgagtt<br>cctgtccgcctggagcacccccagaggttcgagtgtgaccaggaggag<br>ggagccaataccagggcctggagatcctcgagtctcaacgatatttttga<br>agcccaaaaaattgagtggcatgaagattacaaggacgatgacgacaa<br>agactataaggacgacgacgataaggattacaaggatgacgatgataag<br>caccatcatcatcaccatcaccaccaccactga | kedpnppitnlrmkaka<br>qqltwdlnrnvtdiecvk<br>dadysmpavnnsycqf<br>gaislcevtnytvrvanp<br>pfstwilfpensgkpwa<br>gaenltcwihdvdflscs<br>wavgpgapadvqydly<br>lnvanrrqqyeclhyktd<br>aqgtrigcrfddisrlssgs<br>qsshilvrgrsaafgipct<br>dkfvvfsqieiltppnmt<br>akcnkthsfmhwkmr<br>shfnrkfryelqiqkrmq<br>pviteqvrdrtsfqllnpg<br>tytvqirarervyeflsaw<br>stpqrfecdqeegantr<br>awrssslndifeaqkie<br>whedykddddkdykd<br>dddkdykddddkhhh<br>hhhhhhh | SEQ ID NO: 199 (SEQ ID NO: 200) |
| Full-length human CD123 sequence, isoform 2 TRI074 | atggtcctcctttggctcacgctgctcctgatcgccctgccctgtctcctgca<br>aacgaaggaaggtgggaagccttgggcaggtgcggagaatctgacctgc<br>tggattcatgacgtggatttcttgagctgcagctgggcggtaggcccgggg<br>gcccccgcggacgtccagtacgacctgtacttgaacgttgccaacaggcg<br>tcaacagtacgagtgtcttcactacaaaacggatgctcagggaacacgta<br>tcgggtgtcgtttcgatgacatctctcgactctccagcggttctcaaagttc<br>ccacatcctggtgcggggcaggagcgcagccttcggtatcccctgcacag<br>ataagtttgtcgtcttttcacagattgagatattaactccacccaacatgac<br>tgcaaagtgtaataagacacattcctttatgcactggaaaatgagaagtc<br>atttcaatcgcaaatttcgctatgagcttcagatacaaaagagaatgcag<br>cctgtaatcacagaacaggtcagagacagaacctccttccagctactcaa<br>tcctggaacgtacacagtacaaataagagcccgggaaagagtgtatgaa<br>ttcttgagcgcctggagcacccccagcgcttcgagtgcgaccaggagga<br>gggcgcaaacacacgtgcctggcggacgtcgctgctgatcgcgctgggg<br>acgctgctggccctggtctgtgtcttcgtgatctgcagaaggtatctggtga<br>tgcagagactctttccccgcatccctcacatgaaagaccccatcggtgaca<br>gcttccaaaacgacaagctggtggtctgggaggcgggcaaagccggcct<br>ggaggagtgtctggtgactgaagtacaggtcgtgcagaaaactacgcgt<br>acgcggccgctcgagcagaaactcatctcagaagaggatctggcagcaa<br>atgatatcctggattacaaggatgacgacgataaggtttaa | ggkpwagaenltcwih<br>dvdflscswavgpgapa<br>dvqydlylnvanrrqqy<br>eclhyktdaqgtrigcrfd<br>disrlssgsqsshilvrgrs<br>aafgipctdkfvvfsqieil<br>tppnmtakcnkthsfm<br>hwkmrshfnrkfryelq<br>iqkrmqpviteqvrdrts<br>fqllnpgtytvqirarerv<br>yeflsawstpqrfecdq<br>eegantrawrtsllialgtl<br>lalvcvfvicrrylvmqrlf<br>priphmkdpigdsfqn<br>dklwweagkagleecl<br>vtevqvvqkttrtrpleq<br>kliseedlaandildykd<br>dddkv | SEQ ID NO: 201 (SEQ ID NO: 202) |

TABLE 5-continued

| CD123 sequences used for immunization and screening | | | |
|---|---|---|---|
| Name | Nucleotide Sequence | Amino Acid Sequence | SEQ ID NOs: nucleotide (amino acid) |
| Full-length cynomolgus CD123 sequence, isoform 1 TRI114 | atggaagcccccgcccagctgctcttcctgctgctcctgtggctgcctgac accaccggcaaggaagaccccaatgcccccatcaggaacctgagaatga aggagaaggcccagcagctcatgtgggatctgaacaggaacgtgaccga cgtggagtgtatcaagggcaccgactactccatgcccgccatgaataaca gctattgccagttcggcgccatcagcctgtgcgaggtcaccaactacacc gtgagagtggccagcccccccttctccacctggattctgttccctgagaac agcggcacccctagggctggcgctgagaatctgacatgctgggtccatga cgtggacttcctgagctgcagctgggtggtgggacctgctgctcccgctga cgtgcagtacgatctgtatctgaacaaccccaactcccacgagcagtaca ggtgcctgcactacaagacagacgctagaggcacccagatcggctgcag gttcgatgatatcgcccctctgagcaggggatcccagagctcccatatcct ggtgaggggcaggtccgccgctgtgagcattccttgcaccgacaagttcg tcttcttcagccagatcgagaggctgaccccccctaacatgacaggcgag tgcaacgagacccacagcttcatgcactggaagatgaagagccatttcaa caggaaattcaggtacgaactgaggattcagaagagaatgcagcccgtg aggacagagcaggtgagggatacaaccagcttccagctgcccaatcctg gcacctataccgtgcagatcagggctagagagaccgtgtacgagtttctg tccgcctggagcacccccagaggtttgaatgtgaccaggaggagggag cctccagcagggcttggagaaccagcctcctcatcgccctgggcacactg ctggctctgctgtgtgtgttcctgatctgcagaaggtacctggtgatgcaga ggctcttccctaggattccccacatgaaggaccccatcggcgacaccttcc agcaggacaaactggtggtgtgggaagccggaaaggccggcctggagg aatgcctcgtgtccgaggtgcaggtggtggagaagacctaa | kedpnapirnlrmkeka qqlmwdlnrnvtdveci kgtdysmpamnnsyc qfgaislcevtnytvrvas ppfstwilfpensgtpra gaenltcwvhdvdflscs wvvgpaapadvqydly Innpnsheqyrclhykt dargtqigcrfddiaplsr gsqsshilvrgrsaavsip ctdkfvffsqierltppn mtgecnethsfmhwk mkshfnrkfryelriqkr mqpvrteqvrdttsfql pnpgtytvqiraretvye flsawstpqrfecdqee gassrawrtsllialgtllal Icvflicrrylvmqrlfpri phmkdpigdtfqqdkl vvweagkagleeclvse vqvvekt | SEQ ID NO: 203 (SEQ ID NO: 204) |

Preparation of Bispecific CD123-Binding Molecules

Bispecific 00123-binding molecules targeting 00123 and 003 epsilon, TRI129 (SEQ ID NO:129 (nucleic acid), SEQ ID NO:130 (amino acid)); TRI130 (SEQ ID NO:131 (nucleic acid), SEQ ID NO:132 (amino acid)); TRI1123 (SEQ ID NO:133 (nucleic acid), SEQ ID NO:134 (amino acid)); TRI124 (SEQ ID NO: 135 (nucleic acid), SEQ ID NO: 136 (amino acid)); TRI137 (SEQ ID NO: 137 (nucleic acid), SEQ ID NO: 138 (amino acid)); TRI125 (SEQ ID NO: 139 (nucleic acid), SEQ ID NO:140 (amino acid)); TRI126 (SEQ ID NO:141 (nucleic acid), SEQ ID NO:142 (amino acid)); TRI127 (SEQ ID NO:143 (nucleic acid), SEQ ID NO:144 (amino acid)); TRI134 (SEQ ID NO:145 (nucleic acid), SEQ ID NO:146 (amino acid)); TRI128 (SEQ ID NO:147 (nucleic acid), SEQ ID NO:148 (amino acid)); TRI131 (SEQ ID NO:149 (nucleic acid), SEQ ID NO:150 (amino acid)); TRI132 (SEQ ID NO:151 (nucleic acid), SEQ ID NO:152 (amino acid)); TRI138 (SEQ ID NO: 153 (nucleic acid), SEQ ID NO: 154 (amino acid)); and TRI139 (SEQ ID NO: 155 (nucleic acid), SEQ ID NO: 156 (amino acid)), were made using standard molecular biology techniques, starting with existing bispecific binding molecules as templates and using the methods generally disclosed in, e.g., PCT Application Publication No. WO 2007/146968, U.S. Patent Application Publication No. 2006/0051844, PCT Application Publication No. WO 2010/040105, PCT Application Publication No. WO 2010/003108, and U.S. Pat. No. 7,166,707 (see also Table 3). Insertion of the N-terminal anti-CD123 scFv binding domain was accomplished through digestion of the parental template and scFv insert with the restriction enzymes HindIII and XhoI, desired fragments were identified and isolated by agarose gel purification, and ligated. Insertion of the C-terminal anti-CD3 epsilon scFv binding domain was accomplished through digestion of the parental template and scFv insert with the restriction enzymes EcoRI and NotI, desired fragments were identified and isolated by agarose gel purification, and ligated.

Assembly of constructs with human scFv domains was accomplished by a three piece ligation using a HindIII/BamHI fragment, a BamHI/XhoI fragment, and a destination vector cut with HindIII/XhoI. This was used to produce the gene sequences corresponding to the humanized bispecific molecules shown in Table 4.

TABLE 6

| Composition of Initial Humanized Constructs | | | |
|---|---|---|---|
| Construct ID | scFv Orientation | Nucleotide SEQ ID NO | Amino acid SEQ ID NO |
| TRI129 | VHVL | 129 | 130 |
| TRI130 | VLVH | 131 | 132 |
| TRI123 | VHVL | 133 | 134 |
| TRI124 | VLVH | 135 | 136 |
| TRI139 | VHVL | 155 | 156 |
| TRI137 | VHVL | 137 | 138 |
| TRI125 | VHVL | 139 | 140 |
| TRI126 | VHVL | 141 | 142 |
| TRI127 | VLVH | 143 | 144 |
| TRI131 | VHVL | 149 | 150 |
| TRI132 | VHVL | 151 | 152 |
| TRI134 | VHVL | 145 | 146 |
| TRI128 | VHVL | 147 | 148 |
| TRI138 | VHVL | 153 | 154 |

Expression and Purification of CD123-Binding Molecules and Antibodies

Bispecific CD123-binding molecules disclosed herein were produced by both transient transfection of human HEK293 cells and, in some instances, also stable transfection of CHO cells. Transfected cells were purified from cell culture supernatants by Protein A affinity chromatography. If aggregates were detected after affinity chromatography, secondary size exclusion chromatography was also performed to ensure homogeneity of the protein.

Example 2: Binding of CD123-Binding Molecules to CD123(+) Cell Lines

To confirm that binding activity to CD123 on the surface of cancer cells was retained anti-CD123×anti-CD3ε molecules and cross-reactivity to cynomolgus CD123, flow cytometry was used to quantitate binding of constructed CD123-binding molecules to cell lines expressing CD123.

Binding of Monospecific and Bispecific Proteins to CD123 (+) Cell Lines

Binding studies on the CD123(+) Molm-13 (Matsuo, Y et al, 1997, *Leukemia* 11, 1469-1477) cancer cell line and cynomolgus CD123 expressing CHO cells were performed by standard flow cytometry-based staining procedures. The Molm-13 cell line was obtained from DSMZ (Braunschweig, Germany). The Molm-13 cell line was cultured according to the provided protocols. Chinese hamster ovary (CHO) cells stably expressing the full length cynomolgus CD123 protein were developed in-house. A typical experiment would label 100,000 cells per well, in 96-well plates, with a range of 1,000 nM to 0.012 nM binding molecule in 100 μl of PBS buffer with 0.2% BSA and 2 mM EDTA, for 30 min on ice, followed by washes and incubation with PE-labeled minimum cross species reactive secondary antibody, goat anti-human IgG Fcγ, F(ab')2 (Jackson Laboratory) for 30 minutes on ice. Signal from bound molecules was detected using a LSR-II™ flow cytometer (BD Biosciences) and analyzed by FlowJo flow cytometry analysis software. Mean fluorescence intensity (MFI) of bound molecules on cells was determined after exclusion of doublets. Nonlinear regression analysis to determine EC50 values was performed in GraphPad Prism 7© graphing and statistics software.

FIGS. 1A, 1B, 1C and 1D show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in three independent experiments to the CD123 (+) Molm-13 human tumor cell line. These experiments utilized bispecific constructs prepared from transiently transfected HEK293 cells. Four of the molecules demonstrated comparable maximum levels of binding at saturating concentrations. Observed $EC_{50}$ values for TRI125, TRI129, TRI130 and TRI139 were between 2-10 nM. Experiments were repeated for TRI129 and TRI130 from stably transfected CHO cells with similar results (data not shown).

Figure 2A:
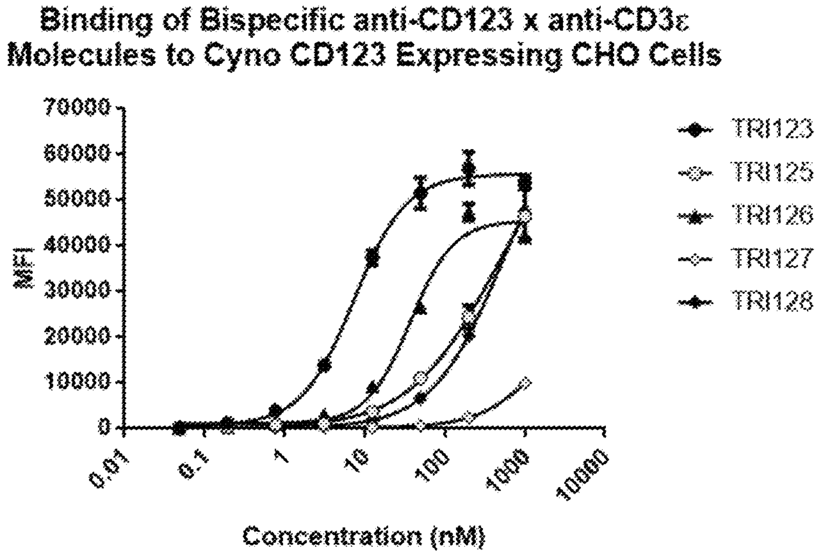
FIG. 2A-FIG. 2C show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments to CHO cells stably expressing cynomolgus CD123 protein.
Figure 2B:
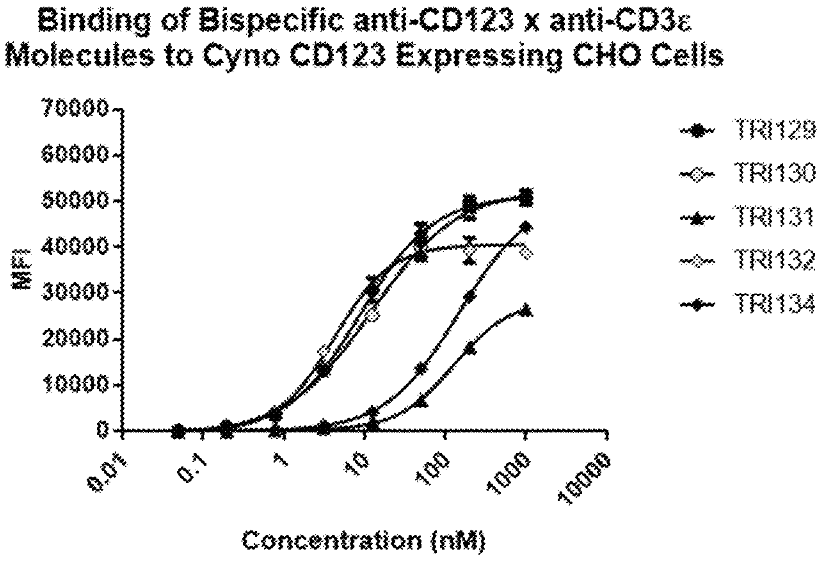
Figure 2C:
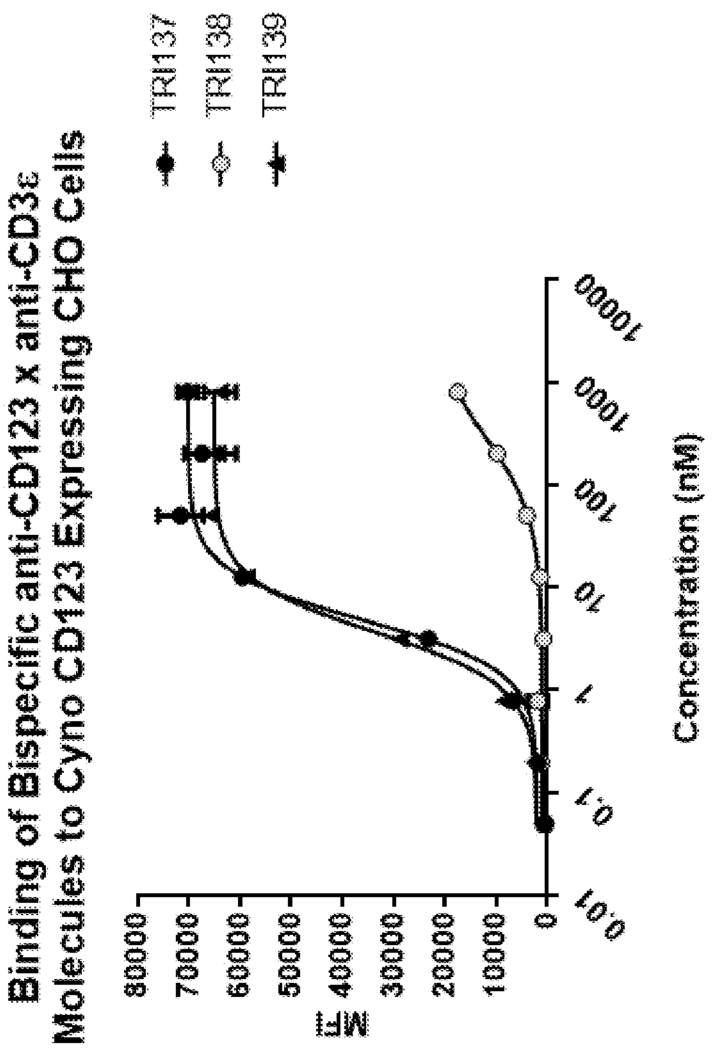

FIGS. 2A, 2B and 2C show the binding of 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments to CHO cells stably expressing cynomolgus CD123 protein. Seven of the molecules demonstrated comparable maximum levels of binding at saturating concentrations. Observed $EC_{50}$ values for TRI123, TRI126, TRI129, TRI130, TRI132, TRI137 and TRI139 were between 3-38 nM.

These results confirm the constructed anti-CD123×anti-CD3ε molecules retain binding activity to human CD123 on the surface of cancer cells and are cross-reactive with cynomolgus CD123.

Example 3: Redirected T Cell Cytotoxicity Assays with CD123(+) Cell Lines

To confirm that bispecific molecules binding to both CD123 and CD3ε could redirect T-cell cytotoxicity against a CD123(+) cell line, chromium-51 release assays were used to quantify target cell lysis induced by T-cells.

Chromium-51 Release Assays with CD123(+) Cell Lines

The Molm-13 human tumor cell line was cultured according to the provided protocols. Peripheral blood mononuclear cells (PBMC) were isolated from human blood using standard ficoll gradients. The isolated cells were washed in saline buffer. PBMC were cultured for 24 hours with Human T-Activator CD3/CD28 Dynabeads® (catalogue #11131D, Gibco Life Technologies, Carlsbad, California, USA) to activate T-cells using the manufacturers protocols. After 24 hours of culture PBMC were harvested and placed in a magnetic field to remove the Dynabeads. The isolated cells were washed in RPMI media+10% human serum. During the assay, concentrations of bispecific molecules with final concentration ranging from 1000 pM to 0.061 pM were added to the activated PBMC (approximately 100,000 per well).

Approximately $2.5\times10^6$ Molm-13 target cells were treated with 0.125 mCi of $^{51}Cr$ and incubated for 90 minutes in a 37° C., 5% $CO_2$ humidified incubator. After incubation, cells were washed 3 times with assay media (RPMI with 10% human serum) and re-suspended in 12.5 mL of assay media. From this suspension, 50 μL was dispensed per well into 96 well U-bottom plates (approximately 10,000 cells per well) to bring the total volume to 200 μL per well, and the PBMC to target cell ratio to 10:1. A zero lysis control was generated by target cells only, omitting the PBMC. A total lysis control was generated by including 0.20% NP-40 as the treatment with target cells only. A background lysis control was generated by target cells with PBMC in the absence of bispecific molecules.

Plates were incubated for 4 hours at 37° C., 5% $CO_2$ in a humidified incubator, after which they were centrifuged at 1000 rpm for 3 minutes, and 25 μL of supernatant was transferred from each well to the corresponding well of a 96-well Luma sample plate. Sample plates were allowed to air dry in a chemical safety hood for 18 hours, and then radioactivity was read on a TopCount microplate scintillation counter (PerkinElmer) using a standard protocol.

Percent specific lysis was calculated using the formula: ((signal in drug treated sample−background signal from samples with Target Cell only)/(signal in total lysis wells−background signal from samples with Target Cell only))×100.

Figure 3A:
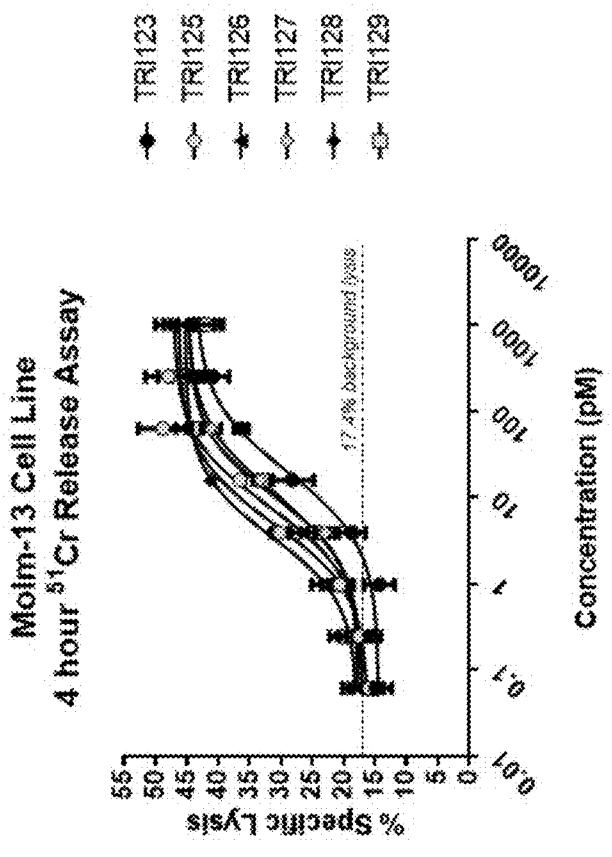
FIG. 3A-FIG. 3C show the results from chromium-51 release assays with the Molm-13 cell line measured at 4 hours using 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments. All of the bispecific anti-CD123×anti-CD3ε molecules showed efficient target cell lysis at 4 hours ranging between 24-48% maximum specific lysis.
Figure 3B:
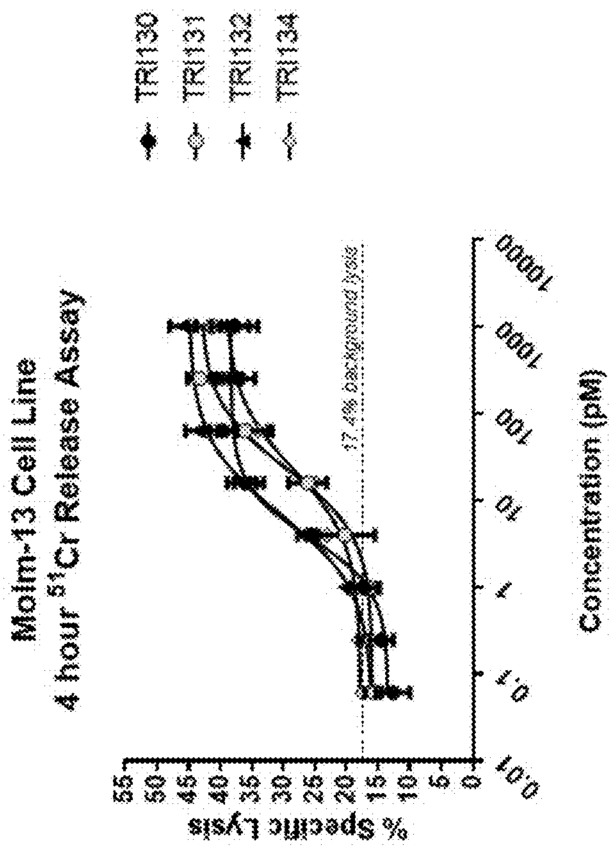
Figure 3C:
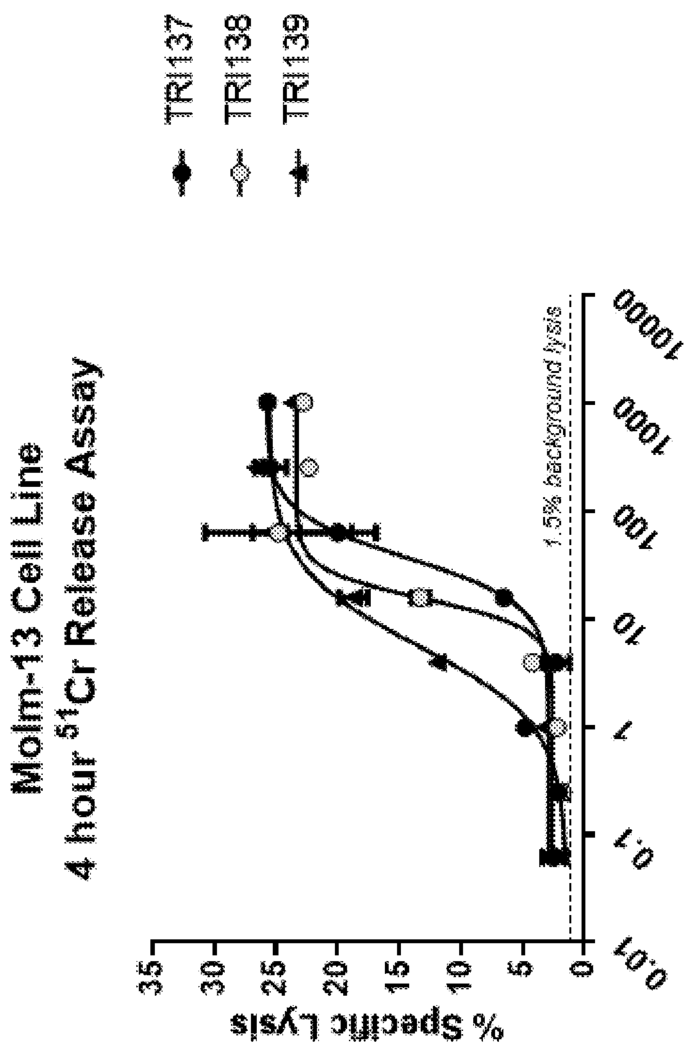

FIGS. 3A, 3B and 3C show chromium-51 release assays with the Molm-13 cell line measured at 4 hours using 13 different bispecific anti-CD123×anti-CD3ε molecules (TRI123, TRI125, TRI126, TRI127, TRI128, TRI129, TRI130, TRI131, TRI132, TRI134, TRI137, TRI138 and TRI139) in two independent experiments. All of the bispecific anti-CD123×anti-CD3ε molecules showed efficient target cell lysis at 4 hours ranging between 24-48% maximum specific lysis. Measured $EC_{50}$ values ranged between 3-37 pM at 4 hours.

Redirected T cell cytotoxicity assays were also performed with CHO cells stably expressing cynomolgus CD123 protein (TRI129 and TRI130) with (i) Molm-13 (human CD123+ cells) and human T-cells, (ii) Molm-13 (human CD123+ cells) and cynomolgous T-cells and (iii) CHO cells stably expressing cynomolgous CD123 and human T-cells. The data show that TRI129 and TRI130 are cross-reactive to human and cynomolgous CD123+ cells and T-cells.

These results confirm that the bispecific molecules binding to both CD123 and CD3ε could redirect T-cell cytotoxicity against a CD123(+) cell line.

Example 4: Target-Dependent T-Cell Proliferation Induced Against CD123(+) Cell Line by Anti-CD123 Bispecific Molecules To compare the effectiveness of different bispecific CD123-binding molecules at inducing target-dependent T-cell proliferation, six different anti-CD123×anti-CD3ε bispecific molecules including TRI123, TRI126, TRI129, TRI130, TRI132 and TRI139 were tested in two independent experiments.

T-cell proliferation was assessed by flow cytometry using a CD123(+) cell line, Molm-13. Peripheral blood mononuclear cells (PBMC) were isolated from human blood using standard density-gradient separation methods. The isolated cells were washed in saline buffer. T-cells were further isolated using a Pan T-cell Isolation Kit II from Miltenyi Biotec (Bergisch Gladbach, Germany) using the manufacturer's protocol. Molm-13 cells were irradiated to prevent cell division using a Faxitron-CellRad X-Ray Irradiation System from Faxitron Bioptics LLC (Tucson, Arizona, USA).

Proliferation was assessed by labeling isolated T-cell populations with CFSE. CFSE-labeled T-cells were plated in U-bottom 96-well plates at 120,000 cells/well, respectively, with 30,000 Molm-13 tumor cells/well, to achieve approximate T-cell to tumor cell ratios of 4:1. Concentrations of test molecules ranging from 2,000 pM to 0.002 pM were added to the cell mixtures to a final volume of 200 μl/well in RPMI 1640 media supplemented with 10% human AB serum, sodium pyruvate, antibiotics and non-essential amino acids. Plates were incubated at 37° C., 5% $CO_2$ in humidified incubators. After 4 days, cells were labeled with antibodies for flow cytometric analysis in original plates to minimize cell losses, using saline buffer with 0.1% bovine serum albumin and 2 mM EDTA. After centrifugation and removal of supernatant, the cell pellets were resuspended with a mixture of the following dye-labeled antibodies in 50 μl volumes: CD5-PE, CD8-Pacific Blue, CD25-PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to calculate the percentages of $CD4^+$ ($CD8^-$) or $CD8^+$ T-cells that had undergone at least one cell division, according to their CFSE profile, by gating sequentially on forward vs side scatter, $7AAD^-$, $CD5^+$, $CD4^+$ or $CD8^+$ T-cells ($7AAD^-$, $CD5^+$ $CD8^-$ or $7AAD^-$ $CD5^+$ $CD8^+$, respectively). Graphs were plotted using GraphPad Prism 7.0.

Figure 4B:
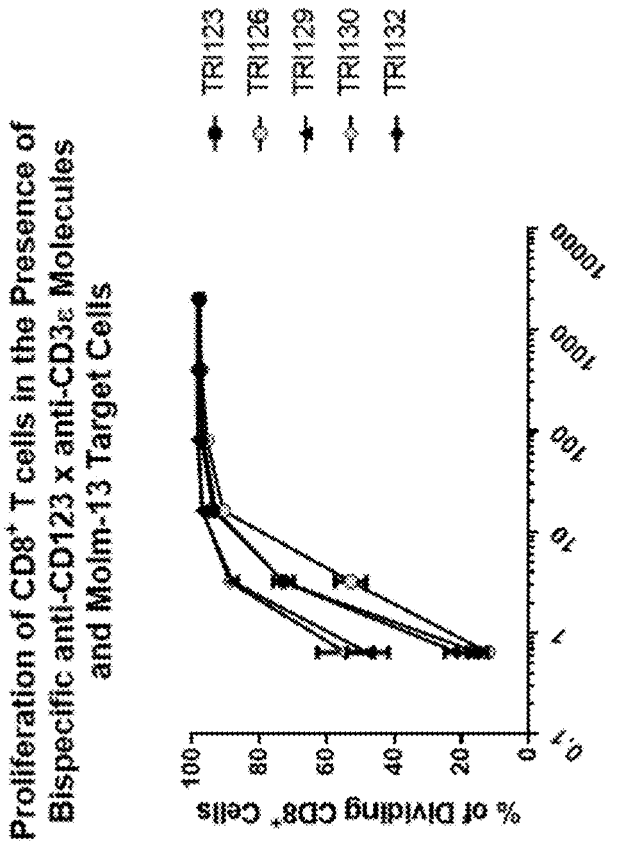
FIG. 4A-FIG. 4D show an induction of T-cell proliferation at low concentrations (10 pM).
Figure 4A:
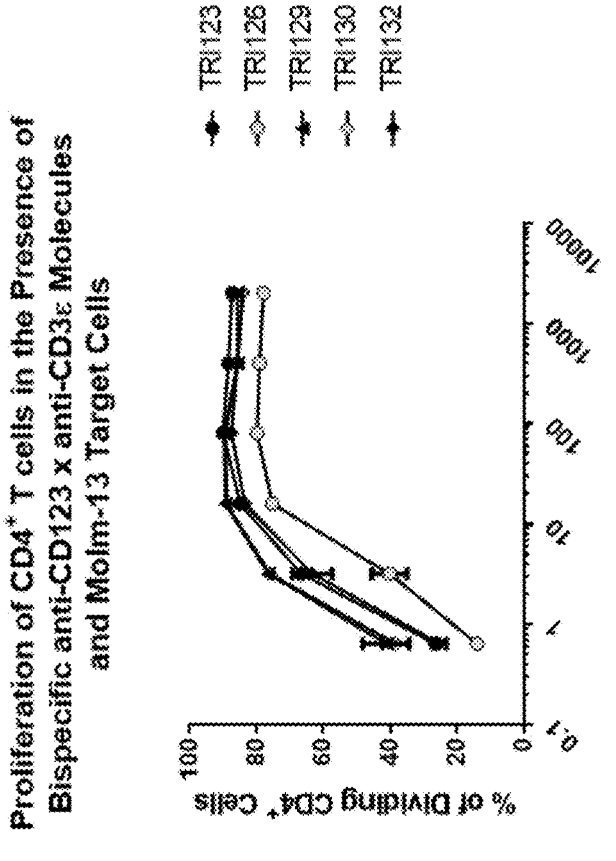
Figure 4C:
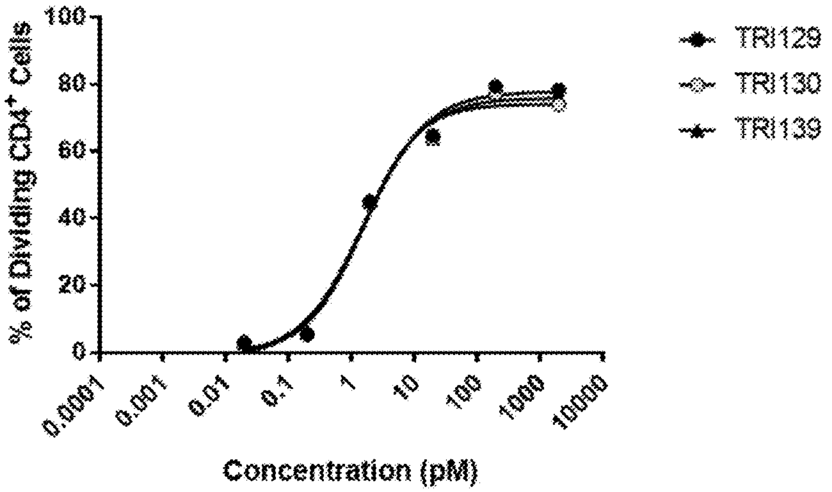
Figure 4D:
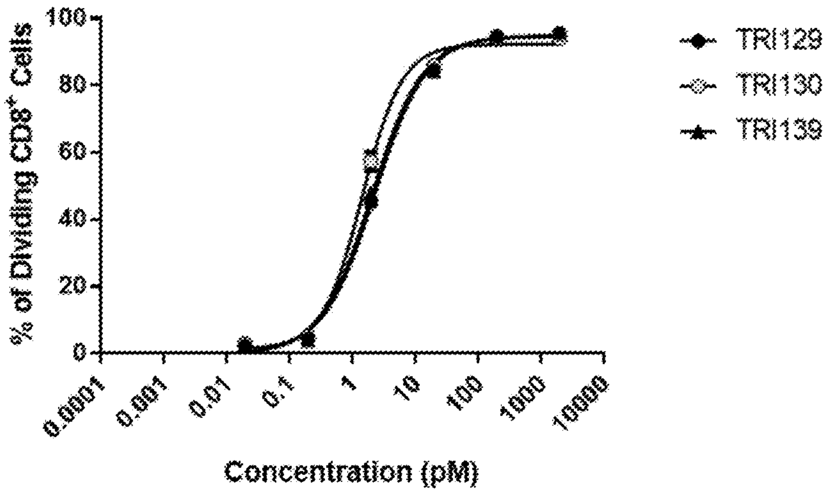
Figure 5A:
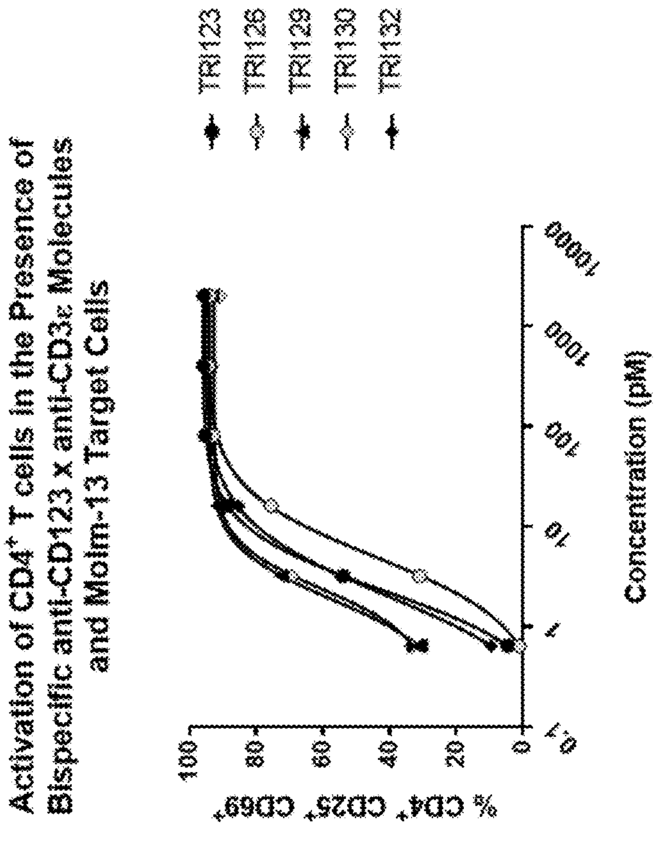
FIG. 5A-FIG. 5D show target dependent activation of $CD4^+$ and $CD8^+$ T-cells in the presence of Molm-13 cells.
Figure 5B:
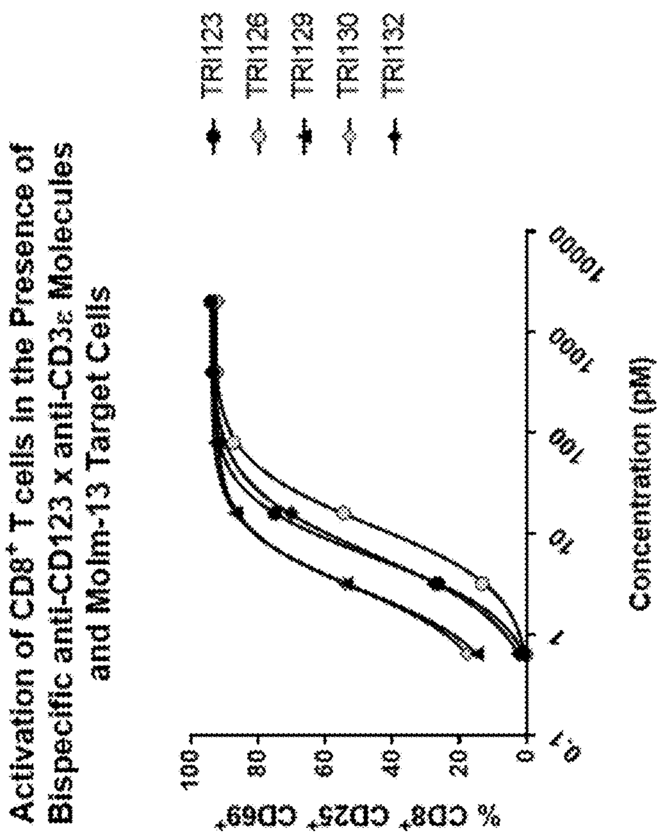
Figure 5C:
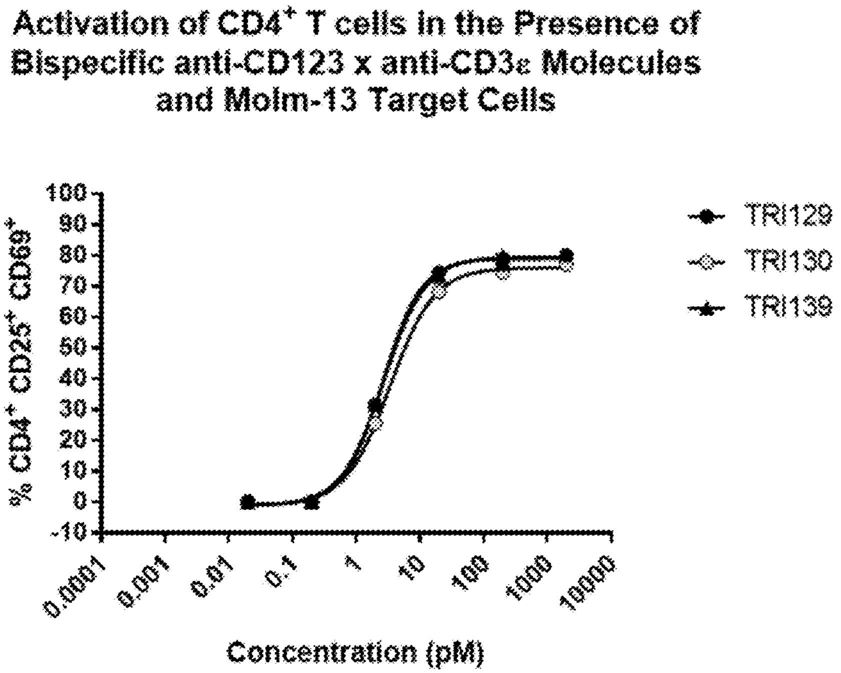
Figure 5D:
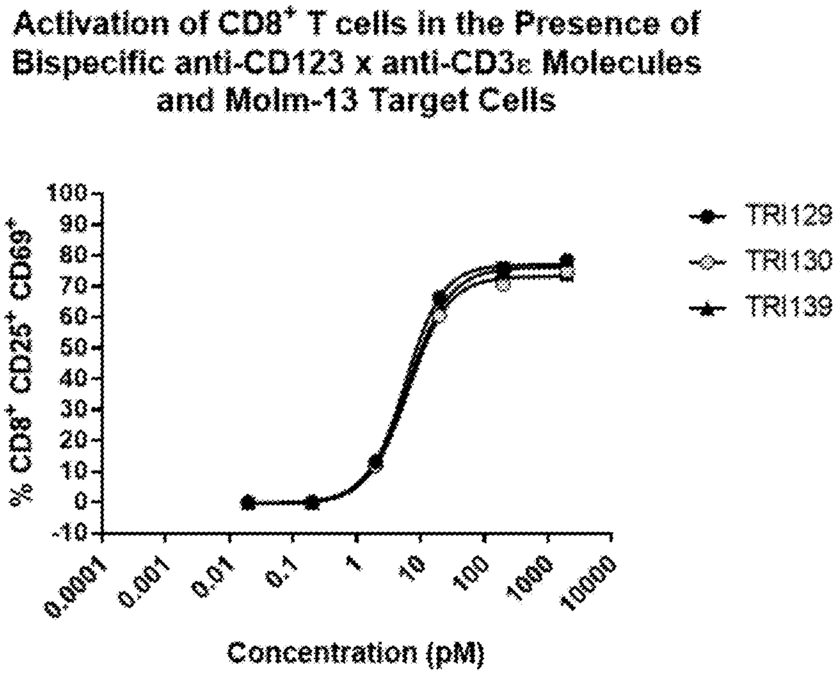

Analysis of dividing T-cell populations (FIGS. 4A and 4B) revealed a significant increase in the percent of proliferating cells in the presence of Molm-13 cells. All molecules showed robust induction of T-cell proliferation at low concentrations (10 pM), and proliferation was slightly higher in the $CD8^+$ (FIG. 4B) than the $CD4^+$ ($CD8^-$) (FIG. 4A) T-cell population. $EC_{50}$ values were determined with TRI129, TRI130 and TRI139 for both CD4 (FIG. 4C) and CD8 (FIG. 4D) populations demonstrating similar potency for all three anti-CD123×anti-CD3ε bispecific molecules.

These results confirm that bispecific molecules binding to both CD123 and CD3ε could induce target-dependent T-cell proliferation against a CD123(+) cell line.

Example 5: Determination of Pharmacokinetics in a Representative Non-Clinical Species To determine the pharmacokinetics in a relevant non-clinical species, a bispecific anti-CD123×anti-CD3 molecule is tested in a Non-Human Primate (NHP) species (e.g., cynomolgus monkeys) for pharmacokinetic (PK) and toxicology assessment of the anti-CD123×anti-CD3 molecule. Cross-reactivity of the anti-CD123 binding domain to NHP CD123 is tested by ELISA or surface plasmon resonance assays (similar to Example 2). Since there is 85.7% sequence identity between NHP and human CD123, equivalent binding is expected. PK and immunogenicity assays can be developed and used to detect and quantify the anti-CD123×anti-CD3 molecule in the presence of cyno serum, as well as to evaluate the immunogenicity response in NHP. Upon successful completion of these tasks to justify cynomolgus monkeys as a relevant tox species for CD123-targeting molecules, a single dose PK/tolerability experiment is performed. The study can be performed at a qualified clinical research organization (CRO). The study results are examined for PK parameters and any adverse events including unexplainable adverse events that cannot be attributed to the mechanism of action of the drug or to anti-drug antibodies (ADA). A toxicologist verifies and interprets the study results and supports continued development of the lead. PK parameters derived from this study are used to design future toxicology studies in non-human primates and/or clinical studies in human patients.

Example 6: Testing of Safety and Tolerability Upon Human Clinical Administration To determine the safety and tolerability in humans of a lead bispecific molecule targeting CD123 and CD3, the following phase 1 clinical trial could be conducted. The first-in-human study of an anti-CD123×anti-CD3 bispecific molecule can be a dose-escalation study to identify the maximum tolerated dose (MTD) in human administration.

As bispecific anti-CD123×anti-CD3 molecules are agonistic, the starting dose is set at a dose producing the Minimum Anticipated Biological Effect Level (MABEL) based on in vitro activity of anti-CD123×anti-CD3. Human pharmacokinetics (PK) are estimated using PK values determined in non-clinical models (mice or non-human primates) and allometric scaling to predict a dose yielding the MABEL. Bispecific molecule is dosed using either intravenous infusion or subcutaneous injection. Dose escalation follows a standard 3+3 design, with an anticipated 12 dose cohorts (N=24-72 patients). Dose frequency is dependent on observed PK in non-clinical studies, but could be weekly (QWA), every other week (Q2W), every third week (Q3W), or monthly (Q4W). Dosing continues until disease progression (as defined by either the immune-related response criteria (irRC) or the response criteria in solid tumors (RECIST)).

Primary endpoint of the study is safety, defining an MTD and any dose limiting toxicities. Secondary endpoints of the study is PK, immunogenicity, and objective responses in tumor volume assessed either by irRC or RECIST criteria. For patients with hematologic malignancies, additional criteria may be assessed, such as the presence of minimal residual disease (MRD status). As appropriate or feasible, biomarker samples are taken from whole blood as well as from lymph node or bone marrow biopsies to monitor the effects on the immune system as well as effects on the cancer or malignancy.

Inclusion criteria for a phase 1 study may be broad and allow for inclusion of patients with refractory or relapsed disease from multiple indications where CD123 expression has been previously shown to be high, such as acute myeloid leukemia (AML), B-lymphoid leukemia, blastic plasmocytoid dendritic neoplasm (BPDCN), and hairy cell leukemia. Patients entering the study require evidence of CD123 expression from immunohistochemical (IHC) analysis from either archival biopsy samples of the primary tumor or from a pre-treatment biopsy of a recurrent tumor from a metastatic site.

A bispecific anti-CD123×anti-CD3 molecule is determined to be sufficiently safe if patients dosed at the MTD or dose levels below the MTD show evidence of clinical benefit, either from objective responses from the irRC or RECIST criteria or changes in potentially prognostic serum biomarkers, such as CTC, PSA, or TAG72.

TABLE 7

Human CD123 isoform sequences (National Center for Biotechnology Information)

| Name | Nucleotide Sequence (mRNA) | Amino Acid Sequence (complete) | SEQ ID NO (Amino Acid SEQ ID NO) |
|---|---|---|---|
| CD123<br>isoform 1<br>NM_002183.3<br>NP_002174.1 | GTCAGGTTCATGGTTACGAAGCTG<br>CTGACCCCAGGATCCCAGCCCGTG<br>GGAGAGAAGGGGGTCTCTGACA<br>GCCCCCACCCCTCCCCACTGCCAG<br>ATCCTTATTGGGTCTGAGTTTCAG<br>GGGTGGGGCCCCAGCTGGAGGT<br>TATAAAACAGCTCAATCGGGGAGT<br>ACAACCTTCGGTTTCTCTTCGGGG<br>AAAGCTGCTTTCAGCGCACACG<br>GGAAGATATCAGAAACATCCTAGG<br>ATCAGGACACCCCAGATCTTCTCA<br>ACTGGAACCACGAAGGCTGTTT<br>CTTCCACACAGTACTTTGATCTCC<br>ATTTAAGCAGGCACCTCTGTCCTG<br>CGTTCCGGAGCTGCGTTCCCGA<br>TGGTCCTCCTTTGGCTCACGCTGC<br>TCCTGATCGCCCTGCCCTGTCTCC<br>TGCAAACGAAGGAAGATCCAAA<br>CCCACCAATCACGAACCTAAGGAT<br>GAAAGCAAAGGCTCAGCAGTTGAC<br>CTGGGACCTTAACAGAAATGTG<br>ACCGATATCGAGTGTGTTAAAGAC<br>GCCGACTATTCTATGCCGGCAGTG<br>AACAATAGCTATTGCCAGTTTG<br>GAGCAATTTCCTTATGTGAAGTGA<br>CCAACTACACCGTCCGAGTGGCCA<br>ACCCACCATTCTCCACGTGGAT<br>CCTCTTCCCTGAGAACAGTGGGAA<br>GCCTTGGGCAGGTGCGGAGAATCT<br>GACCTGCTGGATTCATGACGTG<br>GATTTCTTGAGCTGCAGCTGGGCG<br>GTAGGCCCGGGGGCCCCCGCGGAC<br>GTCCAGTACGACCTGTACTTGA<br>ACGTTGCCAACAGGCGTCAACAGT<br>ACGAGTGTCTTCACTACAAAACGG<br>ATGCTCAGGGAACACGTATCGG<br>GTGTCGTTTCGATGACATCTCTCG<br>ACTCTCCAGCGGTTCTCAAAGTTC<br>CCACATCCTGGTGCGGGGCAGG<br>AGCGCAGCCTTCGGTATCCCCTGC<br>ACAGATAAGTTTGTCGTCTTTTCA<br>CAGATTGAGATATTAACTCCAC<br>CCAACATGACTGCAAAGTGTAATA<br>AGACACATTCCTTTATGCACTGGA<br>AAATGAGAAGTCATTTCAATCG<br>CAAATTTCGCTATGAGCTTCAGAT<br>ACAAAAGAGAATGCAGCCTGTAAT<br>CACAGAACAGGTCAGAGACAGA<br>ACCTCCTTCCAGCTACTCAATCCT<br>GGAACGTACACAGTACAAATAAGA<br>GCCCGGGAAAGAGTGTATGAAT<br>TCTTGAGCGCCTGGAGCACCCCCC<br>AGCGCTTCGAGTGCGACCAGGAGG<br>AGGGCGCAAACACACGTGCCTG<br>GCGGACGTCGCTGCTGATCGCGCT<br>GGGGACGCTGCTGGCCCTGGTCTG<br>TGTCTTCGTGATCTGCAGAAGG<br>TATCTGGTGATGCAGAGACTCTTT<br>CCCCGCATCCCTCACATGAAAGAC<br>CCCATCGGTGACAGCTTCCAAA<br>ACGACAAGCTGGTGGTCTGGGAGG<br>CGGGCAAAGCCGGCCTGGAGGAGT<br>GTCTGGTGACTGAAGTACAGGT<br>CGTGCAGAAAACTTGAGACTGGGG<br>TTCAGGGCTTGTGGGGGTCTGCCT | MVLLWLTLLLIALPCLLQ<br>TKEDPNPPITNLRMKAKA<br>QQLTWDLNRNVTDIECVK<br>DADYSMPAVNNSYCQF<br>GAISLCEVTNYTVRVANP<br>PFSTWILFPENSGKPWAG<br>AENLTCWIHDVDFLSCSW<br>AVGPGAPADVQYDLYL<br>NVANRRQQYECLHYKTDA<br>QGTRIGCRFDDISRLSSG<br>SQSSHILVRGRSAAFGIP<br>CTDKFVVFSQIEILTP<br>PNMTAKCNKTHSFMHWKM<br>RSHFNRKFRYELQIQKRM<br>QPVITEQVRDRTSFQLLN<br>PGTYTVQIRARERVYE<br>FLSAWSTPQRFECDQEEG<br>ANTRAWRTSLLIALGTLL<br>ALVCVFVICRRYLVMQRL<br>FPRIPHMKDPIGDSFQ<br>NDKLVVWEAGKAGLEECL<br>VTEVQVVQKT | SEQ ID NO: 205<br>(SEQ ID NO: 206) |

TABLE 7-continued

Human CD123 isoform sequences (National Center for Biotechnology Information)

| Name | Nucleotide Sequence (mRNA) | Amino Acid Sequence (complete) | SEQ ID NO (Amino Acid SEQ ID NO) |
|---|---|---|---|
| | CAATCTCCCTGGCCGGGCCAGG CGCCTGCACAGACTGGCTGCTGGA CCTGCGCACGCAGCCCAGGAATGG ACATTCCTAACGGGTGGTGGGC ATGGGAGATGCCTGTGTAATTTCG TCCGAAGCTGCCAGGAAGAAGAAC AGAACTTTGTGTGTTTATTTCA TGATAAAGTGATTTTTTTTTTTTT AACCCAAAA | | |
| CD123 isoform 2 NM_001267713.1 NP_001251642.1 | GTCAGGTTCATGGTTACGAAGCTG CTGACCCCAGGATCCCAGCCCGTG GGAGAGAAGGGGGTCTCTGACA GCCCCCACCCCTCCCCACTGCCAG ATCCTTATTGGGTCTGAGTTTCAG GGGTGGGGCCCCAGCTGGAGGT TATAAAACAGCTCAATCGGGGAGT ACAACCTTCGGTTTCTCTTCGGGG AAAGCTGCTTTCAGCGCACACG GGAAGATATCAGAAACATCCTAGG ATCAGGACACCCCAGATCTTCTCA ACTGGAACCACGAAGGCTGTTT CTTCCACACAGTACTTTGATCTCC ATTTAAGCAGGCACCTCTGTCCTG CGTTCCGGAGCTGCGTTCCCGA TGGTCCTCCTTTGGCTCACGCTGC TCCTGATCGCCCTGCCCTGTCTCC TGCAAACGAAGGAAGGTGGGAA GCCTTGGGCAGGTGCGGAGAATCT GACCTGCTGGATTCATGACGTGGA TTTCTTGAGCTGCAGCTGGGCG GTAGGCCCGGGGGCCCCCGCGGAC GTCCAGTACGACCTGTACTTGAAC GTTGCCAACAGGCGTCAACAGT ACGAGTGTCTTCACTACAAAACGG ATGCTCAGGGAACACGTATCGGGT GTCGTTTCGATGACATCTCTCG ACTCTCCAGCGGTTCTCAAAGTTC CCACATCCTGGTGCGGGGCAGGAG CGCAGCCTTCGGTATCCCCTGC ACAGATAAGTTTGTCGTCTTTTCA CAGATTGAGATATTAACTCCACCC AACATGACTGCAAAGTGTAATA AGACACATTCCTTTATGCACTGGA AAATGAGAAGTCATTTCAATCGCA AATTTCGCTATGAGCTTCAGAT ACAAAAGAGAATGCAGCCTGTAAT CACAGAACAGGTCAGAGACAGAAC CTCCTTCCAGCTACTCAATCCT GGAACGTACACAGTACAAATAAGA GCCCGGGAAAGAGTGTATGAATTC TTGAGCGCCTGGAGCACCCCCC AGCGCTTCGAGTGCGACCAGGAGG AGGGCGCAAACACACGTGCCTGGC GGACGTCGCTGCTGATCGCGCT GGGGACGCTGCTGGCCCTGGTCTG TGTCTTCGTGATCTGCAGAAGGTA TCTGGTGATGCAGAGACTCTTT CCCCGCATCCCTCACATGAAAGAC CCCATCGGTGACAGCTTCCAAAAC GACAAGCTGGTGGTCTGGGAGG CGGGCAAAGCCGGCCTGGAGGAGT GTGTGGTGACTGAAGTACAGGTCG TGCAGAAAACTTGAGACTGGGG TTCAGGGCTTGTGGGGGTCTGCCT CAATCTCCCTGGCCGGGCCAGGCG CCTGCACAGACTGGCTGCTGGA CCTGCGCACGCAGCCCAGGAATGG ACATTCCTAACGGGTGGTGGGCAT GGGAGATGCCTGTGTAATTTCG TCCGAAGCTGCCAGGAAGAAGAAC AGAACTTTGTGTGTTTATTTCATG | MVLLWLTLLLIALPCLLQ TKEGGKPWAGAENLTCWI HDVDFLSCSWAVGPGAPA DVQYDLYLNVANRRQQ YECLHYKTDAQGTRIGCR FDDISRLSSGSQSSHILV RGRSAAFGIPCTDKFWF SQIEILTPPNMTAKCN KTHSFMHWKMRSHFNRKF RYELQIQKRMQPVITEQV RDRTSFQLLNPGTYTVQI RARERVYEFLSAWSTP QRFECDQEEGANTRAWRT SLLIALGTLLALVCVFVI CRRYLVMQRLFPRIPHMK DPIGDSFQNDKLVVWE AGKAGLEECLVTEVQVVQ KT | SEQ ID NO: 207 (SEQ ID NO: 208) |

TABLE 7-continued

| Human CD123 isoform sequences (National Center for Biotechnology Information) | | | |
|---|---|---|---|
| Name | Nucleotide Sequence (mRNA) | Amino Acid Sequence (complete) | SEQ ID NO (Amino Acid SEQ ID NO) |
| | ATAAAGTGATTTTTTTTTTTTT AACCCAAAA | | |

Example 7: Target-Dependent T-Cell Activation Induced Against CD123(+) Cell Line by Anti-CD123 Bispecific Molecules To compare the effectiveness of different bispecific 00123-binding molecules at inducing target-dependent T-cell activation of $CD4^+$ and $CD8^+$ T-cells, six different anti-CD123×anti-CD3ε bispecific molecules including TRI123, TRI126, TRI129, TRI130, TRI132 and TRI139 were tested in two independent experiments.

T-cell activation was assessed by flow cytometry using a CD123(+) cell line, Molm-13. Peripheral blood mononuclear cells (PBMC) were isolated from human blood using standard density-gradient separation methods. The isolated cells were washed in saline buffer. T-cells were further isolated using a Pan T-cell Isolation Kit II from Miltenyi Biotec (Bergisch Gladbach, Germany) using the manufacturer's protocol.

T-cells were plated in U-bottom 96-well plates at 120,000 cells/well, respectively, with 30,000 Molm-13 tumor cells/well, to achieve approximate T-cell to tumor cell ratios of 4:1. Concentrations of test molecules ranging from 2,000 pM to 0.002 pM were added to the cell mixtures to a final volume of 200 μl/well in RPMI 1640 media supplemented with 10% human AB serum, sodium pyruvate, antibiotics and non-essential amino acids. Plates were incubated at 37° C., 5% $CO_2$ in humidified incubators. After 20 hours, cells were labeled with antibodies for flow cytometric analysis in original plates to minimize cell losses, using saline buffer with 0.1% bovine serum albumin and 2 mM EDTA. After centrifugation and removal of supernatant, the cell pellets were resuspended with a mixture of the following dye-labeled antibodies in 50 μl volumes: CD69-FITC, CD5-PE, CD8-Pacific Blue, CD4-APC, CD25-PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to calculate the percentages of $CD4^+$ ($CD8^-$) or $CD8^+$ T-cells that had upregulated CD69 and CD25, by gating sequentially on forward vs side scatter, $7AAD^-$, $CD5^+$, $CD4^+$ or $CD8^+$ T-cells ($7AAD^-$, $CD5^+$ $CD4^+$ or $7AAD^-$ $CD5^+$ $CD8^+$, respectively). Graphs were plotted using GraphPad Prism 7.0.

Analysis of activated T-cells after 20 hours (FIG. 5) revealed a significant increase in the percent of activated $CD4^+$ and $CD8^+$ T-cells in the presence of Molm-13 cells. All molecules tested induced maximal activation of T-cells in the presence of Molm-13 target cells at low concentrations ranging from 1-100 pM (FIG. 5). $EC_{50}$ values were determined with TRI129, TRI130 and TRI139 for both $CD4^+$ (FIG. 5C) and $CD8^+$ (FIG. 5D) $CD25^+$ $CD69^+$ populations demonstrating similar potency for all three anti-CD123×anti-CD3ε bispecific molecules.

These results demonstrate that bispecific molecules binding to both CD123 and CD3ε could induce target-dependent T-cell activation against a CD123(+) cell line.

Example 8: Binding of Bispecific Proteins to CD123

To determine the kinetics and affinity of the bispecific to CD123, the TRI-129 and TRI-130 bispecific proteins were expressed via transient transfection in HEK293 cells and purified using a combination of affinity purification and size exclusion purification. The extracellular domain of CD123 was transiently expressed with an affinity tag on the C-terminus and purified using a combination of affinity purification and size exclusion purification. The analyses were performed using a BIACORE™ T200 instrument (Biacore Inc., Piscataway, NJ). The BIACORE™ T200 is a surface plasmon resonance (SPR)-based biosensor system that is designed to provide real-time kinetic binding data.

SPR binding studies of bispecific molecules to recombinant monomeric CD123 ectodomain (ECD) were conducted at 25° C. in HBS-EP+ buffer. AffiniPure F(ab')2 fragment Goat anti-human IgG Fcγ fragment-specific (Jackson Immuno Research) at 20 μg/mL in 10 mM sodium acetate (pH 4.5) was immobilized at a density of 3600 response units (RU) on the surface of a CM5 research-grade sensor chip (R-1005-30, GE Healthcare) by standard amine coupling chemistry. The bispecific molecules at 200 nM in HBS-EP+ buffer were captured by the immobilized anti-Fc F(ab')2 fragment at a flow rate of 30 μL/min for 120 sec to reach a stable 2000 RU response. Different concentrations of CD123 ECD (3-48 nM by 2-fold dilutions, including buffer as blank) were flowed over the captured bispecific molecules at 30 μL/min for 120 sec followed by a 300 sec dissociation period. Optimal regeneration was achieved by one injection of 10 mM glycine (pH 1.7) at a flow rate of 30 μL/min for 15 sec followed by one injection of 50 mM NaOH at 30 μL/min for 15 sec. A two minute stabilization with HBS-EP+ buffer was completed before the subsequent run.

Sensorgrams obtained from kinetic SPR measurements were analyzed by the double subtraction method. The signal from the reference flow cell was subtracted from the analyte binding response obtained from flow cells with immobilized or captured ligands. Buffer reference responses were then averaged from multiple injections. The averaged buffer reference responses were then subtracted from analyte binding responses, and the final double-referenced data were analyzed with BIACORE™ T200 Evaluation software (2.0, GE Healthcare), globally fitting data to derive kinetic parameters (Table 8). All sensorgrams were fitted using a simple one-to-one binding model.

TABLE 8

| Derived kinetic parameters for αCD123 bispecific molecules to CD123 ECD. | | | |
|---|---|---|---|
| Molecule | $K_a$ (1/Ms) | $k_d$ (1/s) | KD (nM) |
| TRI-129 | $1.79 \times 10^5$ | $2.05 \times 10^{-3}$ | 11.4 |
| TRI-130 | $1.72 \times 10^5$ | $4.72 \times 10^{-4}$ | 2.7 |

Figure 6:
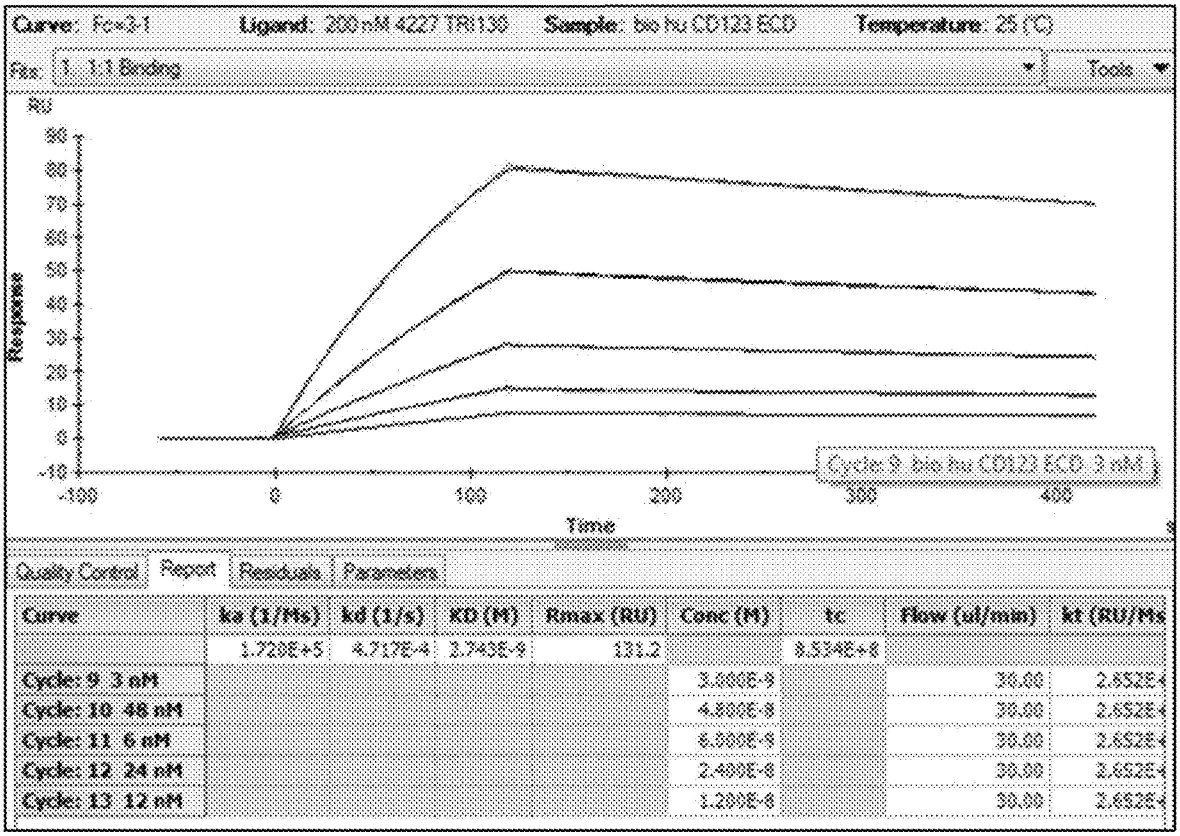
FIG. 6 shows an example of SPR analysis of TRI-130 at different ECD concentrations.

An example of the SPR analysis of TRI-130 at different ECD concentrations ranging from 3 nM to 48 nM is shown in FIG. 6. Thermodynamic and kinetic rate constants of binding were calculated using the BIACORE™ Evaluation software. For example, the affinity (KD) of TRI-130 for CD123 extracellular domain (ECD) was determined to be $2.74\times10^{-9}$ M with a ka of $1.72\times10^5$ $M^{-1}s^{-1}$ and a kd of $4.72\times10^{-4}$ $s^{-1}$. The affinity of TRI-129 for the CD123 was determined to be $1.14\times10^{-8}$ M with a ka of $1.79\times10^5$ $M^{-1}s^{-1}$ and a kd of $2.05\times10^{-3}$ $s^{-1}$.

Example 9: Differential Scanning Calorimetry

Thermal stability of the CD123 binding domain was assessed using Differential Scanning Calorimetry (DSC). DSC measures heat capacity changes associated with the molecule's thermal denaturation when heated at a constant rate. Tm (thermal transition midpoint) value of CD123 binding domain scfv, which is a measure of its stability, can be extracted from the melting curve.

DSC thermal stability study was conducted using a MicroCal VP-Capillary DSC system (Malvern Instrument). An exact match of buffer, PBS pH7.4, was used as the reference. 500 uL of a 0.5 mg/mL solution of each protein sample with reference was loaded on the instrument and heated from 25° C. to 100° C. at a rate of one degree celsius per minute. Melting curve was analyzed using Origin 7 platform software "MicroCal VP-Capillary DSC Automated Analysis Software." Tm of each melting transition was calculated using "non-2 state curser integration" method.

TABLE 9

| Assessment of thermal stability of domains | | | | |
|---|---|---|---|---|
| Sample | TmOnset | Tm1 (αCD3 scFv) | Tm2 (αCD123 scFv and Fc CH2) | Tm3 (Fc CH3) |
| TRI129 | 51.19 | 59.59 | 64.48 | 83.87 |
| TRI130 | 53.19 | 59.59 | 65.71 | 84.64 |

Example 10: Pharmacokinetic Activity

To determine the pharmacokinetic activity of bispecific molecules, female Balb/c mice were injected intravenously (IV) with 200 mg (~10 mg/kg) of either TRI129 or TRI130 (n=30 for each molecule, TRI129 or TRI130). At each time point, blood was collected by cardiac puncture from 3 mice. Time points were: 15 minutes, 2, 6, 24, 48, 72, 96, 168, 336 and 504 hours. Blood was processed to serum, aliquoted and frozen. TRI129 and TRI130 concentrations in serum samples were determined by enzyme linked immunosorbent assay (ELISA). Serum concentrations over time were used to determine PK parameter estimates by non-compartmental analysis (NCA) and compartmental analysis. Serum concentration over time profiles were analyzed with Phoenix 64 software. Graphs were plotted using GraphPad Prism 7.0. NCA parameter analysis of the resulting data is provided in Table 10.

TABLE 10

| NCA parameter analysis of data | | | | |
|---|---|---|---|---|
| Bispecific | T ½ | Clearance | Volume | AUC |
| TRI-129 | 229 hours (9.5 days) | 0.204 ml/hr/kg | 67.54 ml/kg | 38750 hr*μg/ml |
| TRI-130 | 301 hours (12.5 days) | 0.186 ml/hr/kg | 80.84 ml/kg | 37309 hr*μg/ml |

Figure 7:
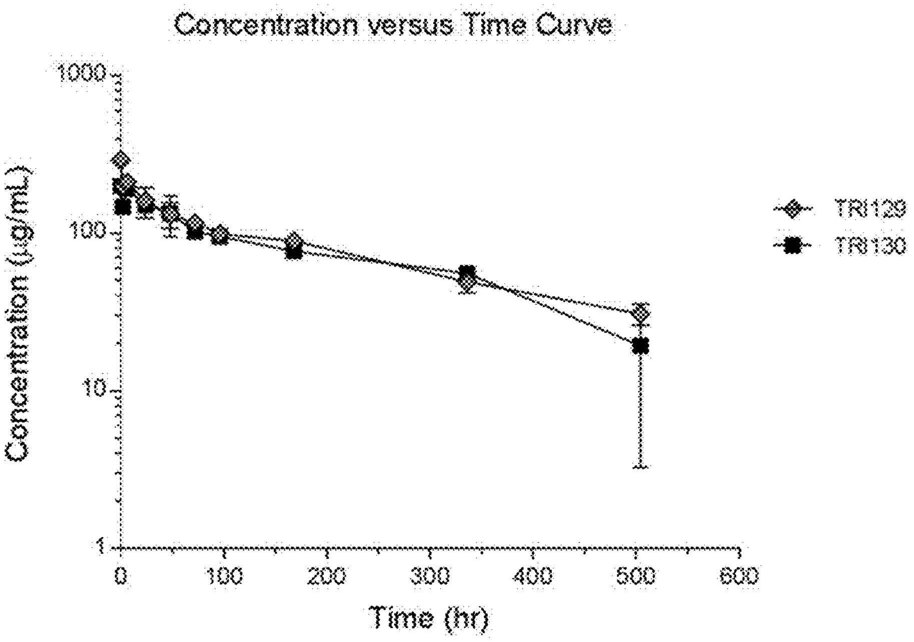
FIG. 7 shows concentration versus time curves for TRI129 and TRI130 bispecific molecules.

FIG. 7 shows concentration versus time curves for TRI129 and TRI130 bispecific molecules.

Example 11: In Vivo Efficacy of Anti-CD123×Anti-CD3 Binding Molecules

Figure 8:
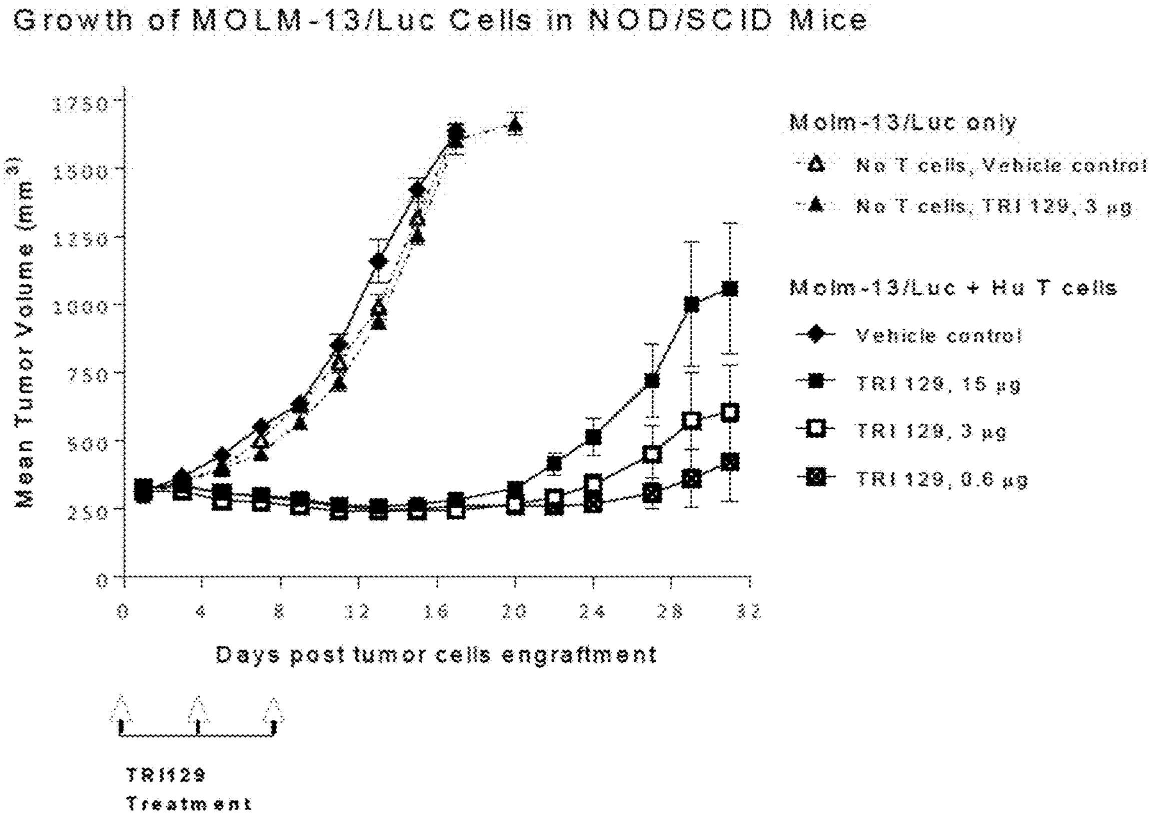
FIG. 8 shows reduction in tumor volume in a mouse tumor model treated with TRI129.
Figure 9:
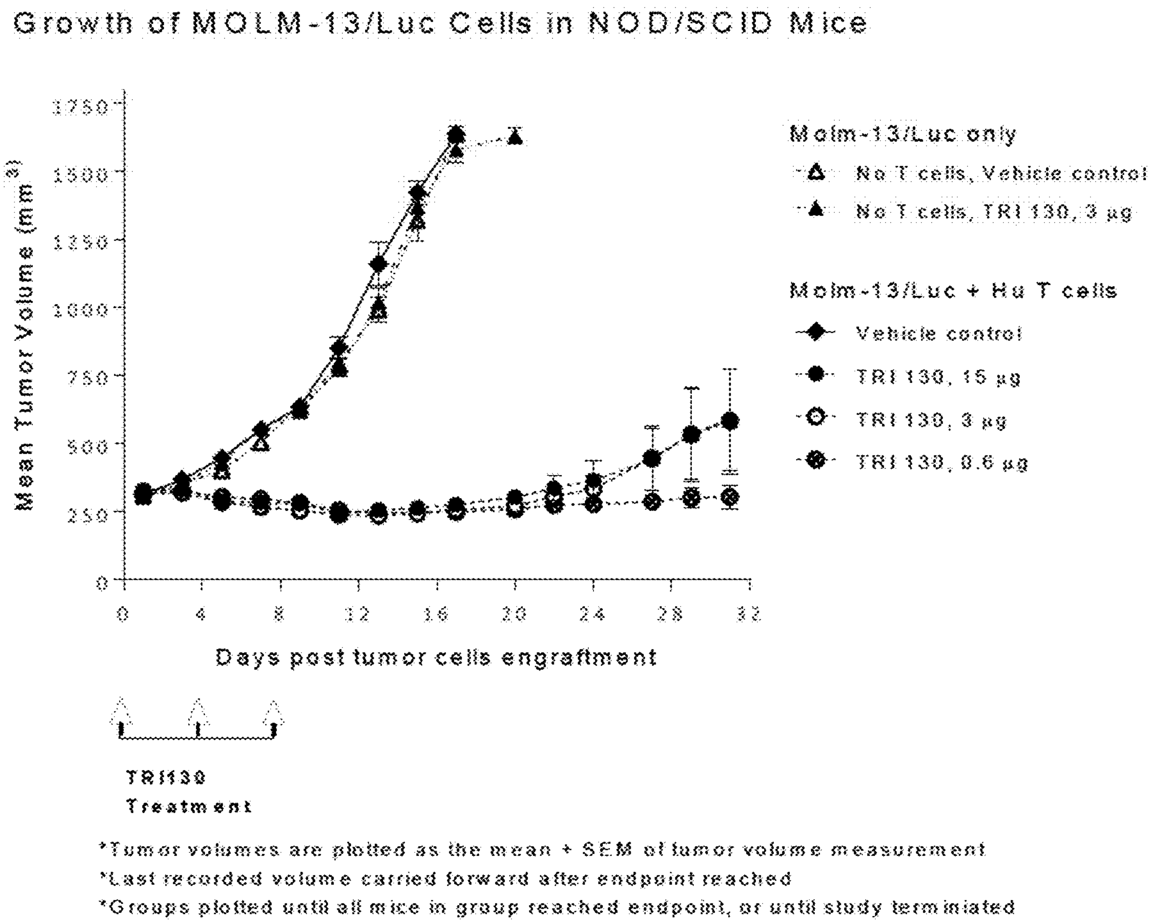
FIG. 9 shows reduction in tumor volume in a mouse tumor model treated with TRI130.
Figure 10:
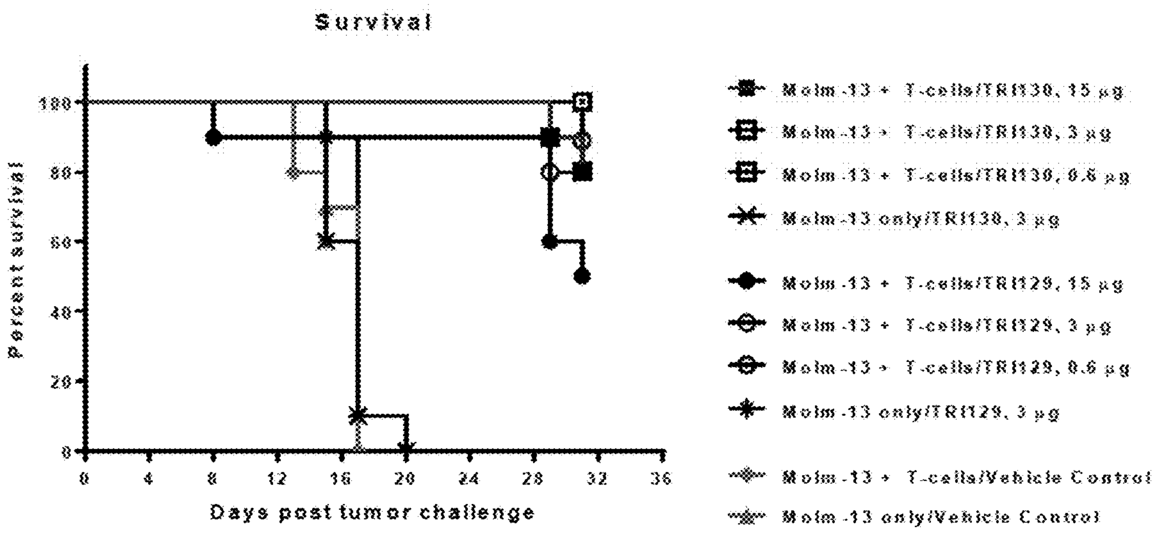
FIG. 10 shows that treatment of a mouse tumor model with TRI129 or TRI130 results in increase in survival.

To determine if TRI129 and TRI130 are capable of inhibiting tumor growth and prolonging survival in vivo, a rodent model of human acute myeloid leukemia was utilized. MOLM-13/LUC cells were co-mixed with donor T-cells and matrigel and implanted into the flank of NOD/SCID mice on day 0 of the study. Animals were treated in groups of 10 mice per group with T-cells from one donor with vehicle, TRI129 or TRI130 on study Day 0, 4 and 8 at doses of 15, 3 and 0.6 μg of protein in a total volume of 200 μl. Tumor growth was measured with calipers over time during the study and survival events were recorded each time a mouse reached the endpoint (tumor volume≥1500 $mm^3$) and was euthanized. As shown FIGS. 8 and 9 there was minimal impact of TRI129 and TRI130 in the absence of donor T-cells and minimal impact of T-cells on tumor growth by the donor T-cells alone. Significant inhibition of tumor growth was seen after treatment with both TRI129 and TRI130 at all doses tested in the presence of donor T-cells. Significant differences in median survival of mice were determined using Kaplan-Meier survival analysis with a log-rank test for comparing survival curves. As shown FIG. 10, the survival of mice treated with all tested doses of TRI129 and TRI130 in the presence of co-implanted human T-cells was significantly prolonged relative to all control groups. Neither the co-implantation of T-cells with vehicle treatment nor the treatment of tumors with TRI129 or TRI130 in the absence of human T-cells extended survival compared to mice implanted with tumor cells alone and treated with vehicle. This result demonstrates both TRI129 and TRI130 are capable of driving inhibition of tumor growth and prolonging survival in a Xenograft model of acute myeloid leukemia.

Example 12: TRI-130 Cytotoxicity is Specific to CD123 Expressing Cell Lines

Figure 12:
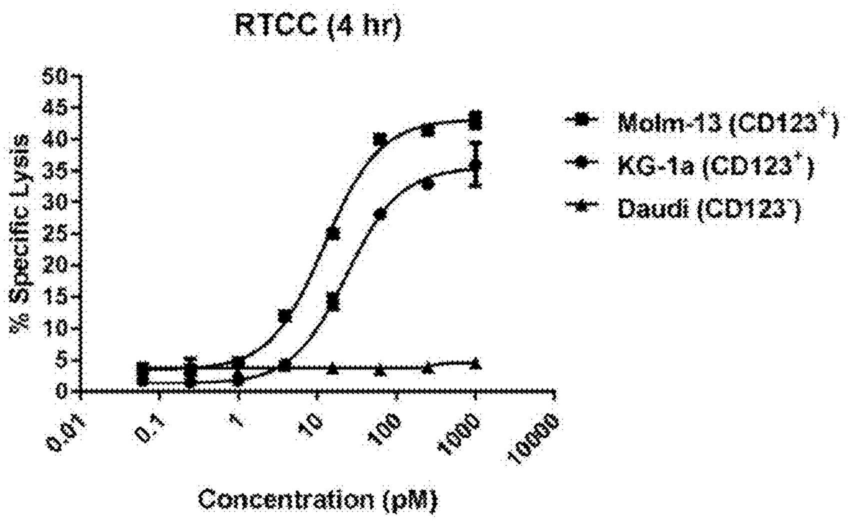
FIG. 12 shows the results from a chromium-51 release assay with the Molm-13, KG-1a and Daudi cell lines measured at 4 hours using the TRI130 bispecific anti-CD123×anti-CD3ε molecule. This assay measured the cytotoxicity of TRI130 incubated with CD123-positive or C123-negative tumor cell lines and purified human T-cells.
Figure 12:
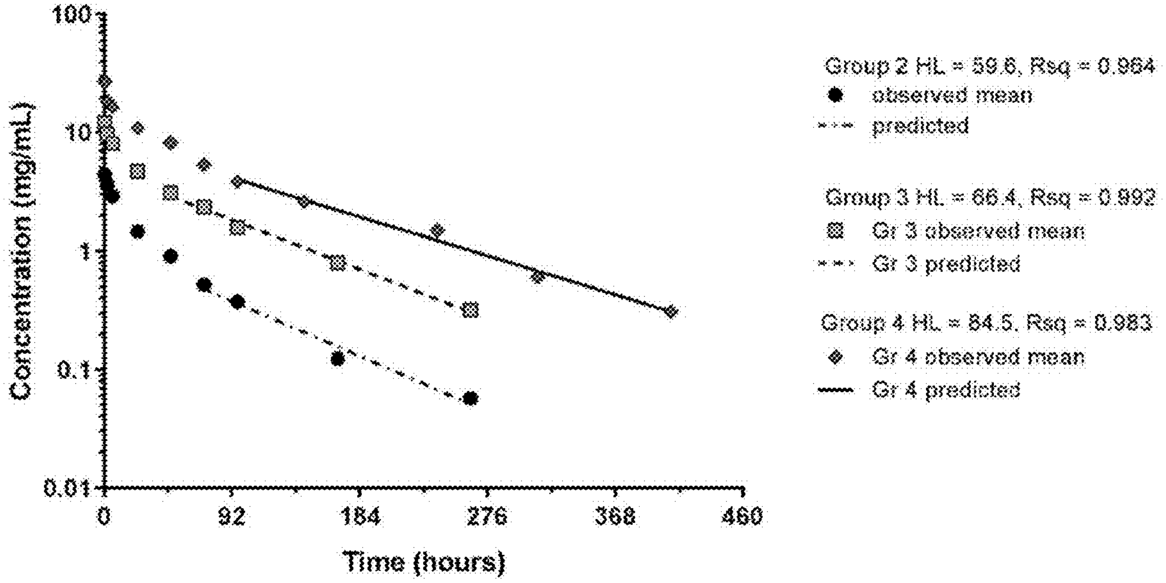

To confirm the specificity of TRI130 and compare its cytotoxic activity on tumor cell lines expressing different levels of CD123, chromium-51 release assays were used to quantify target cell lysis induced by T cells. CD123 expression levels on the CD123 positive MOLM-13 and KG-1a AML tumor cells lines were compared to the CD123 negative Daudi Burkitt's lymphoma tumor cell line by flow cytometry. CD123 expression was detected using a commercially available human CD123 phycoerythrin (PE) conjugated antibody. Positive CD123 expression was detected on MOLM-13 and KG-1a but not on Daudi cells. MOLM-13 and KG-1a cells expressed 10,000 and 2,000 receptors on average per cell respectively (data not shown). Different concentrations of TRI130 were incubated with MOLM-13, KG-1a or Daudi cell lines and purified human T-cells freshly isolated from human peripheral blood then pre-activated with anti-CD3×anti-CD28 coupled beads for 24 hours. TRI130 induced cytotoxicity only in the cell lines which were positive for CD123 expression and demonstrated comparable potency between the MOLM-13 and KG-1a AML tumor cell lines (FIG. 12). Cytotoxicity was measured as percent of specific tumor cell lysis, estimated using a chromium-51 release assay with 4 hr and 24 hr time points (data not shown). These results confirm that TRI130 induced redirected T-cell cytotoxicity is specific to CD123 expressing target cells and demonstrate potent TRI130 cytotoxicity on AML tumor cell lines expressing different levels of the CD123 protein.

Example 13: TRI130 Induced Cytotoxicity with Naïve T-Cells at Different Effector to Target Cell Ratios To examine TRI130 induced cytotoxicity activity at different effector to target cell ratios, KG-1a cells which express moderate levels of CD123 were incubated with different concentrations of TRI130 and purified T-cells from five different human donors that were not pre-activated. KG-1a target cells were cultured with T-cells at effector to target cell ratios of 10:1, 5:1 and 1:1. TRI130 induced cytotoxic activity at all effector to target cell ratios tested was comparable across all five donors (data not shown). Cytotoxicity was measured as percent of specific tumor cell lysis, which was estimated using a 24-hour chromium-51 release assay. These results demonstrate potent TRI130 induced cytotoxicity at different effector to target cell ratios with naïve T-cells and minimal variability in activity between normal donors.

Example 14: Single-Dose Pharmacokinetic and Tolerability Study in Cynomolgus Monkeys A single-dose pharmacokinetic and tolerability study was conducted to determine the tolerability, immunogenicity and pharmacokinetic characteristics following intravenous administration of TRI130. The study design is shown in Table 11. The intravenous route of administration was selected for the study as this is the intended route for human dosing.

Binding to NHP CD3ε was determined using the anti-CD3 binding domain in a monospecific scFv-Fc fusion format. The anti-CD3 scFv-Fc was tested on Chinese cynomolgus macaque T-cells by flow cytometry. Binding levels were variable, with individual monkeys showing high, intermediate or low levels of binding compared to human cells (data not shown).

TABLE 11

Experimental Design of Pharmacokinetic Study in Cynomolgus Monkeys

| Group No. | No. of Males[a] | Test Material | Dosing Day and Time[b] | Dose Level (mg/kg) | Dose Concentration (mg/mL) | Dose Volume (mL/kg) |
|---|---|---|---|---|---|---|
| 1 | 3 | Control | Day 1 | 0 | 0 | 5 |
| 2 | 3 | TRI130 | Day 1 | 0.25 | 0.05 | 5 |
| 3 | 3 | TRI130 | Day 1: 2 hr | 0.5 | 0.1 | 5 |
| 4 | 3 | TRI130 | Day 1: 24 hr | 1.0 | 0.2 | 5 |

[a]Animals were released from study on Day 36.

[b]Dosing for Groups 1 and 2 was started consecutively, without a delay between groups. Dosing was delayed by 2 hour from the end of the third animal in Group 2 and the start of the first animal in Group 3; Dosing for Group 4 was delayed by 24 hours from the start of dosing for Group 1.

The following parameters and end points were evaluated in the single dose NHP study: clinical signs, body weights, food consumption, clinical pathology parameters (hematology, coagulation, and clinical chemistry), pharmacokinetics (PK), immunogenicity, cytokine profiles, and flow cytometry.

Dose levels tested ranged from the expected maximum human dose to high multiples of the expected human dose (Table 12). The anticipated pharmacologically active dose (PAD) in humans is in the range of 0.4 mcg/kg based on the in vivo xenograft model (Example 11), which is 625× below the dose of Group 2. However, based on in vitro activity assays (T-cell activation, proliferation and cytokine release), there is a 10 to 100-fold reduction in the response of cynomolgus T-cells to TRI130 compared to that of human T-cells. Therefore, the dose in Group 2 is expected to be ~6.25 to 62.5× the biologic equivalent to the human PAD. Groups 3 and 4 evaluate a 2 and 4-fold excess of the latter dose.

TRI130 interacts with CD3 on T-cells, and with the target molecule CD123 on immune cell populations including plasmacytoid dendritic cells (pDC) and basophils, which express high levels of CD123, but make up less than 1% of circulating leukocytes. Published data describing other bispecifics targeting CD123 noted significant cytokine release (Chichili et al. Sci Transl Med. 2015 May 27; 7(289): 289ra82).

Due to the expectation for cytokine release, this study was conducted in 2 phases. In Phase 1, two sentinel animals received TRI130 to determine appropriate dose levels for Phase II, which would include treatment Groups 2-4. A dose level of 0.05 mg/kg (initially anticipated as the Phase II mid-dose level) was chosen for the first sentinel, and this animal was closely monitored for signs of cytokine release syndrome, including collection of post-dose observations, body temperatures, and blood samples for cytokine analysis. The dose was well tolerated, and 24 hours later, a second sentinel animal was dosed at 0.25 mg/kg (initially anticipated as the Phase II high dose level) which was also well tolerated.

Dose levels for Phase II were selected in an attempt to produce graded responses to TRI130, and incorporated results of the Phase I sentinels. Because dose levels in Phase I were well tolerated by sentinel animals, with no abnormal clinical observations, elevated cytokine release levels, or increased body temperature, the Phase II dose levels selected were 0.25, 0.5 and 1 mg/kg, which are 2500 times the expected human PAD equivalent (Table 12). Adjusting this margin by up to 100-fold difference in activity, this study achieved up to 25-fold higher doses than the human PAD.

TABLE 12

Dose Equivalents of TRI130 Compared to Expected Pharmacologically Active Dose (PAD)

| Group No. | Test Material | Dose Level (mg/kg) | Mass Equivalent to Expected PAD (~0.4 mcg/kg) | Adjusted Dose Equivalence Based on Cyno Response |
|---|---|---|---|---|
| 1 | Control | 0 | 0 | 0 |
| 2 | TRI130 | 0.25 | 625X | 6.25X |
| 3 | TRI130 | 0.5 | 1250X | 12.5X |
| 4 | TRI130 | 1 | 2500X | 25X |

Pharmacokinetics of Single Dose TRI130 in Cynomolgus Monkeys

Serum concentrations were determined using a standard ELISA method using the extracellular domain of CD123 to capture TRI130, and a biotinylated anti-ID antibody (5H5) recognizing the anti-CD3 binding domain to detect bound TRI130. For most animals a rapid drop in serum concentration at late time points corresponded to the presence of anti-drug antibodies (ADA). A standard bridging ELISA using TRI130+/−biotin was used to measure ADA titers in serum samples collected at late time points. ADA titers were relatively low for 7 of the 9 animals treated with TRI30, and titer values tended to increase over time (data not shown). However, titer also appeared to decrease with increasing doses of TRI130, and the onset of ADA was later for higher doses, meaning that higher doses were not correlated to increased levels of immunogenicity, as would normally be expected. Because TRI130 is a human protein, detecting ADA at late time points in NHP serum samples is considered a normal response, and immunogenicity in NHP is not predictive of human responses.

Non-compartmental analysis (NCA) of serum concentrations detected in the ELISA assay calculated a mean terminal half-life for TR8134 of up to 84 hours in animals dosed with 1 mg/kg (Table 13). Individually, one animal in group 4 had apparent subcutaneous accumulation of TRI130, while another in the group had significant early induction of ADA resulting in a much shorter half-life. Sparse sampling and uniform weighting were used for NCA, and serum concentrations clearly influenced by ADA were excluded from the analysis.

TABLE 13

NCA PK Parameter Estimates for Individual Animals Dosed with TRI130

| NCA with Sparse sampling | | Uniform Weighting | | |
|---|---|---|---|---|
| Parameter | Units | Group 2 | Group 3 | Group 4 |
| Rsq adjusted | | 0.964 | 0.992 | 0.983 |
| HL Lambda z | hr | 59.55 | 66.44 | 84.46 |
| Tmax | hr | 0.25 | 0.25 | 0.25 |
| Cmax | ug/ml | 4.386 | 12.124 | 27.075 |
| Cmax/D | kg*ug/ml/ug | 0.018 | 0.024 | 0.027 |
| Tlast | hr | 264 | 264 | 408 |
| Clast | ug/ml | 0.0573 | 0.317 | 0.309 |
| AUCall | hr*ug/ml | 143.7 | 515.8 | 1329.7 |
| AUCINF | hr*ug/ml | 148.6 | 546.2 | 1367.4 |
| AUCINF/D | hr*kg*ug/ml/ug | 0.594 | 1.092 | 1.367 |
| Vz | ml/kg | 144.57 | 87.75 | 89.11 |
| Cl | ml/hr/kg | 1.683 | 0.915 | 0.731 |
| MRTlast | hr | 49.45 | 64.30 | 88.42 |

TABLE 13-continued

| NCA PK Parameter Estimates for Individual Animals Dosed with TRI130 | | | | |
|---|---|---|---|---|
| NCA with Sparse sampling | | Uniform Weighting | | |
| Parameter | Units | Group 2 | Group 3 | Group 4 |
| MRTINF | hr | 59.41 | 80.75 | 100.58 |
| Vss | ml/kg | 99.96 | 73.92 | 73.56 |

In addition to NCA, compartmental analysis was run for individual animals and the treatment groups, using precompiled WinNonlin® 2 compartment models, with the appropriate dosing and weighting schemes. Results are shown in FIG. 13 and were similar to NCA parameter estimates, with half-life for the one animal in group 4 (4003) without significant ADA or partial subcutaneous dosing, determined to be almost 89 hours. Animal 4002 in group 4 had a gradual increase in serum drug levels over time, and a Tmax at 6 hours (Table 14); therefore, its data was best fit using a 2-compartment model for extravascular dosing, instead of IV bolus dosing.

PK parameter estimates determined using NCA or compartmental analysis, were not similar across treatment groups in that half-life increased and clearance decreased with increasing doses, likely due to target mediated binding of TRI130.

TABLE 14

| Compartmental Analysis for NHP Given a Single IV Dose of TRI130 | | | | | | | | | | |
|---|---|---|---|---|---|---|---|---|---|---|
| Treatment (Dose/Route) | NHP ID | V1 (mL/hr) | CL (mL/hr/kg) | V2 (mL/hr) | CLD2 (mL/hr/kg) | AUC (hr*µg/mL) | Alpha HL (hr) | Beta HL (hr) | Cmax (µg/mL) | Tmax (hr) |
| 0.25 mg/kg IV | 2001 | 59.32 | 2.463 | 24.36 | 4.427 | 101.5 | 2.568 | 24.79 | 4.22 | .25 |
| 0.25 mg/kg IV | 2002 | 50.87 | 1.864 | 32.19 | 1.820 | 134.1 | 6.293 | 36.85 | 4.91 | .25 |
| 0.25 mg/kg IV | 2003 | 61.16 | 1.470 | 43.41 | 3.341 | 170.1 | 4.859 | 53.46 | 4.09 | .25 |
| Group 2 mean | | 56.54 | 1.917 | 32.7 | 3.028 | 130.4 | 4.32 | 35.45 | 4.42 | .25 |
| 0.5 mg/kg IV | 3001 | 41.664 | 0.874 | 25.193 | 1.293 | 572 | 7.569 | 58.99 | 12.0 | .25 |
| 0.5 mg/kg IV | 3002 | 45.703 | 1.072 | 41.354 | 3.339 | 467 | 4.180 | 60.72 | 10.94 | .25 |
| 0.5 mg/kg IV | 3003 | 38.939 | 1.058 | 28.973 | 2.692 | 473 | 3.966 | 47.98 | 12.84 | .25 |
| Group 3 mean | | 41.87 | 1.002 | 32.43 | 2.540 | 499 | 4.608 | 55.65 | 11.94 | .25 |
| 1 mg/kg IV | 4101 | 27.93 | 0.926 | 22.08 | 16.533 | 1080 | 0.511 | 37.85 | 35.81 | .25 |
| 1 mg/kg IV | *4002 | 76.83 | 0.854 | 16.024 | 0.133 | 1172 | 46.2 | 112.6 | 11.27 | 6 |
| 1 mg/kg IV | 4003 | 48.22 | 0.706 | 25.34 | 0.492 | 1417 | 18.996 | 88.92 | 20.74 | .25 |
| Group 4 mean | | 39.31 | 0.826 | 45.2 | 5.22 | 74.22 | 4.15 | 5.6 | 74.22 | 2.17 |

*Received at least part of the TRI130 dose SC, and parameter estimates were analyzed using a SC model Group means were analyzed using the WinNonlin® precompiled model #7 with sparse sampling and appropriate weighting V1: Volume for the $1^{st}$ (central) compartment CL: Clearance from the central or $1^{st}$ compartment V2: Volume for the $2^{nd}$ compartment CLD2: Clearance from the $2^{nd}$ compartment AUC: Area under the concentration time curve Alpha HL: Half-life associated with the macro constant Alpha Beta HL: Half-life associated with the macro constant Beta Cmax: Maximum observed concentration Tolerability of Single Dose TRI130 in Cynomolgus Monkeys A single dose administration of TRI130 to cynomolgus monkeys was clinically well-tolerated at dose levels up to and including 1 mg/kg. At these doses, there were no test-article related clinical observations or changes to body weights, food consumption, clinical chemistry or coagulation parameters.

Administration of TRI130 was associated with decreased lymphocytes in peripheral blood (FIG. 14). TRI130-related, transient decreases in lymphocytes were observed at the 2-hour post-dose time point at all doses. In addition, there appeared to be a reduction in basophil counts in Groups 2 and 3 by hematology measurements (FIG. 15), with a slightly longer time to return to baseline levels, compared to the vehicle control (Group 1). The mean reduction in lymphocytes and basophils was less in Group 4, in part due to one animal that had a limited response and one animal that had apparent subcutaneous rather than intravenous injection, therefore Group 4 was excluded from the mean lymphocyte and basophil data shown in FIGS. 14 and 15. All groups dosed with TRI130 had an increase in neutrophils compared to the vehicle control group (data not shown). The changes noted with the hematology panel were mostly back to baseline levels by about 1 week after dosing.

Administration of TRI130 was not associated with changes in clinical chemistry, including CRP, or with changes in coagulation parameters.

The serum cytokine measurements indicated a minimal spike in some cytokines, including the T cell cytokines IL-10 and IL-2 and secondary cytokines such as MCP-1. The peak levels of cytokine detected were at 2 or 6 hours post-dose. In total, a bead based multi-plex cytokine kit was used to determine the levels of 23 individual cytokines, including T-specific cytokines (such as IL-2, IL-4, IL-5, IL-6, IL-10, IL-17, IFNγ, TNFα), and cytokines that are made by other cell types (such as MCP-1). Examples of cytokines detected in the study are presented in Table 15. Notably, the levels detected in the 1 mg/kg dose were lower than the mid and low dose group, however animal 4003, with more normal IV bolus pharmacokinetic parameters had responses more similar to the other groups. The other animal in Group 4 with an apparent subcutaneous dose (4002) had delayed peak response for some cytokines, consistent with a later Tmax. In general, cytokine levels returned to baseline levels by 96 hours post dose. The minimal cytokine secretion did not translate into any observable clinical post-dose event or changes in body weight or food intake (as noted above). The cytokine secretion is consistent with the mechanism of action of TRI130, which, when the target protein (CD123) is present, would result in some activation of T-cells in the system.

Administration of TRI130 by single intravenous (slow bolus) injection was well-tolerated in cynomolgus monkeys at levels of 0.25, 0.5 and 1 mg/kg. Based on these results, the no-observed-adverse-effect level (NOAEL) was considered to be 1 mg/kg. The serum half-life estimate for TRI130 was 84 hours, with normal clearance and volume of distribution in the high dose group. Lower doses had faster clearance and shorter half-life estimates, suggesting target mediated binding of TRI130 to target cells in cynomolgus monkeys. These observations will be confirmed and extended to higher dose levels in the 28-day repeat-dose GLP toxicology study in cynomolgus monkeys.

TABLE 15

Serum Cytokine Measurements of Dose Groups in Pilot Tolerability and PK

IL-2 (pg/mL)
Animal Number

| Time (hr) | 1001 | 1002 | 1003 | 2001 | 2002 | 2003 | 3001 | 3002 | 3003 | 4002** | 4003 | 4101 |
|---|---|---|---|---|---|---|---|---|---|---|---|---|
| −2 | 42.99 | 52.08 | 70.02 | 76.99 | 60.12 | 81.64 | 76.9 | 41.08 | 97.16 | 78.73 | 106.78 | 107.28 |
| 2* | 55.76 | 51.55 | 53.32 | 246.18 | 159.64 | 221.29 | 166.71 | 86.29 | 192.19 | 109.13 | 223.75 | 137.68 |
| 6 | 82.8 | 60.68 | 58.67 | 190.48 | 117.8 | 178.14 | 115.89 | 74.43 | 136.17 | 107.15 | 157.95 | 164.69 |
| 24 | 69.55 | 55.59 | 69.55 | 143.35 | 78.45 | 119.31 | 88.21 | 56.5 | 139.8 | 137.23 | 103.91 | 120.8 |
| 48 | 50.47 | 58.67 | 62.33 | 91.49 | 54.72 | 99.24 | 74.84 | 41.08 | 102.32 | 89.56 | 88.89 | 120.57 |
| 96 | 40.83 | 60.84 | 63.64 | 69.51 | 62.99 | 75.07 | 74.84 | 36.36 | 101.84 | 83.33 | 79.99 | 136.56 |

IL-10 (pg/mL)

| Time (hr) | 1001 | 1002 | 1003 | 2001 | 2002 | 2003 | 3001 | 3002 | 3003 | 4002 | 4003 | 4101 |
|---|---|---|---|---|---|---|---|---|---|---|---|---|
| −2 | 40.27 | 35.8 | 78.98 | 39.22 | 16.6 | 71.08 | 15.15 | | 28.55 | 24.47 | 62.01 | 78.63 |
| 2 | 46.96 | 31.32 | 44.73 | 630.12 | 174.18 | 576.67 | 115.32 | 26.19 | 216.4 | 55.71 | 410.84 | 90.55 |
| 6 | 74.59 | 43.62 | 43.62 | 372.62 | 84.78 | 179.93 | 74.77 | 14.35 | 97.4 | 66.75 | 100.11 | 157.86 |
| 24 | 71.28 | 43.62 | 59.15 | 150.06 | 31.29 | 100.78 | 48.18 | | 123.88 | 69.12 | 63.59 | 60.43 |
| 48 | 38.04 | 34.68 | 56.94 | 49.44 | 29.02 | 71.08 | 21.47 | | 41.12 | 27.57 | 83.39 | 64.38 |
| 96 | 35.8 | 48.07 | 55.83 | 44.9 | 26.76 | 60.82 | 30.13 | | 48.96 | 41.58 | 37.67 | 85.77 |

IL-1ra (pg/mL)

| Time (hr) | 1001 | 1002 | 1003 | 2001 | 2002 | 2003 | 3001 | 3002 | 3003 | 4002 | 4003 | 4101 |
|---|---|---|---|---|---|---|---|---|---|---|---|---|
| −2 | 29.81 | 10.23 | 21.72 | 14.83 | 7.73 | 27.36 | 17.29 | 7.12 | 21.98 | 10.52 | 24.41 | 26.4 |
| 2 | 39.08 | 14.46 | 20.93 | 91.35 | 31.08 | 73.18 | 38.46 | 21.7 | 69.77 | 22.41 | 51.87 | 36.56 |
| 6 | 48.42 | 22.51 | 16.11 | 253.47 | 21.34 | 102.43 | 36.06 | 23.07 | 135.59 | 18.67 | 48.27 | 59.32 |
| 24 | 33.55 | 10.66 | 18.14 | 101.05 | 13.27 | 26.61 | 59.08 | 7.7 | 96.11 | 20.97 | 21.69 | 18.1 |
| 48 | 15.29 | 10.66 | 20.14 | 15.99 | 21.72 | 21.34 | 8.56 | 2.69 | 21.7 | 11.99 | 21.83 | 20.11 |
| 96 | 11.09 | 15.29 | 13.21 | 13.27 | 6.1 | 15.21 | 11.13 | 5.08 | 14.51 | 9.63 | 12.14 | 26.11 |

IL-6 (pg/mL)

| Time (hr) | 1001 | 1002 | 1003 | 2001 | 2002 | 2003 | 3001 | 3002 | 3003 | 4002 | 4003 | 4101 |
|---|---|---|---|---|---|---|---|---|---|---|---|---|
| −2 | | | | | | | | | | | 1.61 | |
| 2 | 4.46 | 8.2 | 28.17 | 40.23 | 11.18 | 46.47 | 7.41 | | 59.97 | 4.71 | 29.12 | 9.24 |
| IL-2 (pg/mL) Animal Number | | | | | | | | | | | | |
| 6 | 7.29 | 11.3 | | 9.75 | | 34.34 | 15.76 | | 6.65 | 3.31 | 13.75 | 58.68 |
| 24 | 26.34 | | | 0.03 | | 5.95 | 135.1 | | | 0.42 | | 0.88 |
| 48 | | | | | | | | | | | | |
| 96 | | | | | | | | | | | | 0.3 |

TABLE 15-continued

| Serum Cytokine Measurements of Dose Groups in Pilot Tolerability and PK | | | | | | | | | | | | |
|---|---|---|---|---|---|---|---|---|---|---|---|---|
| MCP-1 (pg/mL) | | | | | | | | | | | | |
| Time (hr) | 1001 | 1002 | 1003 | 2001 | 2002 | 2003 | 3001 | 3002 | 3003 | 4002 | 4003 | 4101 |
| −2 | 255.62 | 294.77 | 362.89 | 390.54 | 391.05 | 445.7 | 342.49 | 158.31 | 547.6 | 618.1 | 769.48 | 807.72 |
| 2 | 386.37 | 322.52 | 281.46 | 5860.97 | 1690.25 | 3737.21 | 1429.67 | 520.19 | 3744.09 | 918.3 | 5948.11 | 1144.13 |
| 6 | 563.16 | 393.99 | 316.14 | 2747.2 | 936.33 | 1720.26 | 669.27 | 491.71 | 1119.4 | 1063.89 | 1565.33 | 1972.29 |
| 24 | 484.46 | 346.71 | 378.37 | 1188.25 | 571.67 | 874.9 | 508.46 | 288.4 | 1126.98 | 1287.69 | 781.38 | 1043.59 |
| 48 | 285.74 | 398.27 | 379.72 | 518.2 | 435.71 | 634.29 | 358.73 | 211.71 | 672.02 | 789.58 | 706.93 | 1084.58 |
| 96 | 254.56 | 400.97 | 366.57 | 404.11 | 416.68 | 433.94 | 380.1 | 193.43 | 599.64 | 666.4 | 526.84 | 1167.58 |

**animal 4002 had a serum concentration of TRIBO Tmax at 6 hrs that suggested a subcutaneous route of administration, and indicated a slower accumulation of TRI130 in the animal. This animal's peak cytokine levels were somewhat delayed compared to the other animals.

Example 15: Therapeutic Efficacy of TRI130 in a Disseminated Xenograft Mouse Model of Acute Myeloid Leukemia (AML)

To examine the therapeutic efficacy of TRI130 in mice with established disseminated tumors, a rodent model of human acute myeloid leukemia was utilized. MOLM-13 cells modified to express firefly luciferase were used to allow tumor quantification by bioluminescent imaging. For the study, 100,000 MOLM-13 Luc cells were injected intravenously into the lateral tail vein of 24 NSG male mice. MOLM-13 Luc cells were allowed to establish in the mice for 4 days prior to initiation of treatments. Mice were assigned into 3 groups of 8 mice each. One group received no additional treatments as a control. The remaining two groups received 7 million human T-cells with the first treatments. Treatments consisted of PBS vehicle control or TRI130 at 3 μg on days 4, 8 and 12. Treatments were administered intravenously via the tail vein. Treatments were delivered in 0.2 mL of Dulbecco's Phosphate Buffered Saline (PBS) containing no molecule (vehicle control) or 3 μg of TRI130. The injection included 7 million purified human T-cells for the day 4 treatment only. TRI130 treatment resulted in a rapid significant reduction in skeletal tumor burden (FIG. 16, FIG. 17 and Table 16). Residual non-skeletal tumor burden expanded following TRI130 treatments. Upon necropsy and the end of the study, it was determined this residual tumor burden was associated with the male reproductive tract and was observed in both the vehicle and the TRI130 group with the main difference between the being the absence of skeletal tumor burden. Treatment of established disseminated MOLM-13 Luc tumors in male mice with TRI130 resulted in a significant reduction in tumor burden, $p<0.0001$, relative to T-cell only controls (Table 16). There was no significant difference between the MOLM-13 Luc only and vehicle control groups. Tumor burden distribution was altered by TRI130 treatment with skeletal sites cleared of bioluminescent signal.

TABLE 16

| Statistical Comparison of Mean Tumor Volume through Day 14 | |
|---|---|
| JMP Repeated-Measures ANOVA Analysis with Tukey's HSD Method | |
| Treatment | p-Value |
| Vehicle vs. 3 μg TRI130 | <.0001* |
| Vehicle vs. MOLM-13 only | 0.5385 |
| MOLM-13 only vs. 3 μg TRI130 | <.0001* |

*indicates p-value <0.05 significant difference

Example 16: Construction of an Anti-CD123×Anti-CD3 MGD006-Like Molecule

In order to compare TRI130 activity to another bispecific format an anti-CD123×anti-CD3 bispecific was generated containing the CD123 and CD3 binding domain sequences of MGD006 obtained from WO 2015/026892 (nucleic acid sequences corresponded to SEQ ID NOs: 2 and 4; amino acid sequences corresponded to SEQ ID Nos: 1 and 3) engineered in the format reported in Chichili et al. Sci Transl Med. 2015 May 27; 7(289):289ra82 with an added Avidin-Flag-HIS sequence to enable purification. The resulting MGD006-like construct is referred to as TRI168.

Example 17: Human T-Cell Activation, Cytotoxicity and Cytokine Release in Response to TRI130 and TRI168

To compare the activity of TRI130 and the TRI168 proteins in vitro, T-cells were isolated from normal donor peripheral blood mononuclear cells (PBMC) and incubated with various concentrations of TRI130 and TRI168 in the presence of CD123+ tumor cells (MOLM-13).

T-cell activation was assessed after 24 hours of culture by flow cytometry. After centrifugation and removal of supernatant, the cell pellets were resuspended with a mixture of the following dye-labeled antibodies in 50 μl volumes: CD69-FITC, CD5-PE, CD8-Pacific Blue, CD4-APC, CD25-PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to calculate the percentages of CD4+ (CD8−) or CD8+ T-cells that had upregulated CD69 and CD25, by gating sequentially on forward vs side scatter, 7AAD−, CD5+, CD4+ or CD8+ T-cells (7AAD−, CD5+ CD4+ or 7AAD− CD5+CD8+, respectively). Graphs were plotted using GraphPad Prism 7.0. TRI130 and TRI168 induced similar, dose-dependent T-cell activation in the presence of CD123+ target cells with both donors tested (FIG. 18). The figure shows the percentage of CD4+ and CD8+ T-cells that were CD69 and CD25 positive. EC50 values were determined with TRI130 and TRI168 for both CD4+ and CD8+CD25+CD69+ populations demonstrating similar potency for both molecules. No T-cell activation was observed in the absence of CD123+ target cells (Not Shown).

Molm-13 cytotoxicity was assessed after 24 hours of culture by flow cytometry as described above. The sample files were analyzed using FlowJo software to quantitate cytotoxicity by gating sequentially on forward vs side scatter, 7AAD−, CD5− cells. Graphs were plotted using GraphPad Prism 7.0. TRI130 and TRI168 induced similar, dose-dependent Molm-13 cytoxicity with both donors tested (FIG. 19). The figure shows the total number of viable Molm-13 cells after 24 hours of culture with purified T-cells, TRI130 and TRI168.

Levels of a selected subset of cytokines commonly produced by activated T-cells including IFNγ, IL-2, TNFα and IL-10 were measured in the 24-hour culture supernatants using multiplexed analyte assays. TRI168 induced higher levels of cytokine secretion compared to TRI130 with both donors tested in the presence of CD123+ Molm-13 target cells (FIG. 20).

Rare normal immune cell populations including plasmacytoid dendritic cells and basophils expressing high levels of CD123 are present in PBMC samples and represent targets for anti-CD123×anti-CD3 bispecific molecules. To examine the levels of cytokine secretion induced by TRI130 and TRI168 in the absence of exogenously added target cells, normal donor PBMC were cultured for 24 hours with various concentrations of both proteins and cytokines measured in the resulting supernatants using multiplexed analyte assays. Similar to cultures with purified T-cells and MOLM-13 cells, TRI168 induced higher levels of IFNγ, IL-2, TNFα and IL-10 compared to TRI130 (FIG. 21).

Taken together these results demonstrate comparable in vitro T-cell activation and cytotoxicity of exogenously added CD123+ tumor cells with TRI130 and the MGD006-like anti-CD123×anti-CD3 bispecific TRI168. Notably, TRI168 induces much higher levels of secreted T-cell cytokines in cultures of both purified T-cells with Molm-13 tumor cells and normal donor PBMC samples compared to TRI130. In the clinic, drugs that induce strong T-cell activation can cause a series of adverse events, termed "cytokine release syndrome" (CRS), due to excessive cytokine release. Released cytokines cause a systemic inflammatory response that can lead to life-threatening complications which can limit drug administration.

Example 18: TRI130 Induced Cytotoxicity of AML Cell Samples

To determine if TRI130 is capable of inducing cytotoxicity in primary AML cells, PBMC samples from AML subjects were cultured for several days with various concentrations of TRI130. Cytotoxicity of AML cells was assessed by flow cytometry after four days of culture. After centrifugation and removal of supernatant, the cell pellets were resuspended with a mixture including the following dye-labeled antibodies in 50 μl volumes: CD69-FITC, CD5-APC, CD19-Pacific Blue, CD25-PE-Cy7, and 7AAD, and incubated for 30 min on ice. Cells were washed twice and resuspended in 120 μl volumes immediately prior to acquisition of 50% of each well in a BD LSRII flow cytometer. The sample files were analyzed using FlowJo software to quantitate cytotoxicity in the non-B, non-T cell compartment by gating sequentially on forward vs side scatter, 7AAD−, CD5−, CD19−, CD25− cells. Graphs were plotted using GraphPad Prism 7.0. TRI130 induced a dose dependent loss of non-B, non-T AML cell samples in both donors tested (FIG. 22). The figure shows the total number of viable non-B, non-T-cells after 96 hours of culture. Similar results were obtained at 24 and 48 hours (data not shown). These results demonstrate that TRI130 is capable of inducing cytotoxicity in cultures of primary human AML PBMC samples.

The invention claimed is:

1. A recombinant polypeptide comprising a CD123-binding domain and a CD3-binding domain, wherein the CD123-binding domain comprises (i) an immunoglobulin light chain variable region comprising LCDR1, LCDR2, and LCDR3, and (ii) an immunoglobulin heavy chain variable region comprising HCDR1, HCDR2, and HCDR3, wherein the LCDR1 comprises the amino acid sequence set forth in SEQ ID NO:6; the LCDR2 comprises the amino acid sequence set forth in SEQ ID NO:8; the LCDR3 comprises the amino acid sequence set forth in SEQ ID NO:10, the HCDR1 comprises the amino acid sequence set forth in SEQ ID NO:12; the HCDR2 comprises the amino acid sequence set forth in SEQ ID NO:14; and the HCDR3 comprises the amino acid sequence set forth in SEQ ID NO: 16;

wherein the CD3-binding domain comprises: (i) an immunoglobulin light chain variable region comprising LCDR1, LCDR2, and LCDR3, and (ii) an immunoglobulin heavy chain variable region comprising HCDR1, HCDR2, and HCDR3, wherein (a) the LCDR1, LCDR2 and LCDR3 of the CD3-binding domain comprise the amino acid sequences set forth in SEQ ID NO:162, SEQ ID NO:163, and SEQ ID NO:164, respectively, and the HCDR1, HCDR2, and HCDR3 of the CD3-binding domain comprise the amino acid sequences set forth in SEQ ID NO: 165, SEQ ID NO:166, and SEQ ID NO:167, respectively;

(b) the LCDR1, LCDR2 and LCDR3 of the CD3-binding domain comprise the amino acid sequences set forth in SEQ ID NO:168, SEQ ID NO:169, and SEQ ID NO:170, respectively, and the HCDR1, HCDR2, and HCDR3 of the CD3-binding domain comprise the amino acid sequences set forth in SEQ ID NO: 171, SEQ ID NO:172, and SEQ ID NO:173, respectively;

(c) the LCDR1, LCDR2 and LCDR3 of the CD3-binding domain comprise the amino acid sequences set forth in SEQ ID NO: 307, SEQ ID NO: 308 and SEQ ID NO:309, respectively, and the HCDR1, HCDR2, and HCDR3 of the CD3-binding domain comprise the amino acid sequences set forth in SEQ ID NO: 174, SEQ ID NO: 175 and SEQ ID NO:176, respectively;

(d) the LCDR1, LCDR2 and LCDR3 of the CD3-binding domain comprise the amino acid sequences set forth in SEQ ID NO: 310, SEQ ID NO: 177 and SEQ ID NO: 178, respectively, and the HCDR1, HCDR2, and HCDR3 of the CD3-binding domain comprise the amino acid sequences set forth in SEQ ID NO: 179, SEQ ID NO: 180 and SEQ ID NO: 181, respectively, (e) the LCDR1, LCDR2 and LCDR3 of the CD3-binding domain comprise the amino acid sequences set forth in SEQ ID NO: 182, SEQ ID NO: 183 and SEQ ID NO: 184, respectively, and the HCDR1, HCDR2, and HCDR3 of the CD3-binding domain comprise the amino acid sequences set forth in SEQ ID NO: 185, SEQ ID NO: 186 and SEQ ID NO: 187, respectively; or (f) the LCDR1, LCDR2 and LCDR3 of the CD3-binding domain comprise the amino acid sequences set forth in SEQ ID NO: 188, SEQ ID NO: 189 and SEQ ID NO: 190, respectively, and the HCDR1, HCDR2, and HCDR3 of the CD3-binding domain comprise the amino acid sequences set forth in SEQ ID NO: 191, SEQ ID NO: 192 and SEQ ID NO: 193, respectively.

2. The polypeptide of claim 1, wherein the CD3-binding domain comprises an immunoglobulin light chain variable region and an immunoglobulin heavy chain variable region;

wherein the immunoglobulin light chain variable region of the CD3-binding domain comprises the amino acid sequence of SEQ ID NO:160; and wherein the immunoglobulin heavy chain variable region of the CD3-binding domain comprises the amino acid sequence of SEQ ID NO:161.

3. The polypeptide of claim 1, wherein the CD123-binding domain comprises:

(i) an immunoglobulin light chain variable region comprising the amino acid sequence of SEQ ID NO:2; and (ii) an immunoglobulin heavy chain variable region comprising the amino acid sequence of SEQ ID NO:4.

4. The polypeptide of claim 1, wherein the CD123-binding domain is a single chain variable fragment (scFv), and the CD3-binding domain is an scFv.

5. The polypeptide of claim 1, comprising, in order from amino terminus to carboxyl terminus, (i) the CD123-binding domain, (ii) a hinge region, (iii) an immunoglobulin constant region, (iv) a carboxyl-terminus linker, and (v) the CD3-binding domain.

6. The polypeptide of claim 5, wherein the carboxyl-terminus linker comprises an amino acid sequence comprising $(Gly4Ser)_n$, wherein n=1-7 (SEQ ID NO:314).

7. The polypeptide of claim 6, wherein n=3-5.

8. The polypeptide of claim 5, wherein the carboxyl-terminus linker comprises SEQ ID NO:288.

9. The polypeptide of claim 5, wherein the immunoglobulin constant region comprises immunoglobulin CH2 and CH3 domains of IgG1, IgG2, IgG3, IgG4, IgA1, IgA2 or IgD.

10. The polypeptide of claim 5, wherein the immunoglobulin constant region comprises a human IgG1 CH2 domain comprising the substitutions L234A, L235A, G237A, and K322A, according to the EU numbering system.

11. A dimer comprising two identical polypeptides of claim 1.

12. A pharmaceutical composition comprising the polypeptide of claim 1 and a pharmaceutically acceptable carrier, diluent, or excipient.

13. An isolated nucleic acid molecule encoding the recombinant polypeptide of claim 1.

14. An expression vector comprising a nucleic acid segment encoding the polypeptide of claim 1, wherein the nucleic acid segment is operatively linked to regulatory sequences suitable for expression of the nucleic acid segment in a host cell.

15. A recombinant host cell comprising the expression vector of claim 14.

* * * * *